United States Patent
Chen et al.

(10) Patent No.: US 11,408,032 B2
(45) Date of Patent: Aug. 9, 2022

(54) TUBE LENS DESIGN FOR IMPROVED DEPTH-OF-FIELD

(71) Applicant: Element Biosciences, Inc., San Diego, CA (US)

(72) Inventors: Steve Xiangling Chen, San Diego, CA (US); Minghao Guo, San Diego, CA (US); Michael Previte, San Diego, CA (US); Chunhong Zhou, San Diego, CA (US); Derek Fuller, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 17/016,350

(22) Filed: Sep. 9, 2020

(65) Prior Publication Data
US 2021/0223161 A1 Jul. 22, 2021

Related U.S. Application Data

(60) Provisional application No. 63/076,361, filed on Sep. 9, 2020, provisional application No. 62/962,723, filed on Jan. 17, 2020.

(51) Int. Cl.
*G01N 21/64* (2006.01)
*C12Q 1/6869* (2018.01)
(Continued)

(52) U.S. Cl.
CPC ....... *C12Q 1/6869* (2013.01); *C12N 15/1006* (2013.01); *C12Q 1/6806* (2013.01);
(Continued)

(58) Field of Classification Search
CPC ........... G01M 11/0264; G01N 15/1436; G01N 2015/144; G02B 21/006; G02B 21/0016; G02B 21/244; G02B 21/0064
(Continued)

(56) References Cited

U.S. PATENT DOCUMENTS 4,083,057 A 4/1978 Quinn
5,428,441 A 6/1995 Ogino et al.
(Continued)

FOREIGN PATENT DOCUMENTS

CN 102016546 A 4/2011
CN 110248733 A 9/2019
(Continued)

OTHER PUBLICATIONS

Oldenbourg et al., Methods in Molecular Medicine: Analysis of Microtubule Dynamics by Polarized Light. Methods Mol Med 137: 111-123 (2007).
(Continued)

*Primary Examiner* — Isiaka O Akanbi
(74) *Attorney, Agent, or Firm* — Wilson Sonsini Goodrich & Rosati

(57) ABSTRACT

Imaging systems and methods comprising imaging a first interior surface and a second interior surface of a flow cell are described. In some embodiments, the imaging systems may comprise: a) an objective lens; b) at least one image sensor; and c) at least one tube lens disposed in an optical path between the objective lens and the at least one image sensor; wherein the at least one tube lens is configured to correct imaging performance such that images of the first interior surface of the flow cell and the second interior surface of the flow cell have substantially the same optical resolution.

34 Claims, 42 Drawing Sheets

(51) Int. Cl.
  *G01N 15/14* (2006.01)
  *C12N 15/10* (2006.01)
  *C12Q 1/6806* (2018.01)

(52) U.S. Cl.
  CPC ....... *G01N 15/147* (2013.01); *G01N 15/1436* (2013.01); *G01N 15/1484* (2013.01); *G01N 21/6402* (2013.01); *G01N 21/6428* (2013.01); *G01N 21/6456* (2013.01); *G01N 21/6458* (2013.01); *G01N 21/6486* (2013.01); *G01N 2015/144* (2013.01); *G01N 2021/6439* (2013.01); *G01N 2021/6441* (2013.01); *G01N 2021/6463* (2013.01); *G01N 2201/0612* (2013.01)

(58) Field of Classification Search
  USPC ........... 356/124, 456, 602–635, 237.2–237.6
  See application file for complete search history.

(56) References Cited

U.S. PATENT DOCUMENTS

| | | | |
|---|---|---|---|
| 5,512,131 A | 4/1996 | Kumar et al. | |
| 5,547,839 A | 8/1996 | Dower et al. | |
| 5,578,832 A | 11/1996 | Trulson et al. | |
| 5,622,872 A | 4/1997 | Ribi | |
| 5,834,758 A | 11/1998 | Trulson et al. | |
| 6,115,192 A | 9/2000 | McDonald | |
| 6,720,143 B2 | 4/2004 | Juncosa et al. | |
| 6,829,051 B2 | 12/2004 | Abe et al. | |
| 7,126,699 B1* | 10/2006 | Wihl | G01B 11/0608 356/625 |
| 8,039,817 B2 | 10/2011 | Feng et al. | |
| 8,071,962 B1 | 12/2011 | Feng et al. | |
| 8,143,599 B2 | 3/2012 | Feng et al. | |
| 8,242,463 B2 | 8/2012 | Feng et al. | |
| 8,278,630 B1 | 10/2012 | Feng et al. | |
| 8,399,196 B2 | 3/2013 | Hoser | |
| 8,546,772 B2 | 10/2013 | Feng et al. | |
| 8,586,947 B1 | 11/2013 | Feng et al. | |
| 8,698,102 B2 | 4/2014 | Feng et al. | |
| 8,895,249 B2 | 11/2014 | Shen et al. | |
| 9,068,220 B2 | 6/2015 | Feng et al. | |
| 9,193,998 B2 | 11/2015 | Khurana et al. | |
| 9,365,898 B2 | 6/2016 | Feng et al. | |
| 10,001,622 B2* | 6/2018 | Price | H04N 9/09 |
| 10,564,101 B1* | 2/2020 | Néron | G01B 9/02091 |
| 10,634,487 B2* | 4/2020 | Zhao | G01B 11/24 |
| 10,655,176 B2 | 5/2020 | Stromberg et al. | |
| 10,656,368 B1 | 5/2020 | Rosenberry et al. | |
| 10,704,094 B1 | 7/2020 | Arslan et al. | |
| 10,748,730 B2* | 8/2020 | Chuang | H01J 1/34 |
| 10,768,173 B1 | 9/2020 | Arslan et al. | |
| 10,876,148 B2 | 12/2020 | Zhou et al. | |
| 10,982,280 B2 | 4/2021 | Arslan et al. | |
| 10,996,453 B2 | 5/2021 | Newman et al. | |
| 11,047,005 B2 | 6/2021 | Staker et al. | |
| 11,053,540 B1 | 7/2021 | Chen et al. | |
| 11,060,138 B1 | 7/2021 | Chen et al. | |
| 11,060,140 B2 | 7/2021 | Staker et al. | |
| 11,198,121 B1 | 12/2021 | Guo et al. | |
| 11,200,446 B1 | 12/2021 | ChunHong et al. | |
| 2003/0170613 A1 | 9/2003 | Straus | |
| 2003/0186227 A1 | 10/2003 | Balasubramanian et al. | |
| 2004/0095573 A1* | 5/2004 | Tsai | G01N 21/9501 356/237.5 |
| 2004/0248287 A1 | 12/2004 | Hu et al. | |
| 2005/0073675 A1* | 4/2005 | Lo | G01N 21/8806 356/237.2 |
| 2007/0115457 A1* | 5/2007 | Matsuzawa | G01M 11/0264 356/124 |
| 2008/0030721 A1* | 2/2008 | Kepler | H04N 5/2256 356/124 |
| 2008/0274904 A1 | 11/2008 | Gormley et al. | |
| 2008/0274905 A1* | 11/2008 | Greene | G01N 21/6428 506/4 |
| 2009/0047670 A1 | 2/2009 | Miller et al. | |
| 2009/0103792 A1* | 4/2009 | Rahn | G01N 21/4795 382/131 |
| 2009/0186775 A1 | 7/2009 | Nowak et al. | |
| 2009/0272914 A1* | 11/2009 | Feng | G01N 21/05 250/459.1 |
| 2010/0099100 A1 | 4/2010 | Zaccarin et al. | |
| 2010/0298171 A1 | 11/2010 | Shirazi et al. | |
| 2010/0321786 A1* | 12/2010 | Rahn | G01N 21/4795 359/634 |
| 2011/0165652 A1 | 7/2011 | Hardin et al. | |
| 2011/0220775 A1* | 9/2011 | Triener | G01N 21/6456 250/201.1 |
| 2012/0105858 A1* | 5/2012 | Popescu | G01N 15/1434 356/450 |
| 2012/0148141 A1 | 6/2012 | Ozcan et al. | |
| 2012/0214171 A1 | 8/2012 | Kotseroglou | |
| 2013/0100272 A1* | 4/2013 | Price | H04N 9/09 348/E5.045 |
| 2013/0235388 A1* | 9/2013 | Segale | C12Q 1/6874 356/609 |
| 2013/0274119 A1* | 10/2013 | Knutson | G01N 33/5029 506/9 |
| 2013/0280715 A1 | 10/2013 | Bornhop et al. | |
| 2014/0139840 A1* | 5/2014 | Judkewitz | G02B 21/367 356/456 |
| 2015/0160450 A1 | 6/2015 | Ou et al. | |
| 2016/0041095 A1 | 2/2016 | Rothberg et al. | |
| 2016/0216208 A1 | 7/2016 | Kim et al. | |
| 2016/0281150 A1* | 9/2016 | Rawlings | G01N 35/1095 |
| 2017/0315341 A1* | 11/2017 | Fuller | G02B 21/365 |
| 2017/0341075 A1 | 11/2017 | Sirkis et al. | |
| 2018/0178215 A1 | 6/2018 | Fisher et al. | |
| 2018/0209784 A1* | 7/2018 | Zhao | G01B 11/24 |
| 2018/0284010 A1* | 10/2018 | Scarcelli | G01N 15/1475 |
| 2019/0049708 A1* | 2/2019 | Erlbacher | G02B 21/365 |
| 2019/0212266 A1 | 7/2019 | Baker | |
| 2019/0219835 A1 | 7/2019 | Skinner et al. | |
| 2019/0226992 A1 | 7/2019 | Guo | |
| 2019/0276886 A1 | 9/2019 | Skinner et al. | |
| 2019/0374944 A1* | 12/2019 | Lundquist | G02B 21/361 |
| 2020/0026090 A1 | 1/2020 | Hargis et al. | |
| 2020/0139375 A1 | 5/2020 | Buermann et al. | |
| 2020/0142170 A1 | 5/2020 | Cai | |
| 2020/0149095 A1 | 5/2020 | Arslan et al. | |
| 2020/0179921 A1 | 6/2020 | Arslan et al. | |
| 2020/0182792 A1 | 6/2020 | Vaziri | |
| 2020/0182866 A1 | 6/2020 | Arslan et al. | |
| 2020/0192071 A1 | 6/2020 | Newman et al. | |
| 2020/0218052 A1 | 7/2020 | Hong | |
| 2020/0218053 A1 | 7/2020 | Zou et al. | |
| 2020/0347443 A1 | 11/2020 | Arslan et al. | |
| 2020/0370113 A1 | 11/2020 | Kellinger et al. | |
| 2021/0040534 A1 | 2/2021 | Zhou et al. | |
| 2021/0072234 A1 | 3/2021 | Arslan et al. | |
| 2021/0121882 A1 | 4/2021 | Guo et al. | |
| 2021/0123098 A1 | 4/2021 | Previte et al. | |
| 2021/0123911 A1 | 4/2021 | Arslan et al. | |
| 2021/0139884 A1 | 5/2021 | Kellinger et al. | |
| 2021/0139981 A1 | 5/2021 | Arslan et al. | |
| 2021/0223178 A1 | 7/2021 | Guo et al. | |
| 2021/0223530 A1 | 7/2021 | Guo et al. | |
| 2021/0223531 A1 | 7/2021 | Guo et al. | |
| 2021/0247389 A1 | 8/2021 | Arslan et al. | |
| 2021/0269793 A1 | 9/2021 | Kellinger et al. | |
| 2021/0318294 A1 | 10/2021 | Previte et al. | |
| 2021/0318295 A1 | 10/2021 | Arslan et al. | |
| 2021/0332416 A1 | 10/2021 | Chen et al. | |
| 2021/0332430 A1 | 10/2021 | Arslan et al. | |
| 2021/0333210 A1 | 10/2021 | Chen et al. | |
| 2021/0333211 A1 | 10/2021 | Chen et al. | |

(56) References Cited

U.S. PATENT DOCUMENTS

| | | |
|---|---|---|
| 2021/0373000 A1 | 12/2021 | Arslan et al. |
| 2021/0387184 A1 | 12/2021 | Guo et al. |

FOREIGN PATENT DOCUMENTS

| | | |
|---|---|---|
| DE | 10014204 A1 | 10/2001 |
| WO | WO-2019241305 A1 | 12/2019 |
| WO | WO-2020061237 A1 | 3/2020 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021146597 A1 | 7/2021 |
| WO | WO-2021236792 A1 | 11/2021 |
| WO | WO-2021252671 A2 | 12/2021 |

OTHER PUBLICATIONS

U.S. Appl. No. 17/016,353 Non-Final Office Action dated Jan. 13, 2021.

U.S. Appl. No. 17/016,349 Office Action dated Feb. 2, 2021.

PCT/US2021/013696 International Search Report and Written Opinion dated Apr. 7, 2021.

Feiner-Garcia et al., Advanced Optical Microscopy Techniques for the Investigation of Cell-Nanoparticle Interactions. Smart Nanoparticles for Biomedicine: Micro and Nano Technologies, pp. 219-236 (2018).

Lutz, Biological Imaging by Superresolution Light Microscopy. Comprehensive Biotechnology (Second Ed.) vol. 1: 579-589 (2011).

Nylk et al., Light-Sheet Fluorescence Microscopy with Structured Light. Neurophotonics and Biomedical Spectroscopy, pp. 477-501 (2019).

U.S. Appl. No. 17/372,362 Non-Final Office Action dated Dec. 14, 2021.

U.S. Appl. No. 17/372,362 Non-Final Office Action dated Oct. 22, 2021.

U.S. Appl. No. 17/496,710 Non-Final Office Action dated Nov. 30, 2021.

Dover Motion (Microscope calculations: Field of View, Depth of Field, Numerical Aperture, YouTube tutorial Dover motion CTO, Kevin McCathy, DOF05 product Video dated, Aug. 9, 2019). https://dovermotion.com/applications-capabilities/automated-imaging/microscope-calculations/ (Year: 2019).

U.S. Appl. No. 17/151,020 Final Office Action dated Aug. 9, 2021.

U.S. Appl. No. 17/151,020 Non-Final Office Action dated Mar. 26, 2021.

U.S. Appl. No. 17/372,362 Non-Final Office Action dated Apr. 4, 2022.

\* cited by examiner

TUBE LENS DESIGN FOR IMPROVED DEPTH-OF-FIELD

CROSS-REFERENCE

This application claims the benefit of U.S. Provisional Application No. 63/076,361, filed Sep. 9, 2020 and U.S. Provisional Application No. 62/962,723, filed Jan. 17, 2020, each of which is incorporated herein by reference in its entirety.

BACKGROUND

In typical fluorescence-based genomic testing assays, e.g., genotyping or nucleic acid sequencing (using either real time, cyclic, or stepwise reaction schemes), dye molecules that are attached to nucleic acid molecules tethered on a substrate are excited using an excitation light source, a fluorescence photon signal is generated in one or more spatially-localized positions on the substrate, and the fluorescence is subsequently imaged through an optical system onto an image sensor. An analysis process is then used to analyze the images, find the positions of labeled molecules (or clonally amplified clusters of molecules) on the substrate, and quantify the fluorescence photon signal in terms of wavelength and spatial coordinates, which may then be correlated with the degree to which a specific chemical reaction, e.g., a hybridization event or base addition event, occurred in the specified locations on the substrate. Imaging-based methods provide large scale parallelism and multiplexing capabilities, which help to drive down the cost and accessibility of such technologies. However, detection errors that arise from, for example, overly dense packing of labeled molecules (or clonally-amplified clusters of molecules) within a small region of the substrate surface, or due to low contrast-to-noise ratio (CNR) in the image, may lead to errors in attributing the fluorescence signal to the correct molecules (or clonally amplified clusters of molecules).

SUMMARY

Disclosed herein are imaging systems configured to image a first interior surface and a second interior surface of a flow cell, the imaging systems comprising: a) an objective lens; b) at least one image sensor; and c) at least one tube lens disposed in an optical path between the objective lens and the at least one image sensor; wherein said optical system has a numerical aperture (NA) of less than 0.6 and a field-of-view (FOV) of greater than 1.0 mm$^2$; and wherein the at least one tube lens is configured to correct imaging performance such that images of the first interior surface of the flow cell and the second interior surface of the flow cell have substantially the same optical resolution.

In some embodiments, the flow cell has a wall thickness of at least 700 µm and a fluid-filled gap between the first interior surface and the second interior surface of at least 50 µm. In some embodiments, the images of the first interior surface and the second interior surface are acquired without moving an optical compensator into an optical path between said objective lens and said at least one image sensor. In some embodiments, the imaging system has a numerical aperture (NA) of less than 0.6. In some embodiments, the imaging system has a numerical aperture (NA) of greater than 0.3. In some embodiments, the imaging system has a field-of-view (FOV) of greater than 1.5 mm$^2$. In some embodiments, the optical resolution of images of the first interior surface and the second interior surface are diffraction-limited across the entire field-of-view (FOV). In some embodiments, the at least one tube lens comprises, in order, an asymmetric convex-convex lens, a convex-plano lens, an asymmetric concave-concave lens, and an asymmetric convex-concave lens. In some embodiments, the imaging system comprises two or more tube lenses which are designed to provide optimal imaging performance for the first interior surface and the second interior surface at two or more fluorescence wavelengths. In some embodiments, the imaging system further comprises a focusing mechanism configured to refocus the optical system between acquiring images of the first interior surface and the second interior surface. In some embodiments, the imaging system is configured to image two or more fields-of-view on at least one of the first interior surface or the second interior surface. In some embodiments, the first interior surface and second interior surface of the flow cell are coated with a hydrophilic coating layer, and wherein said hydrophilic coating layer further comprises labeled nucleic acid colonies disposed thereon at a surface density of >10,000 nucleic acid colonies/mm$^2$. In some embodiments, an image of the first interior surface or second interior surface acquired using the imaging system shows a contrast to noise ratio (CNR) of at least 5 when the nucleic acid colonies are labeled with cyanine dye 3 (Cy3), the imaging system comprises a dichroic mirror and bandpass filter set optimized for Cy3 emission, and the image is acquired under non-signal saturating conditions while the surface is immersed in 25 mM ACES, pH 7.4 buffer. In some embodiments, said imaging system comprises 1, 2, 3, or 4 imaging channels configured to detect nucleic acid colonies disposed on at least one of said two distinct surfaces that have been labeled with 1, 2, 3, or 4 distinct detectable labels. In some embodiments, the imaging system is used to monitor a sequencing-by-avidity, sequencing-by-nucleotide base-pairing, sequencing-by-nucleotide binding, or sequencing-by-nucleotide incorporation reaction on at least one of the first interior surface and the second interior surface and detect a bound or incorporated nucleotide base. In some embodiments, the imaging system is used to perform nucleic acid sequencing. In some embodiments, the imaging system is used to determine a genotype of a sample, wherein determining the genotype of the sample comprises preparing a nucleic acid molecule extracted from the sample for sequencing, and then sequencing the nucleic acid molecule. In some embodiments, the at least one image sensor comprises pixels having a pixel dimension chosen such that a spatial sampling frequency for the imaging system is at least twice an optical resolution of the imaging system. In some embodiments, a combination of the objective lens and the at least one tube lens is configured to optimize a modulation transfer function in the spatial frequency range from 700 cycles per mm to 1100 cycles per mm in the sample plane. In some embodiments, the at least one tube lens is designed to correct modulation transfer function (MTF) at one or more specified spatial frequencies, defocus, spherical aberration, chromatic aberration, coma, astigmatism, field curvature, image distortion, image contrast-to-noise ratio (CNR), or any combination thereof, for a combination of the objective lens and the at least one tube lens.

Also disclosed herein are methods of sequencing a nucleic acid molecule, the methods comprising: a) imaging a first surface and an axially-displaced second surface using an optical system which comprises an objective lens and at least one image sensor, wherein said optical system has a numerical aperture (NA) of less than 0.6 and a field-of-view (FOV) of greater than 1.0 mm$^2$, and wherein images of the first surface and the axially-displaced second surface having substantially the same optical resolution are acquired without moving an optical compensator into an optical path between said objective lens and said at least one image sensor; and b) detecting a fluorescently-labeled composition comprising the nucleic acid molecule, or a complement thereof, disposed on the first surface or the axially-displaced second surface to determine an identity of a nucleotide in the nucleic acid molecule.

In some embodiments, a focusing mechanism is utilized to refocus the optical system between acquiring images of the first surface and the axially-displaced second surface. In some embodiments, the method further comprises imaging two or more fields-of-view on at least one of the first surface or axially-displaced second surface. In some embodiments, the first surface and the axially-displaced second surface comprise two surfaces of a flow cell. In some embodiments, said two surfaces of the flow cell are coated with a hydrophilic coating layer. In some embodiments, said hydrophilic coating layer further comprises labeled nucleic acid colonies disposed thereon at a surface density of >10,000 nucleic acid colonies/mm$^2$. In some embodiments, an image of a surface of said two surfaces acquired using said optical system shows a contrast to noise ratio (CNR) of at least 5 when the nucleic acid colonies are labeled with cyanine dye 3 (Cy3), the optical system comprises a dichroic mirror and bandpass filter set optimized for Cy3 emission, and the image is acquired under non-signal saturating conditions while the surface is immersed in 25 mM ACES, pH 7.4 buffer. In some embodiments, said optical system comprises 1, 2, 3, or 4 imaging channels configured to detect nucleic acid colonies disposed on at least one of the first surface and the axially-displaced second surface that have been labeled with 1, 2, 3, or 4 distinct detectable labels. In some embodiments, the at least one image sensor comprises pixels having a pixel dimension chosen such that a spatial sampling frequency for the optical system is at least twice an optical resolution of the optical system. In some embodiments, the optical system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 μm and a gap between the first interior surface and the second interior surface of at least 50 μm. In some embodiments, the at least one tube lens comprises, in order, an asymmetric convex-convex lens, a convex-plano lens, an asymmetric concave-concave lens, and an asymmetric convex-concave lens. In some embodiments, the optical system comprises two or more tube lenses which are designed to provide optimal imaging performance at two or more fluorescence wavelengths. In some embodiments, a combination of objective lens and tube lens is configured to optimize a modulation transfer function in the mid to high spatial frequency range. In some embodiments, the imaging performance metric comprises a measurement of modulation transfer function (MTF) at one or more specified spatial frequencies, defocus, spherical aberration, chromatic aberration, coma, astigmatism, field curvature, image distortion, image contrast-to-noise ratio (CNR), or any combination thereof. In some embodiments, the optical resolution of images of the first surface and axially-displaced second surface are diffraction-limited across the entire field-of-view (FOV). In some embodiments, the sequencing of the nucleic acid molecule further comprises performing a sequencing-by-avidity, sequencing-by-nucleotide base-pairing, sequencing-by-nucleotide binding, or sequencing-by-nucleotide incorporation reaction on at least one of the first surface and axially-displaced second surface and detecting a bound or incorporated nucleotide base. In some embodiments, the method further comprises determining a genotype of a sample, wherein determining the genotype of the sample comprises preparing said nucleic acid molecule for sequencing, and then sequencing said nucleic acid molecule.

Disclosed herein are imaging systems configured to image two distinct, axially-displaced surfaces, the imaging systems comprising an objective lens and at least one image sensor, wherein said imaging system has a numerical aperture (NA) of less than 0.6 and a field-of-view (FOV) of greater than 1.0 mm2, and wherein said imaging system is capable of acquiring images of the two distinct, axially-displaced surfaces that have substantially the same optical resolution without moving an optical compensator into an optical path between said objective lens and said at least one image sensor.

In some embodiments, the imaging system has a numerical aperture of greater than 0.3. In some embodiments, the imaging system further comprises a focusing mechanism used to refocus the optical system between acquiring images of the two distinct, axially-displaced surfaces. In some embodiments, the imaging system is configured to image two or more fields-of-view on at least one of said two distinct, axially-displaced surfaces. In some embodiments, said two distinct, axially-displaced surfaces comprise two surfaces of a flow cell. In some embodiments, said two distinct surfaces of the flow cell are coated with a hydrophilic coating layer, and wherein said hydrophilic coating layer further comprises labeled nucleic acid colonies disposed thereon at a surface density of >10,000 nucleic acid colonies/mm$^2$. In some embodiments, said imaging system comprises 1, 2, 3, or 4 imaging channels configured to detect nucleic acid colonies disposed on at least one of said two distinct surfaces that have been labeled with 1, 2, 3, or 4 distinct detectable labels. In some embodiments, the at least one image sensor comprises pixels having a pixel dimension chosen such that a spatial sampling frequency for the imaging system is at least twice an optical resolution of the imaging system. In some embodiments, the imaging system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 μm and a gap between the first interior surface and the second interior surface of at least 50 μm. In some embodiments, the imaging system comprises two or more tube lenses which are designed to provide optimal imaging performance at two or more fluorescence wavelengths. In some embodiments, the optical resolution of images of the two distinct, axially-displaced surfaces are diffraction-limited across the entire field-of-view (FOV).

Disclosed herein are methods of sequencing a nucleic acid molecule, the method comprising: a) imaging a first surface and an axially-displaced second surface using a compensation-free optical system which comprises an objective lens and at least one image sensor, wherein said optical system has a numerical aperture (NA) of less than 0.6 and a field-of-view (FOV) of greater than 1.0 mm$^2$; b) processing the images of the first surface and the axially-displaced second surface to correct for optical aberration such that the images of the first surface and the axially-displaced second surface have substantially the same optical resolution; and c) detecting a fluorescently-labeled composition comprising the nucleic acid molecule, or a complement thereof, disposed on the first surface or the axially-displaced second surface to determine an identity of a nucleotide in the nucleic acid molecule.

In some embodiments, the images of the first surface and the axially-displaced second surface are acquired without moving an optical compensator into an optical path between said objective lens and said at least one image sensor. In some embodiments, the images of the first surface and the axially-displaced second surface are acquired by just refocusing the optical system. In some embodiments, the method further comprises imaging two or more fields-of-view on at least one of the first surface or axially-displaced second surface. In some embodiments, the first surface and the axially-displaced second surface comprise two surfaces of a flow cell. In some embodiments, said two surfaces of the flow cell are coated with a hydrophilic coating layer. In some embodiments, said hydrophilic coating layer further comprises labeled nucleic acid colonies disposed thereon at a surface density of >10,000 nucleic acid colonies/mm$^2$. In some embodiments, an image of a surface of said two surfaces acquired using said optical system shows a contrast to noise ratio (CNR) of at least 5 when the nucleic acid colonies are labeled with cyanine dye 3 (Cy3), the optical system comprises a dichroic mirror and bandpass filter set optimized for Cy3 emission, and the image is acquired under non-signal saturating conditions while the surface is immersed in 25 mM ACES, pH 7.4 buffer. In some embodiments, said optical system comprises 1, 2, 3, or 4 imaging channels configured to detect nucleic acid colonies disposed on at least one of the first surface and the axially-displaced second surface that have been labeled with 1, 2, 3, or 4 distinct detectable labels. In some embodiments, at least one image sensor comprises pixels having a pixel dimension chosen such that a spatial sampling frequency for the optical system is at least twice an optical resolution of the optical system. In some embodiments, the optical system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 μm and a gap between the first interior surface and the second interior surface of at least 50 μm. In some embodiments, the at least one tube lens comprises, in order, an asymmetric convex-convex lens, a convex-plano lens, an asymmetric concave-concave lens, and an asymmetric convex-concave lens. In some embodiments, the optical system comprises two or more tube lenses which are designed to provide optimal imaging performance at two or more fluorescence wavelengths. In some embodiments, a combination of objective lens and tube lens is configured to optimize a modulation transfer function in the mid to high spatial frequency range. In some embodiments, the imaging performance metric comprises a measurement of modulation transfer function (MTF) at one or more specified spatial frequencies, defocus, spherical aberration, chromatic aberration, coma, astigmatism, field curvature, image distortion, image contrast-to-noise ratio (CNR), or any combination thereof. In some embodiments, the optical resolution of images of the first surface and axially-displaced second surface are diffraction-limited across the entire field-of-view (FOV). In some embodiments, the sequencing of the nucleic acid molecule further comprises performing a sequencing-by-avidity, sequencing-by-nucleotide binding, or sequencing-by-nucleotide incorporation reaction on at least one of the first surface and axially-displaced second surface and detecting a bound or incorporated nucleotide base. In some embodiments, the method further comprises determining a genotype of a sample, wherein determining the genotype of the sample comprises preparing said nucleic acid molecule for sequencing, and then sequencing said nucleic acid molecule.

Disclosed herein are systems for sequencing a nucleic acid molecule comprising: a) an optical system comprising an objective lens and at least one image sensor, wherein said optical system has a numerical aperture (NA) of less than 0.6 and a field-of-view (FOV) of greater than 1.0 mm$^2$, and is configured to acquire images of a first surface and an axially-displaced second surface; and b) a processor programmed to: i) process images of the first surface and the axially-displaced second surface to correct for optical aberration such that the images of the first surface and the axially-displaced second surface have substantially the same optical resolution; and ii) detect a fluorescently-labeled composition comprising the nucleic acid molecule, or a complement thereof, disposed on the first surface or the axially-displaced second surface to determine an identity of a nucleotide in the nucleic acid molecule.

In some embodiments, the images of the first surface and the axially-displaced second surface are acquired without moving an optical compensator into an optical path between said objective lens and said at least one image sensor. In some embodiments, the images of the first surface and the axially-displaced second surface are acquired by just refocusing the optical system. In some embodiments, the imaging system has a numerical aperture of greater than 0.3. In some embodiments, the first surface and axially-displaced second surface comprise two surfaces of a flow cell. In some embodiments, said two surfaces of the flow cell are coated with a hydrophilic coating layer, and wherein said hydrophilic coating layer further comprises labeled nucleic acid colonies disposed thereon at a surface density of >10,000 nucleic acid colonies/mm$^2$. In some embodiments, said optical system comprises 1, 2, 3, or 4 imaging channels configured to detect nucleic acid colonies disposed on at least one of the first surface or axially-displaced second surface that have been labeled with 1, 2, 3, or 4 distinct detectable labels. In some embodiments, the at least one image sensor comprises pixels having a pixel dimension chosen such that a spatial sampling frequency for the optical system is at least twice an optical resolution of the optical system. In some embodiments, the system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 μm and a gap between the first interior surface and the second interior surface of at least 50 μm. In some embodiments, the optical system comprises two or more tube lenses which are designed to provide optimal imaging performance at two or more fluorescence wavelengths.

Disclosed herein are fluorescence imaging systems comprising: a) at least one light source configured to provide excitation light within one or more specified wavelength ranges; b) an objective lens configured to collect fluorescence arising from within a specified field-of-view of a sample plane upon exposure of the sample plane to the excitation light, wherein a numerical aperture of the objective lens is at least 0.3, wherein a working distance of the objective lens is at least 700 μm, and wherein the field-of-view has an area of at least 2 mm$^2$; and c) at least one image sensor, wherein the fluorescence collected by the objective lens is imaged onto the image sensor, and wherein a pixel dimension for the image sensor is chosen such that a spatial sampling frequency for the fluorescence imaging system is at least twice an optical resolution of the fluorescence imaging system.

In some embodiments, the numerical aperture is at least 0.75. In some embodiments, the numerical aperture is at least 1.0. In some embodiments, the working distance is at least 850 µm. In some embodiments, the working distance is at least 1,000 µm. In some embodiments, the field-of-view has an area of at least 2.5 mm². In some embodiments, the field-of-view has an area of at least 3 mm². In some embodiments, the spatial sampling frequency is at least 2.5 times the optical resolution of the fluorescence imaging system. In some embodiments, the spatial sampling frequency is at least 3 times the optical resolution of the fluorescence imaging system. In some embodiments, the system further comprises an X-Y-Z translation stage such that the system is configured to acquire a series of two or more fluorescence images in an automated fashion, wherein each image of the series is acquired for a different field-of-view. In some embodiments, a position of the sample plane is simultaneously adjusted in an X direction, a Y direction, and a Z direction to match the position of an objective lens focal plane in between acquiring images for different fields-of-view. In some embodiments, the time required for the simultaneous adjustments in the X direction, Y direction, and Z direction is less than 0.4 seconds. In some embodiments, the system further comprises an autofocus mechanism configured to adjust the focal plane position prior to acquiring an image of a different field-of-view if an error signal indicates that a difference in the position of the focal plane and the sample plane in the Z direction is greater than a specified error threshold. In some embodiments, the specified error threshold is 100 nm. In some embodiments, the specified error threshold is 50 nm. In some embodiments, the system comprises three or more image sensors, and wherein the system is configured to image fluorescence in each of three or more wavelength ranges onto a different image sensor. In some embodiments, a difference in the position of a focal plane for each of the three or more image sensors and the sample plane is less than 100 nm. In some embodiments, a difference in the position of a focal plane for each of the three or more image sensors and the sample plane is less than 50 nm. In some embodiments, the total time required to reposition the sample plane, adjust focus if necessary, and acquire an image is less than 0.4 seconds per field-of-view. In some embodiments, the total time required to reposition the sample plane, adjust focus if necessary, and acquire an image is less than 0.3 seconds per field-of-view.

Also discloser herein are fluorescence imaging systems for dual-side imaging of a flow cell comprising: a) an objective lens configured to collect fluorescence arising from within a specified field-of-view of a sample plane within the flow cell; b) at least one tube lens positioned between the objective lens and at least one image sensor, wherein the at least one tube lens is configured to correct an imaging performance metric for a combination of the objective lens, the at least one tube lens, and the at least one image sensor when imaging an interior surface of the flow cell, and wherein the flow cell has a wall thickness of at least 700 µm and a gap between an upper interior surface and a lower interior surface of at least 50 µm; wherein the imaging performance metric is substantially the same for imaging the upper interior surface or the lower interior surface of the flow cell without moving an optical compensator into or out of an optical path between the flow cell and the at least one image sensor, without moving one or more optical elements of the tube lens along the optical path, and without moving one or more optical elements of the tube lens into or out of the optical path.

In some embodiments, the objective lens is a commercially-available microscope objective. In some embodiments, the commercially-available microscope objective has a numerical aperture of at least 0.3. In some embodiments, the objective lens has a working distance of at least 700 µm. In some embodiments, the objective lens is corrected to compensate for a cover slip thickness (or flow cell wall thickness) of 0.17 mm. In some embodiments, the fluorescence imaging system further comprising an electro-optical phase plate positioned adjacent to the objective lens and between the objective lens and the tube lens, wherein the electro-optical phase plate provides correction for optical aberrations caused by a fluid filling the gap between the upper interior surface and the lower interior surface of the flow cell. In some embodiments, the at least one tube lens is a compound lens comprising three or more optical components. In some embodiments, the at least one tube lens is a compound lens comprising four optical components. In some embodiments, the four optical components comprise, in order, a first asymmetric convex-convex lens, a second convex-plano lens, a third asymmetric concave-concave lens, and a fourth asymmetric convex-concave lens. In some embodiments, the at least one tube lens is configured to correct an imaging performance metric for a combination of the objective lens, the at least one tube lens, and the at least one image sensor when imaging an interior surface of a flow cell having a wall thickness of at least 1 mm. In some embodiments, the at least one tube lens is configured to correct an imaging performance metric for a combination of the objective lens, the at least one tube lens, and the at least one image sensor when imaging an interior surface of a flow cell having a gap of at least 100 µm. In some embodiments, the at least one tube lens is configured to correct an imaging performance metric for a combination of the objective lens, the at least one tube lens, and the at least one image sensor when imaging an interior surface of a flow cell having a gap of at least 200 µm. In some embodiments, the system comprises a single objective lens, two tube lenses, and two image sensors, and each of the two tube lenses is designed to provide optimal imaging performance at a different fluorescence wavelength. In some embodiments, the system comprises a single objective lens, three tube lenses, and three image sensors, and each of the three tube lenses is designed to provide optimal imaging performance at a different fluorescence wavelength. In some embodiments, the system comprises a single objective lens, four tube lenses, and four image sensors, and each of the four tube lenses is designed to provide optimal imaging performance at a different fluorescence wavelength. In some embodiments, the design of the objective lens or the at least one tube lens is configured to optimize the modulation transfer function in the mid to high spatial frequency range. In some embodiments, the imaging performance metric comprises a measurement of modulation transfer function (MTF) at one or more specified spatial frequencies, defocus, spherical aberration, chromatic aberration, coma, astigmatism, field curvature, image distortion, contrast-to-noise ratio (CNR), or any combination thereof. In some embodiments, the difference in the imaging performance metric for imaging the upper interior surface and the lower interior surface of the flow cell is less than 10%. In some embodiments, the difference in imaging performance metric for imaging the upper interior surface and the lower interior surface of the flow cell is less than 5%. In some embodiments, the use of the at least one tube lens provides for an at least equivalent or better improvement in the imaging performance metric for dual-side imaging compared to that for a conventional system comprising an objective lens, a motion-actuated compensator, and an image sensor. In some embodiments, the use of the at least one tube lens provides for an at least 10% improvement in the imaging performance metric for dual-side imaging compared to that for a conventional system comprising an objective lens, a motion-actuated compensator, and an image sensor.

Disclosed herein are illumination systems for use in imaging-based solid-phase genotyping and sequencing applications, the illumination system comprising: a) a light source; and b) a liquid light-guide configured to collect light emitted by the light source and deliver it to a specified field-of-illumination on a support surface comprising tethered biological macromolecules.

In some embodiments, the illumination system further comprises a condenser lens. In some embodiments, the specified field-of-illumination has an area of at least 2 mm$^2$. In some embodiments, the light delivered to the specified field-of-illumination is of uniform intensity across a specified field-of-view for an imaging system used to acquire images of the support surface. In some embodiments, the specified field-of-view has an area of at least 2 mm$^2$. In some embodiments, the light delivered to the specified field-of-illumination is of uniform intensity across the specified field-of-view when a coefficient of variation (CV) for light intensity is less than 10%. In some embodiments, the light delivered to the specified field-of-illumination is of uniform intensity across the specified field-of-view when a coefficient of variation (CV) for light intensity is less than 5%. In some embodiments, the light delivered to the specified field-of-illumination has a speckle contrast value of less than 0.1. In some embodiments, the light delivered to the specified field-of-illumination has a speckle contrast value of less than 0.05.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A: illustration of imaging front and rear interior surfaces of a flow cell. FIG. 1B: illustration of imaging front and rear exterior surfaces of a substrate.

FIG. 2A: top isometric view. FIG. 2B: bottom isometric view.

FIG. 3A: top view. FIG. 3B: side view.

FIG. 6A: schematic illustration of a multichannel fluorescence imaging module comprising four detection channels. FIG. 6B: detail view illustrating the angle of incidence (AOI) of a light beam on a dichroic reflector.

FIG. 9A illustrates the effect of folding angle on image quality degradation induced by the addition of 1 wave of PV spherical power to the last mirror. FIG. 9B illustrates the effect of folding angle on image quality degradation induced by the addition of 0.1 wave of PV spherical power to the last mirror.

FIG. 10A: transmission spectra for an example bandpass dichroic filter at angles of incidence of 40 degrees and 45 degrees, where the incident beam is linearly polarized and is p-polarized with respect to the plane of the dichroic filter. FIG. 10B: changing the orientation of the light source with respect to the dichroic filter, such that the incident beam is s-polarized with respect to the plane of the dichroic filter, results in a substantially sharper edge between the passband and the stopband.

FIG. 11A: first surface. FIG. 11B: second surface.

FIG. 12A: first surface. FIG. 12B: second surface.

FIG. 13A: first surface. FIG. 13B: second surface.

FIG. 14A: first surface. FIG. 14B: second surface.

FIG. 15A: first surface. FIG. 15B: second surface.

FIG. 16A: first surface. FIG. 16B: second surface.

FIG. 17A: plot of the Strehl ratios for imaging a second flow cell surface through a first flow cell surface as a function of the thickness of the intervening fluid layer (fluid channel height) for different objective lens and/or optical system numerical apertures. FIG. 17B: plot of the Strehl ratio as a function of numerical aperture for imaging a second flow cell surface through a first flow cell surface and an intervening layer of water having a thickness of 0.1 mm.

FIG. 36A shows the preparation of one-piece glass flow cell. FIG. 36B shows the preparation of two-piece glass flow cell. FIG. 36C shows the preparation of three-piece glass flow cell.

FIG. 37A shows a one-piece glass flow cell design. FIG. 37B shows a two-piece glass flow cell design. FIG. 37C shows a three-piece glass flow cell design.

DETAILED DESCRIPTION

Figure 1A:
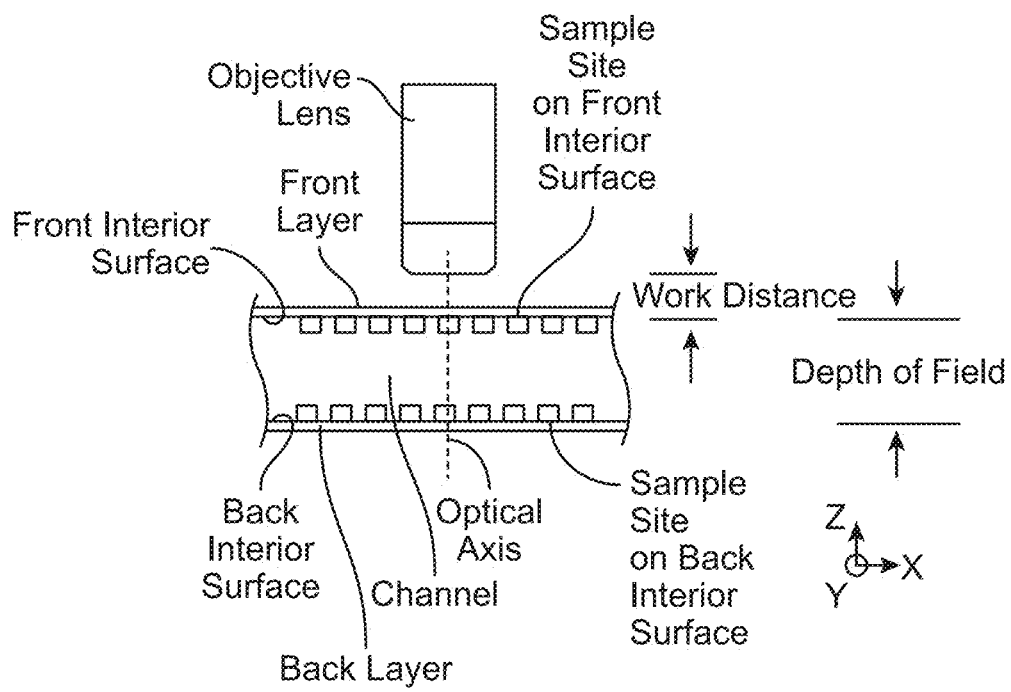
FIGS. 1A-1B schematically illustrate non-limiting examples of imaging dual surface support structures for presenting sample sites for imaging by the imaging systems disclosed herein.

There is a need for fluorescence imaging methods and systems that provide increased optical resolution and improved image quality for genomics applications that lead to corresponding improvements in genomic testing accuracy. Disclosed herein are optical system designs for high-performance fluorescence imaging methods and systems that may provide any one or more of improved optical resolution (including high performance optical resolution), improved image quality, and higher throughput for fluorescence imaging-based genomics applications. The disclosed optical illumination and imaging system designs may provide any one or more of the following advantages: improved dichroic filter performance, increased uniformity of dichroic filter frequency response, improved excitation beam filtering, larger fields-of-view, increased spatial resolution, improved modulation transfer, contrast-to-noise ratio, and image quality, higher spatial sampling frequency, faster transitions between image capture when repositioning the sample plane to capture a series of images (e.g., of different fields-of-view), improved imaging system duty cycle, and higher throughput image acquisition and analysis.

In some instances, improvements in imaging performance, e.g., for dual-side (flow cell) imaging applications comprising the use of thick flow cell walls (e.g., wall (or coverslip) thickness >700 µm) and fluid channels (e.g., fluid channel height or thickness of 50-200 µm) may be achieved using novel objective lens designs that correct for optical aberration introduced by imaging surfaces on the opposite side of thick coverslips and/or fluid channels from the objective.

In some instances, improvements in imaging performance, e.g., for dual-side (flow cell) imaging applications comprising the use of thick flow cell walls (e.g., wall (or coverslip) thickness >700 µm) and fluid channels (e.g., fluid channel height or thickness of 50-200 µm) may be achieved even when using commercially-available, off-the-shelf objectives by using a novel tube lens design that, unlike the tube lens in a conventional microscope that simply forms an image at the intermediate image plane, corrects for the optical aberrations induced by the thick flow cell walls and/or intervening fluid layer in combination with the objective.

In some instances, improvements in imaging performance, e.g., for multichannel (e.g., two-color or four-color) imaging applications, may be achieved by using multiple tube lenses, one for each imaging channel, where each tube lens design has been optimized for the specific wavelength range used in that imaging channel.

In some instances, improvements in imaging performance, e.g., for dual-side (flow cell) imaging applications, may be achieved by using an electro-optical phase plate in combination with an objective lens to compensate for the optical aberrations induced by the layer of fluid separating the upper (near) and lower (far) interior surfaces of a flow cell. In some instances, this design approach may also compensate for vibrations introduced by, e.g., a motion-actuated compensator that is moved in or out of the optical path depending on which surface of the flow cell is being imaged.

Various multichannel fluorescence imaging module designs are disclosed that may include illumination and imaging optical paths comprising folded optical paths (e.g., comprising one or more beam splitters or beam combiners, such as dichroic beam splitters or combiners) that direct an excitation light beam to an objective lens, and direct emission light transmitted through the objective lens to a plurality of detection channels. Some particularly advantageous features of the fluorescence imaging modules described herein include specification of dichroic filter incidence angles that result in sharper and/or more uniform transitions between passband and stopband wavelength regions of the dichroic filters. Such filters may be included within the folded optics and may comprise dichroic beam splitters or combiners. Further advantageous features of the disclosed imaging optics designs may include the position and orientation of one or more excitation light sources and one or more detection optical paths with respect to the objective lens and to a dichroic filter that receives the excitation beam. The excitation beam may also be linearly-polarized and the orientation of the linear polarization may be such that s-polarized light is incident on the dichroic reflective surface of the dichroic filter. Such features may potentially improve excitation beam filtering and/or reduce wavefront error introduced into the emission light beam due to surface deformation of dichroic filters. The fluorescence imaging modules described herein may or may not include any of these features and may or may not include any of these advantages.

Also described herein are devices and systems configured to analyze large numbers of different nucleic acid sequences by imaging, e.g., arrays of immobilized nucleic acid molecules or amplified nucleic acid clusters formed on flow cell surfaces. The devices and systems described herein can also be useful in, e.g., performing sequencing for comparative genomics, tracking gene expression, performing micro RNA sequence analysis, epigenomics, aptamer and phage display library characterization, and for performing other sequencing applications. The devices and systems disclosed herein comprise various combinations of optical, mechanical, fluidic, thermal, electrical, and computing devices/aspects. The advantages conferred by the disclosed flow cell devices, cartridges, and systems include, but are not limited to: (i) reduced device and system manufacturing complexity and cost, (ii) significantly lower consumable costs (e.g., as compared to those for currently available nucleic acid sequencing systems), (iii) compatibility with typical flow cell surface functionalization methods, (iv) flexible flow control when combined with microfluidic components, e.g., syringe pumps and diaphragm valves, etc., and (v) flexible system throughput.

Disclosed herein are capillary flow-cell devices and capillary flow cell cartridges that are constructed from off-the-shelf, disposable, single lumen (e.g., single fluid flow channel) or multi-lumen capillaries that may also comprise fluidic adaptors, cartridge chassis, one or more integrated fluid flow control components, or any combination thereof. Also disclosed herein are capillary flow cell-based systems that may comprise one or more capillary flow cell devices (or microfluidic chips), one or more capillary flow cell cartridges (or microfluidic cartridges), fluid flow controller modules, temperature control modules, imaging modules, or any combination thereof.

The design features of some disclosed capillary flow cell devices, cartridges, and systems include, but are not limited to, (i) unitary flow channel construction, (ii) sealed, reliable, and repetitive switching between reagent flows that can be implemented with a simple load/unload mechanism such that fluidic interfaces between the system and capillaries are reliably sealed, thereby facilitating capillary replacement and system reuse, and enabling precise control of reaction conditions such as reagent concentration, pH, and temperature, (iii) replaceable single fluid flow channel devices or capillary flow cell cartridges comprising multiple flow channels that can be used interchangeably to provide flexible system throughput, and (iv) compatibility with a wide variety of detection methods such as fluorescence imaging.

Although the disclosed capillary flow cell devices and systems, capillary flow cell cartridges, capillary flow cell-based systems, microfluidic devices and cartridges, and microfluidic chip-based systems, are described primarily in the context of their use for nucleic acid sequencing applications, various aspects of the disclosed devices and systems may be applied not only to nucleic acid sequencing but also to any other type of chemical analysis, biochemical analysis, nucleic acid analysis, cell analysis, or tissue analysis application. It shall be understood that different aspects of the disclosed methods, devices, and systems can be appreciated individually, collectively, or in combination with each other. Although discussed herein primarily in the context of fluorescence imaging (including, e.g., fluorescence microscopy imaging, fluorescence confocal imaging, two-photon fluorescence, and the like), it will be understood by those of skill in the art that many of the disclosed optical design approaches and features are applicable to other imaging modes, e.g., bright-field imaging, dark-field imaging, phase contrast imaging, and the like.

Definitions: Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term 'about' a number refers to that number plus or minus 10% of that number. The term 'about' when used in the context of a range refers to that range minus 10% of its lowest value and plus 10% of its greatest value.

As used herein, the phrases "imaging module", "imaging unit", "imaging system", "optical imaging module", "optical imaging unit", and "optical imaging system" are used interchangeably, and may comprise components or sub-systems of a larger system that may also include, e.g., fluidics modules, temperature control modules, translation stages, robotic fluid dispensing and/or microplate handling, processor or computers, instrument control software, data analysis and display software, etc.

As used herein, the term "detection channel" refers to an optical path (and/or the optical components therein) within an optical system that is configured to deliver an optical signal arising from a sample to a detector. In some instances, a detection channel may be configured for performing spectroscopic measurements, e.g., monitoring a fluorescence signal or other optical signal using a detector such as a photomultiplier. In some instances, a "detection channel" may be an "imaging channel", i.e., an optical path (and/or the optical components therein) within an optical system that is configured to capture and deliver an image to an image sensor.

As used herein, a "detectable label" may refer to any of a variety of detectable labels or tags known to those of skill in the art. Examples include, but are not limited to, chromophores, fluorophores, quantum dots, upconverting phosphors, luminescent or chemiluminescent molecules, radioisotopes, magnetic nanoparticles, mass tags, and the like. In some instances, a preferred label may comprise a fluorophore.

As used herein, the term "excitation wavelength" refers to the wavelength of light used to excite a fluorescent indicator (e.g., a fluorophore or dye molecule) and generate fluorescence. Although the excitation wavelength is typically specified as a single wavelength, e.g., 620 nm, it will be understood by those of skill in the art that this specification refers to a wavelength range or excitation filter bandpass that is centered on the specified wavelength. For example, in some instances, light of the specified excitation wavelength comprises light of the specified wavelength±2 nm, ±5 nm, ±10 nm, ±20 nm, ±40 nm, ±80 nm, or more. In some instances, the excitation wavelength used may or may not coincide with the absorption peak maximum of the fluorescent indicator.

As used herein, the term "emission wavelength" refers to the wavelength of light emitted by a fluorescent indicator (e.g., a fluorophore or dye molecule) upon excitation by light of an appropriate wavelength. Although the emission wavelength is typically specified as a single wavelength, e.g., 670 nm, it will be understood by those of skill in the art that this specification refers to a wavelength range or emission filter bandpass that is centered on the specified wavelength. In some instances, light of the specified emission wavelength comprises light of the specified wavelength±2 nm, ±5 nm, ±10 nm, ±20 nm, ±40 nm, ±80 nm, or more. In some instances, the emission wavelength used may or may not coincide with the emission peak maximum of the fluorescent indicator.

As used herein, fluorescence is 'specific' if it arises from fluorophores that are annealed or otherwise tethered to the surface, such as fluorescently labeled nucleic acid sequences having a region of reverse complementarity to a corresponding segment of an oligonucleotide adapter on the surface and annealed to said corresponding segment. This fluorescence is contrasted with fluorescence arising from fluorophores not tethered to the surface through such an annealing process, or in some cases to background florescence of the surface.

As used herein, a "nucleic acid" (also referred to as a "nucleic acid molecule", a "polynucleotide", "oligonucleotide", ribonucleic acid (RNA), or deoxyribonucleic acid (DNA)) is a linear polymer of two or more nucleotides joined by covalent internucleosidic linkages, or variants or functional fragments thereof. In naturally occurring examples of nucleic acids, the internucleoside linkage is typically a phosphodiester bond. However, other examples optionally comprise other internucleoside linkages, such as phosphorothiolate linkages and may or may not comprise a phosphate group. Nucleic acids include double- and single-stranded DNA, as well as double- and single-stranded RNA, DNA/RNA hybrids, peptide-nucleic acids (PNAs), hybrids between PNAs and DNA or RNA, and may also include other types of nucleic acid modifications.

As used herein, a "nucleotide" refers to a nucleotide, nucleoside, or analog thereof. In some cases, the nucleotide is an N- or C-glycoside of a purine or pyrimidine base (e.g., a deoxyribonucleoside containing 2-deoxy-D-ribose or ribonucleoside containing D-ribose). Examples of other nucleotide analogs include, but are not limited to, phosphorothioates, phosphoramidates, methyl phosphonates, chiral-methyl phosphonates, 2-O-methyl ribonucleotides, and the like.

Fluorescence Imaging Viewed as an Information Pipeline:

A useful abstraction of the role that fluorescence imaging systems plays in typical genomic assay techniques (including nucleic acid sequencing applications) is as an information pipeline, where the photon signal enters at one end of the pipeline, e.g., the objective lens used for imaging, and location specific information regarding the fluorescence signal emerges at the other end of the pipeline, e.g., at the position of the image sensor. When more information is pumped through this pipeline, some content, inevitably, will be lost during this transfer process and never recovered. An example of this case is when too many labeled molecules (or clonally-amplified clusters of molecules) are present within a small region of a substrate surface to be clearly resolved in the image; at the position of the image sensor, it becomes difficult to differentiate photon signals arising from adjacent clusters of molecules, thus increasing the probability of attributing the signal to the wrong cluster and leading to detection errors.

Design of Optical Imaging Modules:

The goal of designing an optical imaging module is thus to maximize the flow of information content through this detection pipeline and to minimize detection errors. Several key design elements need to be addressed in the design process, including:

1) Matching the physical feature density on the substrate surface to be imaged with the overall image quality of the optical imaging system and the pixel sampling frequency of the image sensor used. A mismatch of these parameters may result in loss of information or sometimes even the generation of false information, e.g., spatial aliasing may arise when pixel sampling frequency is lower than twice the optical resolution limit.

2) Matching the size of the area to be imaged with the overall image quality of the optical imaging system and focus quality across the entire field of view.

3) Matching the optical collection efficiency, modulation transfer function, and image sensor performance characteristics of the optical system design with the fluorescence photon flux expected for the input excitation photon flux, dye efficiency (related to dye extinction coefficient and fluorescence quantum yield), while accounting for background signal and system noise characteristics.

4) Maximizing the separation of spectral content to reduce cross talk between fluorescence imaging channels.

5) Effective synchronization of image acquisition steps with repositioning of the sample or optics between image capture of different fields-of-view to minimize the down time (or maximize the duty cycle) of the imaging system and thus maximize the overall throughput of the image capture process.

This disclosure describes a systematic way to address each of the design elements outlined above and to create component level specifications for the imaging system.

Improved Optical Resolution and Image Quality to Improve or Maximize Information Transfer and Throughput:

One non-limiting design practice may be to start with the optical resolution required to distinguish two adjacent features as specified in terms of a number, X, of line pairs per mm (lp/mm) and translate it to a corresponding numerical aperture (NA) requirement. The numerical aperture requirement can then be used to assess the resulting impact on modulation transfer function and image contrast.

The standard modulation transfer function (MTF) describes the spatial frequency response for image contrast (modulation) transferred through an optical system; image contrast decreases as a function of spatial frequency and increases with increasing NA. This function limits the contrast/modulation that can be achieved for a given NA. Furthermore, wave front error can negatively impact the MTF, thus making it desirable to improve or optimize the optical system design using the true system MTF instead of that predicted by diffraction-limited optics. Note that, as used herein, MTF will refer to the total system MTF (including the complete optical path from coverslip to image sensor) although design practice may primarily consider the MTF of the objective lens.

In genomic testing applications, where the target to be imaged is an array of high density "spots" on a surface (either randomly distributed or patterned), one can determine the minimum modulation transfer value required by downstream analysis to resolve two adjacent spots and discriminate between four possible states (e.g., ON-OFF, ON-ON, OFF-ON and OFF-OFF). For example, assume that the spots are small enough to be approximated as point sources of light. Assuming that the detection task is to determine if the two adjacent spots separated by a distance, d, are ON or OFF (in other words, bright or dark), and that the contrast-to-noise ratio (CNR) for the fluorescence signals arising from the spots at the sample plane (or object plane) is $C_{sample}$, then under ideal conditions the CNR of the readout signal for the two adjacent spots at the image sensor plane, $C_{image}$, can be closely approximated as $C_{image}=C_{sample}*MTF(1/d)$, where MTF(1/d) is the MTF value at spatial frequency=(1/d).

In a typical design, the value of C may need to be at least 4 so that a simple threshold method can be used to avoid misclassification of fluorescence signals. Assuming a Gaussian distribution of fluorescence signal intensities around a mean value, at $C_{image}>4$, the expected error in correctly classifying fluorescence signals (e.g., as being ON or OFF) is <0.035%. The use of proprietary high CNR sequencing and surface chemistry, such as that described in U.S. patent application Ser. No. 16/363,842, allows one to achieve sample plane CNR ($C_{sample}$) values for clusters of clonally-amplified, labeled oligonucleotide molecules tethered to a substrate surface of greater than 12 (or even much higher) when measured for a sparse field (i.e., at a low surface density of clusters or spots) where the MTF has a value of close to 100%. Assuming a sample plane CNR value of $C_{sample}>12$ and targeting a classification error rate of <0.1% (thus, $C_{image}>4$), in some implementations the minimum value for M(1/d) can be determined as M(1/d)=4/12~33%. Thus, a modulation transfer function threshold of at least 33% may be used to retain the information content of the transferred image.

Design practice can relate the minimum separation distance of two features or spots, d, to the optical resolution requirement (specified as noted above in terms of X (lp/mm)) as d=(1 mm)/X, i.e., d is the minimum separation distance between two features or spots which can be fully resolved by the optical system. In some designs disclosed herein, where the objective of the design analysis is to increase or maximize relevant information transfer, this design criterion can be relaxed to d=(1 mm)/X/A, where 2>A>1. For the same optical resolution of X lp/mm, the value of d, the minimum resolvable spot separation distance at the sample plane, is reduced, thereby enabling the use of higher feature densities.

Design practice determines the minimum spatial sampling frequency at the sample plane using the Nyquist criteria, where spatial sampling frequency S≥2*X (and where X is the optical resolution of the imaging system specified in terms of X lp/mm as noted above). When the system spatial sampling frequency is close to the Nyquist criteria, as is often the case, imaging system resolution of greater than S results in aliasing as the higher frequency information resolved by the optical system cannot be sufficiently sampled by the image sensor.

In the some of the designs disclosed herein, an oversampling scheme based on the relationship S=B*Y (where B>2 and Y is the true optical system MTF limit) may be used to further improve the information transfer capacity of the imaging system. As indicated above, X (lp/mm) corresponds to a practical, non-zero (>33%) minimum modulation transfer value, whereas Y (lp/mm) is the limit of optical resolution so modulation at Y(lp/mm) is 0. Thus, in the disclosed designs, Y (lp/mm) may advantageously be significantly greater than X For values of B≥2, the disclosed designs are oversampling for the sample object frequency X, i.e., S≥B*Y>2*X.

The above relationship can be used to determine the system magnification and may provide an upper bound for image sensor pixel size. The choice of image sensor pixel size is matched to the system optical quality as well to the spatial sampling frequency required to reduce aliasing. The lower bound of image sensor pixel size can be determined based on photon throughput, as relative noise contributions increase with smaller pixels.

Other design approaches are, however, also possible. For example, reducing the NA to less than 0.6 (e.g., 0.5 or less) may provide increased depth of field. Such increased depth of field may enable dual surface imagining wherein two surfaces at different depths can be imaged at the same time with or without refocusing. As discussed above, reducing NA may reduce optical resolution. In some implementations, use of higher excitation beam power, e.g., 1 W or higher, may be employed to produce strong signal. An inherently high contrast sample (i.e., comprising a sample surface that exhibits strong foreground signal and dramatically reduced background signal, may also be used to facilitate acquisition of high contrast-to-noise ratio (CNR) images, e.g., having CNR values of >20, that provide for improved signal discrimination for base-calling in nucleic acid sequencing applications, etc. In some optical system designs disclosed herein, sample support structures such as flow cells having hydrophilic surfaces are used to reduce background noise.

In various implementations, a large field-of-view (FOV) is provided by the disclosed optical systems. For example, a FOV of greater than 2 or 3 mm may be provided with some optical imaging systems comprising, e.g., an objective lens and a tube lens. In some cases, the optical imaging system provides a reduced magnification, for example, a magnification of less than 10×. Such reduced magnification may in some implementations facilitate large FOV designs. Despite a reduced magnification, the optical resolution of such systems can still be sufficient as detector arrays having small pixel size or pitch may be used. In some implementations, image sensors comprising a pixel size that is smaller than twice the optical resolution provided by the optical imaging system (e.g., objective and tube lens) may be used to satisfy the Nyquist theorem.

Still other designs are also possible. In some optical designs configured to provide for dual surface imaging where two surfaces at different depths can be imaged at the same time, the optical imaging system (e.g., the objective lens and/or tube lens) is configured to reduce optical aberration for imaging said two surfaces (e.g., two planes) at those two respective depths more than at other locations (e.g., other planes) at other depths. Additionally, the optical imaging system may be configured to reduce aberration for imaging said two surfaces (e.g., two planes) at those two respective depths through a transmissive layer on said sample support structure (such as a layer of glass (e.g., a cover slip) and through a solution (e.g., an aqueous solution) comprising the sample or in contact with a sample on at least one of said two surfaces.

Multichannel Fluorescence Imaging Modules and Systems:

In some instances, the imaging modules or systems disclosed herein may comprise fluorescence imaging modules or systems. In some instances, the fluorescence imaging systems disclosed herein may comprise a single fluorescence excitation light source (for providing excitation light at a single wavelength or within a single excitation wavelength range) and an optical path configured to deliver the excitation light to a sample (e.g., fluorescently-tagged nucleic acid molecules or clusters thereof disposed on a substrate surface). In some instances, the fluorescence imaging systems disclosed herein may comprise a single fluorescence emission imaging and detection channel, e.g., an optical path configured to collect fluorescence emitted by the sample and deliver an image of the sample (e.g., an image of a substrate surface on which fluorescently-tagged nucleic acid molecules or clusters thereof are disposed) to an image sensor or other photodetection device. In some instances, the fluorescence imaging systems may comprise two, three, four, or more than four fluorescence excitation light sources and/or optical paths configured to deliver excitation light at two, three, four, or more than four excitation wavelengths (or within two, three, four, or more than four excitation wavelength ranges). In some instances, the fluorescence imaging systems disclosed herein may comprise two, three, four, or more than four fluorescence emission imaging and detection channels configured to collect fluorescence emitted by the sample at two, three, four, or more than four emission wavelengths (or within two, three, four, or more than four emission wavelength ranges and deliver an image of the sample (e.g., an image of a substrate surface on which fluorescently-tagged nucleic acid molecules or clusters thereof are disposed) to two, three, four, or more than four image sensors or other photodetection devices.

Figure 1B:
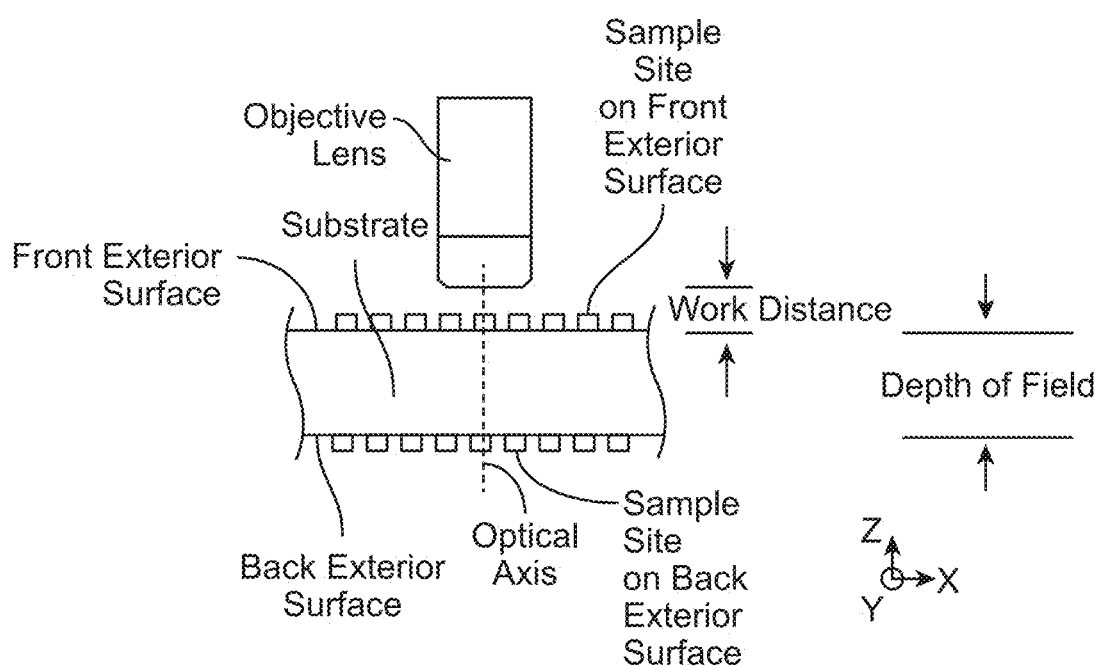

Dual Surface Imaging:

In some instances, the imaging systems disclosed herein, including fluorescence imaging systems, may be configured to acquire high-resolution images of a single sample support structure or substrate surface. In some instances, the imaging systems disclosed herein, including fluorescence imaging systems, may be configured to acquire high-resolution images of two or more sample support structures or substrate surfaces, e.g., two or more surfaces of a flow cell. In some instances, the high-resolution images provided by the disclosed imaging systems may be used to monitor reactions occurring on the two or more surfaces of the flow cell (e.g., nucleic acid hybridization, amplification, and/or sequencing reactions) as various reagents flow through the flow cell or around a flow cell substrate. FIG. 1A and FIG. 1B provide schematic illustrations of such dual surface support structures. FIG. 1A shows a dual surface support structure such as a flow cell that includes an internal flow channel through which an analyte or reagent can be flowed. The flow channel may be formed between first and second, top and bottom, and/or front and back layers such as first and second, top and bottom, and/or front and back plates as shown. One or more of the plates may include a glass plate, such as a coverslip, or the like. In some implementations, the layer comprises borosilicate glass, quartz, or plastic. Interior surfaces of these top and bottom layers provide walls of the flow channel that assist in confining the flow of analyte or reagent through the flow channel of the flow cell. In some designs, these interior surfaces are planar. Similarly, the top and bottom layers may be planar. In some designs, at least one additional layer (not shown) is disposed between the top and bottom layers. This additional layer may have one or more pathways cut therein that assist in defining one or more flow channels and controlling the flow of the analyte or reagent within the flow channel. Additional discussion of sample support structures, e.g., flow cells, can be found below.

FIG. 1A schematically illustrates a plurality of fluorescing sample sites on the first and second, top and bottom, and/or front and back interior surfaces of the flow cell. In some implementations, reactions may occur at these at these sites to bind sample such that fluorescence is emitted from these sites (note that FIG. 1A is schematic and not drawn to scale; for example, the size and spacing of the fluorescing sample sites may be smaller than shown).

FIG. 1B shows another dual surface support structure having two surfaces containing fluorescing sample sites to be imaged. The sample support structure comprises a substrate having first and second, top and bottom, and/or front and back exterior surfaces. In some designs, these exterior surfaces are planar. In various implementations, the analyte or reagent is flowed across these first and second exterior surfaces. FIG. 1B schematically illustrates a plurality of fluorescing sample sites on the first and second, top and bottom, and/or front and back exterior surfaces of the sample support structure. In some implementations, reactions may occur at these at these sites to bind sample such that fluorescence is emitted from these sites (note that FIG. 1B is schematic and not drawn to scale; for example, the size and spacing of the fluorescing sample sites may be smaller than shown).

In some instances, the fluorescence imaging modules and systems described herein may be configured to image such fluorescing sample sites on first and second surfaces at different distances from the objective lens. In some designs, only one of the first or second surfaces is in focus at a time. Accordingly, in such designs, one of the surfaces is imaged at a first time, and the other surface is imaged at a second time. The focus of the fluorescence imaging module may be changed after imaging one of the surfaces in order to image the other surface with comparable optical resolution, as the images of the two surfaces are not simultaneously in focus. In some designs, an optical compensation element may be introduced into the optical path between the sample support structure and the image sensor in order to image one of the two surfaces. The depth of field in such fluorescence imaging configurations may not be sufficiently large to include both the first and second surfaces. In some implementations of the fluorescence imaging modules described herein, both the first and second surfaces may be imaged at the same time, i.e., simultaneously. For example, the fluorescence imaging module may have a depth of field that is sufficiently large to include both surfaces. In some instances, this increased depth of field may be provided by, for example, reducing the numerical aperture of the objective lens (or microscope objective) as will be discussed in more detail below.

As shown in FIGS. 1A and 1B, the imaging optics (e.g., an objective lens) may be positioned at a suitable distance (e.g., a distance corresponding to the working distance) from the first and second surfaces to form in-focus images of the first and second surfaces on an image sensor of a detection channel. As shown in the example of FIGS. 1A and 1B, the first surface may be between said objective lens and the second surface. For example, as illustrated, the objective lens is disposed above both the first and second surfaces, and the first surface is disposed above the second surface. The first and second surfaces, for example, are at different depths. The first and second surfaces are at different distances from any one or more of the fluorescence imaging module, the illumination and imaging module, imaging optics, or the objective lens. The first and second surfaces are separated from each other with the first surface spaced apart above the second surface. In the example shown, the first and second surfaces are planar surfaces and are separated from each other along a direction normal to said first and second planar surfaces. Also, in the example shown, said objective lens has an optical axis and said first and second surfaces are separated from each other along the direction of said optical axis. Similarly, the separation between the first and second surfaces may correspond to the longitudinal distance such as along the optical path of the excitation beam and/or along an optical axis through the fluorescence imaging module and/or the objective lens. Accordingly, these two surfaces may be separated by a distance from each other in the longitudinal (Z) direction, which may be along the direction of the central axis of the excitation beam and/or the optical axis of the objective lens and/or the fluorescence imaging module. This separation may correspond, for example, to a flow channel within a flow cell in some implementations.

In various designs, the objective lens (possibly in combination with another optical component, e.g., a tube lens) have a depth of field and/or depth of focus that is at least as large as the longitudinal separation (in the Z direction) between the first and second surfaces. The objective lens, alone or in combination with the additional optical component, may thus simultaneously form in-focus images of both the first and the second surface on an image sensor of one or more detection channels where these images have comparable optical resolution. In some implementations, the imaging module may or may not need to be re-focused to capture images of both the first and second surfaces with comparable optical resolution. In some implementations, compensation optics need not be moved into or out of an optical path of the imaging module to form in-focus images of the first and second surfaces. Similarly, in some implementations, one or more optical elements (e.g., lens elements) in the imaging module (e.g., the objective lens and/or a tube lens) need not be moved, for example, in the longitudinal direction along the first and/or second optical paths (e.g., along the optical axis of the imaging optics) to form in-focus images of the first surface in comparison to the location of said one or more optical element when used to form in-focus images of the second surface. In some implementations, however, the imaging module includes an autofocus system configured to provide both the first and second surface in focus at the same time. In various implementations, the sample is in focus to sufficiently resolve the sample sites, which are closely spaced together in lateral directions (e.g., the X and Y directions). Accordingly, in various implementations, no optical element enters an optical path between the sample support structure (e.g., between a translation stage that supports the sample support structure) and an image sensor (or photodetector array) in the at least one detection channel in order to form in-focus images of fluorescing sample sites on a first surface of the sample support structure and on a second surface of said sample support structure. Similarly, in various implementations, no optical compensation is used to form an in-focus image of fluorescing sample sites on a first surface of the sample support structure on the image sensor or photodetector array that is not identical to optical compensation used to form an in-focus image of fluorescing sample sites on a second surface of the sample support structure on the image sensor or photodetector array. Additionally, in certain implementations, no optical element in an optical path between the sample support structure (e.g., between a translation stage that supports the sample support structure) and an image sensor in the at least one detection channel is adjusted differently to form an in-focus image of fluorescing sample sites on a first surface of the sample support structure than to form an in-focus image of fluorescing sample sites on a second surface of the sample support structure. Similarly, in some various implementations, no optical element in an optical path between the sample support structure (e.g., between a translation stage that supports the sample support structure) and an image sensor in the at least one detection channel is moved a different amount or a different direction to form an in-focus image of fluorescing sample sites on the a first surface of the sample support structure on the image sensor than to form an in-focus image of fluorescing sample sites on a second surface of said sample support structure on the image sensor. Any combination of the features is possible. For example, in some implementations, in-focus images of the upper interior surface and the lower interior surface of the flow cell can be obtained without moving an optical compensator into or out of an optical path between the flow cell and the at least one image sensor and without moving one or more optical elements of the imaging system (e.g., the objective and/or tube lens) along the optical path (e.g., optical axis) therebetween. For example, in-focus images of the upper interior surface and the lower interior surface of the flow cell can be obtained without moving one or more optical elements of the tube lens into or out of the optical path, or without moving one or more optical elements of the tube lens along the optical path (e.g., optical axis) therebetween.

Any one or more of the fluorescence imaging module, the illumination optical path, the imaging optical path, the objective lens, or the tube lens may be designed to reduce or minimize optical aberration at two locations such as two planes corresponding to two surfaces on a flow cell or other sample support structure, for example, where fluorescing sample sites are located. Any one or more of the fluorescence imaging module, the illumination optical path, the imaging optical path, the objective lens, or the tube lens may be designed to reduce or minimize optical aberration at the selected locations or planes relative to other locations or planes, such as first and second surfaces containing fluorescing sample sites on a dual surface flow cell. For example, any one or more of the fluorescence imaging module, the illumination optical path, the imaging optical path, the objective lens, or the tube lens may be designed to reduce or minimize optical aberration at two depths or planes located at different distances from the objective lens as compared to the aberrations associated with other depths or planes at other distances from the objective lens. For example, optical aberration may be less for imaging the first and second surfaces than elsewhere in a region ranging from about 1 to about 10 mm from the objective lens. Additionally, any one or more of the fluorescence imaging module, the illumination optical path, the imaging optical path, the objective lens, or the tube lens may, in some instances, be configured to compensate for optical aberration induced by transmission of emission light through one or more portions of the sample support structure such as a layer that includes one of the surfaces on which sample adheres as well as possibly a solution that is in contact with the sample. This layer (e.g., a coverslip or the wall of a flow cell) may comprise, e.g., glass, quartz, plastic, or other transparent material having a refractive index and that introduces optical aberration.

Accordingly, the imaging performance may be substantially the same when imaging the first surface and second surface. For example, the optical transfer functions (OTF) and/or modulation transfer functions (MTF) may be the substantially the same for imaging of the first and second surfaces. Either or both of these transfer functions may, for example, be within 20%, within 15%, within 10%, within 5%, within 2.5%, or within 1% of each other, or within any range formed by any of these values at one or more specified spatial frequencies or when averaged over a range of spatial frequencies. Accordingly, an imaging performance metric may be substantially the same for imaging the upper interior surface or the lower interior surface of the flow cell without moving an optical compensator into or out of an optical path between the flow cell and the at least one image sensor, and without moving one or more optical elements of the imaging system (e.g., the objective and/or tube lens) along the optical path (e.g., optical axis) therebetween. For example, an imaging performance metric may be substantially the same for imaging the upper interior surface or the lower interior surface of the flow cell without moving one or more optical elements of the tube lens into or out of the optical path or without moving one or more optical elements of the tube lens along the optical path (e.g., optical axis) therebetween. Additional discussion of MTF is included below and in U.S. Provisional Application No. 62/962,723 filed Jan. 17, 2020, which is incorporated herein by reference in its entirety.

It will be understood by those of skill in the art that the disclosed imaging modules or systems may, in some instances, be stand-alone optical systems designed for imaging a sample or substrate surface. In some instances, they may comprise one or more processors or computers. In some instances, they may comprise one or more software packages that provide instrument control functionality and/or image processing functionality. In some instances, in addition to optical components such as light sources (e.g., solid-state lasers, dye lasers, diode lasers, arc lamps, tungsten-halogen lamps, etc.), lenses, prisms, mirrors, dichroic reflectors, beam splitters, optical filters, optical bandpass filters, light guides, optical fibers, apertures, and image sensors (e.g., complementary metal oxide semiconductor (CMOS) image sensors and cameras, charge-coupled device (CCD) image sensors and cameras, etc.), they may also include mechanical and/or optomechanical components, such as X-Y translation stages, X-Y-Z translation stages, piezoelectric focusing mechanisms, electro-optical phase plates, and the like. In some instances, they may function as modules, components, sub-assemblies, or sub-systems of larger systems designed for, e.g., genomics applications (e.g., genetic testing and/or nucleic acid sequencing applications). For example, in some instances, they may function as modules, components, sub-assemblies, or sub-systems of larger systems that further comprise light-tight and/or other environmental control housings, temperature control modules, flow cells and cartridges, fluidics control modules, fluid dispensing robotics, cartridge- and/or microplate-handling (pick-and-place) robotics, one or more processors or computers, one or more local and/or cloud-based software packages (e.g., instrument/system control software packages, image processing software packages, data analysis software packages), data storage modules, data communication modules (e.g., Bluetooth, WiFi, intranet, or internet communication hardware and associated software), display modules, etc., or any combination thereof. These additional components of larger systems, e.g., systems designed for genomics applications, will be discussed in more detail below.

Figure 2A:
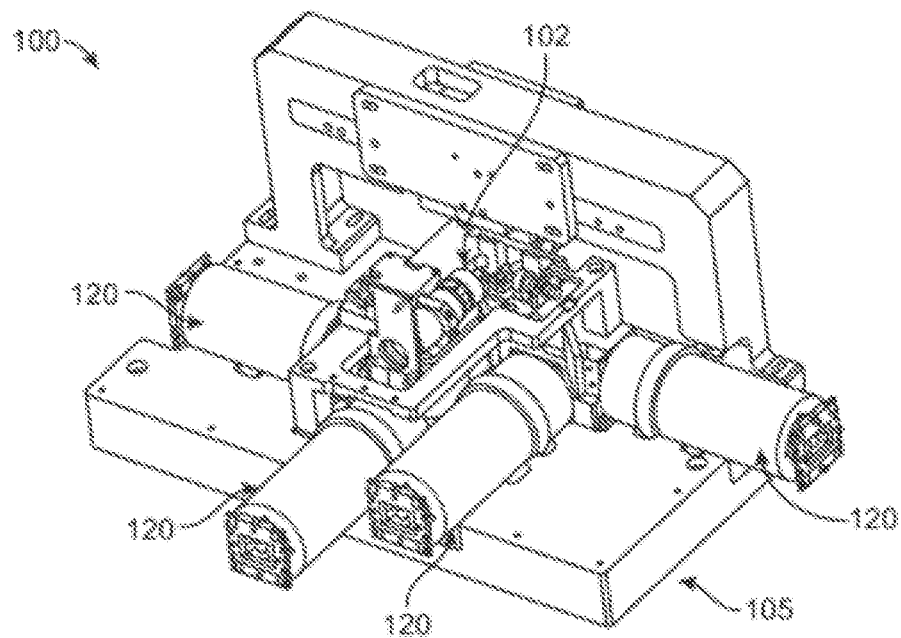
FIGS. 2A-2B illustrate a non-limiting example of a multi-channel fluorescence imaging module comprising a dichroic beam splitter for transmitting an excitation light beam to a sample, and for receiving and redirecting by reflection the resultant fluorescence emission to four detection channels configured for detection of fluorescence emission at four different respective wavelengths or wavelength bands.
Figure 2B:
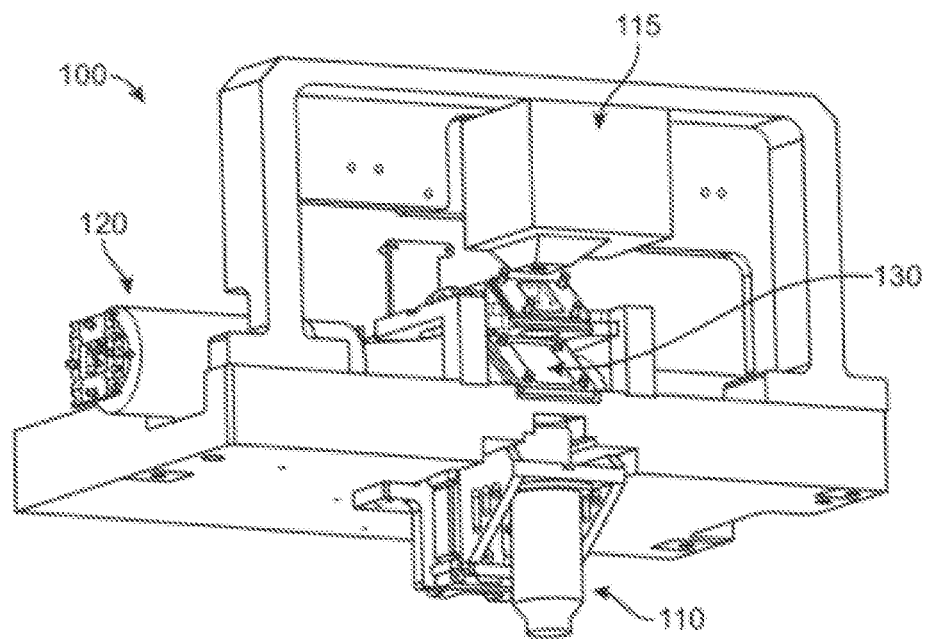

FIGS. 2A and 2B illustrate a non-limiting example of an illumination and imaging module 100 for multi-channel fluorescence imaging. The illumination and imaging module 100 includes an objective lens 110, an illumination source 115, a plurality of detection channels 120, and a first dichroic filter 130, which may comprise a dichroic reflector or beam splitter. An autofocus system, which may include an autofocus laser 102, for example, that projects a spot the size of which is monitored to determine when the imaging system is in-focus may be included in some designs. Some or all components of the illumination and imaging module 100 may be coupled to a baseplate 105.

The illumination or light source 115 may include any suitable light source configured to produce light of at least a desired excitation wavelength (discussed in more detail below). The light source may be a broadband source that emits light within one or more excitation wavelength ranges (or bands). The light source may be a narrowband source that emits light within one or more narrower wavelength ranges. In some instances, the light source may produce a single isolated wavelength (or line) corresponding to the desired excitation wavelength, or multiple isolated wavelengths (or lines). In some instances, the lines may have some very narrow bandwidth. Example light sources that may be suitable for use in the illumination source 115 include, but are not limited to, an incandescent filament, xenon arc lamp, mercury-vapor lamp, a light-emitting diode, a laser source such as a laser diode or a solid-state laser, or other types of light sources. As discussed below, in some designs, the light source may comprise a polarized light source such as a linearly polarized light source. In some implementations, the orientation of the light source is such that s-polarized light is incident on one or more surfaces of one or more optical components such as the dichroic reflective surface of one or more dichroic filters.

The illumination source 115 may further include one or more additional optical components such as lenses, filters, optical fibers, or any other suitable transmissive or reflective optics as appropriate to output an excitation light beam having suitable characteristics toward a first dichroic filter 130. For example, beam shaping optics may be included, for example, to receive light from a light emitter in the light source and produce a beam and/or provide a desired beam characteristic. Such optics may, for example, comprise a collimating lens configured to reduce the divergence of light and/or increase collimation and/or to collimate the light.

In some implementations, multiple light sources are included in the illumination and imaging module 100. In some such implementations, different light sources may produce light having different spectral characteristics, for example, to excite different fluorescence dyes. In some implementations, light produced by the different light sources may directed to coincide and form an aggregate excitation light beam. This composite excitation light beam may be composed of excitation light beams from each of the light sources. The composite excitation light beam will have more optical power than the individual beams that overlap to form the composite beam. For example, in some implementations that include two light sources that produce two excitation light beams, the composite excitation light beam formed from the two individual excitation light beams may have optical power that is the sum of the optical power of the individual beams. Similarly, in some implementations, three, four, five or more light sources may be included, and these light sources may each output excitation light beams that together form a composite beam that that has an optical power that is the sum of the optical power of the individual beams.

In some implementations, the light source 115 outputs a sufficiently large amount of light to produce sufficiently strong fluorescence emission. Stronger fluorescence emission can increase the signal-to-noise ratio (SNR) and the contrast-to-noise ratio (CNR) of images acquired by the fluorescence imaging module. In some implementations, the output of the light source and/or an excitation light beam derived therefrom (including a composite excitation light beam) may range in power from about 0.5 W to about 5.0 W, or more (as will be discussed in more detail below).

Referring again to FIGS. 2A and 2B, the first dichroic filter 130 is disposed with respect to the light source to receive light therefrom. The first dichroic filter may comprise a dichroic mirror, dichroic reflector, dichroic beam splitter, or dichroic beam combiner configured to transmit light in a first spectral region (or wavelength range) and reflect light having a second spectral region (or wavelength range). The first spectral region may include one or more spectral bands, e.g., one or more spectral bands in the ultraviolet and blue wavelength ranges. Similarly, a second spectral region may include one or more spectral bands, e.g., one or more spectral bands extending from the green to red and infrared wavelengths. Other spectral regions or wavelength ranges are also possible.

In some implementations, the first dichroic filter may be configured to transmit light from the light source to a sample support structure such as to a microscope slide, a capillary, a flow cell, a microfluidic chip, or other substrate or support structure. The sample support structure supports and positions the sample, e.g., a composition comprising a fluorescently-labeled nucleic acid molecule or complement thereof, with respect to the illumination and imaging module 100. Accordingly, a first optical path extends from the light source to the sample via the first dichroic filter. In various implementations, the sample support structure includes at least one surface on which the sample is disposed or to which the sample binds. In some instances, the sample may be disposed within or bound to different localized regions or sites on the at least one surface of the sample support structure.

In some instances, the support structure may include two surfaces located at different distances from objective lens 110 (i.e., at different positions or depths along the optical axis of objective lens 110) on which the sample is disposed. As discussed below, for example, a flow cell may comprise a fluid channel formed at least in part by first and second (e.g., upper and lower) interior surfaces, and the sample may be disposed at localized sites on the first interior surface, the second interior surface, or both interior surfaces. The first and second surface may be separated by the region corresponding to the fluid channel through which a solution flows, and thus be at different distances or depth with respect to objective lens 110 of the illumination and imaging module 100.

The objective lens 110 may be included in the first optical path between the first dichroic filter and the sample. This objective lens may be configured, for example, to have a focal length, working distance, and/or be positioned to focus light from the light source(s) onto the sample, e.g., onto a surface of the microscope slide, capillary, flow cell, microfluidic chip, or other substrate or support structure. Similarly, the objective lens 110 may be configured to have suitable focal length, working distance, and/or be positioned to collect light reflected, scattered, or emitted from the sample (e.g., fluorescence emission) and to form an image of the sample (e.g., a fluorescence image).

In some implementations, objective lens 110 may comprise a microscope objective such as an off-the-shelf objective. In some implementations, objective lens 110 may comprise a custom objective. An example of a custom objective lens and/or custom objective—tube lens combination is described below and in U.S. Provisional Application No. 62/962,723 filed on Jan. 17, 2020, which is incorporated herein by reference in its entirety. The objective lens 110 may be designed to reduce or minimize optical aberration at two locations such as two planes corresponding to two surfaces of a flow cell or other sample support structure. The objective lens 110 may be designed to reduce the optical aberration at the selected locations or planes, e.g., the first and second surfaces of a dual surface flow cell, relative to other locations or planes in the optical path. For example, the objective lens 110 may be designed to reduce the optical aberration at two depths or planes located at different distances from the objective lens as compared to the optical aberrations associated with other depths or planes at other distances from the objective. For example, in some instances, optical aberration may be less for imaging the first and second surfaces of a flow cell than that exhibited elsewhere in a region spanning from 1 to 10 mm from the front surface of the objective lens. Additionally, a custom objective lens 110 may in some instances be configured to compensate for optical aberration induced by transmission of fluorescence emission light through one or more portions of the sample support structure, such as a layer that includes one or more of the flow cell surfaces on which a sample is disposed, or a layer comprising a solution filling the fluid channel of a flow cell. These layers may comprise, e.g., glass, quartz, plastic, or other transparent material having a refractive index, and which may introduce optical aberration.

In some implementations, objective lens 110 may have a numerical aperture (NA) of 0.6 or more (as discussed in more detail below). Such a numerical aperture may provide for reduced depth of focus and/or depth of field, improved background discrimination, and increased imaging resolution.

In some implementations, objective lens 110 may have a numerical aperture (NA) of 0.6 or less (as discussed in more detail below). Such a numerical aperture may provide for increased depth of focus and/or depth of field. Such increased depth of focus and/or depth of field may increase the ability to image planes separated by a distance such as that that separates the first and second surfaces of a dual surface flow cell.

As discussed above, a flow cell may comprise, for example, first and second layers comprising first and second interior surfaces respectively that are separated by a fluid channel through which an analyte or reagent can flow. In some implementations, the objective lens 110 and/or illumination and imaging module 100 may be configured to provide a depth of field and/or depth of focus sufficiently large to image both the first and second interior surfaces of the flow cell, either sequentially by re-focusing the imaging module between imaging the first and second surfaces, or simultaneously by ensuring a sufficiently large depth of field and/or depth of focus, with comparable optical resolution. In some instances, the depth of field and/or depth of focus may be at least as large or larger than the distance separating the first and second surfaces of the flow cell to be imaged, such as the first and second interior surfaces of the flow cell. In some instances, the first and second surfaces, e.g., the first and second interior surfaces of a dual surface flow cell or other sample support structure, may be separated, for example, by a distance ranging from about 10 μm to about 700 μm, or more (as will be discussed in more detail below). In some instances, the depth of field and/or depth of focus may thus range from about 10 μm to about 700 μm, or more (as will be discussed in more detail below).

In some designs, compensation optics (e.g., an "optical compensator" or "compensator") may be moved into or out of an optical path in the imaging module, for example, an optical path by which light collected by the objective lens 110 is delivered to an image sensor, to enable the imaging module to image the first and second surfaces of the dual surface flow cell. The imaging module may be configured, for example, to image the first surface when the compensation optics is included in the optical path between the objective lens and an image sensor or photodetector array configured to capture an image of the first surface. In such a design, the imaging module may be configured to image the second surface when the compensation optics is removed from or not included in the optical path between the objective lens 110 and the image sensor or photodetector array configured to capture an image of the second surface. The need for an optical compensator may be more pronounced when using an objective lens 110 with a high numerical aperture (NA) value, e.g., for numerical aperture values of at least 0.6, least 0.65, at least 0.7, at least 0.75, at least 0.8, at least 0.85, at least 0.9, at least 0.95, at least 1.0, or higher. In some implementations, the optical compensation optics (e.g., an optical compensator or compensator) comprises a refractive optical element such as a lens, a plate of optically-transparent material such as glass, a plate of optically-transparent material such as glass, or in the case of polarized light beams, a quarter-wave plate or half-wave plate, etc. Other configurations may be employed to enable the first and second surfaces to be imaged at different times. For example, one or more lenses or optical elements may be configured to be translated in and out of, or along, an optical path between the objective lens 110 and the image sensor.

In certain designs, however, the objective lens 110 is configured to provide sufficiently large depth of focus and/or depth of field to enable the first and second surfaces to be imaged with comparable optical resolution without such compensation optics moving into and out of an optical path in the imaging module, such as an optical path between the objective lens and the image sensor or photodetector array. Similarly, in various designs, the objective lens 110 is configured to provide sufficiently large depth of focus and/or depth of field to enable the first and second surfaces to be imaged with comparable optical resolution without optics being moved, such as one or more lenses or other optical components being translated along an optical path in the imaging module, such as an optical path between the objective lens and the image sensor or photodetector array. Examples of such objective lenses will be described in more detail below.

In some implementations, the objective lens (or microscope objective) 110 may be configured to have reduced magnification. The objective lens 110 may be configured, for example, such that the fluorescence imaging module has a magnification of from less than 2× to less than 10× (as will be discussed in more detail below). Such reduced magnification may alter design constraints such that other design parameters can be achieved. For example, the objective lens 110 may also be configured such that the fluorescence imaging module has a large field-of-view (FOV) ranging, for example, from about 1.0 mm to about 5.0 mm (e.g., in diameter, width, length, or longest dimension) as will be discussed in more detail below.

In some implementations, the objective lens 110 may be configured to provide the fluorescence imaging module with a field-of-view as indicated above such that the FOV has diffraction-limited performance, e.g., less than 0.15 waves of aberration over at least 60%, 70%, 80%, 90%, or 95% of the field, as will be discussed in more detail below.

In some implementations, the objective lens 110 may be configured to provide the fluorescence imaging module with a field-of-view as indicated above such that the FOV has diffraction-limited performance, e.g., a Strehl ratio of greater than 0.8 over at least 60%, 70%, 80%, 90%, or 95% of the field, as will be discussed in more detail below.

Referring again to FIGS. 2A and 2B, the first dichroic beam splitter or beam combiner is disposed in the first optical path between the light source and the sample so as to illuminate the sample with one or more excitation beams. This first dichroic beam splitter or combiner is also in one or more second optical path(s) from the sample to the different optical channels used to detect the fluorescence emission. Accordingly, the first dichroic filter 130 couples the first optical path of the excitation beam emitted by the illumination source 115 and second optical path of the emission light emitted by a sample specimen to the various optical channels where the light is directed to respective image sensors or photodetector arrays for capturing images of the sample.

In various implementations, the first dichroic filter 130, e.g., first dichroic reflector or beam splitter or beam combiner, has a passband selected to transmit light from the illumination source 115 only within a specified wavelength band or possibly a plurality of wavelength bands that include the desired excitation wavelength or wavelengths. For example, the first dichroic beam splitter 130 includes a reflective surface comprising a dichroic reflector that has spectral transmissivity response that is, e.g., configured to transmit light having at least some of the wavelengths output by the light source that form part of the excitation beam. The spectral transmissivity response may be configured not to transmit (e.g., instead to reflect) light of one or more other wavelengths, for example, of one or more other fluorescence emission wavelengths. In some implementations, the spectral transmissivity response may also be configured not to transmit (e.g., instead to reflect) light of one or more other wavelengths output by the light source. Accordingly, the first dichroic filter 130 may be utilized to select which wavelength or wavelengths of light output by the light source reach the sample. Conversely, the dichroic reflector in the first dichroic beam splitter 130 has a spectral reflectivity response that reflects light having one or more wavelengths corresponding to the desired fluorescence emission from the sample and possible reflects light having one or more wavelengths output from the light source that is not intended to reach the sample. Accordingly, in some implementations, the dichroic reflector has a spectral transmissivity that includes one or more pass bands to transmit the light to be incident on the sample and one or more stop bands that reflects light outside the pass bands, for example, light at one or more emission wavelengths and possibly one or more wavelengths output by the light source that are not intended to reach the sample. Likewise, in some implementations the dichroic reflector has a spectral reflectivity that includes one or more spectral regions configured to reflect one or more emission wavelengths and possible one or more wavelengths output by the light source that are not intended to reach the sample and includes one or more regions that transmit light outside these reflection regions. The dichroic reflector included in the first dichroic filter 130 may comprise a reflective filter such as an interference filter (e.g., a quarter-wave stack) configured to provide the appropriate spectral transmission and reflection distributions. FIGS. 2A and 2B also show a dichroic filter 105, which may comprise for example a dichroic beam splitter or beam combiner, that may be used to direct the autofocus laser 102 though the objective and to the sample support structure.

Although the imaging module 100 shown in FIGS. 2A and 2B and discussed above is configured such that the excitation beam is transmitted by the first dichroic filter 130 to the objective lens 110, in some designs the illumination source 115 may be disposed with respect to the first dichroic filter 130 and/or the first dichroic filter is configured (e.g., oriented) such that the excitation beam is reflected by the first dichroic filter 130 to the objective lens 110. Similarly, in some such designs, the first dichroic filter 130 is configured to transmit fluorescence emission from the sample and possibly transmit light having one or more wavelengths output from the light source that is not intended to reach the sample. As will be discussed below, a design where the fluorescence emission is transmitted instead of reflected may potentially reduce wavefront error in the detected emission and/or possibly have other advantages. In either case, in various implementations the first dichroic reflector 130 is disposed in the second optical path so as to receive fluorescence emission from the sample, at least some of which continues on to the detection channels 120.

Figure 3A:
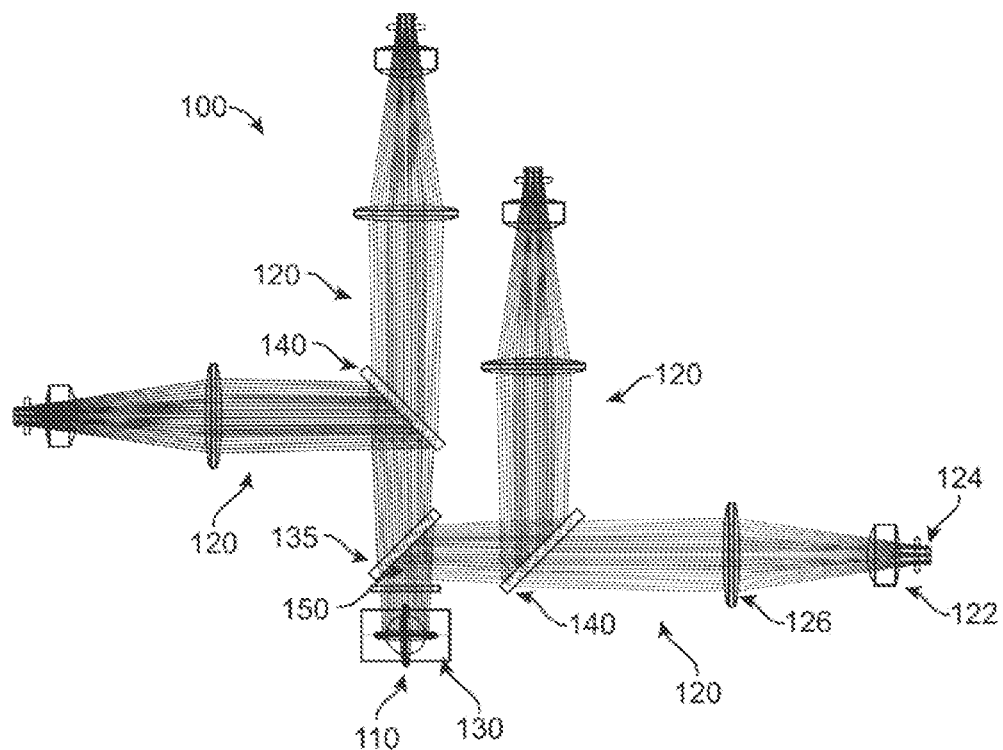
FIGS. 3A-3B illustrate the optical paths within the multi-channel fluorescence imaging module of FIGS. 2A and 2B comprising a dichroic beam splitter for transmitting an excitation light beam to a sample, and for receiving and redirecting by reflection a resultant fluorescence emission to four detection channels for detection of fluorescence emission at four different respective wavelengths or wavelength bands.
Figure 3B:
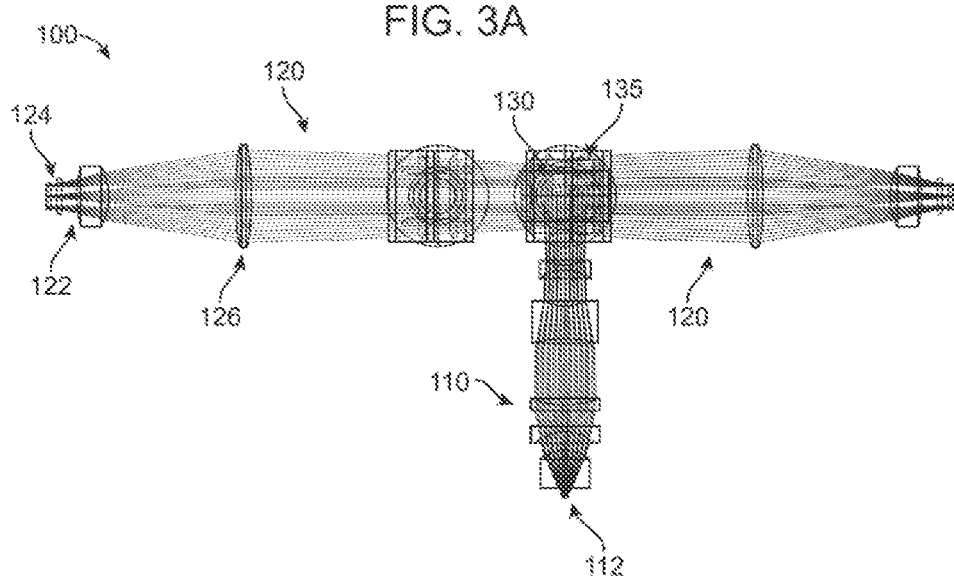

FIGS. 3A and 3B illustrate the optical paths within the multi-channel fluorescence imaging module of FIGS. 2A and 2B. In the example show in FIG. 2A and FIG. 3A, the detection channels 120 are disposed to receive fluorescence emission from a sample specimen that is transmitted by the objective lens 110 and reflected by the first dichroic filter 130. As referred to above and described more below, in some designs the detection channels 120 may be disposed to receive the portion of the emission light that is transmitted, rather than reflected, by the first dichroic filter. In either case, the detection channels 120 may include optics for receiving at least a portion of the emission light. For example, the detection channels 120 may include one or more lenses, such as tube lenses, and may include one or more image sensors or detectors such as photodetector arrays (e.g., CCD or CMOS sensor arrays) for imaging or otherwise producing a signal based on the received light. The tube lenses may, for example, comprise one or more lens elements configured to form an image of the sample onto the sensor or photodetector array to capture an image thereof. Additional discussion of detection channels is included below and in U.S. Provisional Application No. 62/962,723, filed Jan. 17, 2020, which is incorporated herein by reference in its entirety. In some instances, improved optical resolution may be achieved using an image sensor having relatively high sensitivity, small pixels, and high pixel count, in conjunction with a suitable sampling scheme, which may include oversampling or undersampling.

FIGS. 3A and 3B are ray tracing diagrams illustrating optical paths of the illumination and imaging module 100 of FIGS. 2A and 2B. FIG. 3A corresponds to a top view of the illumination and imaging module 100. FIG. 3B corresponds to a side view of the illumination and imaging module 100. The illumination and imaging module 100 illustrated in these figures includes four detection channels 120. However, it will be understood that the disclosed illumination and imaging modules may equally be implemented in systems including more or fewer than four detection channels 120. For example, the multi-channel systems disclosed herein may be implemented with as few as one detection channel 120, or as many as two detection channels 120, three detection channels 120, four detection channels 120, five detection channels 120, six detection channels 120, seven detection channels 120, eight detection channels 120, or more than eight detection channels 120, without departing from the spirit or scope of the present disclosure.

The non-limiting example of imaging module 100 illustrated in FIGS. 3A and 3B includes four detection channels 120, a first dichroic filter 130 that reflects a beam 150 of emission light, a second dichroic filter (e.g., a dichroic beam splitter) 135 that splits the beam 150 into a transmitted portion and a reflected portion, and two channel-specific dichroic filters (e.g., dichroic beam splitters) 140 that further split the transmitted and reflected portions of the beam 150 among individual detection channels 120. The dichroic reflecting surface in the dichroic beam splitters 135 and 140 for splitting the beam 150 among detection channels are shown disposed at 45 degrees relative to a central beam axis of the beam 150 or an optical axis of the imaging module. However, as discussed below, an angle smaller than 45 degrees may be employed and may offer advantages such as sharper transitions from pass band to stop band.

The different detection channels 120 includes imaging devices 124, which may include an image sensor or photo-detector array (e.g., a CCD or CMOS detector array). The different detection channels 120 further include optics 126 such as lenses (e.g., one or more tube lenses each comprising one or more lens elements) disposed to focus the portion of the emission light entering the detection channel 120 at a focal plane coincident with a plane of the photodetector array 124. The optics 126 (e.g., a tube lens) combined with the objective lens 110 are configured to form an image of the sample onto the photodetector array 124 to capture an image of the sample, for example, an image of a surface on the flow cell or other sample support structure after the sample has bound to that surface. Accordingly, such an image of the sample may comprise a plurality of fluorescent emitting spots or regions across a spatial extent of the sample support structure where the sample is emitting fluorescence light. The objective lens 110 together with the optics 126 (e.g., tube lens) may provide a field of view (FOV) that includes a portion of the sample or the entire sample. Similarly, the photodetector array 124 of the different detection channels 120 may be configured to capture images of a full field of view (FOV) provided by the objective lens and the tube lens, or a portion thereof. In some implementations, the photodetector array 124 of some or all detection channels 120 can detect the emission light emitted by a sample disposed on the sample support structure, e.g., a surface of the flow cell, or a portion thereof and record electronic data representing an image thereof. In some implementations, the photodetector array 124 of some or all detection channels 120 can detect features in the emission light emitted by a specimen without capturing and/or storing an image of the sample disposed on the flow cell surface and/or of the full field of view (FOV) provided by the objective lens and optics 126 and/or 122 (e.g., elements of a tube lens). In some implementations, the FOV of the disclosed imaging modules (e.g., that provided by the combination of objective lens 110 and optics 126 and/or 122) may range, for example, between about 1 mm and 5 mm (e.g., in diameter, width, length, or longest dimension) as will be discussed below. The FOV may be selected, for example, to provide a balance between magnification and resolution of the imaging module and/or based on one or more characteristics of the image sensors and/or objective lenses. For example, a relatively smaller FOV may be provided in conjunction with a smaller and faster imaging sensor to achieve high throughput.

Referring again to FIGS. 3A and 3B, in some implementations, the optics 126 in the detection channel (e.g., the tube lens) may be configured to reduce optical aberration in images acquired using optics 126 in combination with objective lens 110. In some implementations comprising multiple detection channels for imaging at different emission wavelengths, the optics 126 (e.g., the tube lens) for different detection channels have different designs to reduce aberration for the respective emission wavelengths at which that particular channel is configured to image. In some implementations, the optics 126 (e.g., the tube lens) may be configured to reduce aberrations when imaging a specific surface (e.g., a plane, object plane, etc.) on the sample support structure comprising fluorescing sample sites disposed thereon as compared to other locations (e.g., other planes in object space). Similarly, in some implementations, the optics 126 (e.g., the tube lens) may be configured to reduce aberrations when imaging first and second surfaces (e.g., first and second planes, first and second object planes, etc.) on a dual surface sample support structure (e.g., a dual surface flow cell) having fluorescing sample sites disposed thereon as compared to other locations (e.g., other planes in object space). For example, the optics 126 in the detection channel (e.g., tube lens) may be designed to reduce the aberration at two depths or planes located at different distances from the objective lens as compared to the aberrations associated with other depths or planes at other distances from the objective. For example, optical aberration may be less for imaging the first and second surfaces than elsewhere in a region from about 1 to about 10 mm from the objective lens. Additionally, custom optic 126 in the detection channel (e.g., a tube lens) may in some embodiments be configured to compensate for aberration induced by transmission of emission light through one or more portions of the sample support structure such as a layer that includes one of the surfaces on which the sample is disposed as well as possibly a solution adjacent to and in contact with the surface on which the sample is disposed. The layer comprising one of the surfaces on which the sample is disposed may comprise, e.g., glass, quartz, plastic, or other transparent material having a refractive index, and which introduces optical aberration. Custom optic 126 in the detection channel (e.g., the tube lens), for example, may in some implementations be configured to compensate for optical aberration induced by a sample support structure, e.g., a coverslip or flow cell wall, or other sample support structure components, as well as possibly a solution adjacent to and in contact with the surface on which the sample is disposed.

In some implementations, the optics 126 in the detection channel (e.g., a tube lens) are configured to have reduced magnification. The optics 126 in the detection channel (e.g., a tube lens) may be configured, for example, such that the fluorescence imaging module has a magnification of less than, for example, 10×, as will be discussed further below. Such reduced magnification may alter design constraints such that other design parameters can be achieved. For example, the optics 126 (e.g., a tube lens) may also be configured such that the fluorescence imaging module has a large field-of-view (FOV), for example, of at least 1.0 mm or larger (e.g., in diameter, width, length, or longest dimension), as will be discussed further below.

In some implementations, the optics 126 (e.g., a tube lens) may be configured to provide the fluorescence imaging module with a field-of-view as indicated above such that the FOV has less than 0.15 waves of aberration over at least 60%, 70%, 80%, 90%, or 95% of the field, as will be discussed further below.

Referring again to FIGS. 3A and 3B, in various implementations, a sample is located at or near a focal position 112 of the objective lens 110. As described above with reference to FIGS. 2A and 2B, a light source such as a laser source provides an excitation beam to the sample to induce fluorescence. At least a portion of fluorescence emission is collected by the objective lens 110 as emission light. The objective lens 110 transmits the emission light toward the first dichroic filter 130, which reflects some or all of the emission light as the beam 150 incident upon the second dichroic filter 135 and to the different detection channels, each comprising optics 126 that form an image of the sample (e.g., a plurality of fluorescing sample sites on a surface of a sample support structure) onto a photodetector array 124.

As discussed above, in some implementations, the sample support structure comprises a flow cell such as a dual surface flow cell having two surfaces (e.g., two interior surfaces, a first surface and a second surface, etc.) containing sample sites that emit fluorescent emission. These two surfaces may be separated by a distance from each other in the longitudinal (Z) direction along the direction of the central axis of the excitation beam and/or the optical axis of the objective lens. This separation may correspond, for example, to a flow channel within the flow cell. Analytes or reagents may be flowed through the flow channel and contact the first and second interior surfaces of the flow cell, which may thereby be contacted with a binding composition such that fluorescence emission is radiated from a plurality of sites on the first and second interior surfaces. The imaging optics (e.g., objective lens 110) may be positioned at a suitable distance (e.g., a distance corresponding to the working distance) from the sample to form in-focus images of the sample on one or more detector arrays 124. As discussed above, in various designs, the objective lens 110 (possibly in combination with the optics 126) may have a depth of field and/or depth of focus that is at least as large as the longitudinal separation between the first and second surfaces. The objective lens 110 and the optics 126 (of each detection channel) can thus simultaneously form images of both the first and the second flow cell surfaces on the photodetector array 124, and these images of the first and second surfaces are both in focus and have comparable optical resolution (or may be brought into focus with only minor refocusing of the objects to acquire images of the first and second surfaces that have comparable optical resolution). In various implementations, compensation optics need not be moved into or out of an optical path of the imaging module (e.g., into or out of the first and/or second optical paths) to form in-focus images of the first and second surfaces that are of comparable optical resolution. Similarly, in various implementations, one or more optical elements (e.g., lens elements) in the imaging module (e.g., the objective lens 110 or optics 126) need not be moved, for example, in the longitudinal direction along the first and/or second optical paths to form in-focus images of the first surface in comparison to the location of said one or more optical elements when used to form in-focus images of the second surface. In some implementations, the imaging module includes an autofocus system configured to quickly and sequentially refocus the imaging module on the first and/or second surface such that the images have comparable optical resolution. In some implementations, objective lens 110 and/or optics 126 are configured such that both the first and second flow cell surfaces are in focus simultaneously with comparable optical resolution without moving an optical compensator into or out of the first and/or second optical path, and without moving one or more lens elements (e.g., objective lens 110 and/or optics 126 (such as a tube lens) longitudinally along the first and/or second optics path. In some implementations, images of the first and/or second surfaces, acquired either sequentially (e.g., with refocusing between surfaces) or simultaneously (e.g., without refocusing between surfaces) using the novel objective lens and/or tube lens designs disclosed herein, may be further processed using a suitable image processing algorithm to enhance the effective optical resolution of the images such that the images of the first and second surfaces have comparable optical resolution. In various implementations, the sample plane is sufficiently in focus to resolve sample sites on the first and/or second flow cell surfaces, the sample sites being closely spaced in lateral directions (e.g., in the X and Y directions).

As discussed above, the dichroic filters may comprise interference filters that selectively transmit and reflect light of different wavelengths based on the principle of thin-film interference, using layers of optical coatings having different refractive indices and particular thickness. Accordingly, the spectral response (e.g., transmission and/or reflection spectra) of the dichroic filters implemented within multi-channel fluorescence imaging modules may be at least partially dependent upon the angle of incidence, or range of angles of incidence, at which the light of the excitation and/or emission beams are incident upon the dichroic filters. Such effects may be especially significant with respect to the dichroic filters of the detection optical path (e.g., the dichroic filters 135 and 140 of FIGS. 3A and 3B).

Figure 4:
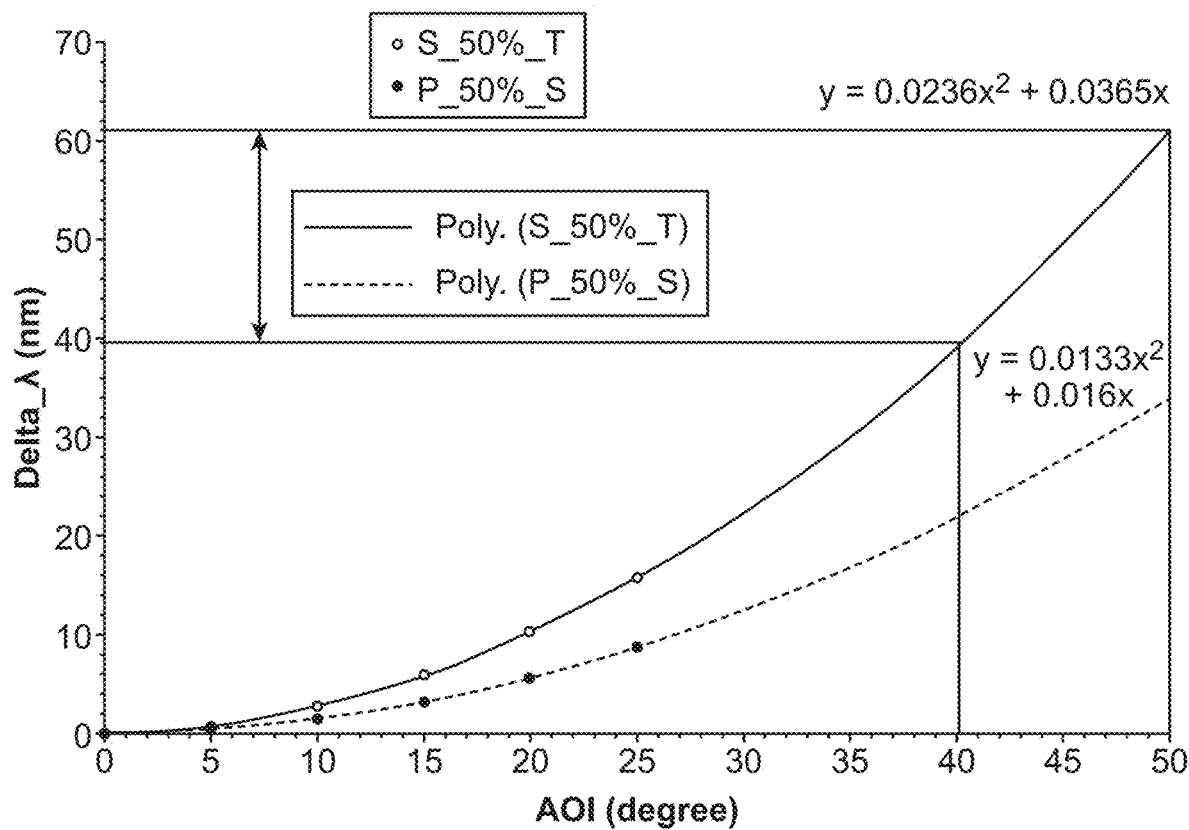
FIG. 4 is a graph illustrating a relationship between dichroic filter performance and beam angle of incidence.

FIG. 4 is a graph illustrating a relationship between dichroic filter performance and beam angle of incidence (AOI). Specifically, the graph of FIG. 4 illustrates the effect of angle of incidence on the transition width or spectral span of a dichroic filter, which corresponds to the range of wavelengths where the spectral response (e.g., transmission spectrum and/or reflection spectrum) transitions between the passband and stopband regions of a dichroic filter. Thus, a transmission edge (or reflection edge) having a relatively small spectral span (e.g., a small delta λ value in the graph of FIG. 4) corresponds to a sharper transition between passband and stopband regions or the transmission and reflection regions (or conversely between reflection and transmission regions), while a transmission edge (or reflection edge) having a relatively large spectral span (e.g., a large delta_λ value in the graph of FIG. 4) corresponds to a less sharp transition between passband and stopband regions. In various implementations, sharper transitions between passband and stopband regions are generally desirable. Moreover, it may also be desirable to have increased consistency or a relatively consistent transition width across all or most of the field of view and/or beam area.

Fluorescence imaging modules, in which the dichroic mirrors are disposed at 45 degrees relative to a central beam axis of the emission light or the optical axis of the optical paths (e.g., of the objective lens and/or tube lens), accordingly can have a transition width of roughly 50 nm for an example dichroic filter, as shown in FIG. 4. Because the emission light beam is not collimated and has some degree of divergence, fluorescence imaging modules may have a range of angles of incidence of approximately 5 degrees between opposing sides of the beam. Thus, as shown in FIG. 4, different portions of the beam of emission light may be incident upon a channel splitting dichroic filter at various angles of incidence between 40 degrees and 50 degrees. This range of relatively large angles of incidence corresponds to a range of transition widths between about 40 nm and about 62 nm. This range of relatively large angles of incidence thereby leads to an increase in transition width of the dichroic filter in the imaging module. Performance of multi-channel fluorescence imaging modules may thus be improved by providing smaller angles of incidence across the full beam, thereby making the transmission edge sharper and allowing better discrimination between different fluorescence emission bands.

Figure 5:
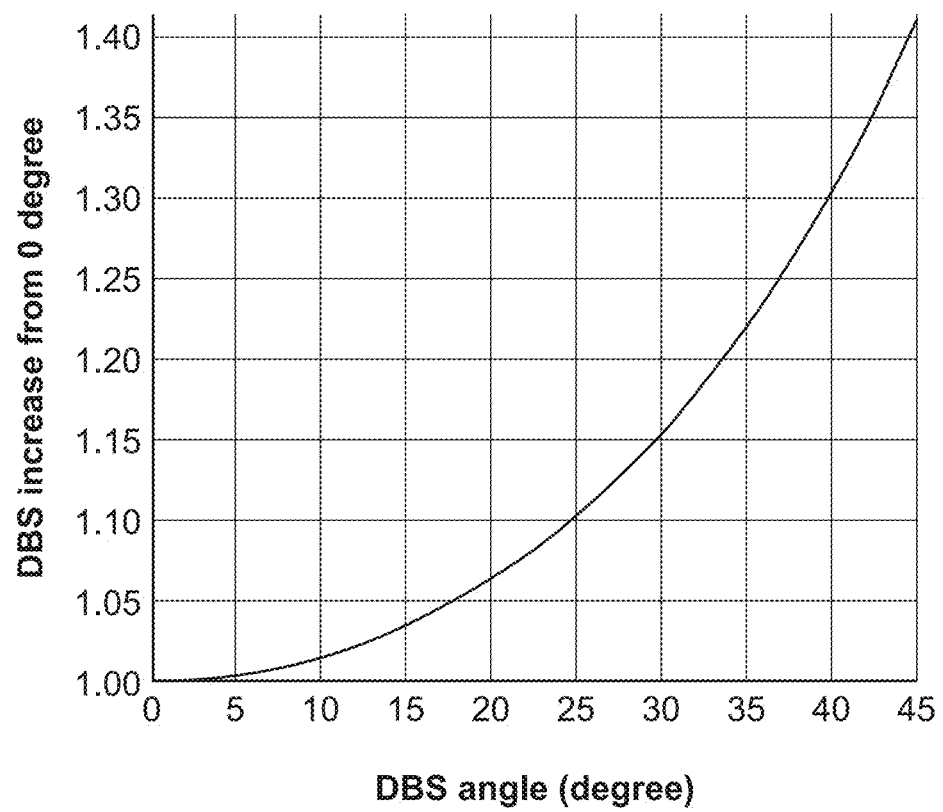
FIG. 5 is a graph illustrating a relationship between beam footprint size and beam angle of incidence on a dichroic filter.

FIG. 5 is a graph illustrating a relationship between beam footprint size (DBS) and beam angle of incidence (DBS angle) on a dichroic filter. In some instances, a smaller beam footprint may be desirable. For example, a small beam footprint allows smaller dichroic filters to be used to split a beam into different wavelength ranges. The use of smaller dichroic filters in turn reduces manufacturing costs and improves the ease of manufacturing suitably flat dichroic filters. As shown in FIG. 5, any angle of incidence greater than 0 degrees (i.e., perpendicular to the surface of the dichroic filter) results in an elliptical beam footprint having an area larger than the cross-sectional area of the beam. An angle of incidence of 45 degrees results in a large beam footprint on the dichroic reflector that is greater than 1.4 times the cross-sectional area of the beam when incident at zero degrees.

Figure 6A:
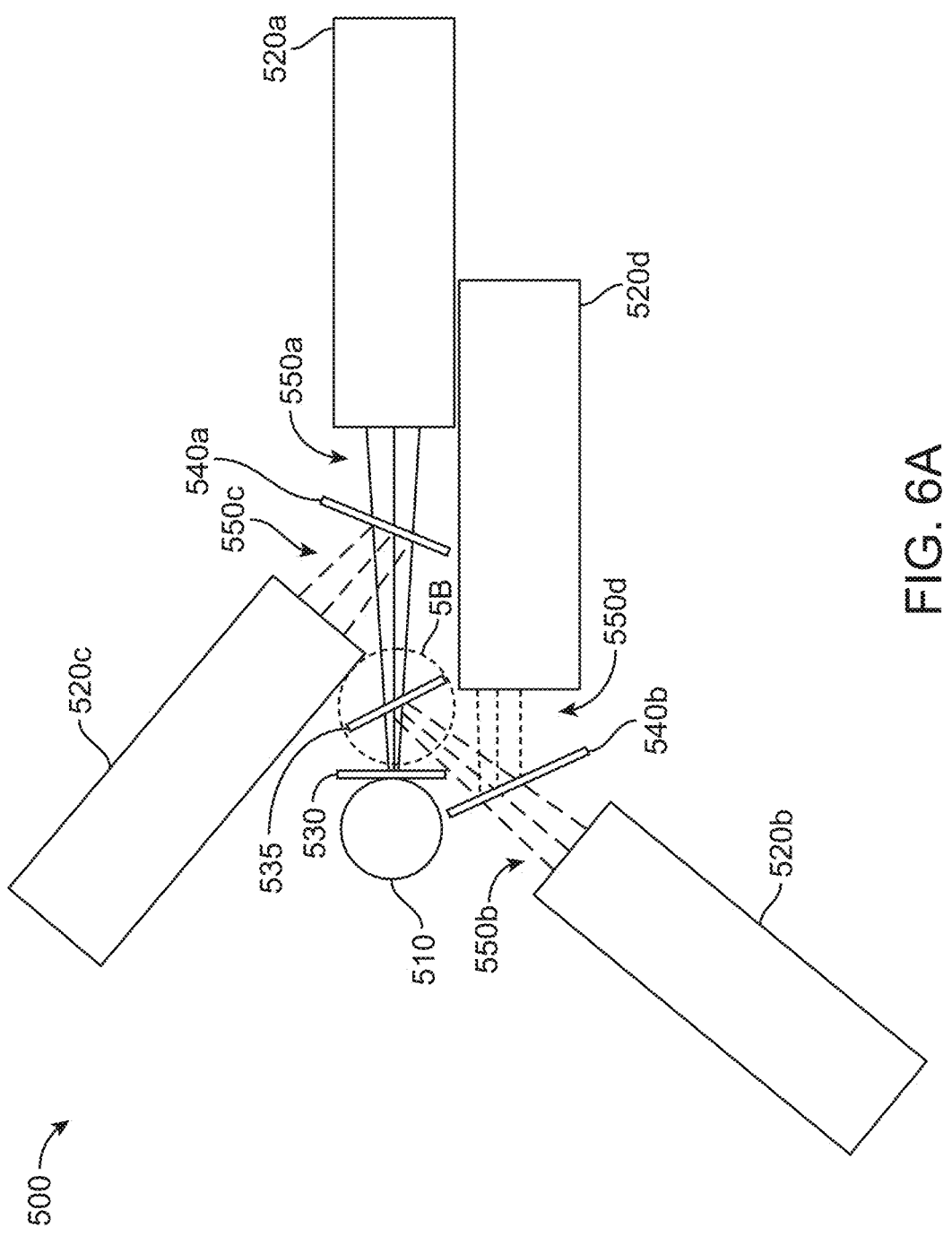
FIGS. 6A-6B schematically illustrate an example configuration of dichroic filters and detection channels of a multi-channel fluorescence imaging module wherein the dichroic filters have reflective surface tilted such that the angle between the incident beam (e.g., the central angle) and the reflective surface of the dichroic filter is less than 45.
Figure 6B:
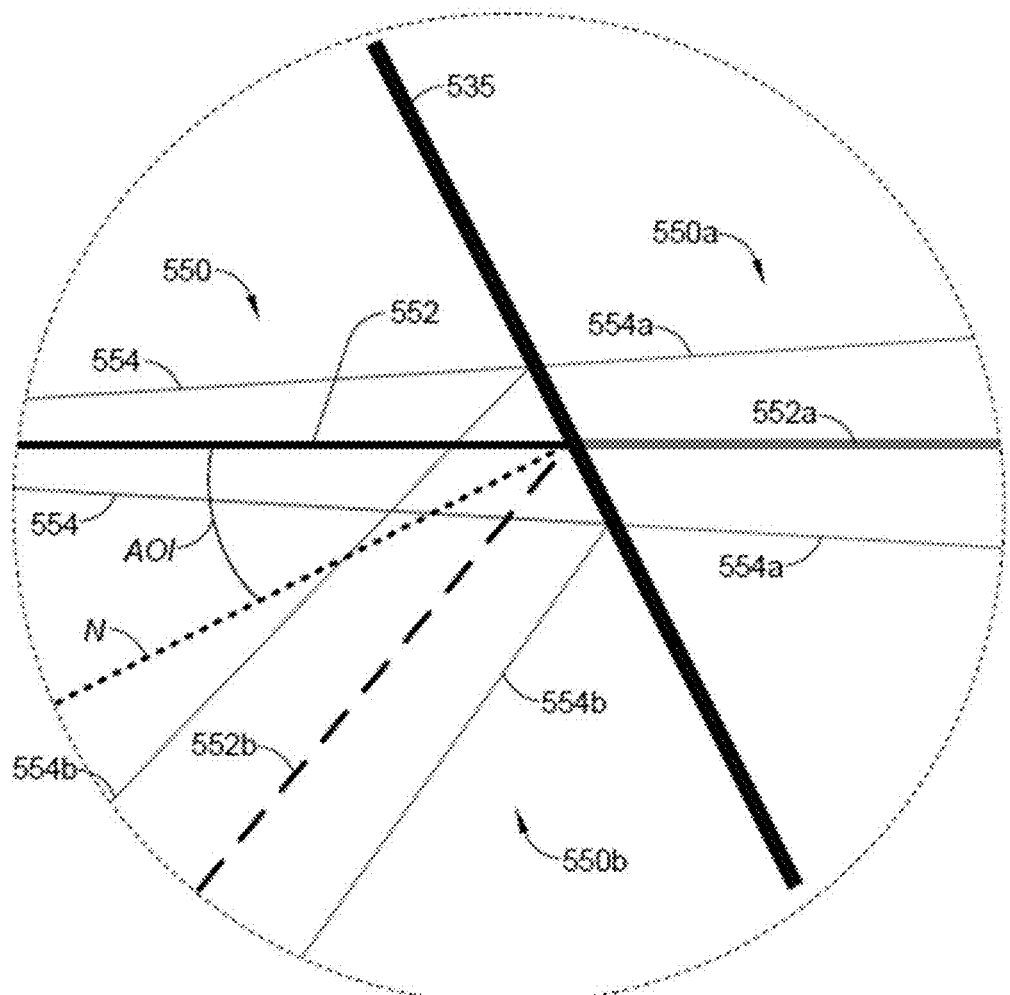

FIGS. 6A and 6B schematically illustrate a non-limiting example configuration of dichroic filters and detection channels in a multi-channel fluorescence imaging module where the dichroic mirrors are disposed at an angle of less than 45 degrees relative to a central beam axis of the emission light or the optical axis of the optical paths (e.g., of the objective lens and/or tube lens). FIG. 6A depicts an imaging module 500 including a plurality of detection channels 520a, 520b, 520c, 520d. FIG. 6B is a detailed view of the portion of the imaging module 500 within the circle 5B as shown in FIG. 6A. As will be described in greater detail, the configuration illustrated in FIGS. 6A and 6B includes a number of aspects that may result in significant improvements over conventional multi-channel fluorescence imaging module designs. In some instances, fluorescence imaging modules and systems of the present disclosure may, however, may be implemented with one or a subset of the features described with respect to FIGS. 6A and 6B without departing from the spirit or scope of the present disclosure.

The imaging module 500 depicted in FIG. 6A includes an objective lens 510 and four detection channels 520a, 520b, 520c, and 520d disposed to receive and/or image emission light transmitted by the objective lens 510. A first dichroic filter 530 is provided to couple the excitation and detection optical paths. In contrast to the design shown in FIGS. 2A and 2B, as well as in FIGS. 3A and 3B, the first dichroic filter 530 (e.g., a dichroic beam splitter or combiner) is configured to reflect light from the light source to the objective lens 510 and sample, and transmit fluorescence emission from the sample to the detection channels 520a, 520b, 520c, and 520d. A second dichroic filter 535 splits a beam of emission light among at least two detection channels 520a, 520b by transmitting a first portion 550a and reflecting a second portion 550b. Additional dichroic filters 540a, 540b are provided to further split the emission light. Dichroic filter 540a transmits at least a portion of the first portion 550a of the emission light and reflects a portion 550c to a third detection channel 520c. Dichroic filter 540b transmits at least a portion of the second portion 550b of the emission light and reflects a portion 550d to a fourth detection channel 520d. Although the imaging module 500 is depicted with four detection channels, in various embodiments the imaging module 500 may include more or fewer detection channels, with a correspondingly larger or smaller number of dichroic filters as appropriate to provide a portion of the emission light to each detection channel. For example, in some embodiments, the features of the imaging module 500 may be implemented with similar advantageous effects in a simplified imaging module including only two detection channels 520a, 520b, and omitting additional dichroic filters 540a, 540b. In some implementations, only one detection channel may be included. Alternatively, three or more detection channels may be employed.

The detection channels 520a, 520b, 520c, 520d illustrated in FIG. 6A may include some or all of the same or similar components to those of the detection channels 120 illustrated in FIGS. 2A-3B. For example, different detection channel 520a, 520b, 520c, 520d may include one or more image sensors or photodetectors arrays, and may include transmissive and/or reflective optics such as one or more lenses (e.g., tube lenses) that focus the light received by the detection channel onto its respective image sensor or photodetector array.

The objective lens 510 is disposed to receive emission light emitted by fluorescence from a specimen. In particular, the first dichroic filter 530 is disposed to receive the emission light collected and transmitted by the objective lens 510. As discussed above and shown in FIG. 6A, in some designs, an illumination source (e.g., the illumination source 115 of FIGS. 2A and 2B) such as a laser source or the like is disposed to provide an excitation beam which is incident on the first dichroic filter 530 such that the first dichroic filter 530 reflects the excitation beam into the same objective lens 510 that transmits the emission light, for example, in an epifluorescence configuration. In some other designs, the illumination source may be directed to the specimen by other optical components along a different optical path that does not include the same objective lens 510. In such configurations, the first dichroic filter 530 may be omitted.

Similarly, as discussed above and shown in FIG. 6A, the detection optics (e.g., including the detection channels 520a, 520b, 520c, 520d and any optical components such as dichroic filters 535, 540a, 540b along the optical path between the objective lens 510 and the detection channels 520a, 520b, 520c, 520d) may be disposed on the transmission path of the first dichroic filter 530, rather than on the reflected path of the first dichroic filter 530. In one example implementation, the objective lens 510 and detection optics are disposed such that the objective lens 510 transmits the beam 550 of emission light directly toward the second dichroic filter 535. The wavefront quality of the emission light may be degraded somewhat by the presence of the first dichroic filter 530 along the path of the beam 550 of emission light (e.g., by imparting some wavefront error to the beam 550). However, the wavefront error introduced by a beam transmitted through a dichroic reflector of a dichroic beam splitter is generally significantly smaller than the wavefront error of a beam reflected from the dichroic reflecting surface of a dichroic beam splitter (e.g., an order of magnitude smaller). Thus, the wavefront quality and subsequent imaging quality of the emission light in a multi-channel fluorescence imaging module may be substantially improved by placing the detection optics along the transmitted beam path of the first dichroic filter 530 rather than along the reflected beam path.

Still referring to FIG. 6A, within the detection optics of the imaging module 500, dichroic filters 535, 540a, and 540b are provided to split the beam 550 of emission light among the detection channels 520a, 520b, 520c, 520d. For example, the dichroic filters 535, 540a, and 540b split the beam 550 on the basis of wavelength, such that a first wavelength or wavelength band of the emission light can be received by the first detection channel 520a, a second wavelength or wavelength band of the emission light can be received by the second detection channel 520b, a third wavelength or wavelength band of the emission light can be received by the third detection channel 520c, and a fourth wavelength or wavelength band of the emission light can be received by the fourth detection channel 520d. In some implementations, multiple separated wavelengths or wavelength bands can be received by the detection channel.

In contrast to the multi-channel fluorescence imaging module design shown in FIGS. 2A and 2B, as well as FIGS. 3A and 3B, the imaging module 500 has dichroic filters 535, 540a, and 540b disposed at angles of incidence of less than 45 degrees with respect to the central beam axis of the incident beams. As shown in FIG. 6B, the different beams 550, 550a, 550b have respective central beam axes 552, 552a, 552b. In various implementations, the central beam axes 552, 552a, 552b is at the center of a cross-section of the beam orthogonal to the propagation direction of the beam. These central beam axes 552, 552a, 552b may correspond to the optical axis of the objective lens and/or the optics within the separate channels, for example, the optical axes of the respective tube lenses. Additional rays 554, 554a, 554b of each beam 550, 550a, 550b are illustrated in FIG. 6B to indicate the diameter of each beam 550, 550a, 550b. Beam diameter may be defined, for example, as a full width at half maximum diameter, a D4σ (i.e., 4 times σ, where σ is the standard deviation of the horizontal or vertical marginal distribution of the beam respectively) or second-moment width, or any other suitable definition of beam diameter.

The central beam axis 552 of the beam 550 of emission light may serve as a reference point for defining the angle of incidence of the beam 550 on the second dichroic filter 535. Accordingly, the "angle of incidence" (AOI) of a beam 550 may be the angle between the central beam axis 552 of the incident beam 550 and a line N normal to the surface the beam is incident on, for example, the dichroic reflective surface. When the beam 550 of emission light is incident upon the dichroic reflective surface of the second dichroic filter 535 at an angle of incidence AOI, the second dichroic filter 535 transmits a first portion 550a of the emission light (e.g., the portion having wavelengths within the passband region of the second dichroic filter 535) and reflects a second portion 550b of the emission light (e.g., the portion having wavelengths within the stopband region of the second dichroic filter 535). The first portion 550a and the second portion 550b may each be similarly described in terms of a central beam axis 552a, 552b. As referred to above, the optical axis may alternatively or additionally be used.

In the example configuration of FIGS. 6A and 6B, the second dichroic filter 535 is disposed such that the central beam axis 552 of the beam 550 is incident at an angle of incidence of 30 degrees. Similarly, the additional dichroic filters 540a, 540b are disposed such that the central beam axes 552a, 552b of the first and second portions 550a, 550b of the beam 550 are also incident at angles of incidence of 30 degrees. However, in various implementations these angles of incidence may be other angles smaller than 45 degrees. In some instances, for example, the angles of incidence may range between about 20 degrees and about 45 degrees, as will be discussed further below. Moreover, the angles of incidence on each of the dichroic filters 535, 540a, 540b need not necessarily be the same. In some embodiments, some or all of the dichroic filters 535, 540a, 540b may be disposed such that their incident beams 550, 550a, 550b have different angles of incidence. As described above, the angle of incidence may be with respect to the optical axis of the optics within the imaging module, for example, the objective lens and/or the optics in the detection channels (e.g., the tube lenses) and the dichroic reflective surface in the respective dichroic beam splitter. The same ranges and values for the angle of incidence apply to the case when the optical axis is used to specify the AOI.

The beams 550, 550a, 550b of emission light in a fluorescence imaging module system are typically diverging beams. As noted above, the beams of emission light can have a beam divergence large enough that regions of the beam within the beam diameter are incident upon the dichroic filters at angles of incidence that differ by up to 5 degrees or more relative to the angle of incidence of the central beam axis and/or optical axis of the optics. In some designs, the objective lens 510 may be configured, for example, to have an f-number or numerical aperture selected to produce a smaller beam diameter for a given field of view of the microscope. In one example, the f-number or numerical aperture of the objective lens 510 may be selected such that the full diameter of the beams 550, 550a, 550b are incident upon dichroic filters 535, 540a, 540b at angles of incidence within, for example, 1 degree, 1.5 degrees, 2 degrees, 2.5 degrees, 3 degrees, 3.5 degrees, 4 degrees, 4.5 degrees, or 5 degrees of the angle of incidence of the central beam axes 552, 552a, 552b.

In some implementations, the focal length of the objective lens that is suitable for producing such a narrow beam diameter may be longer than those typically employed in fluorescence microscopes or imaging systems. For example, in some implementations, the focal length of the objective lens may range between 20 mm and 40 mm, as will be discussed further below. In one example, an objective lens 510 having a focal length of 36 mm may produce a beam 550 characterized by a divergence small enough that light across the full diameter of the beam 550 is incident upon the second dichroic filter 535 at angles within 2.5 degrees of the angle of incidence of the central beam axis.

Figure 7:
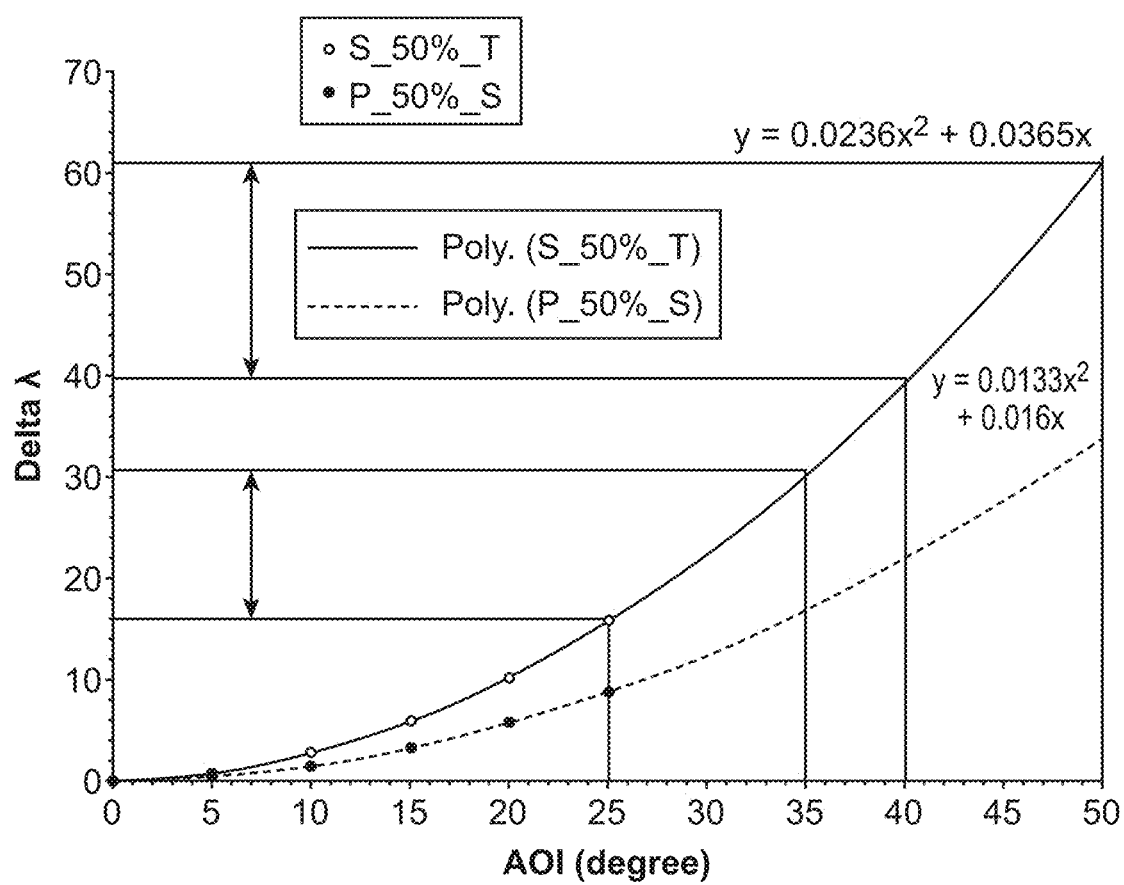
FIG. 7 provides a graph illustrating improved dichroic filter performance corresponding to the imaging module configuration illustrated in FIGS. 6A and 6B.
Figure 8:
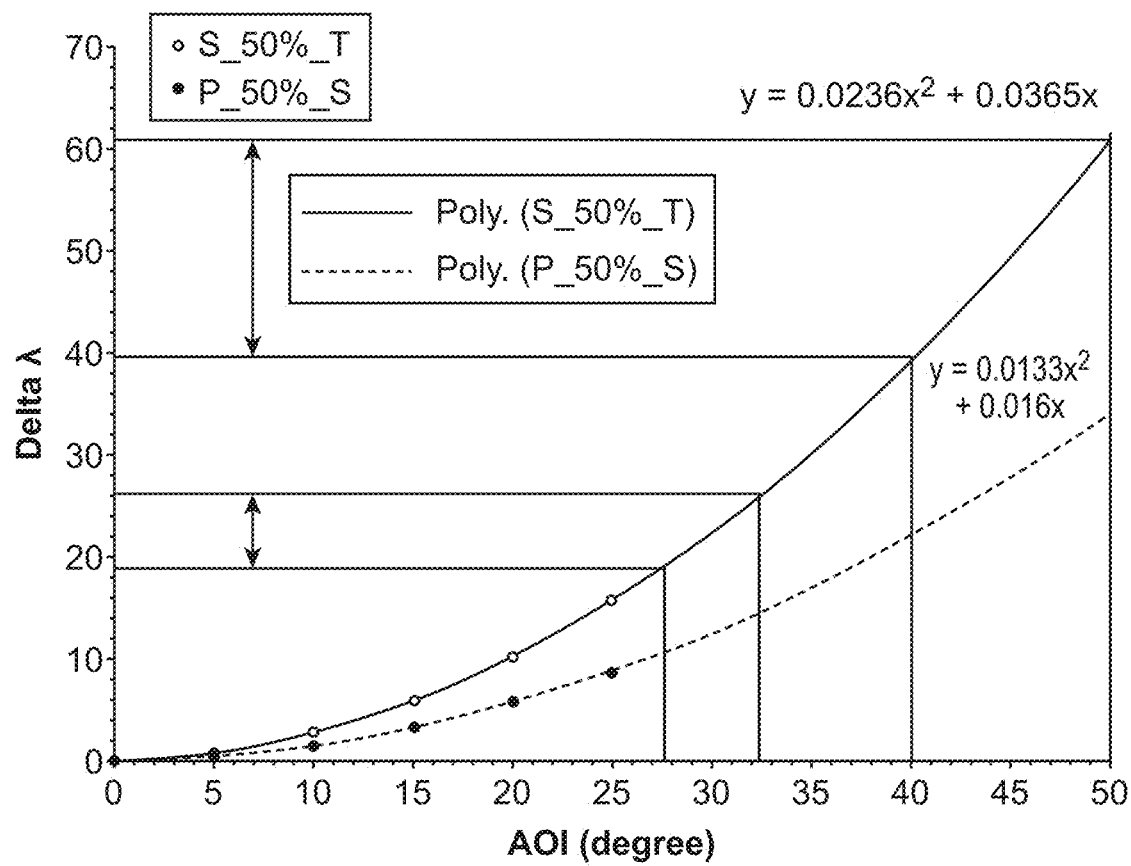
FIG. 8 provides a graph illustrating improved dichroic filter performance corresponding to the imaging module configuration illustrated in FIGS. 6A and 6B.

FIG. 7 and FIG. 8 provide graphs illustrating improved dichroic filter performance due to aspects of the imaging module configuration of FIGS. 6A and 6B (or any of the imaging module configurations disclosed herein). The graph in FIG. 7 is similar to that of FIG. 4 and illustrates the effect of angle of incidence on the transition width (e.g., the spectral span of the transmission edge) of a dichroic filter. FIG. 7 shows an example where the orientation of a dichroic filter (e.g., dichroic filters 535, 540a, and 540b) and the dichroic reflective surface therein is such that its incident beam has an angle of incidence of 30 degrees, rather than 45 degrees. FIG. 7 shows how this reduced angle of incidence significantly improves the sharpness and the uniformity of the transition width across the full beam diameter. For example, while an angle of incidence of 45 degrees at the central beam axis results in a range of transition widths between about 40 nm and about 62 nm, an angle of incidence of 30 degrees at the central beam axis results in a range of transition widths between about 16 nm and about 30 nm. In this example, the average transition width is reduced from about 51 nm to about 23 nm, indicating a sharper transition between passband and stopband. Moreover, the variation in transition widths across the beam diameter is reduced by nearly 40% from a 22 nm range to a 14 nm range, indicating a more uniform sharpness of the transition over the area of the beam.

FIG. 8 illustrates additional advantages that may be realized by selecting the appropriate f-number or numerical aperture for the objective lens to reduce beam divergence in any of the imaging module configurations disclosed herein. In some implementations, a longer focal length is used. In the example of FIG. 8, the objective lens 510 has a focal length of 36 mm, which with the appropriate numerical aperture (e.g., less than 5), reduces the range of angles of incidence within the beam 550 from 30 degrees±5 degrees to 30 degrees±2.5 degrees. With this design, the range of transition widths may be reduced to between about 19 nm and about 26 nm. When compared to the improved system of FIG. 7, although the average transition width is substantially the same (e.g., a spectral span of roughly 23 nm), the variation in transition widths across the beam diameter is further reduced to a 7 nm range, representing a reduction of nearly 70% relative to the range of transition widths illustrated in FIG. 4.

Referring back to FIG. 5, the reduction in angle of incidence from 45 degrees to 30 degrees at the central beam axis is further advantageous because it reduces the beam spot size on the dichroic filter. As shown in FIG. 5, an angle of incidence of 45 degrees results in a beam footprint on the dichroic filter having an area greater than 1.4 times the cross-sectional area of the beam. However, an angle of incidence of 30 degrees results in a beam footprint on the dichroic filter having an area only about 1.15 times the cross-sectional area of the beam. Thus, reducing the angle of incidence at the dichroic filters 535, 540*a*, 540*b* from 45 degrees to 30 degrees results in a reduction of about 18% in the area of the beam footprint on the dichroic filters 535, 540*a*, 540*b*. This reduction in beam footprint area allows smaller dichroic filters to be used.

Figure 9A:
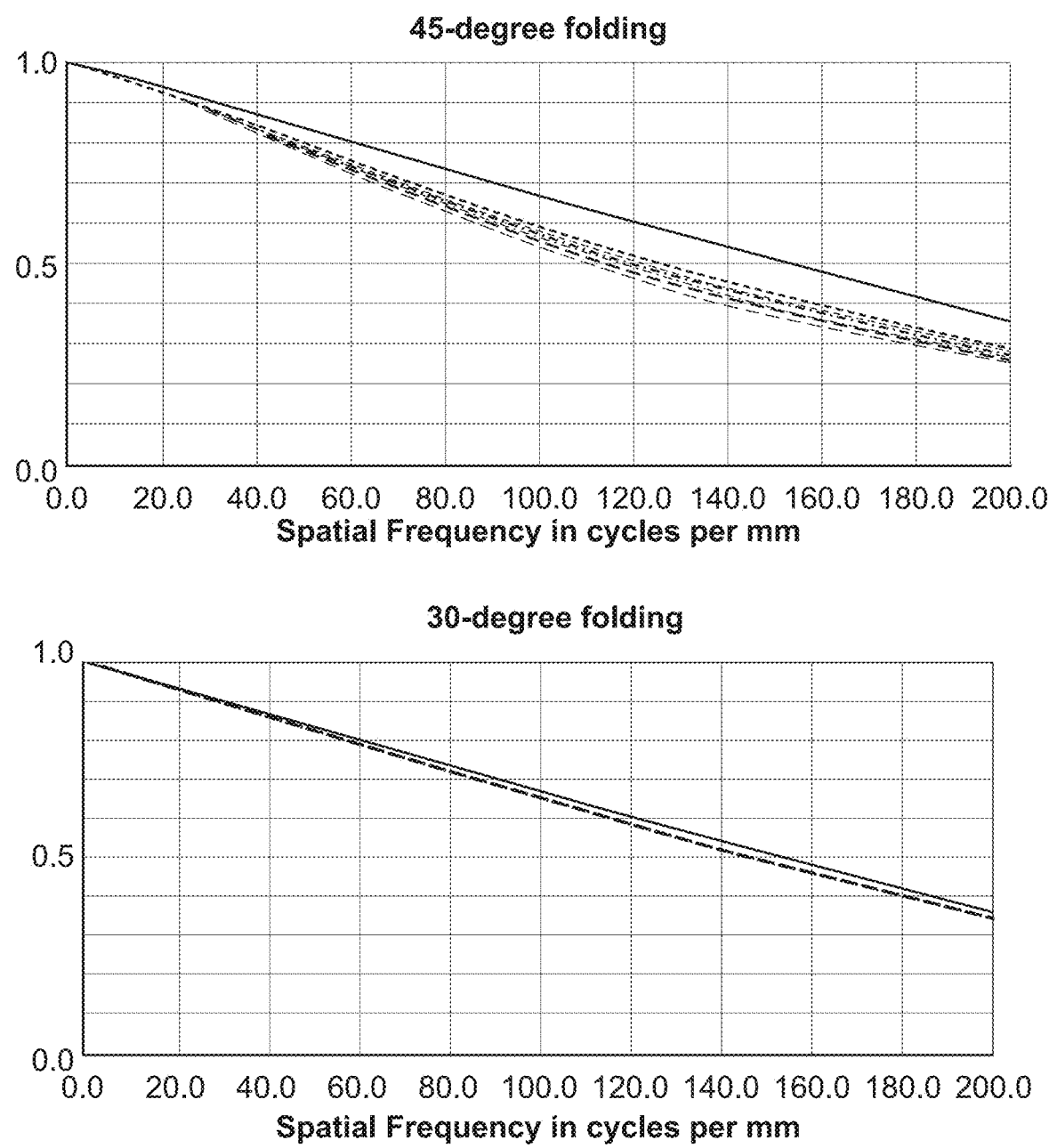
FIGS. 9A-9B provide graphs illustrating reduced surface deformation resulting from the imaging module configuration of FIGS. 6A and 6B.
Figure 9B:
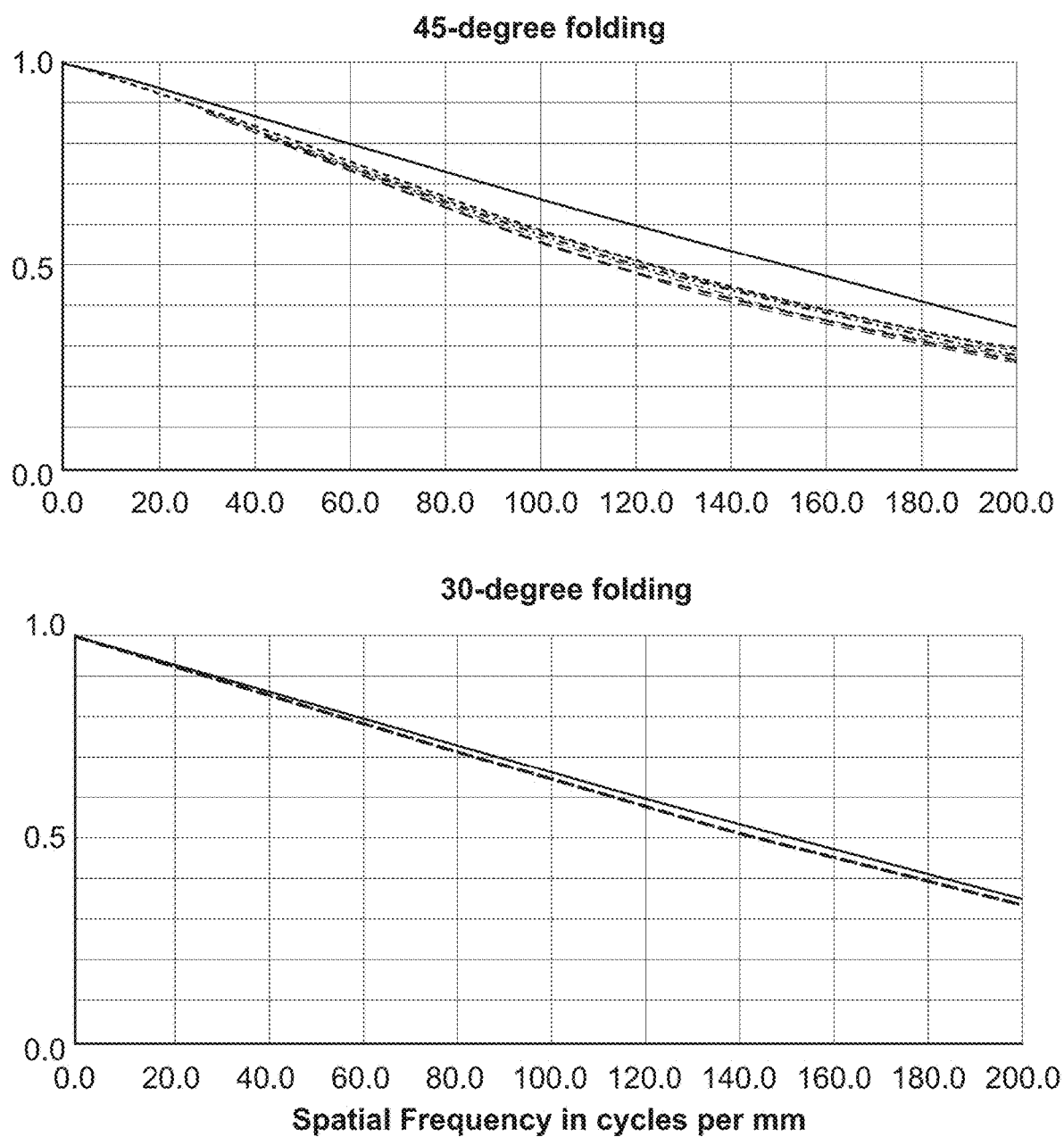

Referring now jointly to FIGS. 9A-B, the reduction in angle of incidence from 45 degrees to 30 degrees may also provide improved performance with regard to surface deformation caused by the dichroic filters in any of the imaging module configurations disclosed herein, as indicated by improvements in the modulation transfer function. In general, the amount of surface deformation increases with larger area optical elements. If a larger area on the dichroic filter is employed, a larger amount of surface deformation is encountered, thereby introducing more wavefront error into the beam. FIG. 9A illustrates the effect of folding angle on image quality degradation induced by the addition of 1 wave of peak-to-valley (PV) spherical power to the last mirror. FIG. 9B illustrates the effect of folding angle on image quality degradation induced by the addition of 0.1 wave of PV spherical power to the last mirror. As shown in FIGS. 9A and 9B, the reduction in angle of incidence to 30 degrees significantly reduces the effect of surface deformation to achieve close to diffraction-limited performance of the detection optics.

In some implementations of the disclosed imaging modules, the polarization state of the excitation beam may be utilized to further improve the performance of the multi-channel fluorescence imaging modules disclosed herein. Referring back to FIGS. 2A, 2B, and 6A, for example, some implementations of the multi-channel fluorescence imaging modules disclosed herein have an epifluorescence configuration in which a first dichroic filter 130 or 530 merges the optical paths of the excitation beam and the beam of emission light such that both the excitation and emission light are transmitted through the objective lens 110, 510. As discussed above, the illumination source 115 may include a light source such as a laser or other source which provides the light that forms the excitation beam. In some designs, the light source comprises a linearly polarized light source and the excitation beam may be linearly polarized. In some designs, polarization optics are included to polarize the light and/or rotate the polarization of the light. For example, a polarizer such as a linear polarizer may be included in an optical path of the excitation beam to polarize the excitation beam. Retarders such as half wave retarders or a plurality of quarter wave retarders or retarders having other amounts of retardance may be included to rotate the linear polarization in some designs.

The linearly polarized excitation beam, when it is incident upon any dichroic filter or other planar interface, may be p-polarized (e.g., having an electric field component parallel to the plane of incidence), s-polarized (e.g., having an electric field component normal to the plane of incidence), or may have a combination of p-polarization and s-polarization states within the beam. The p- or s-polarization state of the excitation beam may be selected and/or changed by selecting the orientation of the illumination source 115 and/or one or more components thereof with respect to the first dichroic filter 130, 530 and/or with respect to any other surfaces with which the excitation beam will interact. In some implementations where the light source output linearly polarized light, the light source can be configured to provide s-polarized light. For example, the light source may comprise an emitter such as a solid-state laser or a laser diode that may be rotated about its optical axis or the central axis of the beam to orient the linearly polarized light output therefrom. Alternatively, or in addition, retarders may be employed to rotate the linear polarization about the optical axis or the central axis of the beam. As discussed above, in some implementations, for example when the light source does not output polarized light, a polarizer disposed in the optical path of the excitation beam can polarize the excitation beam. In some designs, for example, a linear polarizer is disposed in the optical path of the excitation beam. This polarizer may be rotated to provide the proper orientation of the linear polarization to provide s-polarized light.

In some designs, the linear polarization is rotated about the optical axis or the central axis of the beam such that s-polarization is incident on the dichroic reflector of the dichroic beam splitter. When s-polarized light is incident on the dichroic reflector of the dichroic beam splitter the transition between the pass band and the stop band is sharper as opposed to when p-polarized light is incident on the dichroic reflector of the dichroic beam splitter.

Figure 10A:
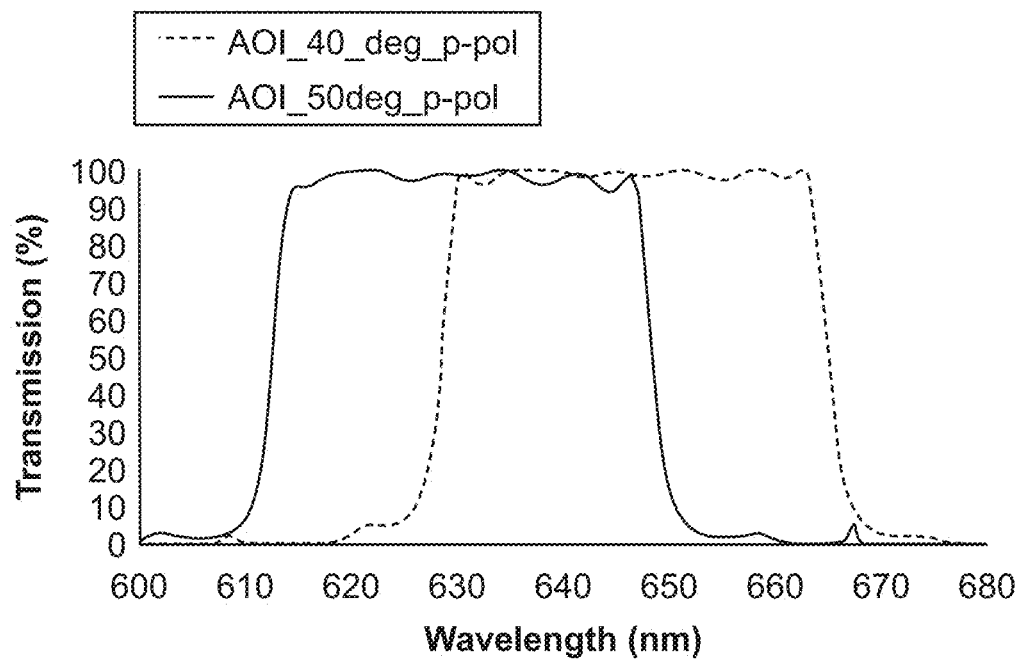
FIGS. 10A-10B provide graphs illustrating improved excitation filter performance (e.g. sharper transitions between pass bands and surrounding stop bands) resulting from use of s-polarization of the excitation beam.
Figure 10B:
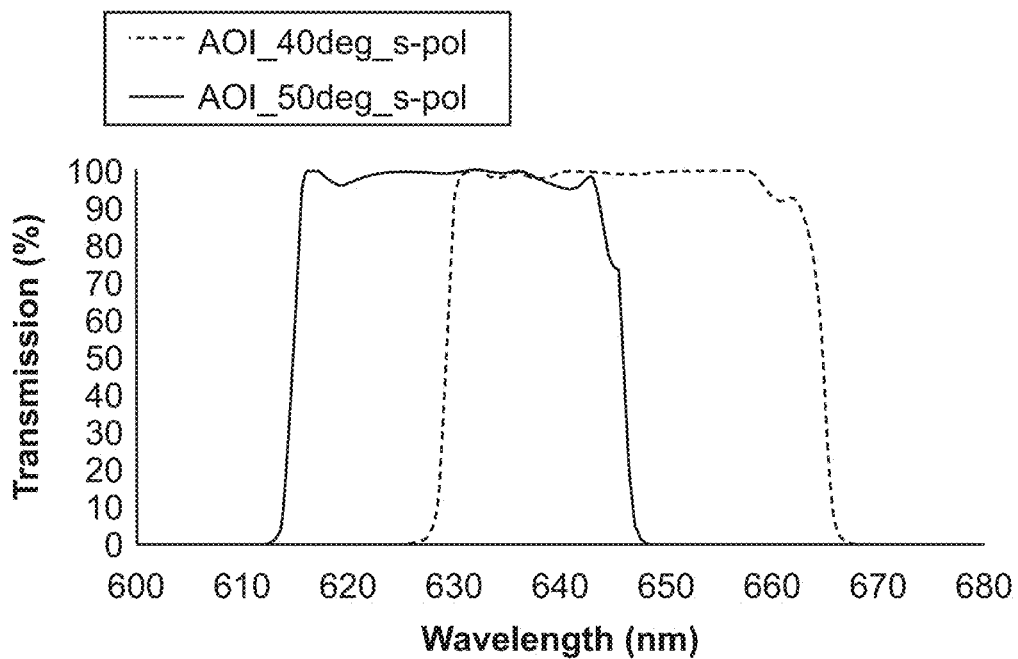

As shown in FIGS. 10A and 10B, use of the p- or s-polarization state of the excitation beam may significantly affect the narrowband performance of any excitation filters such as the first dichroic filter 130, 530. FIG. 10A illustrates a transmission spectrum between 610 nm and 670 nm for an example bandpass dichroic filter at angles of incidence of 40 degrees and 45 degrees, where the incident beam is linearly polarized and is p-polarized with respect to the plane of the dichroic filter. As shown in FIG. 10B, changing the orientation of the light source with respect to the dichroic filter, such that the incident beam is s-polarized with respect to the plane of the dichroic filter, results in a substantially sharper edge between the passband and the stopband of the dichroic filter. Thus, the illumination and imaging modules 100, 500 disclosed herein may advantageously have an illumination source 115 oriented relative to the first dichroic filter 130, 530 such that the excitation beam is s-polarized with respect to the plane of the first dichroic filter 130, 530. As discussed above, in some implementation, a polarizer such as a linear polarizer may be used to polarize the excitation beam. This polarizer may be rotated to provide an orientation of the linearly polarized light corresponding to s-polarized light. Also as discussed above, in some implementations, other approaches to rotating the linearly polarized light may be used. For example, optical retarders such as half wave retarders or multiple quarter wave retarders may be used to rotate the polarization direction. Other arrangements are also possible.

As discussed elsewhere herein, reducing the numerical aperture (NA) of the fluorescence imaging module and/or of the objective lens may increase the depth of field to enable the comparable imaging of the two surfaces. FIGS. 11A-16B, show how the MTF is more similar at first and second surfaces separated by 1 mm of glass for lower numerical apertures than for larger numerical apertures.

Figure 11A:
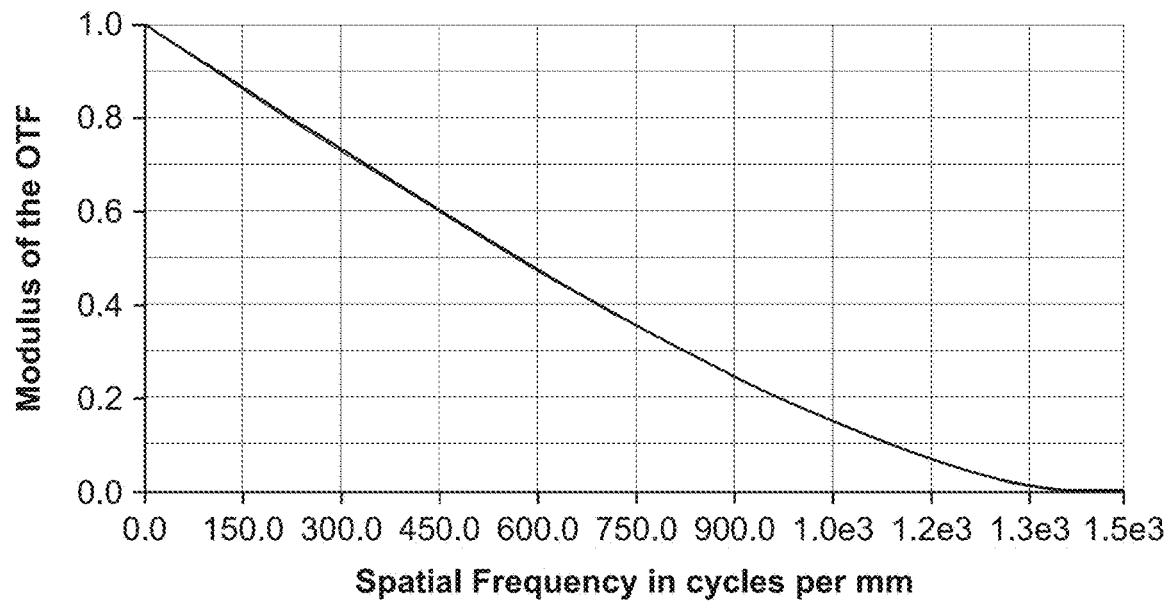
FIGS. 11A-11B illustrate the modulation transfer function (MTF) of an example dual surface imaging system disclosed herein having a numerical aperture (NA) of 0.3.
Figure 11B:
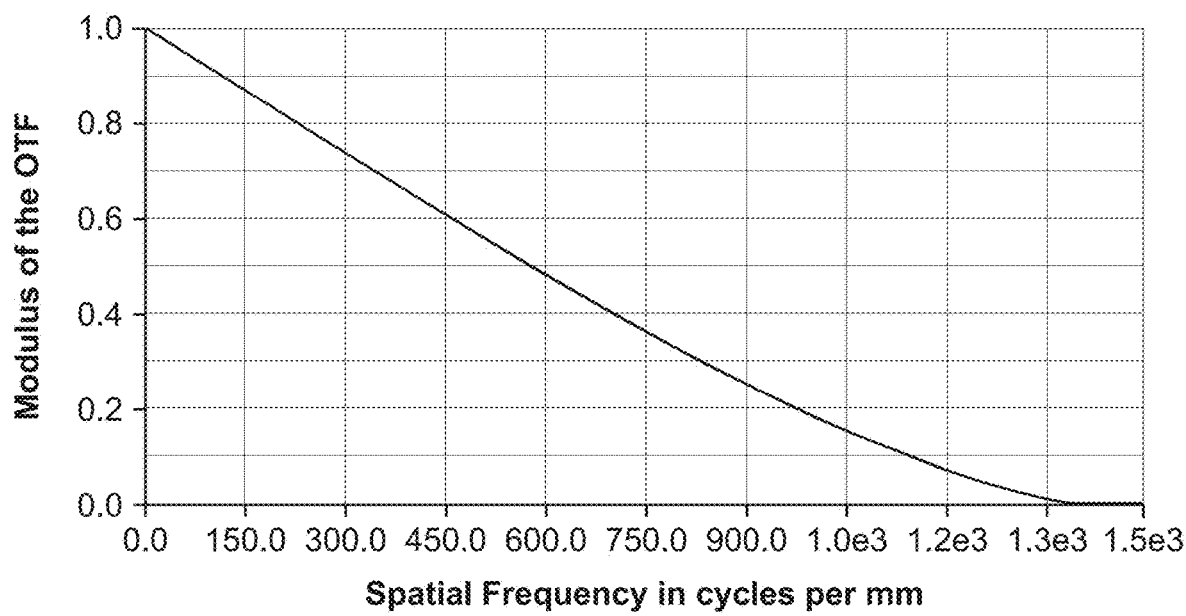

FIGS. 11A and 11B show the MTF at first (FIG. 11A) and second (FIG. 11B) surfaces for an NA of 0.3.

Figure 12A:
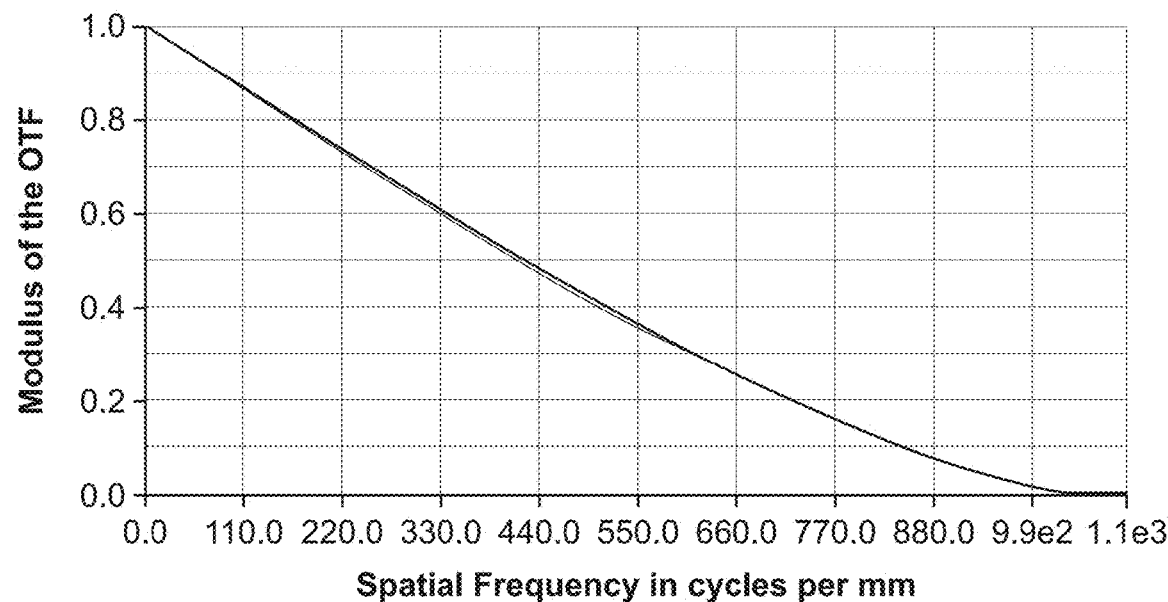
FIGS. 12A-12B illustrate the MTF of an example dual surface imaging system disclosed herein having an NA of 0.4.
Figure 12B:
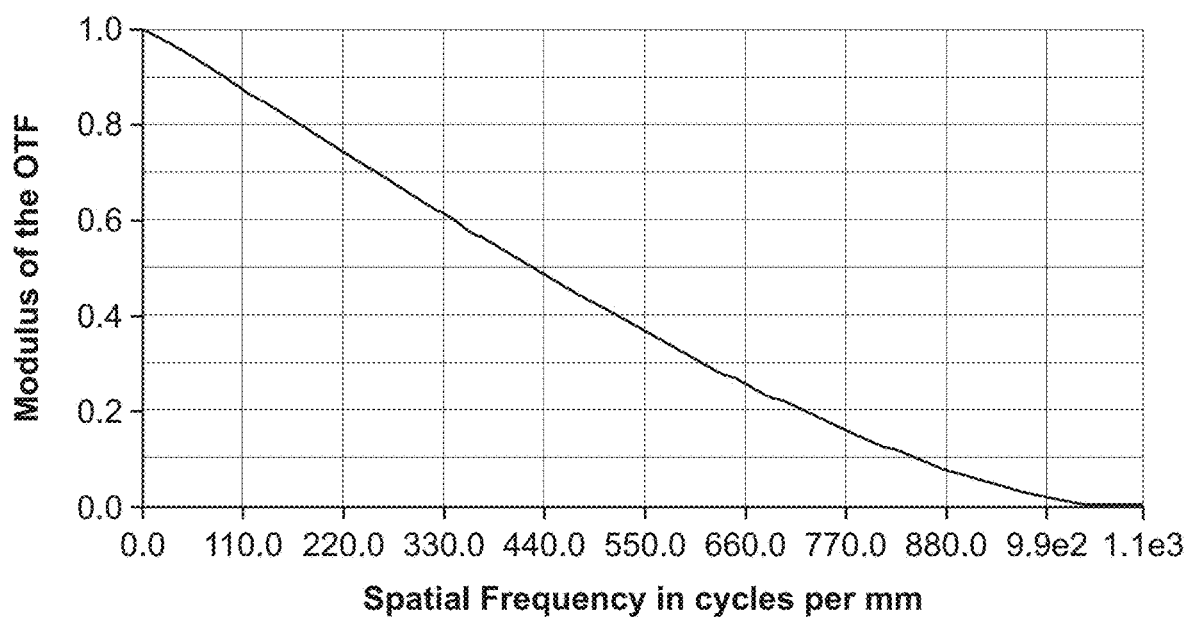

FIGS. 12A and 12B show the MTF at first (FIG. 12A) and second (FIG. 12B) surfaces for an NA of 0.4.

Figure 13A:
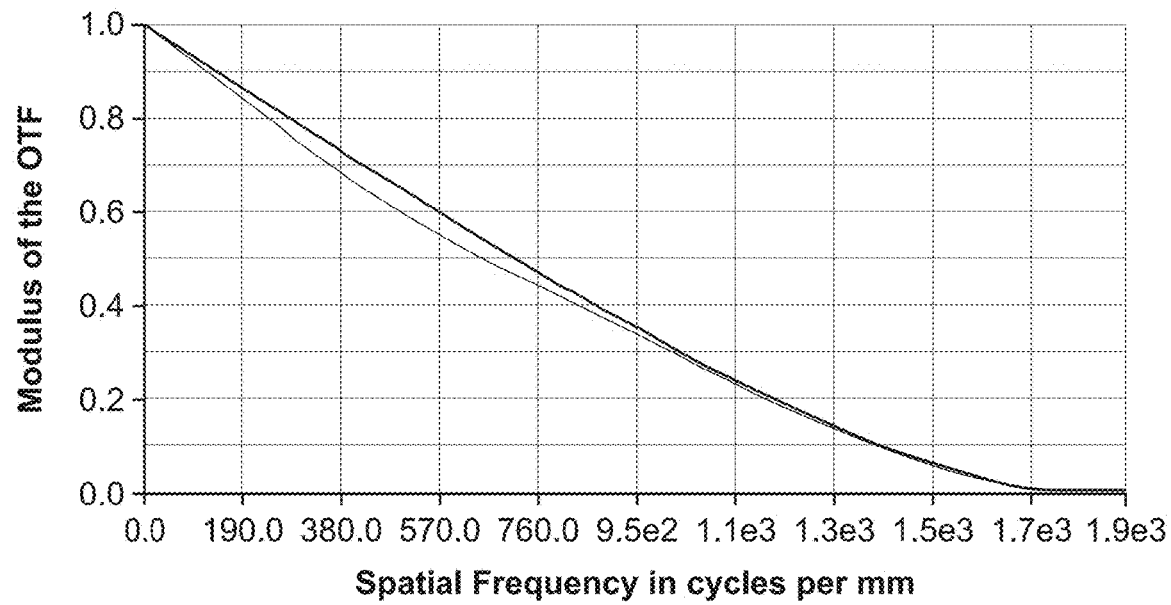
FIGS. 13A-13B illustrate the MTF of an example dual surface imaging system disclosed herein having an NA of 0.5.
Figure 13B:
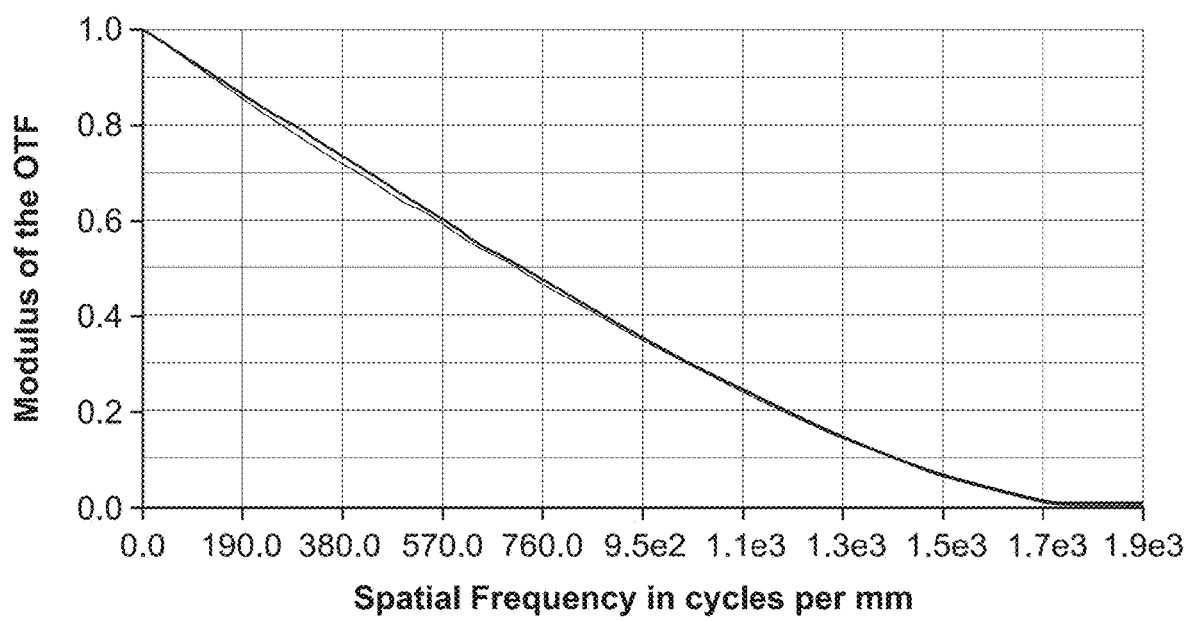

FIGS. 13A and 13B show the MTF at first (FIG. 13A) and second (FIG. 13B) surfaces for an NA of 0.5.

Figure 14A:
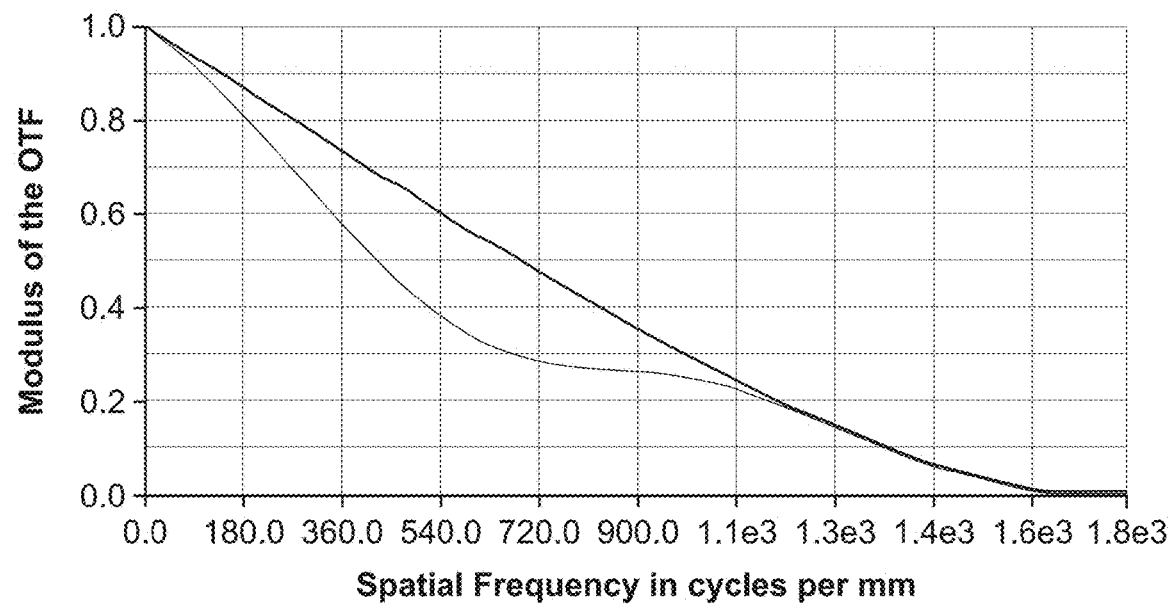
FIGS. 14A-14B illustrate the MTF of an example dual surface imaging system disclosed herein having an NA of 0.6.
Figure 14B:
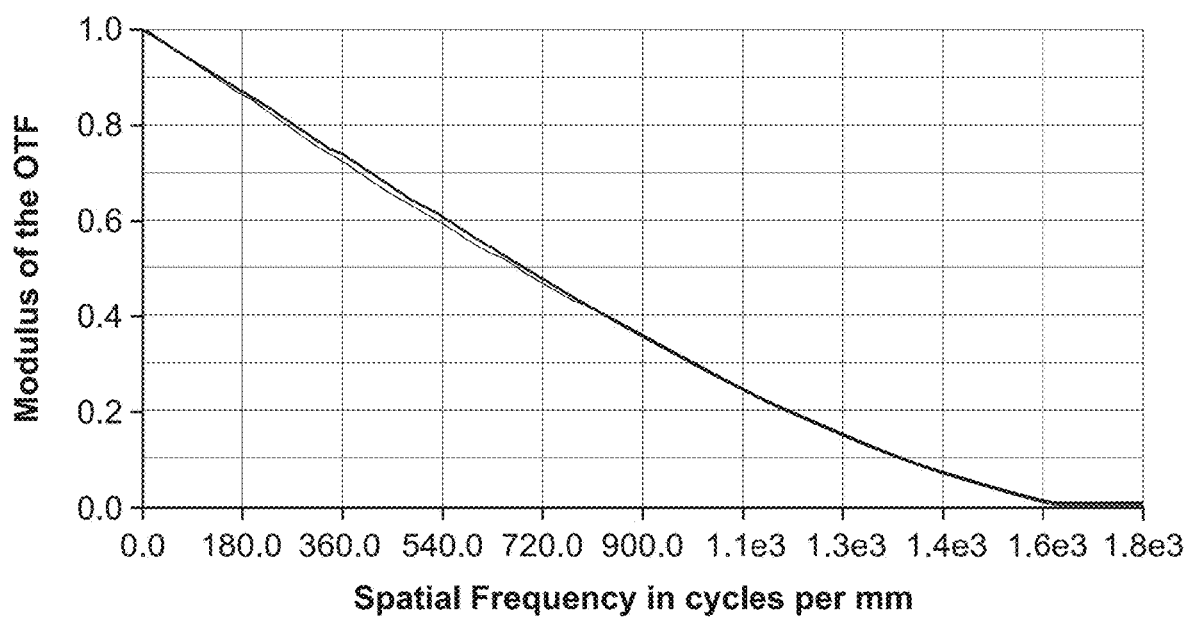

FIGS. 14A and 14B show the MTF at first (FIG. 14A) and second (FIG. 14B) surfaces for an NA of 0.6.

Figure 15A:
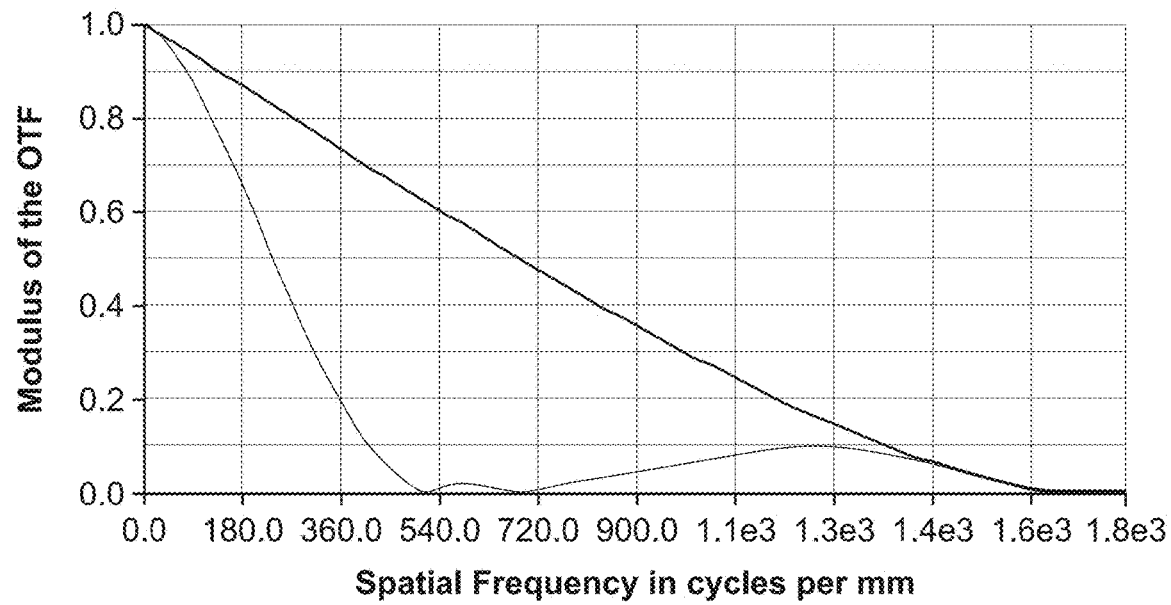
FIGS. 15A-15B illustrate the MTF of an example dual surface imaging system disclosed herein having an NA of 0.7.
Figure 15B:
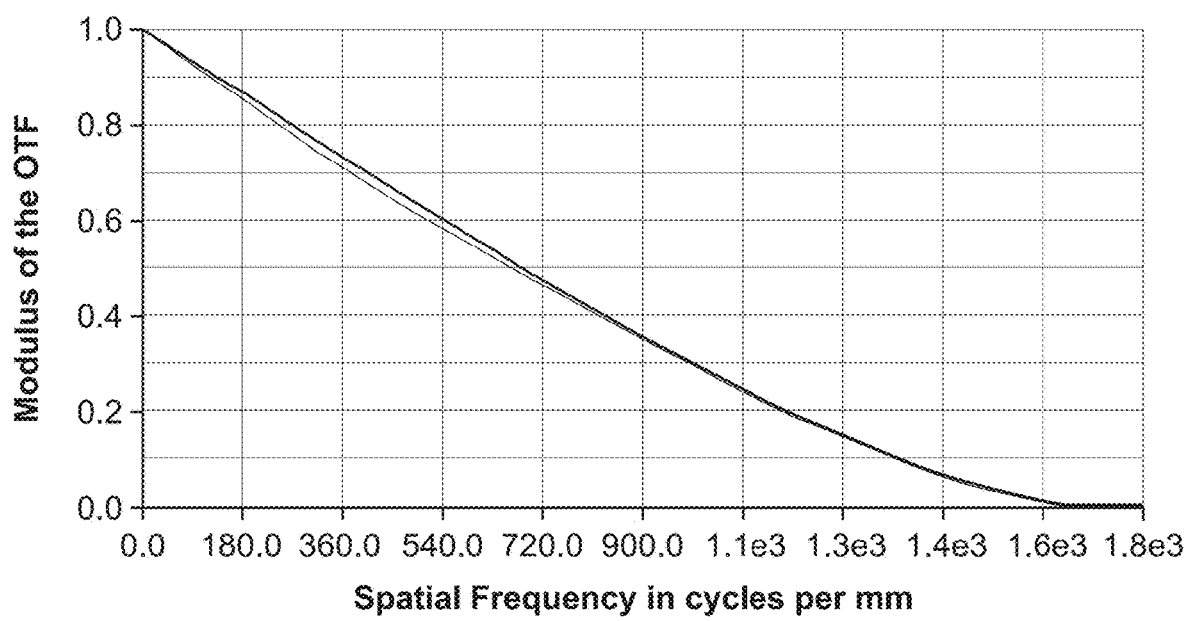

FIGS. 15A and 15B show the MTF at first (FIG. 15A) and second (FIG. 15B) surfaces for an NA of 0.7.

Figure 16A:
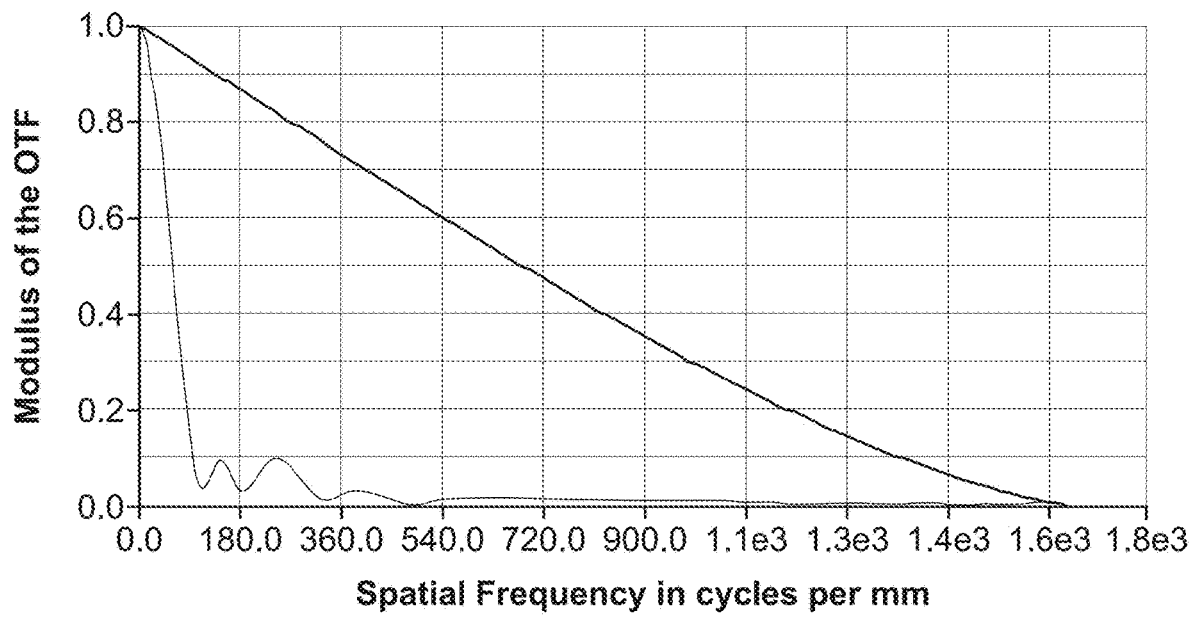
FIGS. 16A-16B illustrate the MTF of an example dual surface imaging system disclosed herein having an NA of 0.8.
Figure 16B:
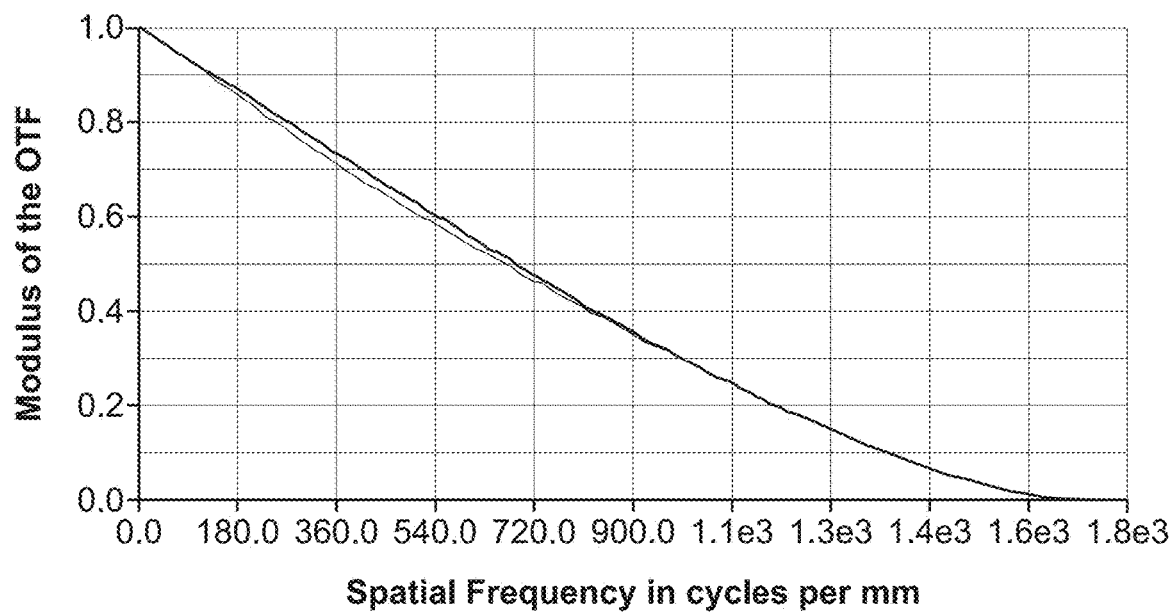

FIGS. 16A and 16B show the MTF at first (FIG. 16A) and second (FIG. 16B) surfaces for an NA of 0.8. The first and second surfaces in each of these figures correspond to, e.g., the top and bottom surfaces of a flow cell.

Figure 17A:
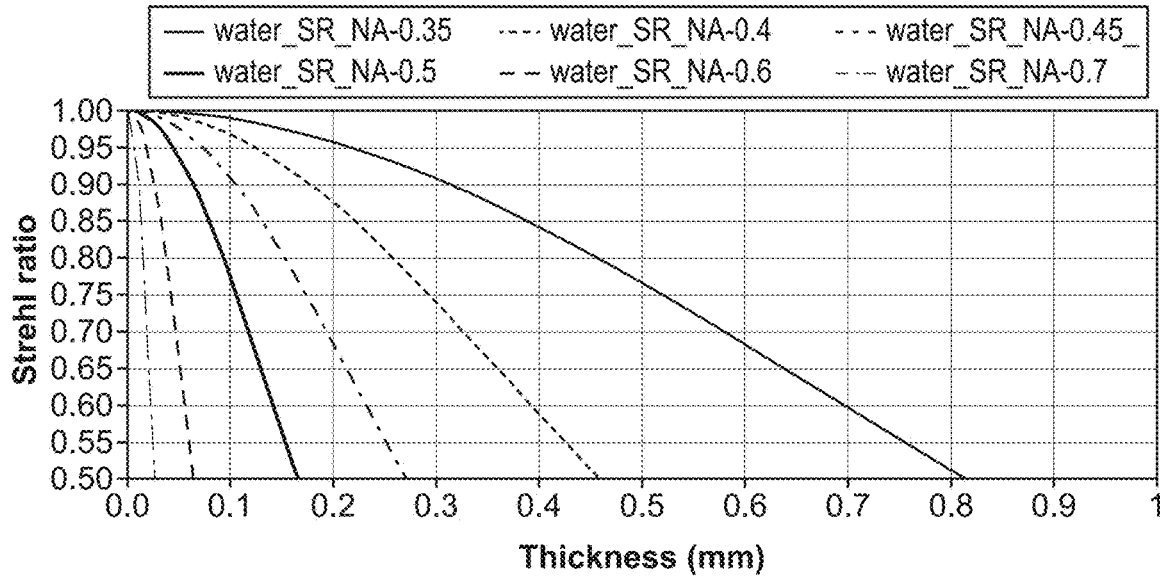
FIGS. 17A-17B provide plots of the calculated Strehl ratio for imaging a second flow cell surface through a first flow cell surface.
Figure 17B:
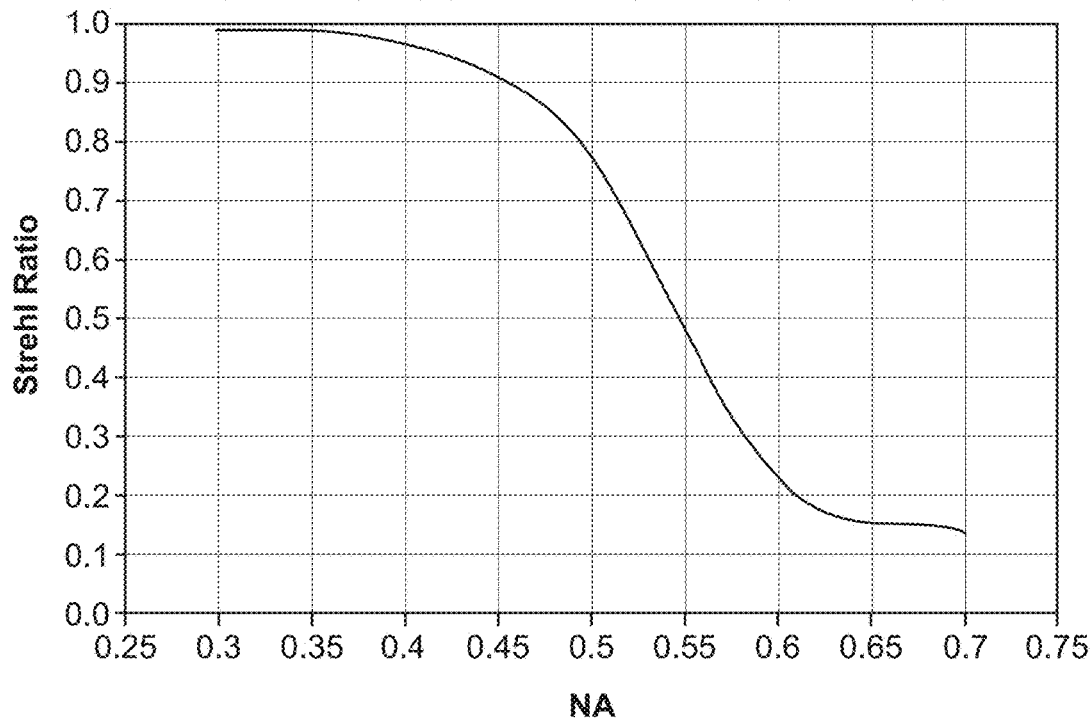

FIGS. 17A-B provide plots of the calculated Strehl ratio (i.e., the ratio of peak light intensity focused or collected by the optical system versus that focused or collected by an ideal optical system and point light source) for imaging a second flow cell surface through a first flow cell surface. FIG. 17A shows a plot of the Strehl ratios for imaging a second flow cell surface through a first flow cell surface as a function of the thickness of the intervening fluid layer (fluid channel height) for different objective lens and/or optical system numerical apertures. As shown, the Strehl ratio decreases with increasing separation between the first and second surfaces. One of the surfaces would thus have deteriorated image quality with increasing separation between the two surfaces. The decrease in second surface imaging performance with increased separation distance between the two surfaces is reduced for imaging systems having smaller numerical apertures as compared to those having larger numerical apertures. FIG. 17B shows a plot of the Strehl ratio as a function of numerical aperture for imaging a second flow cell surface through a first flow cell surface and an intervening layer of water having a thickness of 0.1 mm. The loss of imaging performance at higher numerical apertures may be attributed to the increased optical aberration induced by the fluid for the second surface imaging. With increasing NA, the increased optical aberration introduced by the fluid for the second surface imaging degrades the image quality significantly. In general, however, reducing the numeral aperture of the optical system reduces the achievable resolution. This loss of image quality can be at least partially offset by providing an increased sample plane (or object plane) contrast-to-noise ratio, for example, by using chemistries for nucleic acid sequencing applications that enhance the fluorescence emission for labeled nucleic acid clusters and/or that reduce background fluorescence emission. In some instances, for example, sample support structures comprising hydrophilic substrate materials and/or hydrophilic coatings may be employed. In some cases, such hydrophilic substrates and/or hydrophilic coatings may reduce background noise. Additional discussion of sample support structures, hydrophilic surfaces and coatings, and methods for enhancing contrast-to-noise ratios, e.g., for nucleic acid sequencing applications, can be found below.

In some implementations, any one or more of the fluorescence imaging system, the illumination and imaging module 100, the imaging optics (e.g., optics 126), the objective lens, and/or the tube lens is configured to have reduced magnification, such as a magnification of less than 10×, as will be discussed further below. Such reduced magnification may adjust design constraints such that other design parameters can be achieved. For example, any one or more of the fluorescence microscope, illumination and imaging module 100, the imaging optics (e.g., optics 126), the objective lens or the tube lens may also be configured such that the fluorescence imaging module has a large field-of-view (FOV), for example, a field-of-view of at least 3.0 mm or larger (e.g., in diameter, width, height, or longest dimension), as will be discussed further below. Any one or more of the fluorescence imaging system, the illumination and imaging module 100, the imaging optics (e.g., optics 126), the objective lens and/or the tube lens may be configured to provide the fluorescence microscope with such a field-of-view such that the FOV has less than, e.g., 0.1 waves of aberration over at least 80% of field. Similarly, any one or more of the fluorescence imaging system, illumination and imaging module 100, the imaging optics (e.g., optics 126), the objective lens and/or the tube lens may be configured such that the fluorescence imaging module has such a FOV and is diffraction limited or is diffraction limited over such an FOV.

As discussed above, in various implementations, a large field-of-view (FOV) is provided by the disclosed optical systems. In some implementations, obtaining an increased FOV is facilitated in part by the use of larger image sensors or photodetector arrays. The photodetector array, for example, may have an active area with a diagonal of at least 15 mm or larger, as will be discussed further below. As discussed above, in some implementations the disclosed optical imaging systems provide a reduced magnification, for example, of less than 10× which may facilitate large FOV designs. Despite the reduced magnification, the optical resolution of the imaging module may still be sufficient as detector arrays having small pixel size or pitch may be used. The pixel size and/or pitch may, for example, be about 5 μm or less, as will be discussed in more detail below. In some implementations, the pixel size is smaller than twice the optical resolution provided by the optical imaging system (e.g., objective and tube lens) to satisfy the Nyquist theorem. Accordingly, the pixel dimension and/or pitch for the image sensor(s) may be such that a spatial sampling frequency for the imaging module is at least twice an optical resolution of the imaging module. For example, the spatial sampling frequency for the photodetector array may be is at least 2 times, at least 2.5 times, at least 3 times, at least 4 times, or at least 5 times the optical resolution of the fluorescence imaging module (e.g., the illumination and imaging module, the objective and tube lens, the object lens and optics 126 in the detection channel, the imaging optics between the sample support structure or stage configured to support the sample support stage and the photodetector array) or any spatial sampling frequency in a range between any of these values.

Although a wide range of features are discussed herein with respect to fluorescence imaging modules, any of the features and designs describe herein may be applied to other types of optical imaging systems including without limitation bright-field and dark-field imaging, and may apply to luminescence or phosphorescence imaging.

Figure 18:
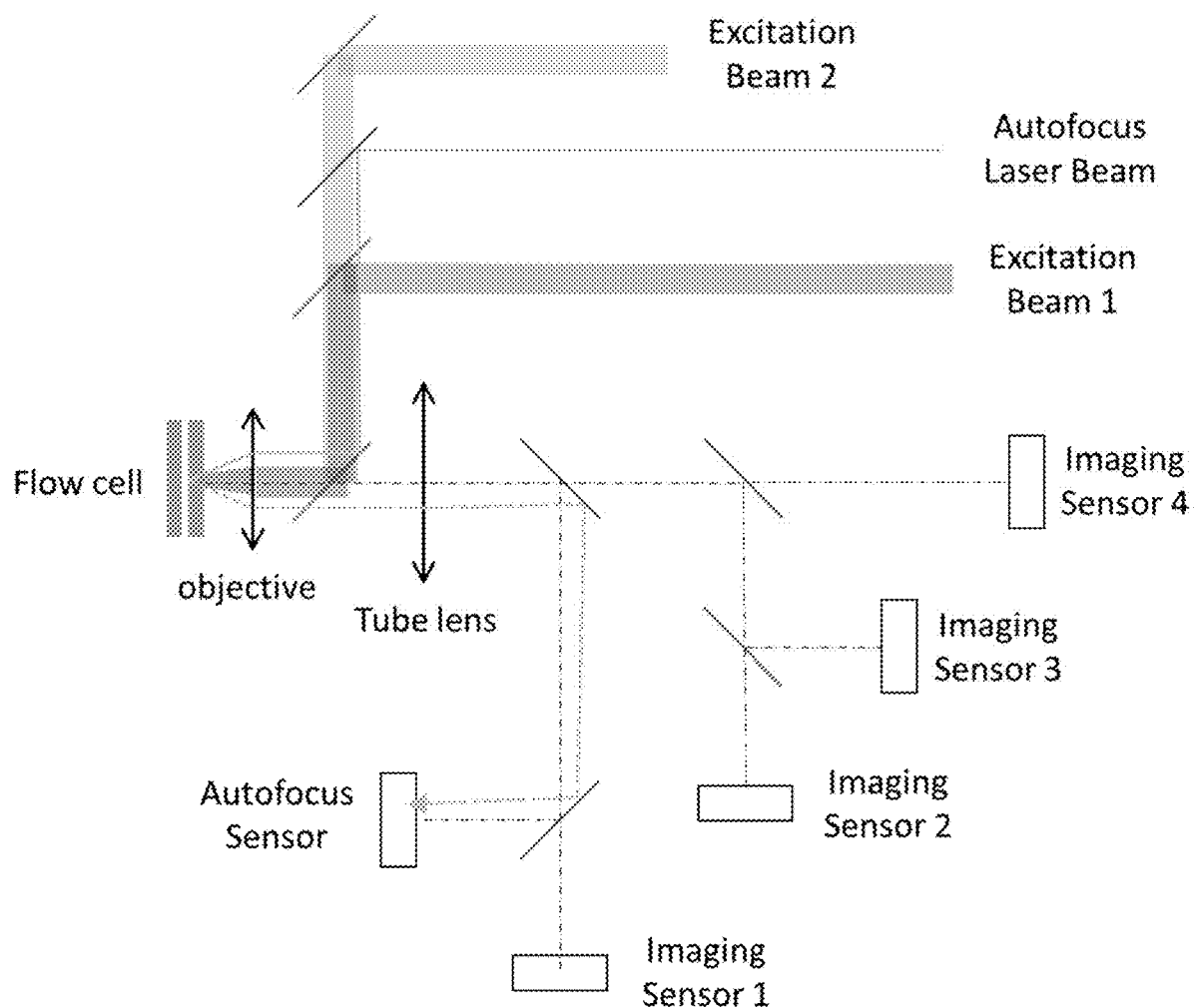
FIG. 18 provides a schematic illustration of a dual-wavelength excitation/four channel emission fluorescence imaging system of the present disclosure.

Dual Wavelength Excitation/Four Channel Imaging System:

FIG. 18 illustrates a dual excitation wavelength/four channel imaging system for dual-side imaging applications that includes an objective and tube lens combination that is scanned in a direction perpendicular to the optical axis to provide for large area imaging, e.g., by tiling several images to create a composite image having a total field-of-view (FOV) that is much larger than that for each individual image. The system comprises two excitation light sources, e.g., lasers or laser diodes, operating at different wavelengths and an autofocus laser. The two excitation light beams and autofocus laser beam are combined using a series of mirrors and/or dichroic reflectors and delivered to an upper or lower interior surface of the flow cell through the objective. Fluorescence that is emitted by labeled oligonucleotides (or other biomolecules) tethered to one of the flow cell surfaces is collected by the objective, transmitted through the tube lens, and directed to one of four imaging sensors according to the wavelength of the emitted light by a series of intermediate dichroic reflectors. Autofocus laser light that has been reflected from the flow cell surface is collected by the objective, transmitted through the tube lens, and directed to an autofocus sensor by a series of intermediate dichroic reflectors. The system allows accurate focus to be maintained (e.g., by adjusting the relative distance between the flow cell surface and the objective using a precision linear actuator, translation stage, or microscope turret-mounted focus adjustment mechanism, to reduce or minimize the reflected light spot size on the autofocus image sensor) while the objective/tube lens combination is scanned in a direction perpendicular to the optical axis of the objective. Dual wavelength excitation used in combination with four channel (i.e. four wavelength) imaging capability provides for high-throughput imaging of the upper (near) and lower (far) interior surfaces of the flow cell.

Improved or Optimized Objective and/or Tube Lens for Use with Thicker Coverslips:

Existing design practice includes the design of objective lenses and/or use of commonly available off-the-shelf microscope objectives to optimize image quality when images are acquired through thin (e.g., <200 μm thick) microscope coverslips. When used to image on both sides of a fluidic channel or flow cell, the extra height of the gap between the two surfaces (i.e., the height of the fluid channel; typically, about 50 μm to 200 μm) introduces optical aberration in images captured for the non-optimal side of the fluidic channel, thereby causing lower optical resolution. This is primarily because the additional gap height is significant compared to the optimal coverslip thickness (typical fluid channel or gap heights of 50-200 μm vs. coverslip thicknesses of <200 μm). Another common design practice is to utilize an additional "compensator" lens in the optical path when imaging is to be performed on the non-optimal side of the fluid channel or flow cell. This "compensator" lens and the mechanism required to move it in or out of the optical path so that either side of the flow cell may be imaged further increases system complexity and imaging system down time, and potentially degrades image quality due to vibration, etc.

In the present disclosure, the imaging system is designed for compatibility with flow cell consumables that comprise a thicker coverslip or flow cell wall (thickness ≥700 μm). The objective lens design may be improved or optimized for a coverslip that is equal to the true cover slip thickness plus half of the effective gap thickness (e.g., 700 μm+½*fluid channel (gap) height). This design significantly reduces the effect of gap height on image quality for the two surfaces of the fluid channel and balances the optical quality for images of the two surfaces, as the gap height is small relative to the total coverslip thickness and thus its impact on optical quality is reduced.

Additional advantages of using a thicker coverslip include improved control of thickness tolerance error during manufacturing, and a reduced likelihood that the coverslip undergoes deformation due to thermal and mounting-induced stress. Coverslip thickness error and deformation adversely impact imaging quality for both the top surface and the bottom surface of a flow cell.

To further improve the dual surface imaging quality for sequencing applications, our optical system design places a strong emphasis on improving or optimizing MTF (e.g., through improving or optimizing the objective lens and/or tube lens design) in the mid- to high-spatial frequency range that is most suitable for imaging and resolving small spots or clusters.

Improved or Optimized Tube Lens Design for Use in Combination with Commercially-Available, Off-the-Shelf Objectives:

For low-cost sequencer design, the use of a commercially-available, off-the-shelf objective lens may be preferred due to its relatively low price. However, as noted above, low-cost, off-the-shelf objectives are mostly optimized for use with thin coverslips of about 170 μm in thickness. In some instances, the disclosed optical systems may utilize a tube lens design that compensates for a thicker flow cell coverslip while enabling high image quality for both interior surfaces of a flow cell in dual-surface imaging applications. In some instances, the tube lens designs disclosed herein enable high quality imaging for both interior surfaces of a flow cell without moving an optical compensator into or out of the optical path between the flow cell and an image sensor, without moving one or more optical elements or components of the tube lens along the optical path, and without moving one or more optical elements or components of the tube lens into or out of the optical path.

Figure 19:
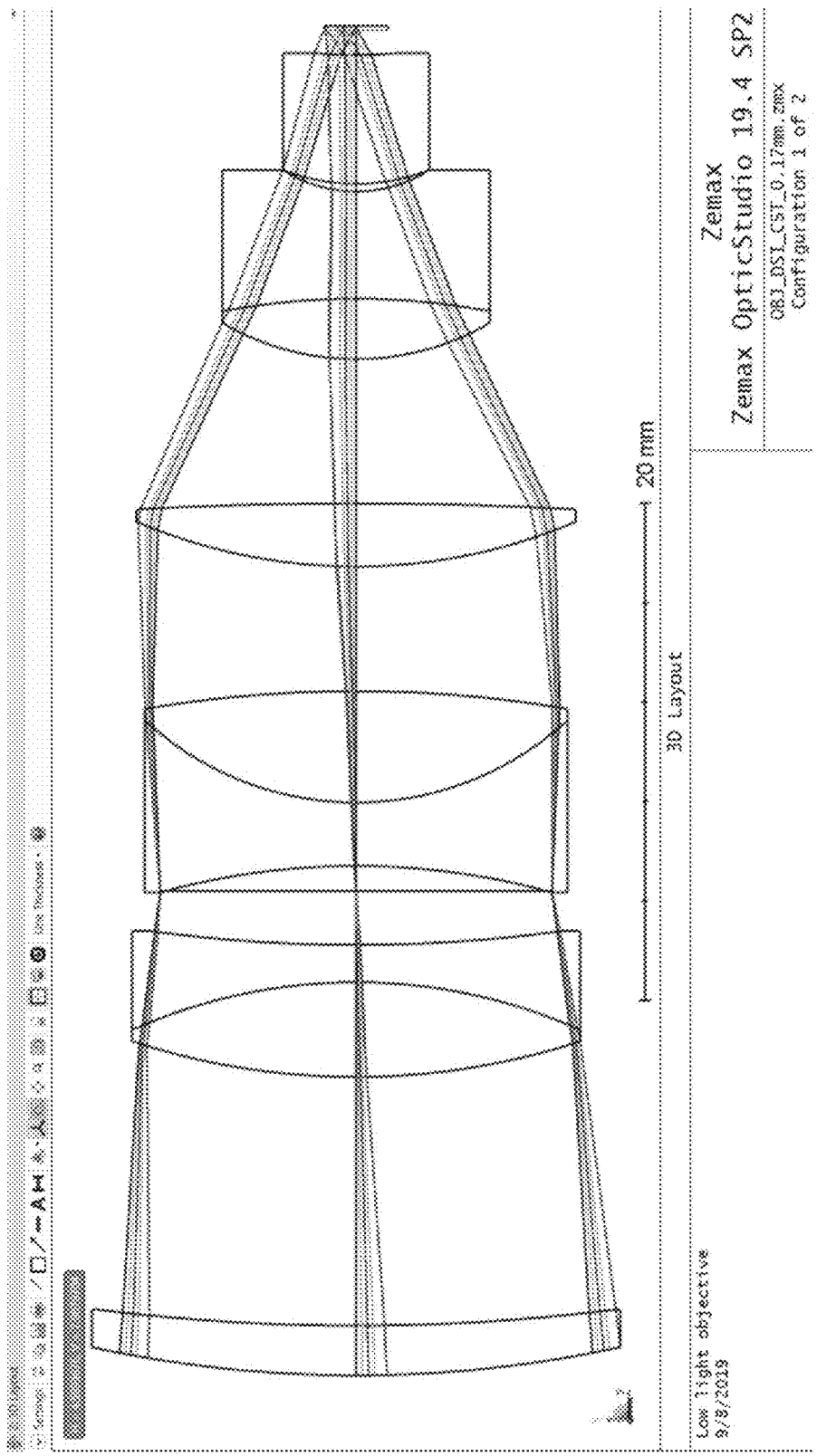
FIG. 19 provides an optical ray tracing diagram for an objective lens design that has been designed for imaging a surface on the opposite side of a 0.17 mm thick coverslip.
Figure 20:
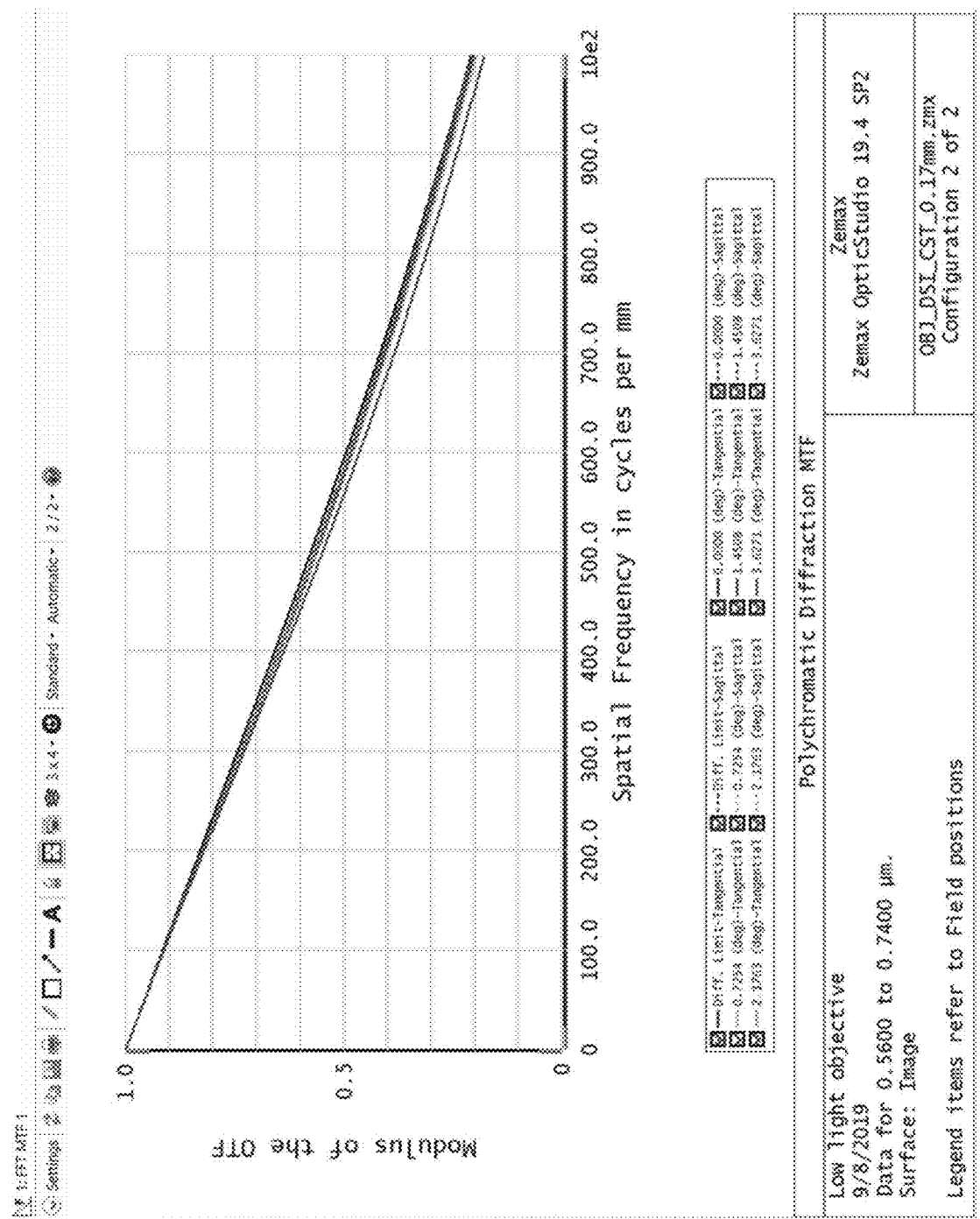
FIG. 20 provides a plot of the modulation transfer function for the objective lens illustrated in FIG. 19 as a function of spatial frequency when used to image a surface on the opposite side of a 0.17 mm thick coverslip.

FIG. 19 provides an optical ray tracing diagram for a low light objective lens design that has been improved or optimized for imaging a surface on the opposite side of a 0.17 mm thick coverslip. The plot of modulation transfer function for this objective, shown in FIG. 20, indicates near-diffraction limited imaging performance when used with the designed—for 0.17 mm thick coverslip.

Figure 21:
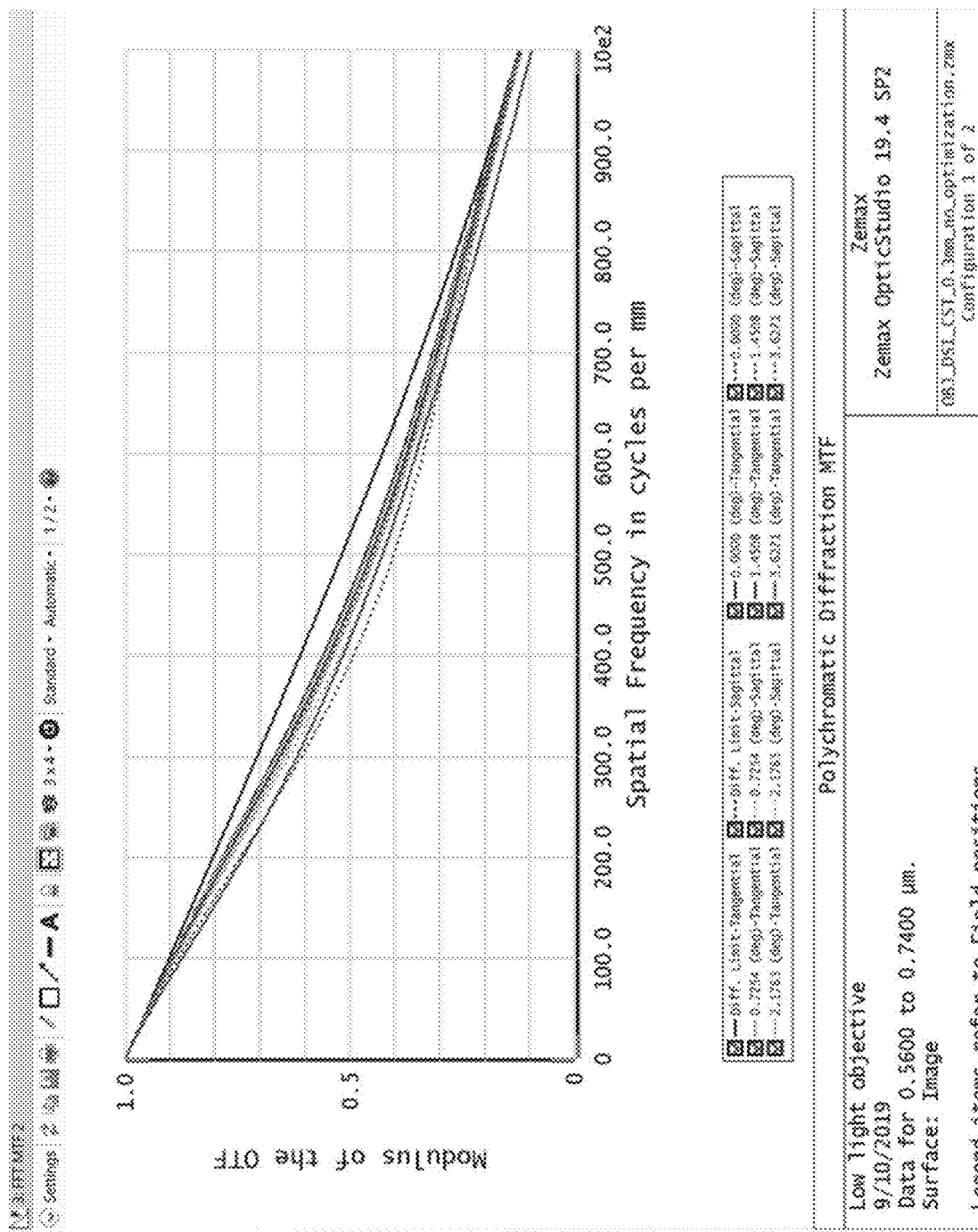
FIG. 21 provides a plot of the modulation transfer function for the objective lens illustrated in FIG. 19 as a function of spatial frequency when used to image a surface on the opposite side of a 0.3 mm thick coverslip.

FIG. 21 provides a plot of the modulation transfer function for the same objective lens illustrated in FIG. 19 as a function of spatial frequency when used to image a surface on the opposite side of a 0.3 mm thick coverslip. The relatively minor deviations of MTF value over the spatial frequency range of about 100 to about 800 lines/mm (or cycles/mm) indicates that the image quality obtained even when using a 0.3 mm thick coverslip is still reasonable.

Figure 22:
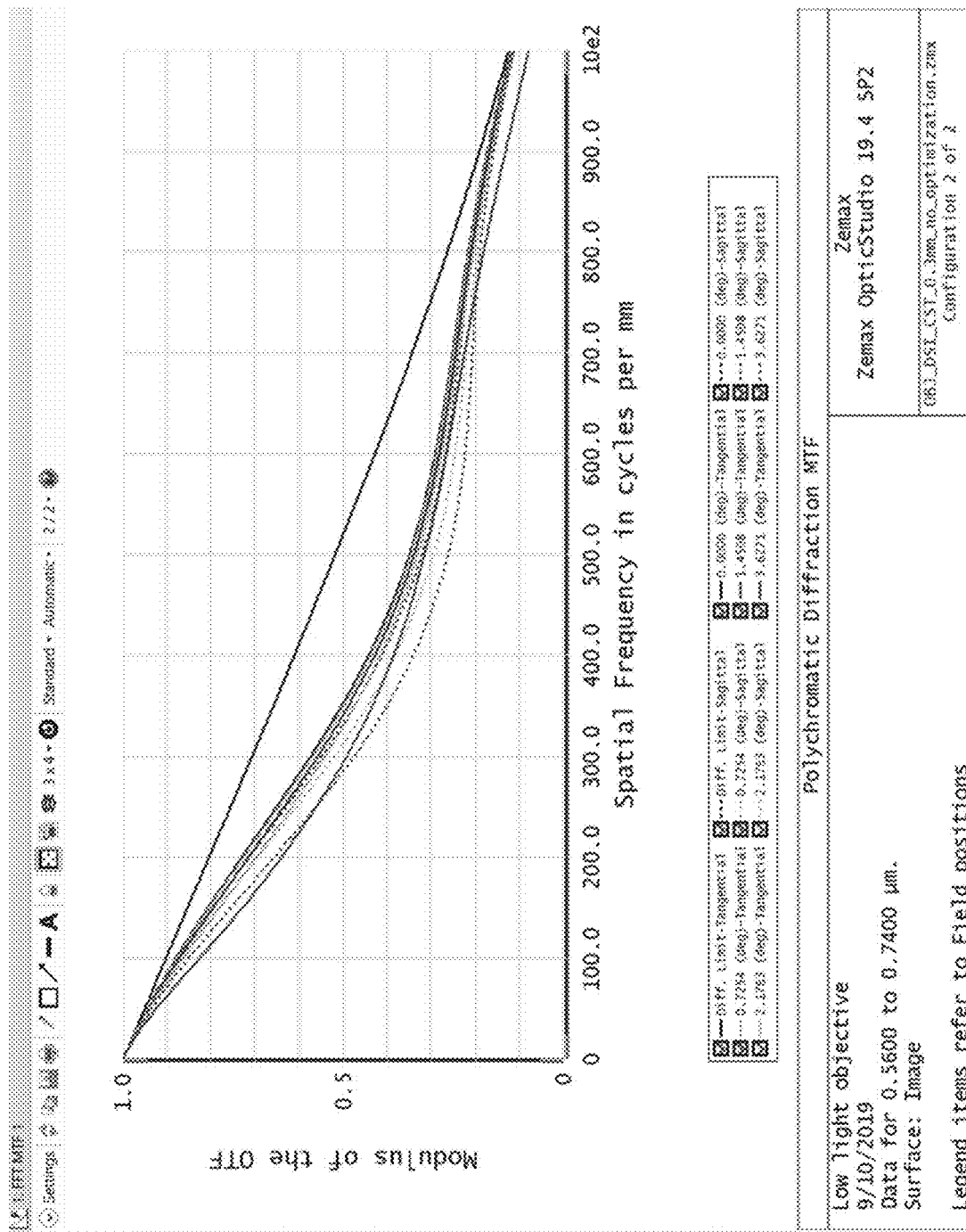
FIG. 22 provides a plot of the modulation transfer function for the objective lens illustrated in FIG. 19 as a function of spatial frequency when used to image a surface that is separated from that on the opposite side of a 0.3 mm thick coverslip by a 0.1 mm thick layer of aqueous fluid.

FIG. 22 provides a plot of the modulation transfer function for the same objective lens illustrated in FIG. 19 as a function of spatial frequency when used to image a surface that is separated from that on the opposite side of a 0.3 mm thick coverslip by a 0.1 mm thick layer of aqueous fluid (i.e., under the kind of conditions encountered for dual-side imaging of a flow cell when imaging the far surface). As can be seen in the plot of FIG. 22, imaging performance is degraded, as indicated by the deviations of the MTF curves from those for the an ideal, diffraction-limited case over the spatial frequency range of about 50 lp/mm to about 900 lp/mm.

Figure 23:
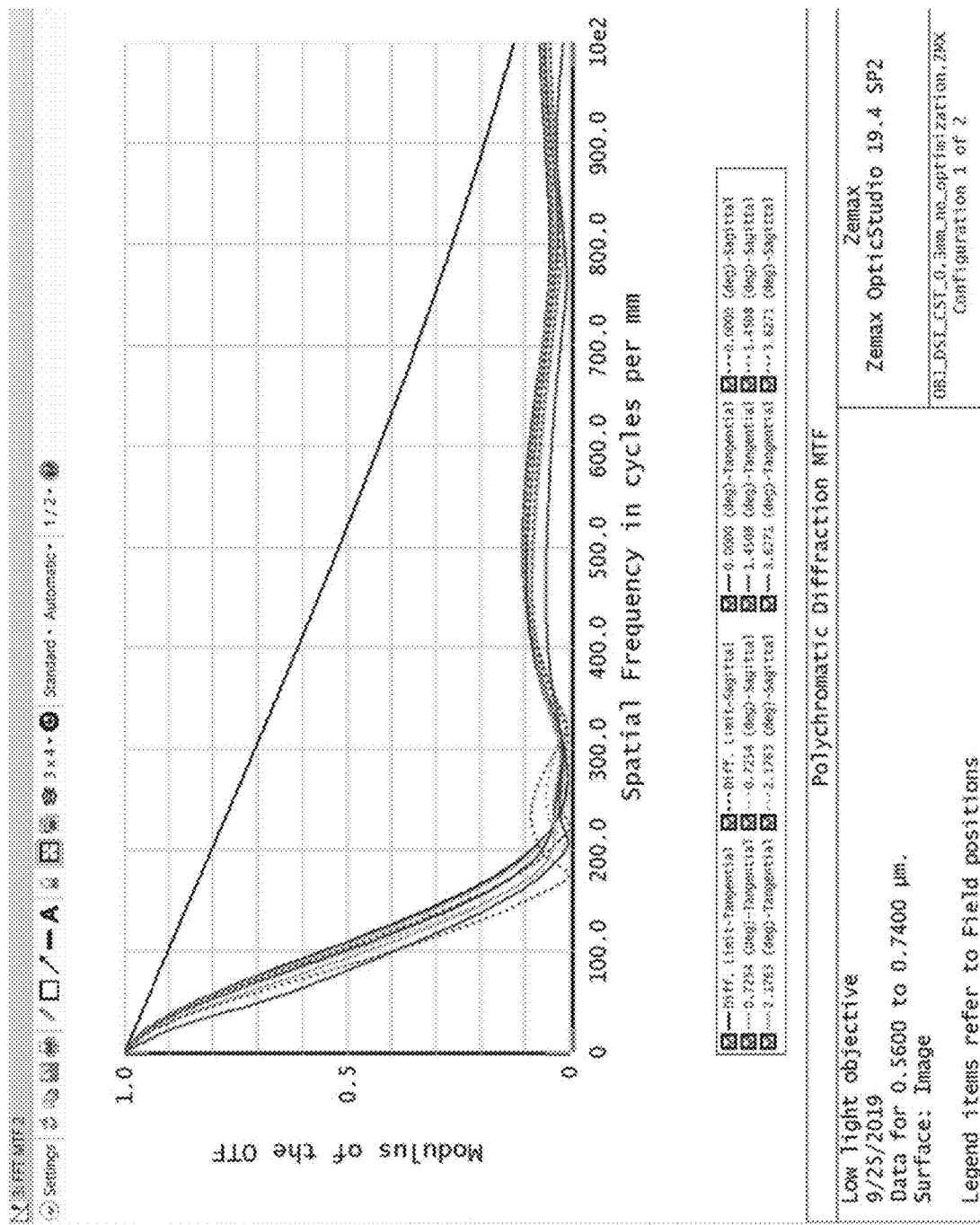
FIG. 23 provides a plot of the modulation transfer function for the objective lens illustrated in FIG. 19 as a function of spatial frequency when used to image a surface on the opposite side of a 1.0 mm thick coverslip.
Figure 24:
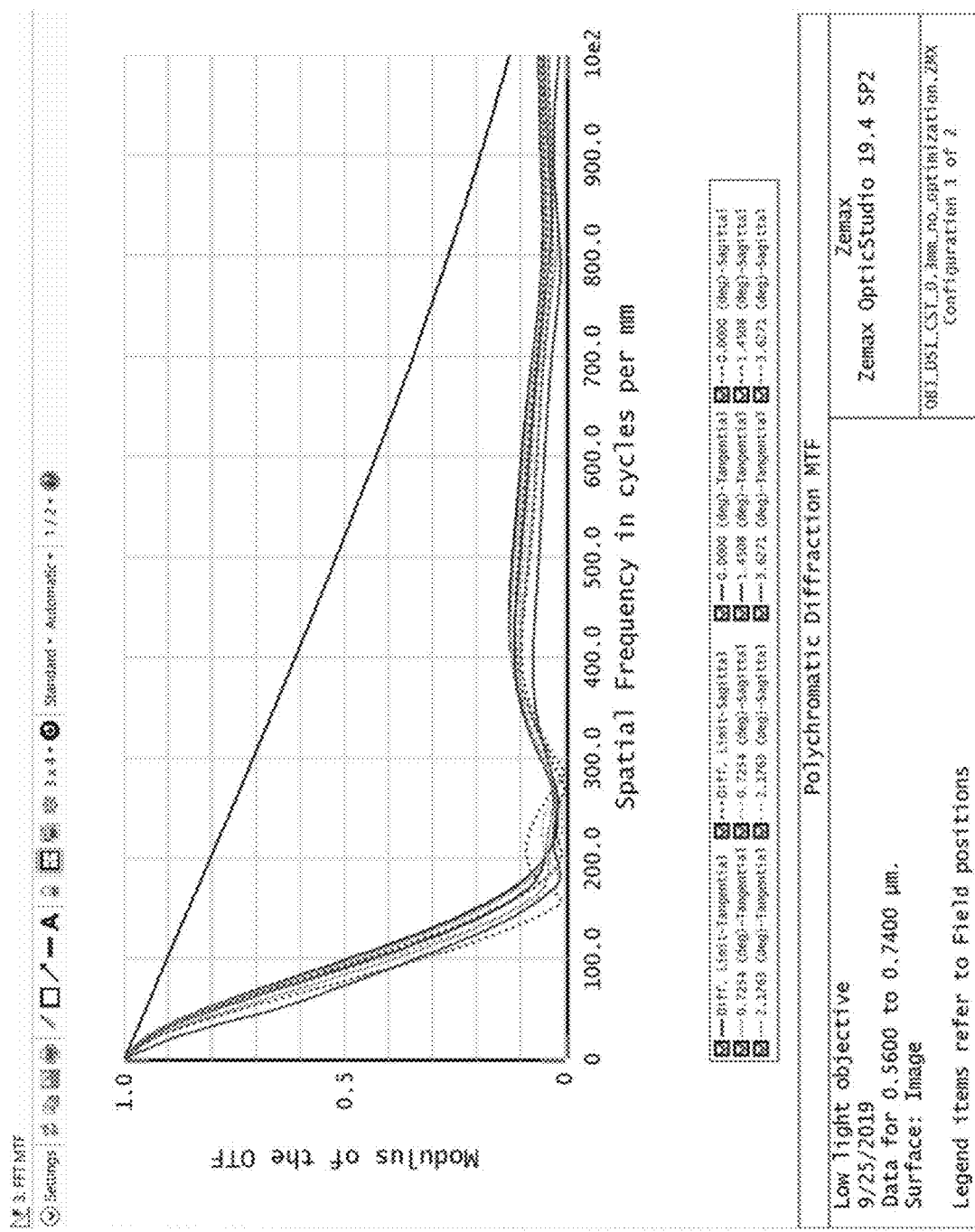
FIG. 24 provides a plot of the modulation transfer function for the objective lens illustrated in FIG. 19 as a function of spatial frequency when used to image a surface that is separated from that on the opposite side of a 1.0 mm thick coverslip by a 0.1 mm thick layer of aqueous fluid.

FIG. 23 and FIG. 24 provide plots of the modulation transfer function as a function of spatial frequency for the upper (or near) interior surface (FIG. 23) and lower (or far) interior surface (FIG. 24) of a flow cell when imaged using the objective lens illustrated in FIG. 19 through a 1.0 mm thick coverslip, and when the upper and lower interior surfaces are separated by a 0.1 mm thick layer of aqueous fluid. As can be seen, imaging performance is significantly degraded for both surfaces.

Figure 25:
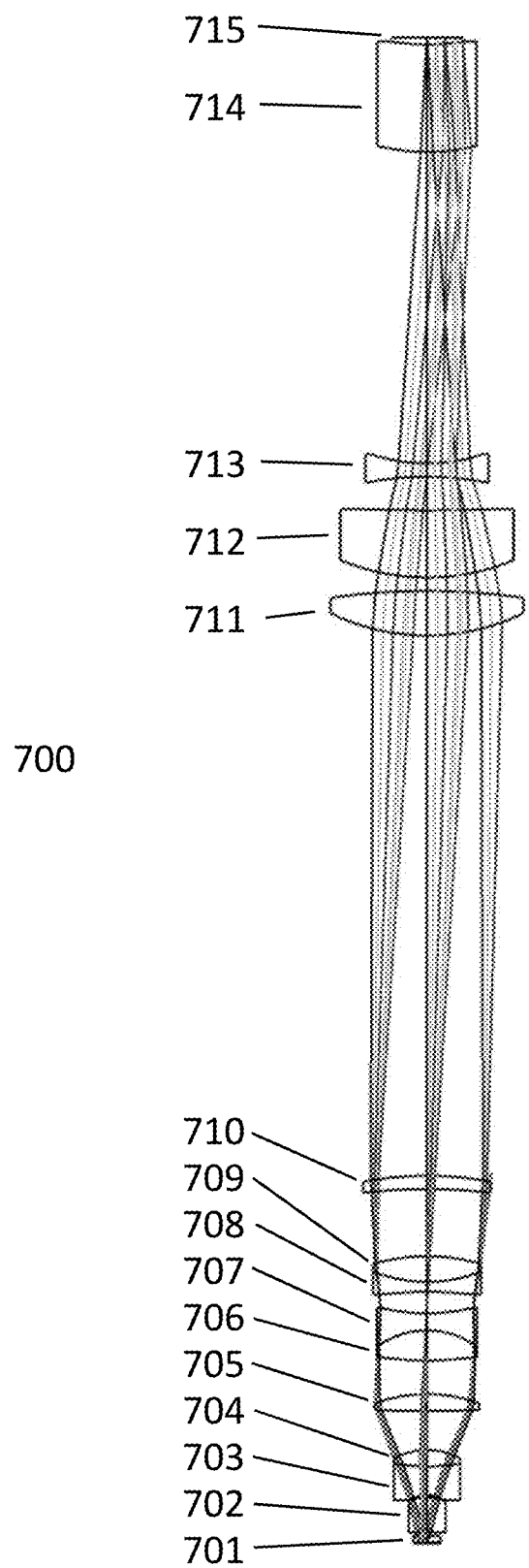
FIG. 25 provides a ray tracing diagram for a tube lens design which, if used in conjunction with the objective lens illustrated in FIG. 19, provides for improved dual-side imaging through a 1 mm thick coverslip.

FIG. 25 provides a ray tracing diagram for a tube lens design which, if used in conjunction with the objective lens illustrated in FIG. 19, provides for improved dual-side imaging through a 1 mm thick coverslip. The optical design 700 comprising a compound objective (lens elements 702, 703, 704, 705, 706, 707, 708, 709, and 710) and a tube lens (lens elements 711, 712, 713, and 714) is improved or optimized for use with flow cells comprising a thick coverslip (or wall), e.g., greater than 700 μm thick, and a fluid channel thickness of at least 50 μm, and transfers the image of an interior surface from the flow cell 701 to the image sensor 715 with dramatically improved optical image quality and higher CNR.

In some instances, the tube lens (or tube lens assembly) may comprise at least two optical lens elements, at least three optical lens elements, at least four optical lens elements, at least five optical lens elements, at least six optical lens elements, at least seven optical lens elements, at least eight optical lens elements, at least nine optical lens elements, at least ten optical lens elements, or more, where the number of optical lens elements, the surface geometry of each element, and the order in which they are placed in the assembly is improved or optimized to correct for optical aberrations induced by the thick wall of the flow cell, and in some instances, allows one to use a commercially-available, off-the-shelf objective while still maintaining high-quality, dual-side imaging capability.

In some instances, as illustrated in FIG. 25, the tube lens assembly may comprise, in order, a first asymmetric convex-convex lens 711, a second convex-plano lens 712, a third asymmetric concave-concave lens 713, and a fourth asymmetric convex-concave lens 714.

Figure 26:
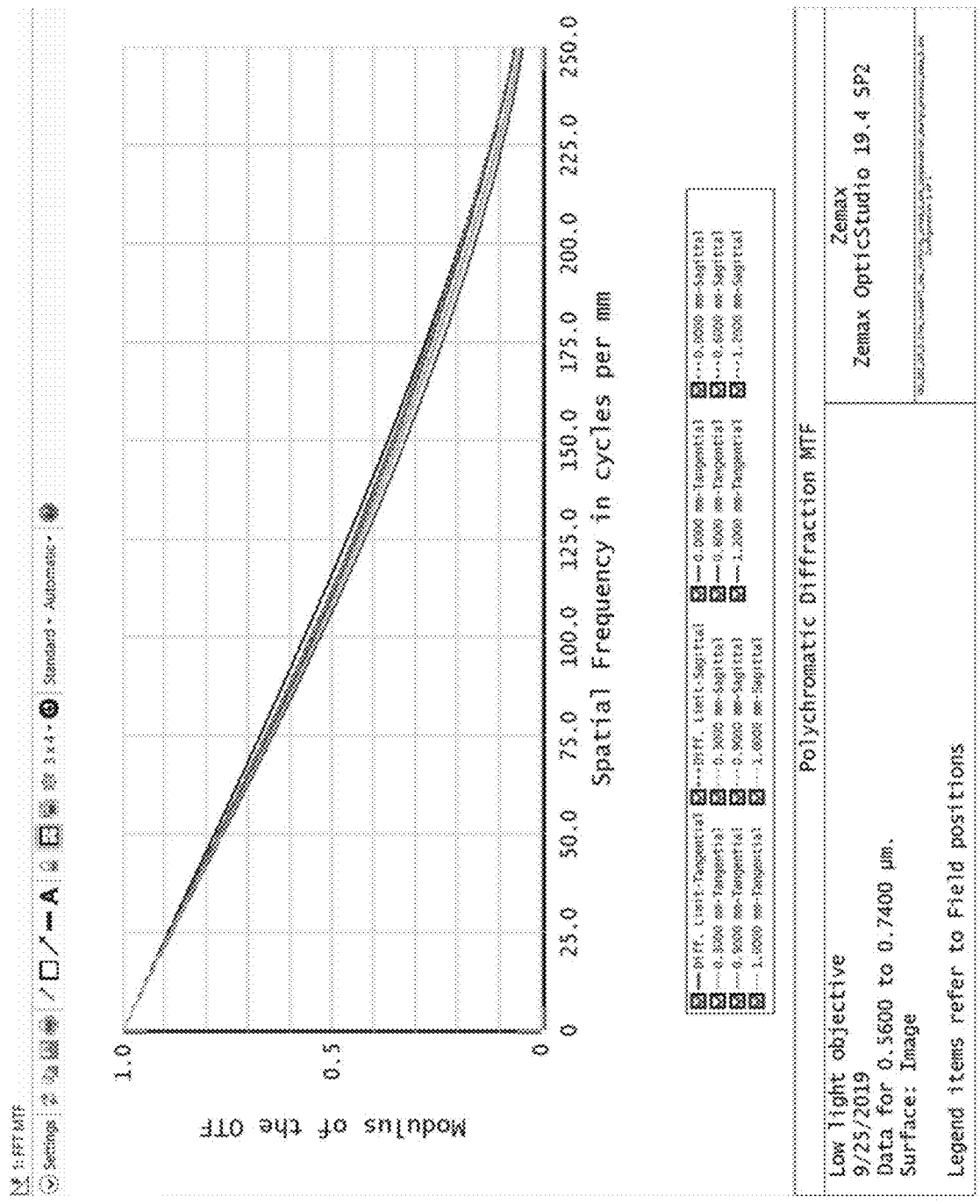
FIG. 26 provides a plot of the modulation transfer function for the combination of objective lens and tube lens illustrated in FIG. 25 as a function of spatial frequency when used to image a surface on the opposite side of a 1.0 mm thick coverslip.
Figure 27:
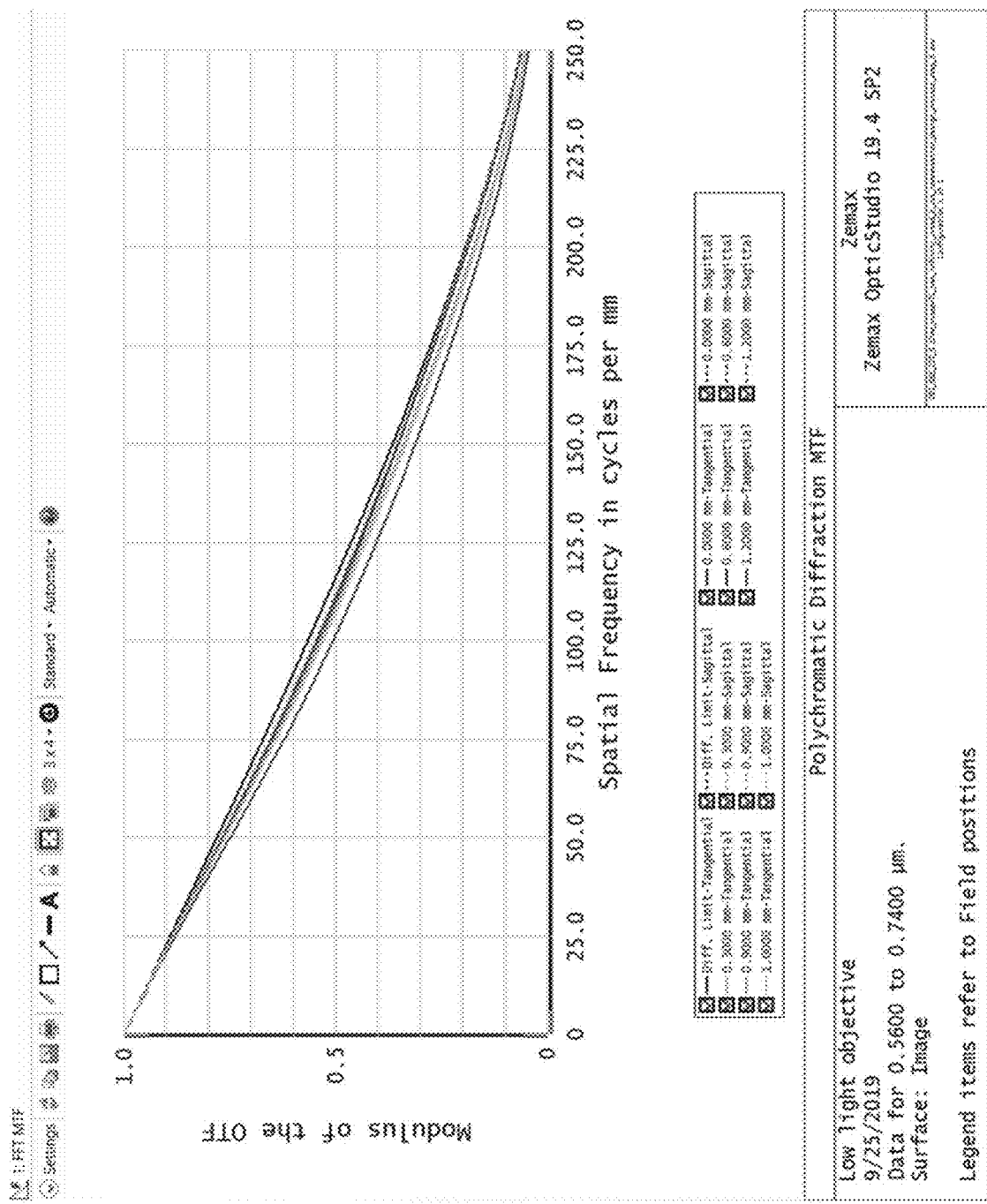
FIG. 27 provides a plot of the modulation transfer function for the combination of objective lens and tube lens illustrated in FIG. 25 as a function of spatial frequency when used to image a surface that is separated from that on the opposite side of a 1.0 mm thick coverslip by a 0.1 mm thick layer of aqueous fluid.

FIG. 26 and FIG. 27 provide plots of the modulation transfer function as a function of spatial frequency for the upper (or near) interior surface (FIG. 26) and lower (or far) interior surface (FIG. 27) of a flow cell when imaged using the objective lens (corrected for a 0.17 mm coverslip) and tube lens combination illustrated in FIG. 25 through a 1.0 mm thick coverslip, and when the upper and lower interior surfaces are separated by a 0.1 mm thick layer of aqueous fluid. As can be seen, the imaging performance achieved is nearly that expected for a diffraction-limited optical design.

Figure 28:
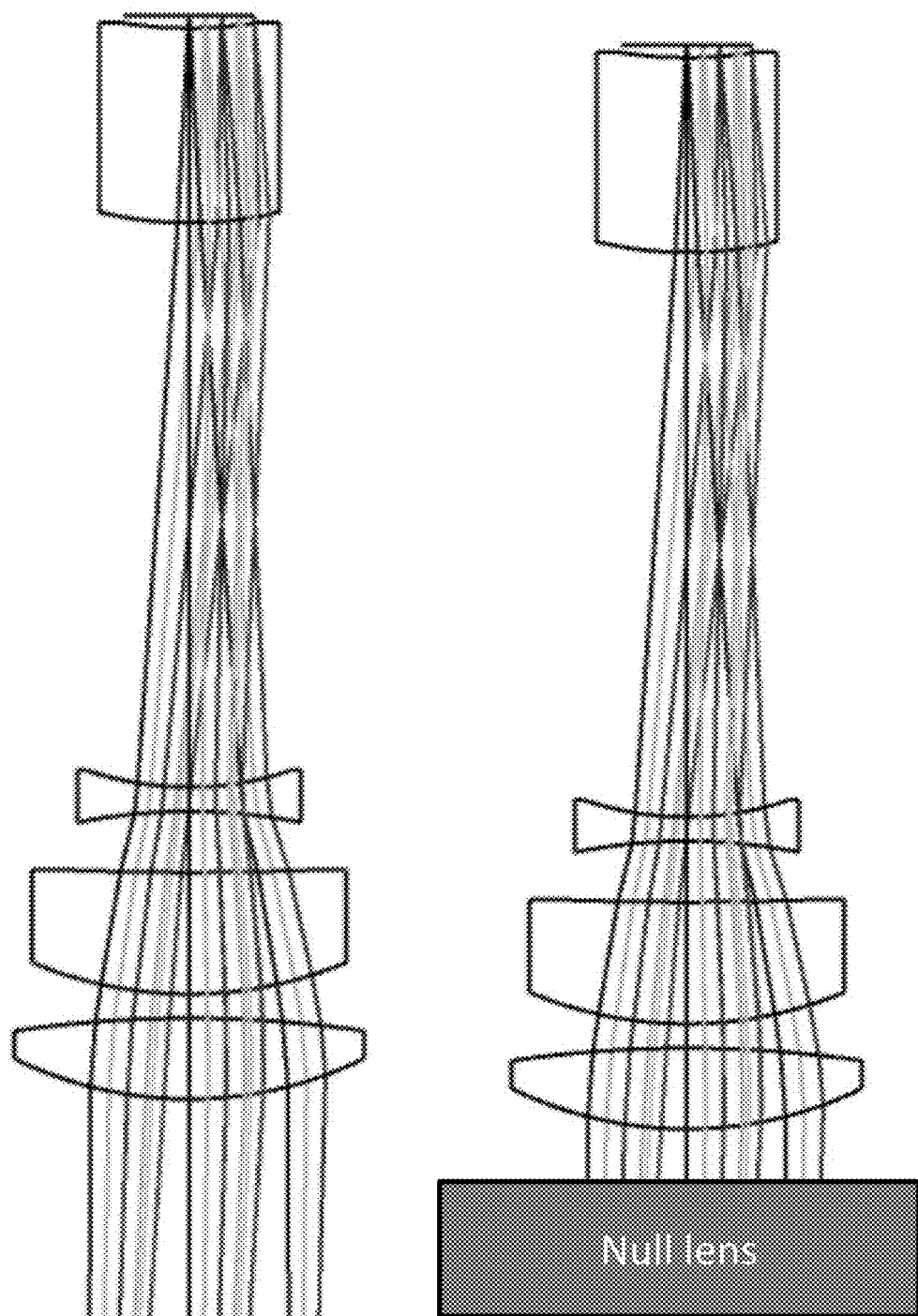
FIG. 28 provides ray tracing diagrams for tube lens design (left) of the present disclosure that has been optimized to provide high-quality, dual-side imaging performance. Because the tube lens is no longer infinity-corrected, an appropriately designed null lens (right) may be used in combination with the tube lens to compensate for the non-infinity-corrected tube lens for manufacturing and testing purposes.

FIG. 28 provides ray tracing diagrams for tube lens design (left) of the present disclosure that has been improved or optimized to provide high-quality, dual-side imaging performance. Because the tube lens is no longer infinity-corrected, an appropriately designed null lens (right) may be used in combination with the tube lens to compensate for the non-infinity-corrected tube lens for manufacturing and testing purposes.

Imaging channel-specific tube lens adaptation or optimization: In imaging system design, it is possible to improve or optimize both the objective lens and the tube lens in the same wavelength region for all imaging channels. Typically, the same objective lens is shared by all imaging channels (see, for example, FIG. 18), and each imaging channel either uses the same tube lens or has a tube lens that shares the same design.

In some instances, the imaging systems disclosed herein may further comprise a tube lens for each imaging channel where the tube lens has been independently improved or optimized for the specific imaging channel to improve image quality, e.g., to reduce or minimize distortion and field curvature, and improve depth-of-field (DOF) performance for each channel. Because the wavelength range (or bandpass) for each specific imaging channel is much narrower than the combined wavelength range for all channels, the wavelength- or channel-specific adaptation or optimization of the tube lens used in the disclosed systems results in significant improvements in imaging quality and performance. This channel-specific adaptation or optimization results in improved image quality for both the top and bottom surfaces of the flow cell in dual-side imaging applications.

Dual-Side Imaging w/o Fluid Present in Flow Cell:

For optimal imaging performance of both top and bottom interior surfaces of a flow cell, a motion-actuated compensator is typically required to correct for optical aberrations induced by the fluid in the flow cell (typically comprising a fluid layer thickness of about 50-200 µm). In some instances of the disclosed optical system designs, the top interior surface of the flow cell may be imaged with fluid present in the flow cell. Once the sequencing chemistry cycle has been completed, the fluid may be extracted from the flow cell for imaging of the bottom interior surface. Thus, in some instances, even without the use of a compensator, the image quality for the bottom surface is maintained.

Compensation for Optical Aberration and/or Vibration Using Electro-Optical Phase Plates:

In some instances, dual-surface image quality may be improved without requiring the removal of the fluid from the flow cell by using an electro-optical phase plate (or other corrective lens) in combination with the objective to cancel the optical aberrations induced by the presence of the fluid. In some instances, the use of an electro-optical phase plate (or lens) may be used to remove the effects of vibration arising from the mechanical motion of a motion-actuated compensator and may provide faster image acquisition times and sequencing cycle times for genomic sequencing applications.

Improved Contrast-to-Noise Ratio (CNR), Field-of-View (FOV), Spectral Separation, and Timing Design to Increase or Maximize Information Transfer and Throughput:

Another way to increase or maximize information transfer in imaging systems designed for genomics applications is to increase the size of the field-of-view (FOV) and reduce the time required to image a specific FOV. With typical large NA optical imaging systems, it may be common to acquire images for fields-of-view that are on the order of 1 mm$^2$ in area, where in the presently disclosed imaging system designs large FOV objectives with long working distances are specified to enable imaging of areas of 2 mm$^2$ or larger.

In some cases, the disclosed imaging systems are designed for use in combination with proprietary low-binding substrate surfaces and DNA amplification processes that reduce fluorescence background arising from a variety of confounding signals including, but are not limited to, nonspecific adsorption of fluorescent dyes to substrate surfaces, nonspecific nucleic acid amplification products (e.g., nucleic acid amplification products that arise the substrate surface in areas between the spots or features corresponding to clonally-amplified clusters of nucleic acid molecules (i.e., specifically amplified colonies), nonspecific nucleic acid amplification products that may arise within the amplified colonies, phased and pre-phased nucleic acid strands, etc. The use of low-binding substrate surfaces and DNA amplification processes that reduce fluorescence background in combination with the disclosed optical imaging systems may significantly cut down on the time required to image each FOV.

The presently disclosed system designs may further reduce the required imaging time through imaging sequence improvement or optimization where multiple channels of fluorescence images are acquired simultaneously or with overlapping timing, and where spectral separation of the fluorescence signals is designed to reduce cross-talks between fluorescence detection channels and between the excitation light and the fluorescence signal(s).

The presently disclosed system designs may further reduce the required imaging time through improvement or optimization of scanning motion sequence. In the typical approach, an X-Y translation stage is used to move the target FOV into position underneath the objective, an autofocus step is performed where optimal focal position is determined and the objective is moved in the Z direction to the determined focal position, and an image is acquired. A sequence of fluorescence images is acquired by cycling through a series of target FOV positions. From an information transfer duty cycle perspective, information is only transferred during the fluorescence image acquisition portion of the cycle. In the presently disclosed imaging system designs, a single-step motion in which all axes (X-Y-Z) are repositioned simultaneously is performed, and the autofocus step is used to check focal position error. The additional Z motion is only commanded if the focal position error (i.e., the difference between the focal plane position and the sample plane position) exceeds a certain limit (e.g., a specified error threshold). Coupled with high speed X-Y motion, this approach increases the duty cycle of the system, and thus increases the imaging throughput per unit time.

Furthermore, by matching the optical collection efficiency, modulation transfer function, and image sensor performance characteristics of the design with the fluorescence photon flux expected for the input excitation photon flux, dye efficiency (related to dye extinction coefficient and fluorescence quantum yield), while accounting for background signal and system noise characteristics, the time required to acquire high quality (high contrast-to-noise ratio (CNR) images) may be reduced or minimized.

The combination of efficient image acquisition and improved or optimized translation stage step and settle times leads to fast imaging times (i.e., the overall time required per field-of-view) and higher throughput imaging system performance.

Along with the large FOV and fast image acquisition duty cycle, the disclosed designs may comprise also specifying image plane flatness, chromatic focus performance between fluorescence detection channels, sensor flatness, image distortion, and focus quality specifications.

Chromatic focus performance is further improved by individually aligning the image sensors for different fluorescence detection channels such that the best focal plane for each detection channel overlaps. The design goal is to ensure that images across more than 90 percent of the field-of-view are acquired within ±100 nm (or less) relative to the best focal plane for each channel, thus increasing or maximizing the transfer of individual spot intensity signals. In some instances, the disclosed designs further ensure that images across 99 percent of the field-of-view are acquired within ±150 nm (or less) relative to the best focal plane for each channel, and that images across more the entire field-of-view are acquired within ±200 nm (or less) relative to the best focal plane for each imaging channel.

Illumination optical path design: Another factor for improving signal-to-noise ratio (SNR), contrast-to-noise ratio (CNR), and/or increasing throughput is to increase illumination power density to the sample. In some instances, the disclosed imaging systems may comprise an illumination path design that utilizes a high-power laser or laser diode coupled with a liquid light guide. The liquid light guide removes optical speckle that is intrinsic to coherent light sources such as lasers and laser diodes. Furthermore, the coupling optics are designed in such a way as to underfill the entrance aperture of the liquid light guide. The underfilling of the liquid light guide entrance aperture reduces the effective numerical aperture of the illumination beam entering the objective lens, and thus improves light delivery efficiency through the objective onto the sample plane. With this design innovation, one can achieve illumination power densities up to 3× that for conventional designs over a large field-of-view (FOV).

By utilizing the angle-dependent discrimination of s- and p-polarization, in some instances, the illumination beam polarization may be orientated to reduce the amount of back-scattered and back-reflected illumination light that reaches the imaging sensors.

Assessing Image Quality:

For any of the embodiments of the optical imaging designs disclosed herein, imaging performance or imaging quality may be assessed using any of a variety of performance metrics known to those of skill in the art. Examples include, but are not limited to, measurements of modulation transfer function (MTF) at one or more specified spatial frequencies, defocus, spherical aberration, chromatic aberration, coma, astigmatism, field curvature, image distortion, contrast-to-noise ratio (CNR), or any combination thereof.

In some instances, the disclosed optical designs for dual-side imaging (e.g., the disclosed objective lens designs, tube lens designs, the use of an electro-optical phase plate in combination with an objective, etc., alone or in combination) may yield significant improvements for image quality for both the upper (near) and lower (far) interior surfaces of a flow cell, such that the difference in an imaging performance metric for imaging the upper interior surface and the lower interior surface of the flow cell is less than 20%, less than 15%, less than 10%, less than 5%, less than 4%, less than 3%, less than 2%, or less than 1% for any of the imaging performance metrics listed above, either individually or in combination.

In some instances, the disclosed optical designs for dual-side imaging (e.g., comprising the disclosed tube lens designs, the use of an electro-optical phase plate in combination with an objective, etc.) may yield significant improvements for image quality such that an image quality performance metric for dual-side imaging provides for an at least 1%, at least 2%, at least 3%, at least 4%, at least 5%, at least 10%, at least 15%, at least 20%, at least 25%, or at least 30% improvement in the imaging performance metric for dual-side imaging compared to that for a conventional system comprising, e.g., an objective lens, a motion-actuated compensator (that is moved out of or into the optical path when imaging the near or far interior surfaces of a flow cell), and an image sensor for any of the imaging performance metrics listed above, either individually or in combination. In some instances, fluorescence imaging systems comprising one or more of the disclosed tube lens designs provides for an at least equivalent or better improvement in an imaging performance metric for dual-side imaging compared to that for a conventional system comprising an objective lens, a motion-actuated compensator, and an image sensor. In some instances, fluorescence imaging systems comprising one or more of the disclosed tube lens designs provides for an at least 5%, 10%, 15%, 20%, 25%, 30%, 35%, 40%, 45%, or 50% improvement in an imaging performance metric for dual-side imaging compared to that for a conventional system comprising an objective lens, a motion-actuated compensator, and an image sensor.

Imaging Module Specifications:

Excitation light wavelength(s): In any of the disclosed optical imaging module designs, the light source(s) of the disclosed imaging modules may produce visible light, such as green light and/or red light. In some instances, the light source(s), alone or in combination with one or more optical components, e.g., excitation optical filters and/or dichroic beam splitters, may produce excitation light at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that the excitation wavelength may have any value within this range, e.g., about 620 nm.

Excitation Light Bandwidths:

In any of the disclosed optical imaging module designs, the light source(s), alone or in combination with one or more optical components, e.g., excitation optical filters and/or dichroic beam splitters, may produce light at the specified excitation wavelength within a bandwidth of ±2 nm, ±5 nm, ±10 nm, ±20 nm, ±40 nm, ±80 nm, or greater. Those of skill in the art will recognize that the excitation bandwidths may have any value within this range, e.g., about ±18 nm.

Light Source Power Output:

In any of the disclosed optical imaging module designs, the output of the light source(s) and/or an excitation light beam derived therefrom (including a composite excitation light beam) may range in power from about 0.5 W to about 5.0 W, or more (as will be discussed in more detail below). In some instances, the output of the light source and/or the power of an excitation light beam derived therefrom may be at least 0.5 W, at least 0.6 W, at least 0.7 W, at least 0.8 W, at least 1 W, at least 1.1 W, at least 1.2 W, at least 1.3 W, at least 1.4 W, at least 1.5 W, at least 1.6 W, at least 1.8 W, at least 2.0 W, at least 2.2 W, at least 2.4 W, at least 2.6 W, at least 2.8 W, at least 3.0 W, at least 3.5 W, at least 4.0 W, at least 4.5 W, or at least 5.0 W. In some implementations, the output of the light source and/or the power of an excitation light beam derived therefrom (including a composite excitation light beam) may be at most 5.0 W, at most 4.5 W, at most 4.0 W, at most 3.5 W, at most 3.0 W, at most 2.8 W, at most 2.6 W, at most 2.4 W, at most 2.2 W, at most 2.0 W, at most 1.8 W, at most 1.6 W, at most 1.5 W, at most 1.4 W, at most 1.3 W, at most 1.2 W, at most 1.1 W, at most 1 W, at most 0.8 W, at most 0.7 W, at most 0.6 W, or at most 0.5 W. Any of the lower and upper values described in this paragraph may be combined to form a range included within the present disclosure, for example, in some instances the output of the light source and/or the power of an excitation light beam derived therefrom (including a composite excitation light beam) may range from about 0.8 W to about 2.4 W. Those of skill in the art will recognize that the output of the light source and/or the power of an excitation light beam derived therefrom (including a composite excitation light beam) may have any value within this range, e.g., about 1.28 W.

Light Source Output Power and CNR:

In some implementations of the disclosed optical imaging module designs, the output power of the light source(s) and/or the power of excitation light beam(s) derived therefrom (including a composite excitation light beam) is sufficient, in combination with an appropriate sample, to provide for a contrast-to-noise ratio (CNR) in images acquired by the illumination and imaging module of at least 5, at least 10, at least 15, at least 20, at least 21, at least 22, at least 23, at least 24, at least 25, at least 30, at least 35, at least 40, or at least 50 or more, or any CNR within any range formed by any of these values.

Fluorescence Emission Bands:

In some instances, the disclosed fluorescence optical imaging modules may be configured to detect fluorescence emission produced by any of a variety of fluorophores known to those of skill in the art. Examples of suitable fluorescence dyes for use in, e.g., genotyping and nucleic acid sequencing applications (e.g., by conjugation to nucleotides, oligonucleotides, or proteins) include, but are not limited to, fluorescein, rhodamine, coumarin, cyanine, and derivatives thereof, including the cyanine derivatives cyanine dye-3 (Cy3), cyanine dye-5 (Cy5), cyanine dye-7 (Cy7), etc.

Fluorescence Emission Wavelengths:

In any of the disclosed optical imaging module designs, the detection channel or imaging channel of the disclosed optical systems may include one or more optical components, e.g., emission optical filters and/or dichroic beam splitters, configured to collect emission light at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that the emission wavelength may have any value within this range, e.g., about 825 nm.

Fluorescence Emission Light Bandwidths:

In any of the disclosed optical imaging module designs, the detection channel or imaging channel may comprise one or more optical components, e.g., emission optical filters and/or dichroic beam splitters, configured to collect light at the specified emission wavelength within a bandwidth of ±2 nm, ±5 nm, ±10 nm, ±20 nm, ±40 nm, ±80 nm, or greater. Those of skill in the art will recognize that the excitation bandwidths may have any value within this range, e.g., about ±18 nm.

Numerical Aperture:

In some instances, the numerical aperture of the objective lens and/or optical imaging module (e.g., comprising an objective lens and/or tube lens) in any of the disclosed optical system designs may range from about 0.1 to about 1.4. In some instances, the numerical aperture may be at least 0.1, at least 0.2, at least 0.3, at least 0.4, at least 0.5, at least 0.6, at least 0.7, at least 0.8, at least 0.9, at least 1.0, at least 1.1, at least 1.2, at least 1.3, or at least 1.4. In some instances, the numerical aperture may be at most 1.4, at most 1.3, at most 1.2, at most 1.1, at most 1.0, at most 0.9, at most 0.8, at most 0.7, at most 0.6, at most 0.5, at most 0.4, at most 0.3, at most 0.2, or at most 0.1. Any of the lower and upper values described in this paragraph may be combined to form a range included within the present disclosure, for example, in some instances the numerical aperture may range from about 0.1 to about 0.6. Those of skill in the art will recognize that the numerical aperture may have any value within this range, e.g., about 0.55.

Optical Resolution:

In some instances, depending on the numerical aperture of the objective lens and/or optical system (e.g., comprising an objective lens and/or tube lens), the minimum resolvable spot (or feature) separation distance at the sample plane achieved by any of the disclosed optical system designs may range from about 0.5 µm to about 2 µm. In some instances, the minimum resolvable spot separation distance at the sample plane may be at least 0.5 µm, at least 0.6 µm, at least 0.7 µm, at least 0.8 µm, at least 0.9 µm, at least 1.0 µm, at least 1.2 µm, at least 1.4 µm, at least 1.6 µm, at least 1.8 µm, or at least 1.0 µm. In some instances, the minimum resolvable spot separation distance may be at most 2.0 µm, at most 1.8 µm, at most 1.6 µm, at most 1.4 µm, at most 1.2 µm, at most 1.0 µm, at most 0.9 µm, at most 0.8 µm, at most 0.7 µm, at most 0.6 µm, or at most 0.5 µm. Any of the lower and upper values described in this paragraph may be combined to form a range included within the present disclosure, for example, in some instances the minimum resolvable spot separation distance may range from about 0.8 µm to about 1.6 µm. Those of skill in the art will recognize that the minimum resolvable spot separation distance may have any value within this range, e.g., about 0.95 µm.

Optical Resolution of First and Second Surfaces at Different Depths:

In some instances, the use of the novel objective lens and/or tube lens designs disclosed herein, in any of the optical modules or systems disclosed herein, may confer comparable optical resolution for first and second surfaces (e.g. the upper and lower interior surfaces of a flow cell) with or without the need to refocus between acquiring the images of the first and second surfaces. In some instances, the optical resolution of the images thus obtained of the first and second surfaces may be with 20%, 18%, 16%, 14%, 12%, 10%, 8%, 6%, 4%, 2%, or 1% of each other, or within any value within this range.

Magnification:

In some instances, the magnification of the objective lens and/or tube lens, and/or optical system (e.g., comprising an objective lens and/or tube lens) in any of the disclosed optical configurations may range from about 2× to about 20×. In some instances, the optical system magnification may be at least 2×, at least 3×, at least 4×, at least 5×, at least 6×, at least 7×, at least 8×, at least 9×, at least 10×, at least 15×, or at least 20×. In some instances, the optical system magnification may be at most 20×, at most 15×, at most 10×, at most 9×, at most 8×, at most 7×, at most 6×, at most 5×, at most 4×, at most 3×, or at most 2×. Any of the lower and upper values described in this paragraph may be combined to form a range included within the present disclosure, for example, in some instances the optical system magnification may range from about 3× to about 10×. Those of skill in the art will recognize that the optical system magnification may have any value within this range, e.g., about 7.5×.

Objective Lens Focal Length:

In some implementations of the disclosed optical designs, the focal length of the objective lens may range between 20 mm and 40 mm. In some instances, the focal length of the objective lens may be at least 20 mm, at least 25 mm, at least 30 mm, at least 35 mm, or at least 40 mm. In some instances, the focal length of the objective lens may be at most 40 mm, at most 35 mm, at most 30 mm, at most 25 mm, or at most 20 mm. Any of the lower and upper values described in this paragraph may be combined to form a range included within the present disclosure, for example, in some instances the focal length of the objective lens may range from 25 mm to 35 mm. Those of skill in the art will recognize that the focal length of the objective lens may have any value within the range of values specified above, e.g., about 37 mm.

Objective lens working distance: In some implementations of the disclosed optical designs, the working distance of the objective lens may range between about 100 μm and 30 mm. In some instances, the working distance may be at least 100 μm, at least 200 μm, at least 300 μm, at least 400 μm, at least 500 μm, at least 600 μm, at least 700 μm, at least 800 μm, at least 900 μm, at least 1 mm, at least 2 mm, at least 4 mm, at least 6 mm, at least 8 mm, at least 10 mm, at least 15 mm, at least 20 mm, at least 25 mm, or at least 30 mm. In some instances, the working distance may be at most 30 mm, at most 25 mm, at most 20 mm, at most 15 mm, at most 10 mm, at most 8 mm, at most 6 mm, at most 4 mm, at most 2 mm, at most 1 mm, at most 900 μm, at most 800 μm, at most 700 μm, at most 600 μm, at most 500 μm, at most 400 μm, at most 300 μm, at most 200 μm, at most 100 μm. Any of the lower and upper values described in this paragraph may be combined to form a range included within the present disclosure, for example, in some instances the working distance of the objective lens may range from 500 μm to 2 mm. Those of skill in the art will recognize that the working distance of the objective lens may have any value within the range of values specified above, e.g., about 1.25 mm.

Objectives Optimized for Imaging Through Thick Coverslips:

In some instances of the disclosed optical designs, the design of the objective lens may be improved or optimized for a different coverslip of flow cell thickness. For example, in some instances the objective lens may be designed for optimal optical performance for a coverslip that is from about 200 μm to about 1,000 μm thick. In some instances, the objective lens may be designed for optimal performance with a coverslip that is at least 200 μm, at least 300 μm, at least 400 μm, at least 500 μm, at least 600 μm, at least 700 μm, at least 800 μm, at least 900 μm, or at least 1,000 μm thick. In some instances, the objective lens may be designed for optimal performance with a coverslip that is at most 1,000 μm, at most 900 μm, at most 800 μm, at most 700 μm, at most 600 μm, at most 500 μm, at most 400 μm, at most 300 μm, or at most 200 μm thick. Any of the lower and upper values described in this paragraph may be combined to form a range included within the present disclosure, for example, in some instances the objective lens may be designed for optimal optical performance for a coverslip that may range from about 300 μm to about 900 μm. Those of skill in the art will recognize that the objective lens may be designed for optimal optical performance for a coverslip that may have any value within this range, e.g., about 725 μm.

Depth of Field and Depth of Focus:

In some instances, the depth of field and/or depth of focus for any of the disclosed imaging module (e.g., comprising an objective lens and/or tube lens) designs may range from about 10 μm to about 800 μm, or more. In some instances, the depth of field and/or depth of focus may be at least 10 μm, at least 20 μm, at least 30 μm, at least 40 μm, at least 50 μm, at least 75 μm, at least 100 μm, at least 125 μm, at least 150 μm, at least 175 μm, at least 200 μm, at least 250 μm, at least 300 μm, at least 300 μm, at least 400 μm, at least 500 μm, at least 600 μm, at least 700 μm, or at least 800 μm, or more. In some instances, the depth of field and/or depth of focus be at most 800 μm, at most 700 μm, at most 600 μm, at most 500 μm, at most 400 μm, at most 300 μm, at most 250 μm, at most 200 μm, at most 175 μm, at most 150 μm, at most 125 μm, at most 100 μm, at most 75 μm, at most 50 μm, at most 40 μm, at most 30 μm, at most 20 μm, at most 10 μm, or less. Any of the lower and upper values described in this paragraph may be combined to form a range included within the present disclosure, for example, in some instances the depth of field and/or depth of focus may range from about 100 μm to about 175 μm. Those of skill in the art will recognize that the depth of field and/or depth of focus may have any value within the range of values specified above, e.g., about 132 μm.

Field of View (FOV):

In some implementations, the FOV of any of the disclosed imaging module designs (e.g., that provided by a combination of objective lens and detection channel optics (such as a tube lens)) may range, for example, between about 1 mm and 5 mm (e.g., in diameter, width, length, or longest dimension). In some instances, the FOV may be at least 1.0 mm, at least 1.5 mm, at least 2.0 mm, at least 2.5 mm, at least 3.0 mm, at least 3.5 mm, at least 4.0 mm, at least 4.5 mm, or at least 5.0 mm (e.g., in diameter, width, length, or longest dimension). In some instances, the FOV may be at most 5.0 mm, at most 4.5 mm, at most 4.0 mm, at most 3.5 mm, at most 3.0 mm, at most 2.5 mm, at most 2.0 mm, at most 1.5 mm, or at most 1.0 mm (e.g., in diameter, width, length, or longest dimension). Any of the lower and upper values described in this paragraph may be combined to form a range included within the present disclosure, for example, in some instances the FOV may range from about 1.5 mm to about 3.5 mm (e.g., in diameter, width, length, or longest dimension). Those of skill in the art will recognize that the FOV may have any value within the range of values specified above, e.g., about 3.2 mm (e.g., in diameter, width, length, or longest dimension).

Field-of-view (FOV) area: In some instances of the disclosed optical system designs, the area of the field-of-view may range from about 2 mm$^2$ to about 5 mm$^2$. In some instances, the field-of-view may be at least 2 mm$^2$, at least 3 mm$^2$, at least 4 mm$^2$, or at least 5 mm$^2$ in area. In some instances, the field-of-view may be at most 5 mm$^2$, at most 4 mm$^2$, at most 3 mm$^2$, or at most 2 mm$^2$ in area. Any of the lower and upper values described in this paragraph may be combined to form a range included within the present disclosure, for example, in some instances the field-of-view may range from about 3 mm$^2$ to about 4 mm$^2$ in area. Those of skill in the art will recognize that the area of the field-of-view may have any value within this range, e.g., 2.75 mm$^2$.

Optimization of Objective Lens and/or Tube Lens MTF:

In some instances, the design of the objective lens and/or at least one tube lens in the disclosed imaging modules and systems is configured to optimize the modulation transfer function in the mid to high spatial frequency range. For example, in some instances, the design of the objective lens and/or at least one tube lens in the disclosed imaging modules and systems is configured to optimize the modulation transfer function in the spatial frequency range from 500 cycles per mm to 900 cycles per mm, from 700 cycles per mm to 1100 cycles per mm, from 800 cycles per mm to 1200 cycles per mm, or from 600 cycles per mm to 1000 cycles per mm in the sample plane.

Optical Aberration and Diffraction-Limited Imaging Performance:

In some implementations of any of the optical imaging module designs disclosed herein, the objective lens and/or tube lens may be configured to provide the imaging module with a field-of-view as indicated above such that the FOV has less than 0.15 waves of aberration over at least 60%, 70%, 80%, 90%, or 95% of the field. In some implementations, the objective lens and/or tube lens may be configured to provide the imaging module with a field-of-view as indicated above such that the FOV has less than 0.1 waves of aberration over at least 60%, 70%, 80%, 90%, or 95% of the field. In some implementations, the objective lens and/or tube lens may be configured to provide the imaging module with a field-of-view as indicated above such that the FOV has less than 0.075 waves of aberration over at least 60%, 70%, 80%, 90%, or 95% of the field. In some implementations, the objective lens and/or tube lens may be configured to provide the imaging module with a field-of-view as indicated above such that the FOV is diffraction-limited over at least 60%, 70%, 80%, 90%, or 95% of the field.

Angle of Incidence of Light Beams on Dichroic Reflectors, Beam Splitter, and Beam Combiners:

In some instances of the disclosed optical designs, the angles of incidence for a light beam incident on a dichroic reflector, beam splitter, or beam combiner may range between about 20 degrees and about 45 degrees. In some instances, the angles of incidence may be at least 20 degrees, at least 25 degrees, at least 30 degrees, at least 35 degrees, at least 40 degrees, or at least 45 degrees. In some instances, the angles of incidence may be at most 45 degrees, at most 40 degrees, at most 35 degrees, at most 30 degrees, at most 25 degrees, or at most 20 degrees. Any of the lower and upper values described in this paragraph may be combined to form a range included within the present disclosure, for example, in some instances the angles of incidence may range from about 25 degrees to about 40 degrees. Those of skill in the art will recognize that the angles of incidence may have any value within the range of values specified above, e.g., about 43 degrees.

Image Sensor (Photodetector Array) Size:

In some instances, the disclosed optical systems may comprise image sensor(s) having an active area with a diagonal ranging from about 10 mm to about 30 mm, or larger. In some instances, the image sensors may have an active area with a diagonal of at least 10 mm, at least 12 mm, at least 14 mm, at least 16 mm, at least 18 mm, at least 20 mm, at least 22 mm, at least 24 mm, at least 26 mm, at least 28 mm, or at least 30 mm. In some instances, the image sensors may have an active area with a diagonal of at most 30 mm, at most 28 mm, at most 26 mm, at most 24 mm, at most 22 mm, at most 20 mm, at most 18 mm, at most 16 mm, at most 14 mm, at most 12 mm, or at most 10 mm. Any of the lower and upper values described in this paragraph may be combined to form a range included within the present disclosure, for example, in some instances the image sensor(s) may have an active area with a diagonal ranging from about 12 mm to about 24 mm. Those of skill in the art will recognize that the image sensor(s) may have an active area with a diagonal having any value within the range of values specified above, e.g., about 28.5 mm.

Image Sensor Pixel Size and Pitch:

In some instances, the pixel size and/or pitch selected for the image sensor(s) used in the disclosed optical system designs may range in at least one dimension from about 1 μm to about 10 μm. In some instances, the pixel size and/or pitch may be at least 1 μm, at least 2 μm, at least 3 μm, at least 4 μm, at least 5 μm, at least 6 μm, at least 7 μm, at least 8 μm, at least 9 μm, or at least 10 μm. In some instances, the pixel size and/or pitch may be at most 10 μm, at most 9 μm, at most 8 μm, at most 7 μm, at most 6 μm, at most 5 μm, at most 4 μm, at most 3 μm, at most 2 μm, or at most 1 μm. Any of the lower and upper values described in this paragraph may be combined to form a range included within the present disclosure, for example, in some instances the pixel size and/or pitch may range from about 3 μm to about 9 μm. Those of skill in the art will recognize that the pixel size and/or pitch may have any value within this range, e.g., about 1.4 μm.

Oversampling:

In some instances of the disclosed optical designs, a spatial oversampling scheme is utilized wherein the spatial sampling frequency is at least 2×, 2.5×, 3×, 3.5×, 4×, 4.5×, 5×, 6×, 7×, 8×, 9×, or 10× the optical resolution X(lp/mm).

Maximum Translation Stage Velocity:

In some instances of the disclosed optical imaging modules, the maximum translation stage velocity on any one axis may range from about 1 mm/sec to about 5 mm/sec. In some instances, the maximum translation stage velocity may be at least 1 mm/sec, at least 2 mm/sec, at least 3 mm/sec, at least 4 mm/sec, or at least 5 mm/sec. In some instances, the maximum translation stage velocity may be at most 5 mm/sec, at most 4 mm/sec, at most 3 mm/sec, at most 2 mm/sec, or at most 1 mm/sec. Any of the lower and upper values described in this paragraph may be combined to form a range included within the present disclosure, for example, in some instances the maximum translation stage velocity may range from about 2 mm/sec to about 4 mm/sec. Those of skill in the art will recognize that the maximum translation stage velocity may have any value within this range, e.g., about 2.6 mm/sec.

Maximum Translation Stage Acceleration:

In some instances of the disclosed optical imaging modules, the maximum acceleration on any one axis of motion may range from about 2 mm/sec$^2$ to about 10 mm/sec$^2$. In some instances, the maximum acceleration may be at least 2 mm/sec$^2$, at least 3 mm/sec$^2$, at least 4 mm/sec$^2$, at least 5 mm/sec$^2$, at least 6 mm/sec$^2$, at least 7 mm/sec$^2$, at least 8 mm/sec$^2$, at least 9 mm/sec$^2$, or at least 10 mm/sec$^2$. In some instances, the maximum acceleration may be at most 10 mm/sec$^2$, at most 9 mm/sec$^2$, at most 8 mm/sec$^2$, at most 7 mm/sec$^2$, at most 6 mm/sec$^2$, at most 5 mm/sec$^2$, at most 4 mm/sec$^2$, at most 3 mm/sec$^2$, or at most 2 mm/sec$^2$. Any of the lower and upper values described in this paragraph may be combined to form a range included within the present disclosure, for example, in some instances the maximum acceleration may range from about 2 mm/sec$^2$ to about 8 mm/sec$^2$. Those of skill in the art will recognize that the maximum acceleration may have any value within this range, e.g., about 3.7 mm/sec$^2$.

Translation Stage Positioning Repeatability:

In some instances of the disclosed optical imaging modules, the repeatability of positioning for any one axis may range from about 0.1 µm to about 2 µm. In some instances, the repeatability of positioning may be at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, at least 1.0 µm, at least 1.2 µm, at least 1.4 µm, at least 1.6 µm, at least 1.8 µm, or at least 2.0 µm. In some instances, the repeatability of positioning may be at most 2.0 µm, at most 1.8 µm, at most 1.6 µm, at most 1.4 µm, at most 1.2 µm, at most 1.0 µm, at most 0.9 µm, at most 0.8 µm, at most 0.7 µm, at most 0.6 µm, at most 0.5 µm, at most 0.4 µm, at most 0.3 µm, at most 0.2 µm, or at most 0.1 µm. Any of the lower and upper values described in this paragraph may be combined to form a range included within the present disclosure, for example, in some instances the repeatability of positioning may range from about 0.3 µm, µm to about 1.2 µm. Those of skill in the art will recognize that the repeatability of positioning may have any value within this range, e.g., about 0.47 µm.

FOV Repositioning Time:

In some instances of the disclosed optical imaging modules, the maximum time required to reposition the sample plane (field-of-view) relative to the optics, or vice versa, may range from about 0.1 sec to about 0.5 sec. In some instances, the maximum repositioning time (i.e., the scan stage step and settle time) may be at least 0.1 sec, at least 0.2 sec, at least 0.3 sec, at least 0.4 sec, or at least 0.5 sec. In some instances, the maximum repositioning time may be at most 0.5 sec, at most 0.4 sec, at most 0.3 sec, at most 0.2 sec, or at most 0.1 sec. Any of the lower and upper values described in this paragraph may be combined to form a range included within the present disclosure, for example, in some instances the maximum repositioning time may range from about 0.2 sec to about 0.4 sec. Those of skill in the art will recognize that the maximum repositioning time may have any value within this range, e.g., about 0.45 sec.

Error Threshold for Autofocus Correction:

In some instances of the disclosed optical imaging modules, the specified error threshold for triggering an autofocus correction may range from about 50 nm to about 200 nm. In some instances, the error threshold may be at least 50 nm, at least 75 nm, at least 100 nm, at least 125 nm, at least 150 nm, at least 175 nm, or at least 200 nm. In some instances, the error threshold may be at most 200 nm, at most 175 nm, at most 150 nm, at most 125 nm, at most 100 nm, at most 75 nm, or at most 50 nm. Any of the lower and upper values described in this paragraph may be combined to form a range included within the present disclosure, for example, in some instances the error threshold may range from about 75 nm to about 150 nm. Those of skill in the art will recognize that the error threshold may have any value within this range, e.g., about 105 nm.

Image Acquisition Time:

In some instances of the disclosed optical imaging modules, the image acquisition time may range from about 0.001 sec to about 1 sec. In some instances, the image acquisition time may be at least 0.001 sec, at least 0.01 sec, at least 0.1 sec, or at least 1 sec. in some instances, the image acquisition time may be at most 1 sec, at most 0.1 sec, at most 0.01 sec, or at most 0.001 sec. Any of the lower and upper values described in this paragraph may be combined to form a range included within the present disclosure, for example, in some instances the image acquisition time may range from about 0.01 sec to about 0.1 sec. Those of skill in the art will recognize that the image acquisition time may have any value within this range, e.g., about 0.250 seconds.

Imaging Time Per FOV:

In some instances, the imaging times may range from about 0.5 seconds to about 3 seconds per field-of-view. In some instances, the imaging time may be at least 0.5 seconds, at least 1 second, at least 1.5 seconds, at least 2 seconds, at least 2.5 seconds, or at least 3 seconds per FOV. In some instances, the imaging time may be at most 3 seconds, at most 2.5 seconds, at most 2 seconds, at most 1.5 seconds, at most 1 second, or at most 0.5 seconds per FOV. Any of the lower and upper values described in this paragraph may be combined to form a range included within the present disclosure, for example, in some instances the imaging time may range from about 1 second to about 2.5 seconds. Those of skill in the art will recognize that the imaging time may have any value within this range, e.g., about 1.85 seconds.

Flatness of Field:

In some instances, images across 80%, 90%, 95%, 98%, 99%, or 100% percent of the field-of-view are acquired within ±200 nm, ±175 nm, ±150 nm, ±125 nm, ±100 nm, ±75 nm, or ±50 nm relative to the best focal plane for each fluorescence (or other imaging mode) detection channel.

Systems and System Components for Genomics and Other Applications:

As noted above, in some implementations, the disclosed optical imaging modules may function as modules, components, sub-assemblies, or sub-systems of larger systems configured for performing, e.g., genomics applications (e.g., genetic testing and/or nucleic acid sequencing applications) or other chemical analysis, biochemical analysis, nucleic acid analysis, cell analysis or tissue analysis applications. In addition to one, two, three, four, or more than four imaging modules as disclosed herein (each of which may comprise one or more illumination optical paths and/or one or more detection optical paths (e.g., one or more detection channels configured for imaging fluorescence emission within a specified wavelength range onto an image sensor)), such systems may comprise one or more X-Y translation stages, one or more X-Y-Z translation stages, flow cells or cartridges, fluidics systems and fluid flow control modules, temperature control modules, fluid dispensing robotics, cartridge- and/or microplate-handling (pick-and-place) robotics, light-tight housings and/or environmental control chambers, one or more processors or computers, data storage modules, data communication modules (e.g., Bluetooth, WiFi, intranet, or internet communication hardware and associated software), display modules, one or more local and/or cloud-based software packages (e.g., instrument/ system control software packages, image processing software packages, data analysis software packages), etc., or any combination thereof.

Translation Stages:

In some implementations of the imaging and analysis systems (e.g., nucleic acid sequencing systems) disclosed herein, the system may comprise one or more (e.g., one, two, three, four, or more than four) high precision X-Y (or in some cases, X-Y-Z) translation stage(s) for re-positioning one or more sample support structure(s) (e.g., flow cell(s)) in relation to the one or more imaging modules, for example, in order to tile one or more images, each corresponding to a field-of-view of the imaging module, to reconstruct composite image(s) of an entire flow cell surface. In some implementations of the imaging systems and genomics analysis systems (e.g., nucleic acid sequencing systems) disclosed herein, the system may comprise one or more (e.g., one, two, three, four, or more than four) high precision X-Y (or in some cases, X-Y-Z) translation stage(s) for re-positioning the one or more imaging modules in relation to one or more sample support structure(s) (e.g., flow cell(s)), for example, in order to tile one or more images, each corresponding to a field-of-view of the imaging module, to reconstruct composite image(s) of an entire flow cell surface.

Suitable translation stages are commercially available from a variety of vendors, for example, Parker Hannifin. Precision translation stage systems typically comprise a combination of several components including, but not limited to, linear actuators, optical encoders, servo and/or stepper motors, and motor controllers or drive units. High precision and repeatability of stage movement is required for the systems and methods disclosed herein in order to ensure accurate and reproducible positioning and imaging of, e.g., fluorescence signals when interspersing repeated steps of reagent delivery and optical detection.

Consequently, the systems disclosed herein may comprise specifying the precision with which the translation stage is configured to position a sample support structure in relation to the illumination and/or imaging optics (or vice versa). In one aspect of the present disclosure, the precision of the one or more translation stages is between about 0.1 µm and about 10 µm. In other aspects, the precision of the translation stage is about 10 µm or less, about 9 µm or less, about 8 µm or less, about 7 µm or less, about 6 µm or less, about 5 µm or less, about 4 µm or less, about 3 µm or less, about 2 µm or less, about 1 µm or less, about 0.9 µm or less, about 0.8 µm or less, about 0.7 µm or less, about 0.6 µm or less, about 0.5 µm or less, about 0.4 µm or less, about 0.3 µm or less, about 0.2 µm or less, or about 0.1 µm or less. Those of skill in the art will appreciate that, in some instances, the positioning precision of the translation stage may fall within any range bounded by any of two of these values (e.g. from about 0.5 µm to about 1.5 µm). In some instances, the positioning precision of the translation stage may have any value within the range of values included in this paragraph, e.g., about 0.12 µm.

Flow Cells, Microfluidic Devices, and Cartridges:

The flow cell devices and flow cell cartridges disclosed herein may be used as components of systems designed for a variety of chemical analysis, biochemical analysis, nucleic acid analysis, cell analysis, or tissue analysis application. In general, such systems may comprise one or more one or more of the disclosed single capillary flow cell devices, multiple capillary flow cell devices, capillary flow cell cartridges, and/or microfluidic devices and cartridges described herein. Additional description of the disclosed flow cell devices and cartridges may be found in PCT Patent Application Publication WO 2020/118255, which is incorporated herein by reference in its entirety.

In some instances, the systems disclosed herein may comprise 1, 2, 3, 4, 5, 6, 7, 8, 9, 10, or more than 10 single capillary flow cell devices, multiple capillary flow cell devices, capillary flow cell cartridges, and/or microfluidic devices and cartridges. In some instances, the single capillary flow cell devices, multiple capillary flow cell devices, and/or microfluidic devices and cartridges may be fixed components of the disclosed systems. In some instances, the single capillary flow cell devices, multiple capillary flow cell devices, and/or microfluidic devices and cartridges may be removable, exchangeable components of the disclosed systems. In some instances, the single capillary flow cell devices, multiple capillary flow cell devices, and/or microfluidic devices and cartridges may be disposable or consumable components of the disclosed systems.

In some implementations, the disclosed single capillary flow cell devices (or single capillary flow cell cartridges) comprise a single capillary, e.g., a glass or fused-silica capillary, the lumen of which forms a fluid flow path through which reagents or solutions may flow, and the interior surface of which may form a sample support structure to which samples of interest are bound or tethered. In some implementations, the multi-capillary capillary flow cell devices (or multi-capillary flow cell cartridges) disclosed herein may comprise 2, 3, 4, 5, 6, 7, 8, 9, 10, 11, 12, 13, 14, 15, 16, 17, 18, 19, 20, or more than 20 capillaries configured for performing an analysis technique that further comprises imaging as a detection method.

In some instances, one or more capillaries may be packaged within a chassis to form a cartridge that facilitates ease-of-handling, incorporates adapters or connectors for making external fluid connections, and may optionally include additional integrated functionality such as reagent reservoirs, waste reservoirs, valves (e.g., microvalves), pumps (e.g., micropumps), etc., or any combination thereof.

Figure 29:
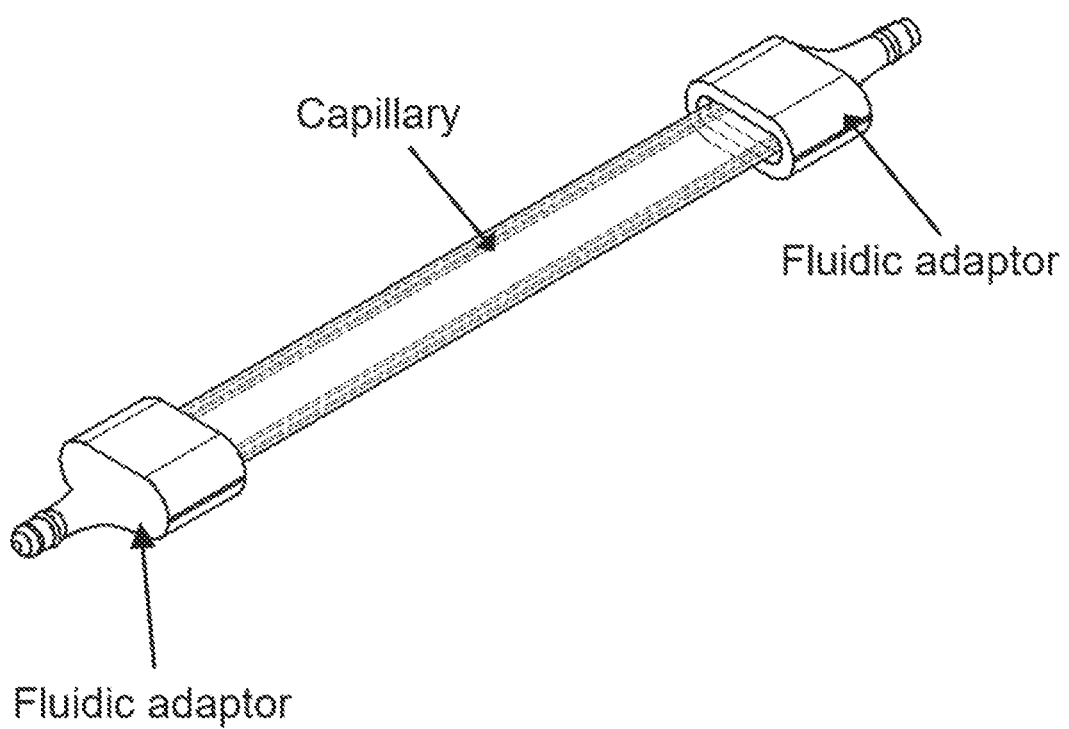
FIG. 29 illustrates one non-limiting example of a single capillary flow cell having 2 fluidic adaptors.

FIG. 29 illustrates one non-limiting example of a single glass capillary flow cell device that comprises two fluidic adaptors—one affixed to each end of the piece of glass capillary—that are designed to mate with standard OD fluidic tubing to provide for convenient, interchangeable fluid connections with an external fluid flow control system. The fluidic adaptors can be attached to the capillary using any of a variety of techniques known to those of skill in the art including, but not limited to, press fit, adhesive bonding, solvent bonding, laser welding, etc., or any combination thereof.

In general, the capillaries used in the disclosed capillary flow cell devices and capillary flow cell cartridges will have at least one internal, axially-aligned fluid flow channel (or "lumen") that runs the full length of the capillary. In some instances, the capillary may have two, three, four, five, or more than five internal, axially-aligned fluid flow channels (or "lumen").

A number specified cross-sectional geometries for suitable capillaries (or the lumen thereof) are consistent with the disclosure herein including, but not limited to, circular, elliptical, square, rectangular, triangular, rounded square, rounded rectangular, or rounded triangular cross-sectional geometries. In some instances, the capillary (or lumen thereof) may have any specified cross-sectional dimension or set of dimensions. For example, in some instances the largest cross-sectional dimension of the capillary lumen (e.g. the diameter if the lumen is circular in shape, or the diagonal if the lumen is square or rectangular in shape) may range from about 10 µm to about 10 mm. In some aspects, the largest cross-sectional dimension of the capillary lumen may be at least 10 µm, at least 25 µm, at least 50 µm, at least 75 µm, at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In some aspects, the largest cross-sectional dimension of the capillary lumen may be at most 10 mm, at most 9 mm, at most 8 mm, at most 7 mm, at most 6 mm, at most 5 mm, at most 4 mm, at most 3 mm, at most 2 mm, at most 1 mm, at most 900 µm, at most 800 µm, at most 700 µm, at most 600 µm, at most 500 µm, at most 400 µm, at most 300 µm, at most 200 µm, at most 100 µm, at most 75 µm, at most 50 µm, at most 25 µm, or at most 10 µm. Any of the lower and upper values described in this paragraph may be combined to form a range included within the present disclosure, for example, in some instances the largest cross-sectional dimension of the capillary lumen may range from about 100 µm to about 500 µm. Those of skill in the art will recognize that the largest cross-sectional dimension of the capillary lumen may have any value within this range, e.g., about 124 µm.

In some instances, e.g., wherein the lumen of the one or more capillaries in a flow cell device or cartridge has a square or rectangular cross-section, the distance between a first interior surface (e.g., a top or upper surface) and a second interior surface (e.g., a bottom or lower surface) that defines the gap height or thickness of a fluid flow channel may range from about 10 µm to about 500 µm. In some instances, the gap height may be at least 10 µm, at least 20 µm, at least 30 µm, at least 40 µm, at least 50 µm, at least 60 µm, at least 70 µm, at least 80 µm, at least 90 µm, at least 100 µm, at least 125 µm, at least 150 µm, at least 175 µm, at least 200 µm, at least 225 µm, at least 250 µm, at least 275 µm, at least 300 µm, at least 325 µm, at least 350 µm, at least 375 µm, at least 400 µm, at least 425 µm, at least 450 µm, at least 475 µm, or at least 500 µm. In some instances, the gap height may be at most 500 µm, at most 475 µm, at most 450 µm, at most 425 µm, at most 400 µm, at most 375 µm, at most 350 µm, at most 325 µm, at most 300 µm, at most 275 µm, at most 250 µm, at most 225 µm, at most 200 µm, at most 175 µm, at most 150 µm, at most 125 µm, at most 100 µm, at most 90 µm, at most 80 µm, at most 70 µm, at most 60 µm, at most 50 µm, at most 40 µm, at most 30 µm, at most 20 µm, or most 10 µm. Any of the lower and upper values described in this paragraph may be combined to form a range included within the present disclosure, for example, in some instances the gap height may range from about 40 µm to about 125 µm. Those of skill in the art will recognize that the gap height may have any value within the range of values in this paragraph, e.g., about 122 µm.

In some instances, the length of the one or more capillaries used to fabricate the disclosed capillary flow cell devices or flow cell cartridges may range from about 5 mm to about 5 cm or greater. In some instances, the length of the one or more capillaries may be less than 5 mm, at least 5 mm, at least 1 cm, at least 1.5 cm, at least 2 cm, at least 2.5 cm, at least 3 cm, at least 3.5 cm, at least 4 cm, at least 4.5 cm, or at least 5 cm. In some instances, the length of the one or more capillaries may be at most 5 cm, at most 4.5 cm, at most 4 cm, at most 3.5 cm, at most 3 cm, at most 2.5 cm, at most 2 cm, at most 1.5 cm, at most 1 cm, or at most 5 mm. Any of the lower and upper values described in this paragraph may be combined to form a range included within the present disclosure, for example, in some instances the length of the one or more capillaries may range from about 1.5 cm to about 2.5 cm. Those of skill in the art will recognize that the length of the one or more capillaries may have any value within this range, e.g., about 1.85 cm. In some instances, devices or cartridges may comprise a plurality of two or more capillaries that are the same length. In some instances, devices or cartridges may comprise a plurality of two or more capillaries that are of different lengths.

The capillaries used for constructing the disclosed capillary flow cell devices or capillary flow cell cartridges may be fabricated from any of a variety of materials known to those of skill in the art including, but not limited to, glass (e.g., borosilicate glass, soda lime glass, etc.), fused silica (quartz), polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) as more chemically inert alternatives, or any combination thereof. PEI is somewhere between polycarbonate and PEEK in terms of both cost and chemical compatibility. FFKM is also known as Kalrez.

The one or more materials used to fabricate the capillaries are often optically transparent to facilitate use with spectroscopic or imaging-based detection techniques. In some instances, the entire capillary will be optically transparent. Alternately, in some instances, only a portion of the capillary (e.g., an optically transparent "window") will be optically transparent.

The capillaries used for constructing the disclosed capillary flow cell devices and capillary flow cell cartridges may be fabricated using any of a variety of techniques known to those of skill in the art, where the choice of fabrication technique is often dependent on the choice of material used, and vice versa. Examples of suitable capillary fabrication techniques include, but are not limited to, extrusion, drawing, precision computer numerical control (CNC) machining and boring, laser photoablation, and the like.

In some implementations, the capillaries used in the disclosed capillary flow cell devices and cartridges may be off-the-shelf commercial products. Examples of commercial vendors that provide precision capillary tubing include Accu-Glass (St. Louis, Mo.; precision glass capillary tubing), Polymicro Technologies (Phoenix, Ariz.; precision glass and fused-silica capillary tubing), Friedrich & Dimmock, Inc. (Millville, N.J.; custom precision glass capillary tubing), and Drummond Scientific (Broomall, Pa.; OEM glass and plastic capillary tubing).

The fluidic adapters that are attached to the capillaries of the capillary flow cell devices and cartridges disclosed herein, and other components of the capillary flow cell devices or cartridges, may be fabricated using any of a variety of suitable techniques (e.g., extrusion molding, injection molding, compression molding, precision CNC machining, etc.) and materials (e.g., glass, fused-silica, ceramic, metal, polydimethylsiloxane, polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), etc.), where again the choice of fabrication technique is often dependent on the choice of material used, and vice versa.

Figure 30:
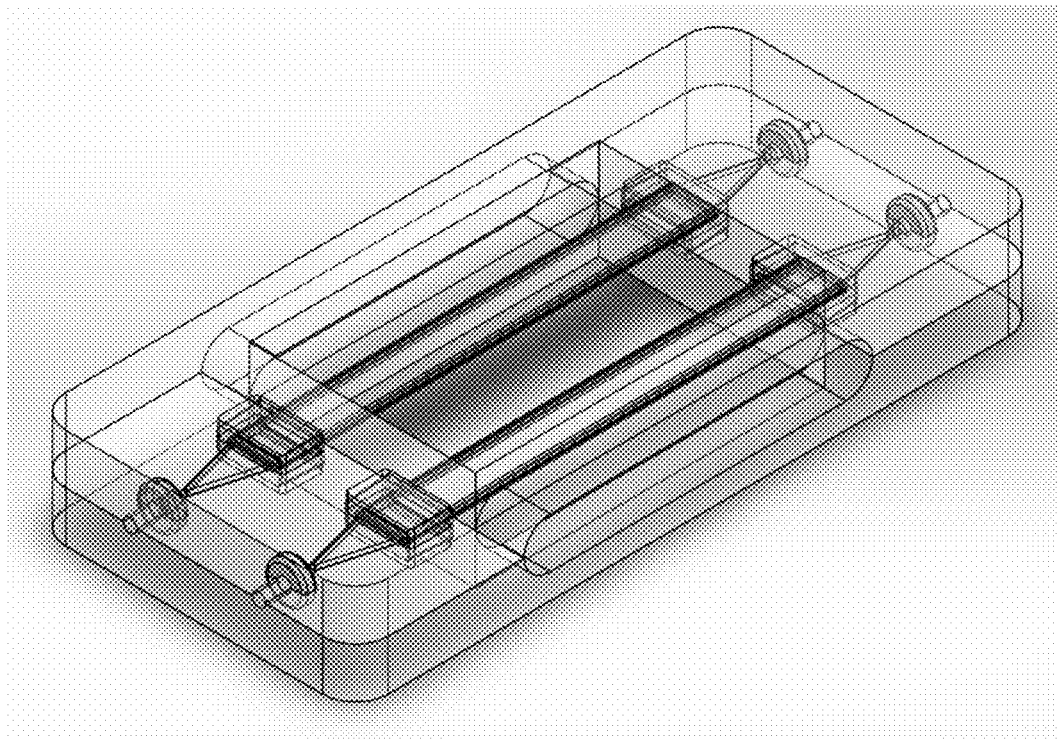
FIG. 30 illustrates one non-limiting example of a flow cell cartridge comprising a chassis, fluidic adapters, and optionally other components, that is designed to hold two capillaries.

FIG. 30 provides a non-limiting example of capillary flow cell cartridge that comprises two glass capillaries, fluidic adaptors (two per capillary in this example), and a cartridge chassis that mates with the capillaries and/or fluidic adaptors such that the capillaries are held in a fixed orientation relative to the cartridge. In some instances, the fluidic adaptors may be integrated with the cartridge chassis. In some instances, the cartridge may comprise additional adapters that mate with the capillaries and/or capillary fluidic adapters. As noted elsewhere herein, in some instances, the cartridge may comprise additional functional components. In some instances, the capillaries are permanently mounted in the cartridge. In some instances, the cartridge chassis is designed to allow one or more capillaries of the flow cell cartridge to be interchangeable removed and replaced. For example, in some instances, the cartridge chassis may comprise a hinged "clamshell" configuration which allows it to be opened so that one or more capillaries may be removed and replaces. In some instances, the cartridge chassis is configured to mount on, for example, the stage of a fluorescence microscope or within a cartridge holder of a fluorescence imaging module or instrument system of the present disclosure.

In some instances, the disclosed flow cell devices may comprise microfluidic devices (or "microfluidic chips") and cartridges, where the microfluidic devices are fabricated by forming fluid channels in one or more layers of a suitable material and comprise one or more fluid channels (e.g., "analysis" channels) configured for performing an analysis technique that further comprises imaging as a detection method. In some implementations, the microfluidic devices or cartridges disclosed herein may comprise 1, 2, 3, 4, 5, 6, 7, 8, 9, 10, 11, 12, 13, 14, 15, 16, 17, 18, 19, 20, or more than 20 fluid channels (e.g., "analysis" fluid channels) configured for performing an analysis technique that further comprises imaging as a detection method. In some instances, the disclosed microfluidic devices may further comprise additional fluid channels (e.g., for dilution or mixing of reagents), reagent reservoirs, waste reservoirs, adapters for making external fluid connections, and the like, to provide integrated "lab-on-a-chip" functionality within the device.

A non-limiting example of microfluidic flow cell cartridge comprises a chip having two or more parallel glass channels formed on the chip, fluidic adaptors coupled to the chip, and a cartridge chassis that mates with the chip and/or fluidic adapters such that the chip is posited in a fixed orientation relative to the cartridge. In some instances, the fluidic adaptors may be integrated with the cartridge chassis. In some instances, the cartridge may comprise additional adapters that mate with the chip and/or fluidic adapters. In some instances, the chip is permanently mounted in the cartridge. In some instances, the cartridge chassis is designed to allow one or more chips of the flow cell cartridge to be interchangeably removed and replaced. For example, in some instances, the cartridge chassis may comprise a hinged "clamshell" configuration which allows it to be opened so that one or more chips may be removed and replaces. In some instances, the cartridge chassis is configured to mount on, for example, the stage of a microscope system or within a cartridge holder of an imaging system. Even through only one chip is described in the non-limiting example, it is understood that more than one chip can be used in the microfluidic flow cell cartridge. The flow cell cartridges of the present disclosure may comprise a single microfluidic chip or a plurality of microfluidic chips. In some instances, the flow cell cartridges of the present disclosure may comprise 2, 3, 4, 5, 6, 7, 8, 9, 10, 11, 12, 13, 14, 15, 16, 17, 18, 19, 20, or more than 20 microfluidic chips. The packaging of one or more microfluidic devices within a cartridge may facilitate ease-of-handling and correct positioning of the device within the optical imaging system.

The fluid channels within the disclosed microfluidic devices and cartridges may have an of a variety of cross-sectional geometries including, but not limited to, circular, elliptical, square, rectangular, triangular, rounded square, rounded rectangular, or rounded triangular cross-sectional geometries. In some instances, the fluid channels may have any specified cross-sectional dimension or set of dimensions. For example, in some instances, the height (e.g., gap height), width, or largest cross-sectional dimension of the fluid channels (e.g., the diagonal if the fluid channel has a square, rounded square, rectangular, or rounded rectangular cross-section) may range from about 10 μm to about 10 mm. In some aspects, the height (e.g., gap height), width, or largest cross-sectional dimension of the fluid channels may be at least 10 μm, at least 25 μm, at least 50 μm, at least 75 μm, at least 100 μm, at least 200 μm, at least 300 μm, at least 400 μm, at least 500 μm, at least 600 μm, at least 700 μm, at least 800 μm, at least 900 μm, at least 1 mm, at least 2 mm, at least 3 mm, at least 4 mm, at least 5 mm, at least 6 mm, at least 7 mm, at least 8 mm, at least 9 mm, or at least 10 mm. In some aspects, the height (e.g., gap height), width, or largest cross-sectional dimension of the fluid channels may be at most 10 mm, at most 9 mm, at most 8 mm, at most 7 mm, at most 6 mm, at most 5 mm, at most 4 mm, at most 3 mm, at most 2 mm, at most 1 mm, at most 900 μm, at most 800 μm, at most 700 μm, at most 600 μm, at most 500 μm, at most 400 μm, at most 300 μm, at most 200 μm, at most 100 μm, at most 75 μm, at most 50 μm, at most 25 μm, or at most 10 μm. Any of the lower and upper values described in this paragraph may be combined to form a range included within the present disclosure, for example, in some instances the height (e.g., gap height), width, or largest cross-sectional dimension of the fluid channels may range from about 20 μm to about 200 μm. Those of skill in the art will recognize that the height (e.g., gap height), width, or largest cross-sectional dimension of the fluid channels may have any value within this range, e.g., about 122 μm.

In some instances, the length of the fluid channels in the disclosed microfluidic devices and cartridges may range from about 5 mm to about 10 cm or greater. In some instances, the length of the fluid channels may be less than 5 mm, at least 5 mm, at least 1 cm, at least 1.5 cm, at least 2 cm, at least 2.5 cm, at least 3 cm, at least 3.5 cm, at least 4 cm, at least 4.5 cm, at least 5 cm, at least 6 cm, at least 7 cm, at least 8 cm, at least 9 cm, or at least 10 cm. In some instances, the length of the fluid channels may be at most 10 cm, at most 9 cm, at most 8 cm, at most 7 cm, at most 6 cm, at most 5 cm, at most 4.5 cm, at most 4 cm, at most 3.5 cm, at most 3 cm, at most 2.5 cm, at most 2 cm, at most 1.5 cm, at most 1 cm, or at most 5 mm. Any of the lower and upper values described in this paragraph may be combined to form a range included within the present disclosure, for example, in some instances the length of the fluid channels may range from about 1.5 cm to about 2.5 cm. Those of skill in the art will recognize that the length of the fluid channels may have any value within this range, e.g., about 1.35 cm. In some instances, the microfluidic devices or cartridges may comprise a plurality of fluid channels that are the same length.

In some instances, the microfluidic devices or cartridges may comprise a plurality of fluid channels that are of different lengths.

The disclosed microfluidic devices will comprise at least one layer of material having one or more fluid channels formed therein. In some instances, the microfluidic chip may include two layers bonded together to form one or more fluid channels. In some instances, the microfluidic chip may include three or more layers bonded together to form one or more fluid channels. In some instances, the microfluidic fluid channels may have an open top. In some instances, the microfluidic fluid channels may be fabricated within one layer, e.g., the top surface of a bottom layer, and sealed by bonding the top surface of the bottom layer to the bottom surface of a top layer of material. In some instances, the microfluidic channels may be fabricated within one layer, e.g., as patterned channels the depth of which extends through the full thickness of the layer, which is then sandwiched between and bonded to two non-patterned layers to seal the fluid channels. In some instances, the microfluidic channels are fabricated by the removal of a sacrificial layer on the surface of a substrate. This method does not require the bulk substrate (e.g., a glass or silicon wafer) to be etched away. Instead, the fluid channels are located on the surface of the substrate. In some instances, the microfluidic channels may be fabricated in or on the surface of a substrate and then sealed by deposition of a conformal film or layer on the surface of the substrate to create sub-surface or buried fluid channels in the chip.

The microfluidic chips can be manufactured using a combination of microfabrication processes. Because the devices are microfabricated, substrate materials will typically be selected based upon their compatibility with known microfabrication techniques, e.g., photolithography, wet chemical etching, laser ablation, laser irradiation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electromagnetic (e.g. light) or electric fields.

The disclosed microfluidic chips may be fabricated from any of a variety of materials known to those of skill in the art including, but not limited to, glass (e.g., borosilicate glass, soda lime glass, etc.), fused-silica (quartz), silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) (as more chemically inert alternatives), or any combination thereof. In some preferred instances, the substrate material(s) may include silica-based substrates, such as borosilicate glass, and quartz, as well as other substrate materials.

The disclosed microfluidic devices may be fabricated using any of a variety of techniques known to those of skill in the art, where the choice of fabrication technique is often dependent on the choice of material used, and vice versa. The microfluidic channels on the chip can be constructed using techniques suitable for forming micro-structures or micro-patterns on the surface of a substrate. In some instances, the fluid channels are formed by laser irradiation. In some instances, the microfluidic channels are formed by focused femtosecond laser radiation. In some instances, the microfluidic channels are formed by photolithography and etching including, but not limited to, chemical etching, plasma etching, or deep reactive ion etching. In some instances, the microfluidic channels are formed using laser etching. In some instances, the microfluidic channels are formed using a direct-write lithography technique. Examples of direct-write lithography include electron beam direct-write and focused ion beam milling.

In additional preferred instances, the substrate material(s) may comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates may be readily patterned or micromachined using available microfabrication techniques, such as those described above. In some instances, microfluidic chips may be fabricated from polymeric materials, e.g., from microfabricated masters, using well known molding techniques, such as injection molding, embossing, stamping, or by polymerizing the polymeric precursor material within a mold (see, e.g., U.S. Pat. No. 5,512,131). In some instances, such polymeric substrate materials are preferred for their ease of manufacture, low cost, and disposability, as well as their general inertness to most extreme reaction conditions. As with flow cell devices fabricated from other materials, e.g., glass, flow cell devices fabricated from these polymeric materials may include treated surfaces, e.g., derivatized or coated surfaces, to enhance their utility in the microfluidic system, as will be discussed in more detail below.

The fluid channels and/or fluid chambers of the microfluidic devices are typically fabricated into the upper surface of a first substrate as microscale channels (e.g., grooves, indentations, etc.) using the above described microfabrication techniques. The first substrate comprises a top side having a first planar surface and a bottom side. In the microfluidic devices prepared in accordance with the methods described herein, the plurality of fluid channels (e.g., grooves and/or indentations) are formed on the first planar surface. In some instances, the fluid channels (e.g., grooves and/or indentations) formed in the first planar surface (prior to bonding to a second substrate) have a bottom and side walls, with the top remaining open. In some instances, the fluid channels (e.g., grooves and/or indentations) formed in the first planar surface (prior to bonding to a second substrate) have a bottom and side walls and the top remaining closed. In some instances, the fluid channels (e.g., grooves and/or indentations) formed in the first planar surfaces (prior to bonding to a second substrate) have only side walls and no top or bottom surface (i.e., the fluid channels span the full thickness of the first substrate.

Fluid channels and chambers may be sealed by placing the first planar surface of the first substrate in contact with, and bonding to, the planar surface of a second substrate to form the channels and/or chambers (e.g., the interior portion) of the device at the interface of these two components. In some instances, after the first substrate is bonded to a second substrate, the structure may further be placed in contact with and bonded to a third substrate. In some instances, the third substrate may be placed in contact with the side of the first substrate that is not in contact with the second substrate. In some instances, the first substrate is placed between the second substrate and the third substrate. In some instances, the second substrate and the third substrate can cover and/or seal the grooves, indentations, or apertures formed on the first substrate to form the channels and/or chambers (e.g., the interior portion) of the device at the interface of these components.

The device can have openings that are oriented such that they are in fluid communication with at least one of the fluid channels and/or fluid chambers formed in the interior portion of the device, thereby forming fluid inlets and/or fluid outlets. In some instances, the openings are formed on the first substrate. In some instances, the openings are formed on the first and the second substrate. In some instances, the openings are formed on the first, the second, and the third substrate. In some instances, the openings are positioned at the top side of the device. In some instances, the openings are positioned at the bottom side of the device. In some instances, the openings are positioned at the first and/or the second ends of the device, and the channels run along the direction from the first end to the second end.

Conditions under which substrates may be bonded together are generally widely understood by those of skill in the art, and such bonding of substrates is generally carried out by any of a variety of methods, the choice of which may vary depending upon the nature of the substrate materials used. For example, thermal bonding of substrates may be applied to a number of substrate materials including, e.g., glass or silica-based substrates, as well as some polymer based-substrates. Such thermal bonding techniques typically comprise mating the substrate surfaces that are to be bonded under conditions of elevated temperature and, in some cases, application of external pressure. The precise temperatures and pressures utilized will generally vary depending upon the nature of the substrate materials used.

For example, for silica-based substrate materials, i.e., glass (borosilicate glass, Pyrex™, soda lime glass, etc.), fused-silica (quartz), and the like, thermal bonding of substrates is typically carried out at temperatures ranging from about 500° C. to about 1400° C., and preferably, from about 500° C. to about 1200° C. For example, soda lime glass is typically bonded at temperatures of around 550° C., whereas borosilicate glass is typically thermally bonded at or near 800° C. Quartz substrates, on the other hand, are typically thermally bonded at temperatures at or near 1200° C. These bonding temperatures are typically achieved by placing the substrates to be bonded into high temperature annealing ovens.

Polymeric substrates that are thermally bonded, on the other hand, will typically utilize lower temperatures and/or pressures than silica-based substrates, in order to prevent excessive melting of the substrates and/or distortion, e.g., flattening of the interior portion of the device (i.e., the fluid channels or chambers). Generally, such elevated temperatures for bonding polymeric substrates will vary from about 80° C. to about 200° C., depending upon the polymeric material used, and will preferably be between about 90° C. and about 150° C. Because of the significantly reduced temperatures required for bonding polymeric substrates, such bonding may typically be carried out without the need for the high temperature ovens used in the bonding of silica-based substrates. This allows incorporation of a heat source within a single integrated bonding system, as described in greater detail below.

Adhesives may also be used to bond substrates together according to well-known methods, which typically comprise applying a layer of adhesive between the substrates that are to be bonded and pressing them together until the adhesive sets. A variety of adhesives may be used in accordance with these methods, including, e.g., UV curable adhesives, that are commercially available. Alternative methods may also be used to bond substrates together in accordance with the present invention, including e.g., acoustic or ultrasonic welding and/or solvent welding of polymeric parts.

Typically, a number of the described microfluidic chips or devices will be manufactured at the same time, e.g., using "wafer-scale" fabrication. For example, polymeric substrates may be stamped or molded in large separable sheets which can then be mated and bonded together. Individual devices or bonded substrates may then be separated from the larger sheet by cutting or dicing. Similarly, for silica-based substrates, individual devices can be fabricated from larger substrate wafers or plates, allowing higher throughput of the manufacturing process. Specifically, a plurality of fluid channel structures can be fabricated on a first substrate wafer or plate, which is then overlaid with and bonded to a second substrate wafer or plate, and optionally further overlaid with and bonded to a third substrate wafer or plate. The individual devices are then segmented from the larger substrates using known methods, such as sawing, scribing and breaking, and the like.

As noted above, the top or second substrate is overlaid upon the bottom or first substrate to seal the various channels and chambers. In carrying out the bonding process according to the methods of the present disclosure, the bonding of the first and second substrates may be carried out using vacuum and/or pressure to maintain the two substrate surfaces in optimal contact. In particular, the bottom substrate may be maintained in optimal contact with the top substrate by, e.g., mating the planar surface of the bottom substrate with the planar surface of the top substrate and applying a vacuum through holes that are disposed through the top substrate. Typically, application of a vacuum to holes in the top substrate is carried out by placing the top substrate on a vacuum chuck, which typically comprises a mounting table or surface, having an integrated vacuum source. In the case of silica-based substrates, the bonded substrates are subjected to elevated temperatures in order to create an initial bond, so that the bonded substrates may then be transferred to the annealing oven, without any shifting relative to each other.

Alternate bonding systems for incorporation with the apparatus described herein include, e.g., adhesive dispensing systems, for applying adhesive layers between the two planar surfaces of the substrates. This may be done by applying the adhesive layer prior to mating the substrates, or by placing an amount of the adhesive at one edge of the adjoining substrates and allowing the wicking action of the two mated substrates to draw the adhesive across the space between the two substrates.

In certain instances, the overall bonding system can include automatable systems for placing the top and bottom substrates on the mounting surface and aligning them for subsequent bonding. Typically, such systems include translation systems for moving either the mounting surface or one or more of the top and bottom substrates relative to each other. For example, robotic systems may be used to lift, translate and place each of the top and bottom substrates upon the mounting table, and within the alignment structures, in turn. Following the bonding process, such systems also can remove the finished product from the mounting surface and transfer these mated substrates to a subsequent operation, e.g., a separation or dicing operation, an annealing oven for silica-based substrates, etc., prior to placing additional substrates thereon for bonding.

In some instances, the manufacturing of the microfluidic chip includes the layering or laminating of two or more layers of substrate, e.g., patterned and non-patterned polymeric sheets, in order to produce the chip. For example, in microfluidic devices, the microfluidic features of the device are typically produced by laser irradiation, etching, or otherwise fabricating features into the surface of a first layer. A second layer is then laminated or bonded to the surface of the first to seal these features and provide the fluidic elements of the device, e.g., the fluid channels.

As noted above, in some instances one or more capillary flow cell devices or microfluidic chips may be mounted in a cartridge chassis to form a capillary flow cell cartridge or microfluidic cartridge. In some instances, the capillary flow cell cartridge or microfluidic cartridge may further comprise additional components that are integrated with the cartridge to provide enhanced performance for specific applications. Examples of additional components that may be integrated into the cartridge include, but are not limited to, adapters or connectors for making fluidic connections to other components of the system, fluid flow control components (e.g., miniature valves, miniature pumps, mixing manifolds, etc.), temperature control components (e.g., resistive heating elements, metal plates that serve as heat sources or sinks, piezoelectric (Peltier) devices for heating or cooling, temperature sensors), or optical components (e.g., optical lenses, windows, filters, mirrors, prisms, fiber optics, and/or light-emitting diodes (LEDs) or other miniature light sources that may collectively be used to facilitate spectroscopic measurements and/or imaging of one or more capillary or fluid flow channels.

The fluidic adaptors, cartridge chassis, and other cartridge components may be attached to the capillaries, capillary flow cell device(s), microfluidic chip(s) (or fluid channels within the chip) using any of a variety of techniques known to those of skill in the art including, but not limited to, press fit, adhesive bonding, solvent bonding, laser welding, etc., or any combination thereof. In some instances, the inlet(s) and/or outlet(s) of the microfluidic channels in the microfluidic chip are apertures on the top surface of the chip, and the fluidic adaptors can be attached or coupled to the inlet(s) and/or outlet(s) of the microfluidic channels within the chip. In some instances, the cartridge may comprise additional adapters (i.e., in addition to the fluidic adapters) that mate with the chip and/or fluidic adapters and help to position the chip within the cartridge. These adapters may be constructed using the same fabrication techniques and materials as those outlined above for the fluidic adapters.

The cartridge chassis (or "housing") may be fabricated from metal and/or polymer materials such as aluminum, anodized aluminum, polycarbonate (PC), acrylic (PMMA), or Ultem (PEI), while other materials are also consistent with the present disclosure. A housing may be fabricated using CNC machining and/or molding techniques, and designed so that one, two, or more than two capillaries or microfluidic chips are constrained by the chassis in a fixed orientation to create one or more independent flow channels. The capillaries or chips may be mounted in the chassis using, e.g., a compression fit design, or by mating with compressible adapters made of silicone or a fluoroelastomer. In some instances, two or more components of the cartridge chassis (e.g., an upper half and a lower half) are assembled using, e.g., screws, clips, clamps, or other fasteners so that the two halves are separable. In some instances, two or more components of the cartridge chassis are assembled using, e.g., adhesives, solvent bonding, or laser welding so that the two or more components are permanently attached.

Flow Cell Surface Coatings:

In some instances, one or more interior surfaces of the capillary lumens or microfluidic channels in the disclosed flow cell devices may be coated using any of a variety of surface modification techniques or polymer coatings known to those of skill in the art. In some instances, the coatings may be formulated to increase or maximize the number of available binding sites (e.g., tethered oligonucleotide adapter/primer sequences) on the one or more interior surfaces to increase or maximize a foreground signal, e.g., a fluorescence signal arising from labeled nucleic acid molecules hybridized to tethered oligonucleotide adapter/primer sequences. In some instances, the coatings may be formulated to decrease or minimize nonspecific binding of fluorophores and other small molecules, or labeled or unlabeled nucleotides, proteins, enzymes, antibodies, oligonucleotides, or nucleic acid molecules (e.g., DNA, RNA, etc.), in order to decrease or minimize a background signal, e.g., background fluorescence arising from the nonspecific binding of labeled biomolecules or from autofluorescence of a sample support structure. The combination of increased foreground signal and reduced background signal that may be achieved in some instances through the use of the disclosed coatings may thus provide improved signal-to-noise ratio (SNR) in spectroscopic measurements or improved contrast-to-noise ratio (CNR) in imaging methods.

As will be discussed in more detail below, the disclosed hydrophilic, polymer-coated flow cell devices, optionally used in combination with the improved hybridization and/or amplification protocols, yield solid-phase bioassay reactions that exhibit: (i) negligible non-specific binding of protein and other reaction components (thus reducing or minimizing substrate background), (ii) negligible non-specific nucleic acid amplification product, and (iii) provide tunable nucleic acid amplification reactions. Although described herein primarily in the context of nucleic acid hybridization, amplification, and sequencing assays, it will be understood by those of skill in the art that the disclosed low-binding supports may be used in any of a variety of other bioassay formats including, but not limited to, sandwich immunoassays, enzyme-linked immunosorbent assays (ELISAs), etc.

In a preferred aspect, one or more layers of a coating material may be applied to the interior flow cell device surfaces, where the number of layers and/or the material composition of each layer is chosen to adjust one or more surface properties of the interior flow cell device surfaces, as noted in U.S. patent application Ser. No. 16/363,842. Examples of surface properties that may be adjusted include, but are not limited to, surface hydrophilicity/hydrophobicity, overall coating thickness, the surface density of chemically-reactive functional groups, the surface density of grafted linker molecules or oligonucleotide adapters/primers, etc. In some preferred applications, one or more surface properties of the capillary or channel lumen are adjusted to, for example, (i) provide for very low non-specific binding of proteins, oligonucleotides, fluorophores, and other molecular components of chemical or biological analysis applications, including solid-phase nucleic acid amplification and/or sequencing applications, (ii) provide for improved solid-phase nucleic acid hybridization specificity and efficiency, and (iii) provide for improved solid-phase nucleic acid amplification rate, specificity, and efficiency.

Any of a variety of molecules known to those of skill in the art including, but not limited to, silanes, amino acids, peptides, nucleotides, oligonucleotides, other monomers or polymers, or combinations thereof may be used in creating the one or more chemically-modified layers on the interior flow cell device surfaces, where the choice of components used may be varied to alter one or more properties of the support surface, e.g., the surface density of functional groups and/or tethered oligonucleotide primers, the hydrophilicity/hydrophobicity of the support surface, or the three three-dimensional nature (i.e., "thickness") of the support surface.

The attachment chemistry used to graft a first chemically-modified layer to an interior surface of the flow cell (capillary or channel) will generally be dependent on both the material from which the flow cell device is fabricated and the chemical nature of the layer. In some instances, the first layer may be covalently attached to the interior flow cell device surfaces. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the support surface. For example, glass or silicon surfaces may be acid-washed using a Piranha solution (a mixture of sulfuric acid ($H_2SO_4$) and hydrogen peroxide ($H_2O_2$)) and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding support surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Examples of preferred polymers that may be used to create one or more layers of low non-specific binding material in any of the disclosed support surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the support surface and/or to cross-link the layers to each other include, but are not limited to, biotin-streptavidin interactions (or variations thereof), His tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

In some instances, the number of layers of polymer or other chemical layers on the interior flow cell device surfaces may range from 1 to about 10, or greater than 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, the one or more layers may all comprise the same material. In some instances, each layer may comprise a different material. In some instances, a plurality of layers may comprise a plurality of materials.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches. Molecules often exhibit a 'power of 2' number of branches, such as 2, 4, 8, 16, 32, 64, or 128 branches.

In some instances, the resulting functional end groups distal from the surface following the deposition of one or more layers, e.g., polymer layers can include, but are not limited to, biotin, methoxy ether, carboxylate, amine, NHS ester, maleimide, and bis-silane.

Linear, branched, or multi-branched polymers used to create one or more layers of any of the multi-layered surfaces disclosed herein may have a molecular weight of at least 500 Daltons, at least 1,000 Daltons, at least 1,500 Daltons, at least 2,000 Daltons, at least 2,500 Daltons, at least 3,000 Daltons, at least 3,500 Daltons, at least 4,000 Daltons, at least 4,500 Daltons, at least 5,000 Daltons, at least 7,500 Daltons, at least 10,000 Daltons, at least 12,500 Daltons, at least 15,000 Daltons, at least 17,500 Daltons, at least 20,000 Daltons, at least 25,000 Daltons, at least 30,000 Daltons, at least 35,000 Daltons, at least 40,000 Daltons, at least 45,000 Daltons, or at least 50,000 Daltons. In some instances, the linear, branched, or multi-branched polymers used to create one or more layers of any of the multi-layered surfaces disclosed herein may have a molecular weight of at most 50,000 Daltons, at most 45,000 Daltons, at most 40,000 Daltons, at most 35,000 Daltons, at most 30,000 Daltons, at most 25,000 Daltons, at most 20,000 Daltons, at most 17,500 Daltons, at most 15,000 Daltons, at most 12,500 Daltons, at most 10,000 Daltons, at most 7,500 Daltons, at most 5,000 Daltons, at most 4,500 Daltons, at most 4,000 Daltons, at most 3,500 Daltons, at most 3,000 Daltons, at most 2,500 Daltons, at most 2,000 Daltons, at most 1,500 Daltons, at most 1,000 Daltons, or at most 500 Daltons. Any of the lower and upper values described in this paragraph may be combined to form a range included within the present disclosure, for example, in some instances the molecular weight of linear, branched, or multi-branched polymers used to create one or more layers of any of the multi-layered surfaces disclosed herein may range from about 1,500 Daltons to about 20,000 Daltons. Those of skill in the art will recognize that the molecular weight of linear, branched, or multi-branched polymers used to create one or more layers of any of the multi-layered surfaces disclosed herein may have any value within this range, e.g., about 1,260 Daltons.

In some instances, two or more layers may be covalently coupled to each other or internally cross-linked to improve the stability of the resulting surface. In some instances, e.g., wherein at least one layer of a multi-layered surface comprises a branched polymer, the number of covalent bonds between a branched polymer molecule of the layer being deposited and molecules of the previous layer may range from about one covalent linkage per molecule and about 32 covalent linkages per molecule. In some instances, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32, or more than 32 covalent linkages per molecule. In some instances, the number of covalent bonds between a branched polymer molecule of the new layer and molecules of the previous layer may be at most 32, at most 30, at most 28, at most 26, at most 24, at most 22, at most 20, at most 18, at most 16, at most 14, at most 12, at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of covalent bonds between a branched polymer molecule of the new layer and molecules of the previous layer may range from about 4 to about 16. Those of skill in the art will recognize that the number of covalent bonds between a branched polymer molecule of the new layer and molecules of the previous layer may have any value within this range, e.g., about 11 in some instances, or an average number of about 4.6 in other instances.

Any reactive functional groups that remain following the coupling of a material layer to the interior flow cell device surfaces may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

In order to scale binding site surface density, e.g., oligonucleotide adapter/primer surface density, and add additional dimensionality to hydrophilic or amphoteric surfaces, substrates comprising multi-layer coatings of PEG and other hydrophilic polymers have been developed. By using hydrophilic and amphoteric surface layering approaches that include, but are not limited to, the polymer/co-polymer materials described below, it is possible to increase adapter/primer loading density on the surface significantly. Traditional PEG coating approaches use monolayer primer deposition, which has been tested and reported for single molecule sequencing applications but do not yield high copy numbers for nucleic acid amplification applications. As described herein, "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, polyacrylamide, polyester, dextran, poly-lysine, and copolymers of poly-lysine and PEG.

In some instances, the different layers may be cross-linked to each other through any of a variety of conjugation reactions including, but not limited to, biotin-streptavidin binding, azide-alkyne click reaction, amine-NETS ester reaction, thiol-maleimide reaction, and ionic interactions between positively charged polymer and negatively charged polymer. In some instances, high adapter/primer density materials may be constructed in solution and subsequently layered onto the surface in multiple steps.

Exemplary PEG multilayers include PEG (8 arm, 16 arm, 8 arm) on PEG-amine-APTES. Similar concentrations were observed for 3-layer multi-arm PEG (8 arm, 16 arm, 8 arm) and (8 arm, 64 arm, 8 arm) on PEG-amine-APTES exposed to 8 uM primer, and 3-layer multi-arm PEG (8 arm, 8 arm, 8 arm) using star-shape PEG-amine to replace 16 arm and 64 arm. PEG multilayers having comparable first, second and third PEG layers are also contemplated.

In some instances, the resultant surface density of binding sites on the interior flow cell device surfaces, e.g., oligonucleotide adapter/primer surface densities, may range from about 100 primer molecules per $\mu m^2$ to about 1,000,000 primer molecules per $\mu m^2$. In some instances, the surface density of binding sites may be at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per $\mu m^2$. In some instances, the surface density of binding sites may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, or at most 100 molecules per $\mu m^2$. Any of the lower and upper values described in this paragraph may be combined to form a range included within the present disclosure, for example, in some instances the surface density of binding sites may range from about 10,000 molecules per $\mu m^2$ to about 100,000 molecules per $\mu m^2$. Those of skill in the art will recognize that the surface density of binding sites may have any value within this range, e.g., about 3,800 molecules per $\mu m^2$ in some instances, or about 455,000 molecules per $\mu m^2$ in other instances. In some instances, as will be discussed further below for nucleic acid sequencing applications, the surface density of template library nucleic acid sequences (e.g., sample DNA molecules) initially hybridized to adapter or primer sequences tethered to the interior flow cell device surfaces may be less than or equal to that indicated for the surface density of binding sites. In some instances, as will also be discussed further below, the surface density of clonally-amplified template library nucleic acid sequences hybridized to adapter or primer sequences on the interior flow cell device surfaces may span the same range or a different range as that indicated for the surface density of tethered oligonucleotide adapters or primers.

Local surface densities of binding sites on the interior flow cell device surfaces as listed above do not preclude variation in density across a surface, such that a surface may comprise a region having a binding site density of, for example, 500,000/um$^2$, while also comprising at least a second region having a substantially different local surface density.

In some instances, capture probes, e.g., oligonucleotide primers with different base sequences and base modifications (or other biomolecules, e.g., enzymes or antibodies) may be tethered to one or more layers of the resulting surface at various surface densities. In some instances, for example, both surface functional group density and the capture probe concentration used for coupling may be varied to target a certain capture probe surface density range. Additionally, capture probe surface density may be controlled by diluting capture probes with other "inert" molecules that carry the same reactive functional group for coupling to the surface. For example, amine-labeled oligonucleotide probes can be diluted with amine-labeled polyethylene glycol in a reaction with an NETS-ester coated surface to reduce the final primer density. In the case of oligonucleotide adapters/primers, probe sequences with different lengths of linker between the hybridization region and the surface attachment functional group may also be applied to vary surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure or estimate the capture probe surface density, fluorescently-labeled capture probes may be tethered to the surface and a fluorescence reading then compared with that for a calibration solution comprising a known concentration of the fluorophore.

In some instances, the degree of hydrophilicity (or "wettability" with aqueous solutions) of the disclosed support surfaces, e.g., interior flow cell device surfaces, may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surfaced disclosed herein may range from about 0 degrees to about 50 degrees. In some instances, the water contact angle for the hydrophilic, low-binding support surfaced disclosed herein may no more than 50 degrees, 45 degrees, 40 degrees, 35 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than any value within this range, e.g., no more than 40 degrees. Those of skill in the art will realize that a given hydrophilic, low-binding support surface of the present disclosure may exhibit a water contact angle having a value of anywhere within this range, e.g., about 27 degrees. In some instances, the disclosed low nonspecific binding surfaces have a water contact angle of less than 45 degrees. In some instances, the disclosed low nonspecific binding surfaces have a water contact angle of less than 35 degrees.

As noted, the hydrophilic coated interior flow cell device surfaces of the present disclosure exhibit reduce non-specific binding of proteins, nucleic acids, fluorophores, and other components of biological and biochemical assay methods. The degree of non-specific binding exhibited by a given support surface, e.g., an interior flow cell device surface, may be assessed either qualitatively or quantitatively. For example, in some instances, exposure of the surface to fluorescent dyes (e.g., cyanine dye 3 (Cy3), cyanine dye 5 (Cy5), etc.), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different support surface formulations of the present disclosure.

In some instances, the degree of non-specific binding exhibited by the disclosed low nonspecific binding support surfaces may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of non-specific binding exhibited by a given support surface formulation may thus be assessed in terms of the number of non-specifically bound protein molecules (or other molecules) per unit area. In some instances, the low nonspecific binding supports of the present disclosure may exhibit nonspecific protein binding (or nonspecific binding of other specified molecules, e.g., cyanine dye 3 (Cy3) of less than 0.001 molecule per µm$^2$, less than 0.01 molecule per µm$^2$, less than 0.1 molecule per µm², less than 0.25 molecule per µm², less than 0.5 molecule per µm², less than 1 molecule per µm², less than 10 molecules per µm², less than 100 molecules per µm², or less than 1,000 molecules per µm². Those of skill in the art will realize that a given support surface of the present disclosure may exhibit nonspecific binding falling anywhere within this range, for example, of less than 86 molecules per µm². For example, some modified surfaces disclosed herein exhibit nonspecific protein binding of less than 0.5 molecule/µm² following contact with a 1 uM solution of Cy3 labeled streptavidin (GE Amersham) in phosphate buffered saline (PBS) buffer for 15 minutes, followed by 3 rinses with deionized water. Some modified surfaces disclosed herein exhibit nonspecific binding of Cy3 dye molecules of less than 0.25 molecules per µm2. In independent nonspecific binding assays, 1 µM labeled Cy3 SA (ThermoFisher), 1 uM Cy5 SA dye (ThermoFisher), 10 uM Aminoallyl-dUTP—ATTO-647N (Jena Biosciences), 10 uM Aminoallyl-dUTP—ATTO-Rho11 (Jena Biosciences), 10 uM Aminoallyl-dUTP—ATTO-Rho11 (Jena Biosciences), 10 uM 7-Propargylamino-7-deaza-dGTP—Cy5 (Jena Biosciences, and 10 uM 7-Propargylamino-7-deaza-dGTP—Cy3 (Jena Biosciences) were incubated on the low nonspecific binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon(GE Healthcare Lifesciences, Pittsburgh, Pa.) instrument using the Cy3, AF555, or Cy5 filter sets (according to dye test performed) as specified by the manufacturer at a PMT gain setting of 800 and resolution of 50-100 µm. For higher resolution imaging, images were collected on an Olympus IX83 microscope (Olympus Corp., Center Valley, Pa.) with a total internal reflectance fluorescence (TIRF) objective (20×, 0.75 NA or 100×, 1.5 NA, Olympus), an sCMOS Andor camera (Zyla 4.2. Dichroic mirrors were purchased from Semrock (IDEX Health & Science, LLC, Rochester, N.Y.), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per µm².

In some instances, the coated flow cell device surfaces disclosed herein may exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

In some instances, one or more surface modification and/or polymer layers may be applied to the interior flow cell device surfaces using a technique such as chemical vapor deposition (CVD). In some instances, one or more surface modification and/or polymer layers may be applied to the interior flow cell device surfaces by flowing one or more appropriate chemical coupling or coating reagents through the capillaries or fluid channels prior to use for their intended application. In some instances, one or more coating reagents may be added to a buffer used, e.g., a nucleic acid hybridization, amplification reaction, and/or sequencing reaction buffer to provide for dynamic coating of the interior flow cell device surfaces.

In some instances, the chemical modification layers may be applied uniformly across the surface of the substrate or support structure. Alternately, the surface of the substrate or support structure may be non-uniformly distributed or patterned, such that the chemical modification layers are confined to one or more discrete regions of the substrate. For example, the substrate surface may be patterned using photolithographic techniques to create an ordered array or random pattern of chemically-modified regions on the surface. Alternately or in combination, the substrate surface may be patterned using, e.g., contact printing and/or ink-jet printing techniques. In some instances, an ordered array or random patter of chemically-modified discrete regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions, or any intermediate number of discrete regions spanned by the range herein.

In some instances, fluorescence images of the disclosed low nonspecific binding surfaces when used, e.g., in nucleic acid hybridization or amplification applications to create clusters of hybridized or clonally-amplified nucleic acid molecules (e.g., "discrete regions" that have been directly or indirectly labeled with a fluorophore) exhibit contrast-to-noise ratios (CNRs) of at least 5, 10, 20, 30, 40, 50, 60, 70, 80, 90, 100, 110, 120, 130, 140, 150, 160, 170, 180, 190, 20, 210, 220, 230, 240, 250, or greater than 250 when the nucleic acid molecules are labeled with Cy3 and the images are acquired using an Olympus IX83 inverted fluorescence microscope equipped with a 20×, 0.75 NA objective, a 532 nm light source, a bandpass and dichroic mirror filter set adapted or optimized for 532 nm long-pass excitation and Cy3 fluorescence emission filter, a Semrock 532 nm dichroic reflector, and a camera (Andor sCMOS, Zyla 4.2) where the excitation light intensity is adjusted to avoid signal saturation, and the surface is immersed in a buffer (e.g., 25 mM ACES, pH 7.4 buffer) while the image is acquired. As used herein, contrast-to-noise ratio (CNR) is calculated as:

$$CNR=(S-B)/\text{Noise}$$

where S=foreground signal (e.g., the fluorescence signal as measured in the image that arises from a labeled nucleic acid colony or cluster on a sample support surface), B=background signal (where $B=B_{inter}+B_{intra}$), $B_{inter}$=background signal measured at a location on the sample support surface that is between labeled nucleic acid colonies or clusters, $B_{intra}$=background signal measured at the location of a nucleic acid colony or cluster (determined, e.g., by contacting the sample support surface with a labeled, non-complementary oligonucleotide and measuring the resulting fluorescence), and Noise=the signal noise. The contrast-to-noise ratio (CNR) of images of sequencing surfaces, for example, provides a key metric in assessing nucleic acid amplification specificity and non-specific binding on the support. While signal-to-noise ratio (SNR) is often considered to be a benchmark of overall signal quality, it can be shown that improved CNR can provide a significant advantage over SNR as a benchmark for signal quality in imaging applications that require rapid image capture (e.g., nucleic acid sequencing applications for which cycle times must be minimized).

In some instances, polymer-coated sample support structures, e.g., interior flow cell device surfaces comprising the disclosed hydrophilic polymer coatings, may exhibit improved stability to repetitive exposure to solvents, changes in temperature, changes in pH, or long-term storage.

Fluidics systems and fluid flow control modules: in some implementations, the disclosed imaging and/or analysis systems may provide fluid flow control capability for delivering samples or reagents to the one or more flow cell devices or flow cell cartridges (e.g., single capillary flow cell device or microfluidic channel flow cell device) connected to the system. Reagents and buffers may be stored in bottles, reagent and buffer cartridges, or other suitable containers that are connected to the flow cell inlets by means of tubing and valve manifolds. The disclosed systems may also include processed sample and waste reservoirs in the form of bottles, cartridges, or other suitable containers for collecting fluids downstream of the capillary flow cell devices or capillary flow cell cartridges. In some embodiments, the fluid flow (or "fluidics") control module may provide programmable switching of flow between different sources, e.g. sample or reagent reservoirs or bottles located in the instrument, and the inlet(s) to a central region (e.g., a capillary flow cell or microfluidic device, or a large fluid chamber such as a large fluid chamber within a microfluidic device). In some instances, the fluid flow control module may provide programmable switching of flow between outlet(s) from the central region (e.g., a capillary flow cell or microfluidic device) and different collection points, e.g., processed sample reservoirs, waste reservoirs, etc., connected to the system. In some instances, samples, reagents, and/or buffers may be stored within reservoirs that are integrated into the flow cell cartridge or microfluidic cartridge itself. In some instances, processed samples, spent reagents, and/or used buffers may be stored within reservoirs that are integrated into the flow cell cartridge or microfluidic device cartridge itself.

In some implementations, one or more fluid flow control modules may be configured to control the delivery of fluids to one or more capillary flow cells, capillary flow cell cartridges, microfluidic devices, microfluidic cartridges, or any combination thereof. In some instances, the one or more fluidics controllers may be configured to control volumetric flow rates for one or more fluids or reagents, linear flow velocities for one or more fluids or reagents, mixing ratios for one or more fluids or reagents, or any combination thereof. Control of fluid flow through the disclosed systems will typically be performed using pumps (or other fluid actuation mechanisms) and valves (e.g., programmable pumps and valves). Examples of suitable pumps include, but are not limited to, syringe pumps, programmable syringe pumps, peristaltic pumps, diaphragm pumps, and the like. Examples of suitable valves include, but are not limited to, check valves, electromechanical two-way or three-way valves, pneumatic two-way and three-way valves, and the like. In some instances, fluid flow through the system may be controlled by means of applying positive pneumatic pressure to one or more inlets of the reagent and buffer containers, or to inlets incorporated into flow cell cartridge(s) (e.g., capillary flow cell or microfluidic cartridges). In some embodiments, fluid flow through the system may be controlled by means of drawing a vacuum at one or more outlets of waste reservoir(s), or at one or more outlets incorporated into flow cell cartridge(s) (e.g., capillary flow cell or microfluidic cartridges).

In some instances, different modes of fluid flow control are utilized at different points in an assay or analysis procedure, e.g. forward flow (relative to the inlet and outlet for a given capillary flow cell device), reverse flow, oscillating or pulsatile flow, or combinations thereof. In some applications, oscillating or pulsatile flow may be applied, for example, during assay wash/rinse steps to facilitate complete and efficient exchange of fluids within the one or more flow cell devices or flow cell cartridges (e.g., capillary flow cell devices or cartridges, and microfluidic devices or cartridges).

Similarly, in some cases different fluid flow rates may be utilized at different locations within a flow cell device or at different points in the assay or analysis process workflow, for example, in some instances, the volumetric flow rate may vary from −100 ml/sec to +100 ml/sec. In some embodiment, the absolute value of the volumetric flow rate may be at least 0.001 ml/sec, at least 0.01 ml/sec, at least 0.1 ml/sec, at least 1 ml/sec, at least 10 ml/sec, or at least 100 ml/sec. In some embodiments, the absolute value of the volumetric flow rate may be at most 100 ml/sec, at most 10 ml/sec, at most 1 ml/sec, at most 0.1 ml/sec, at most 0.01 ml/sec, or at most 0.001 ml/sec. The volumetric flow rate at a given location with the flow cell device or at a given point in time may have any value within this range, e.g. a forward flow rate of 2.5 ml/sec, a reverse flow rate of −0.05 ml/sec, or a value of 0 ml/sec (i.e., stopped flow).

In some implementations, the fluidics system may be designed to minimize the consumption of key reagents (e.g., expensive reagents) required for performing, e.g., genomic analysis applications. For example, in some implementations the disclosed fluidics systems may comprise a first reservoir housing a first reagent or solution, a second reservoir housing a second reagent or solution, and a central region, e.g., a central capillary flow cell or microfluidic device, where an outlet from the first reservoir and an outlet from the second reservoir are fluidically coupled to an inlet of the central capillary flow cell or microfluidic device through at least one valve such that the volume of the first reagent or solution flowing per unit time from the outlet of the first reservoir to the inlet of the central capillary flow cell or microfluidic device is less than the volume of the second reagent or solution flowing per unit time from the outlet of the second reservoir to the inlet of the central region. In some implementations, the first reservoir and second reservoir may be integrated into a capillary flow cell cartridge or microfluidic cartridge. In some instances, the at least one valve may also be integrated into the capillary flow cell cartridge or microfluidic cartridge.

In some instances, the first reservoir is fluidically coupled to the central capillary flow cell or microfluidic device through a first valve, and the second reservoir is fluidically coupled to the central capillary flow cell or microfluidic device through a second valve. In some instances, the first and/or second valves may be, e.g., a diaphragm valve, pinch valve, gate valve, or other suitable valve. In some instances, the first reservoir is positioned in close proximity to the inlet of the central capillary flow cell or microfluidic device to reduce dead volume for delivery of the first reagent solution. In some instances, the first reservoir is placed in closer proximity to the inlet of the central capillary flow cell or microfluidic device than is the second reservoir. In some instances, the first reservoir is positioned in close proximity to the second valve so as to reduce the dead volume for delivery of the first reagent relative to that for delivery of a plurality of "second" reagents (e.g., two, three, four, five, or six or more "second" reagents) from a plurality of "second" reservoirs (e.g., two, three, four, five, or six or more "second" reservoirs).

The first and second reservoirs described above may be used to house the same or different reagents or solutions. In some instances, the first reagent that is housed in the first reservoir is different from the second reagent that is housed in the second reservoir, and the second reagent comprises at least one reagent that is used in common by a plurality of reactions occurring in the central a central capillary flow cell or microfluidic device. In some instances, e.g., in fluidics systems configured for performing nucleic acid sequencing chemistry within the central capillary flow cell or microfluidic device, the first reagent comprises at least one reagent selected from the group consisting of a polymerase, nucleotide, and a nucleotide analog. In some instances, the second reagent comprises a low-cost reagent, e.g., a solvent.

In some instances, the interior volume of the central region, e.g., a central capillary flow cell cartridge, or microfluidic device comprising one or more fluid channels or fluid chambers, can be adjusted based on the specific application to be performed, e.g., nucleic acid sequencing. In some embodiments, the central region comprises an interior volume suitable for sequencing a eukaryotic genome. In some embodiments, the central region comprises an interior volume suitable for sequencing a prokaryotic genome. In some embodiments, the central region comprises an interior volume suitable for sequencing a viral genome. In some embodiments, the central region comprises an interior volume suitable for sequencing a transcriptome. For example, in some embodiments, the interior volume of the central region may comprise a volume of less than 0.05 µl, between 0.05 µl and 0.1 µl, between 0.05 µl and 0.2 µl, between 0.05 µl and 0.5 µl, between 0.05 µl and 0.8 µl, between 0.05 µl and 1 µl, between 0.05 µl and 1.2 µl, between 0.05 µl and 1.5 µl, between 0.1 µl and 1.5 µl, between 0.2 µl and 1.5 µl, between 0.5 µl and 1.5 µl, between 0.8 µl and 1.5 µl, between 1 µl and 1.5 µl, between 1.2 µl and 1.5 µl, or greater than 1.5 µl, or a range defined by any two of the foregoing. In some embodiments, the interior volume of the central region may comprise a volume of less than 0.5 µl, between 0.5 µl and 1 µl, between 0.5 µl and 2 µl, between 0.5 µl and 5 µl, between 0.5 µl and 8 µl, between 0.5 µl and 10 µl, between 0.5 µl and 12 µl, between 0.5 µl and between 1 µl and 15 µl, between 2 µl and 15 µl, between 5 µl and 15 µl, between 8 µl and 15 µl, between 10 µl and 15 µl, between 12 µl and 15 or greater than 15 or a range defined by any two of the foregoing. In some embodiments, the interior volume of the central region may comprise a volume of less than 5 µl, between 5 µl and 10 µl, between 5 µl and 20 µl, between 5 µl and 500 µl, between 5 µl and 80 µl, between 5 µl and 100 µl, between 5 µl and 120 µl, between 5 µl and 150 µl, between 10 µl and 150 µl, between 20 µl and 150 µl, between 50 µl and 150 µl, between 80 µl and 150 µl, between 100 µl and 150 µl, between 120 µl and 150 or greater than 150 or a range defined by any two of the foregoing. In some embodiments, the interior volume of the central region may comprise a volume of less than 50 µl, between 50 µl and 100 µl, between 50 µl and 200 between 50 µl and 500 µl, between 50 µl and 800 µl, between 50 µl and 1000 µl, between 50 µl and 1200 µl, between 50 µl and 1500 µl, between 100 µl and 1500 µl, between 200 µl and 1500 µl, between 500 µl and 1500 µl, between 800 µl and 1500 µl, between 1000 µl and 1500 µl, between 1200 µl and 1500 µl, or greater than 1500 or a range defined by any two of the foregoing. In some embodiments, the interior volume of the central region may comprise a volume of less than 500 µl, between 500 µl and 1000 µl, between 500 µl and 2000 µl, between 500 µl and 5 ml, between 500 µl and 8 ml, between 500 µl and 10 ml, between 500 µl and 12 ml, between 500 µl and 15 ml, between 1 ml and 15 ml, between 2 ml and 15 ml, between 5 ml and 15 ml, between 8 ml and 15 ml, between 10 ml and 15 ml, between 12 ml and 15 ml, or greater than 15 ml, or a range defined by any two of the foregoing. In some embodiments, the interior volume of the central region may comprise a volume of less than 5 ml, between 5 ml and 10 ml, between 5 ml and 20 ml, between 5 ml and 50 ml, between 5 ml and 80 ml, between 5 ml and 100 ml, between 5 ml and 120 ml, between 5 ml and 150 ml, between 10 ml and 150 ml, between 20 ml and 150 ml, between 50 ml and 150 ml, between 80 ml and 150 ml, between 100 ml and 150 ml, between 120 ml and 150 ml, or greater than 150 ml, or a range defined by any two of the foregoing. In some embodiments, the systems described herein comprise an array or collection of flow cell devices or systems comprising multiple discrete capillaries, microfluidic channels, fluidic channels, chambers, or lumenal regions, wherein the combined interior volume is, comprises, or includes one or more of the values within a range disclosed herein.

In some instances, the ratio of volumetric flow rate for the delivery of the first reagent to the central capillary flow cell or microfluidic device to that for delivery of the second reagent to the central capillary flow cell or microfluidic device may be less than 1:20, less than 1:16, least than 1:12, less than 1:10, less than 1:8, less than 1:6, or less than 1:2. In some instances, the ratio of volumetric flow rate for the delivery of the first reagent to the central capillary flow cell or microfluidic device to that for delivery of the second reagent to the central capillary flow cell or microfluidic device may have any value with the range spanned by these values, e.g., less than 1:15.

As noted, the flow cell devices and/or fluidics systems disclosed herein may be configured to achieve a more efficient use of the reagents than that achieved by, e.g., other sequencing devices and systems, particularly for the costly reagents used in a variety of sequencing chemistry steps. In some instances, the first reagent comprises a reagent that is more expensive than the second reagent. In some instances, the first reagent comprises a reaction-specific reagent and the second reagent comprises a nonspecific reagent common to all reactions performed in the central capillary flow cell or microfluidic device region, and wherein the reaction specific reagent is more expensive than the nonspecific reagent.

In some instances, utilization of the flow cell devices and/or fluidic systems disclosed herein may convey advantages in terms of reduced consumption of costly reagents. In some instances, for example, utilization of the flow cell devices and/or fluidic systems disclosed herein may results in at least a 5%, at least a 7.5%, at least a 10%, at least a 12.5%, at least a 15%, at least a 17.5%, at least a 20%, at least a 22.5%, at least a 25%, at least a 30%, at least a 35%, at least a 40%, at least a 45%, or at least a 50% reduction in reagent consumption compared to the reagent consumption encountered when operating, e.g., current commercially-available nucleic acid sequencing systems.

Figure 31:
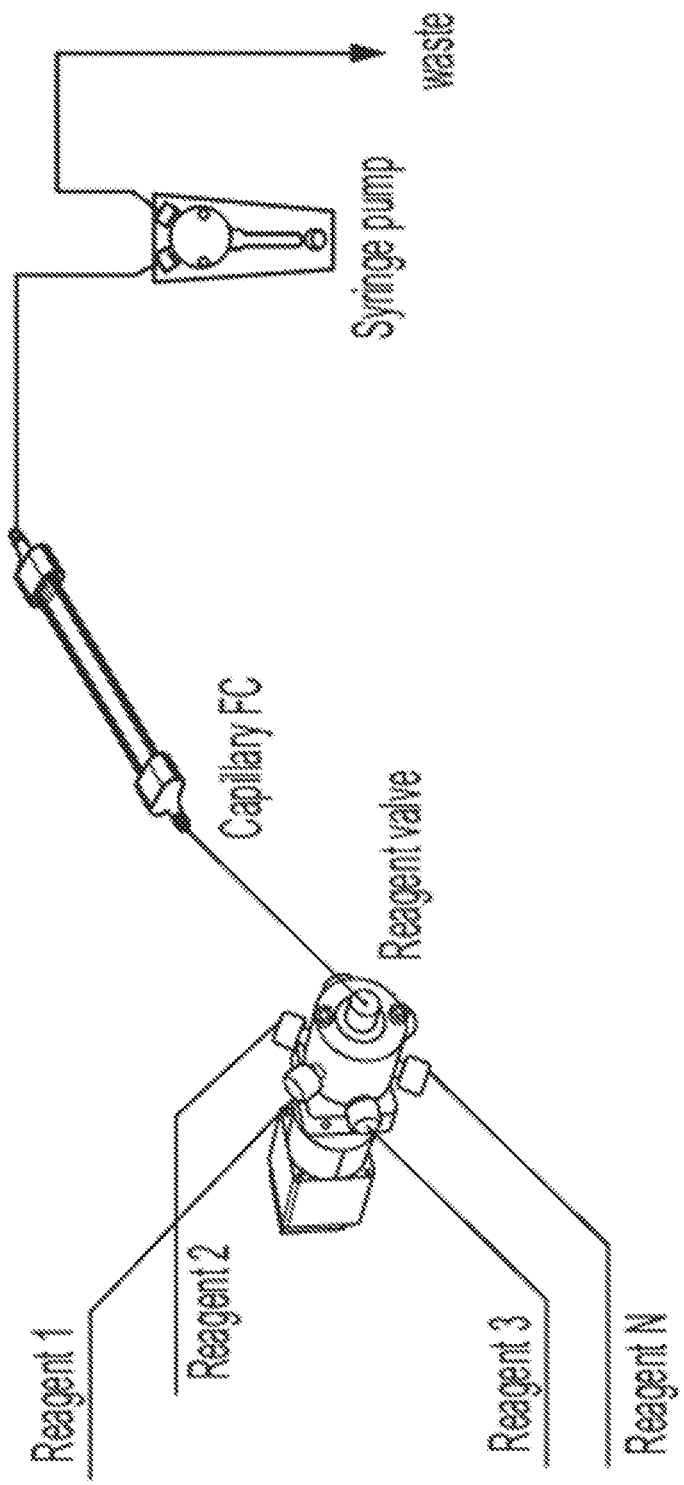
FIG. 31 illustrates one non-limiting example of a system comprising a single capillary flow cell connected to various fluid flow control components, where the single capillary is compatible with mounting on a microscope stage or in a custom imaging instrument for use in various imaging applications.

FIG. 31 illustrates a non-limiting example of a simple fluidics system comprising a single capillary flow cell connected to various fluid flow control components, where the single capillary is optically accessible and compatible with mounting on a microscope stage or in a custom imaging instrument for use in various imaging applications. A plurality of reagent reservoirs is fluidically-coupled with the inlet end of the single capillary flow cell device, where the reagent flowing through the capillary at any given point in time is controlled by means of a programmable rotary valve that allows the user to control the timing and duration of reagent flow. In this non-limiting example, fluid flow is controlled by means of a programmable syringe pump that provides precise control and timing of volumetric fluid flow and fluid flow velocity.

Figure 32:
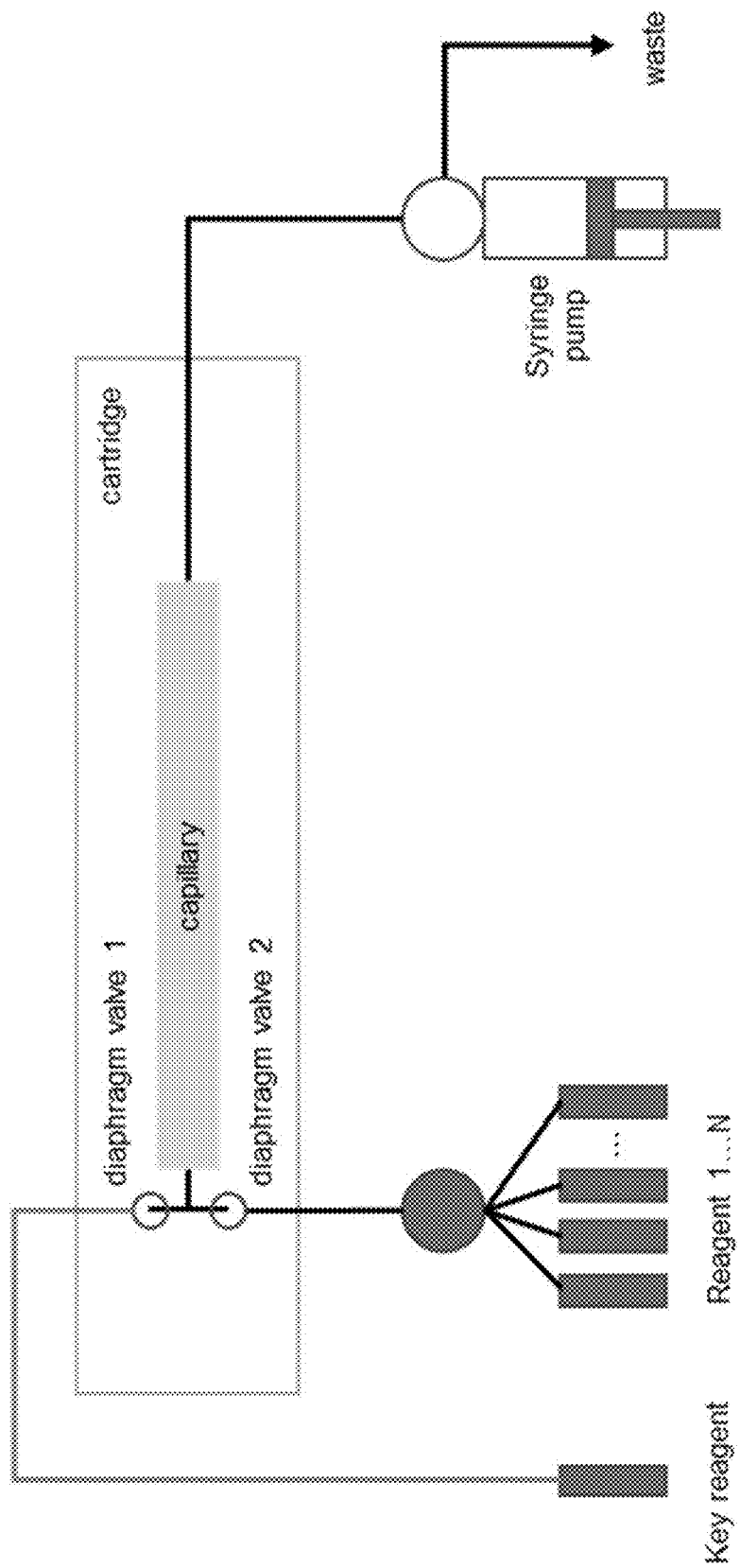
FIG. 32 illustrates one non-limiting example of a system that comprises a capillary flow cell cartridge having integrated diaphragm valves to reduce or minimize dead volume and conserve certain key reagents.

FIG. 32 illustrates a non-limiting example of a fluidics system that comprises a capillary flow cell cartridge having integrated diaphragm valves to reduce or minimize dead volume and conserve certain key reagents. The integration of miniature diaphragm valves into the cartridge allows the valve to be positioned in close proximity to the inlet of the capillary, thereby reducing or minimizing dead volume within the device and reducing the consumption of costly reagents. The integration of valves and other fluid control components within the capillary flow cell cartridge also allows greater fluid flow control functionality to be incorporated into the cartridge design.

Figure 33:
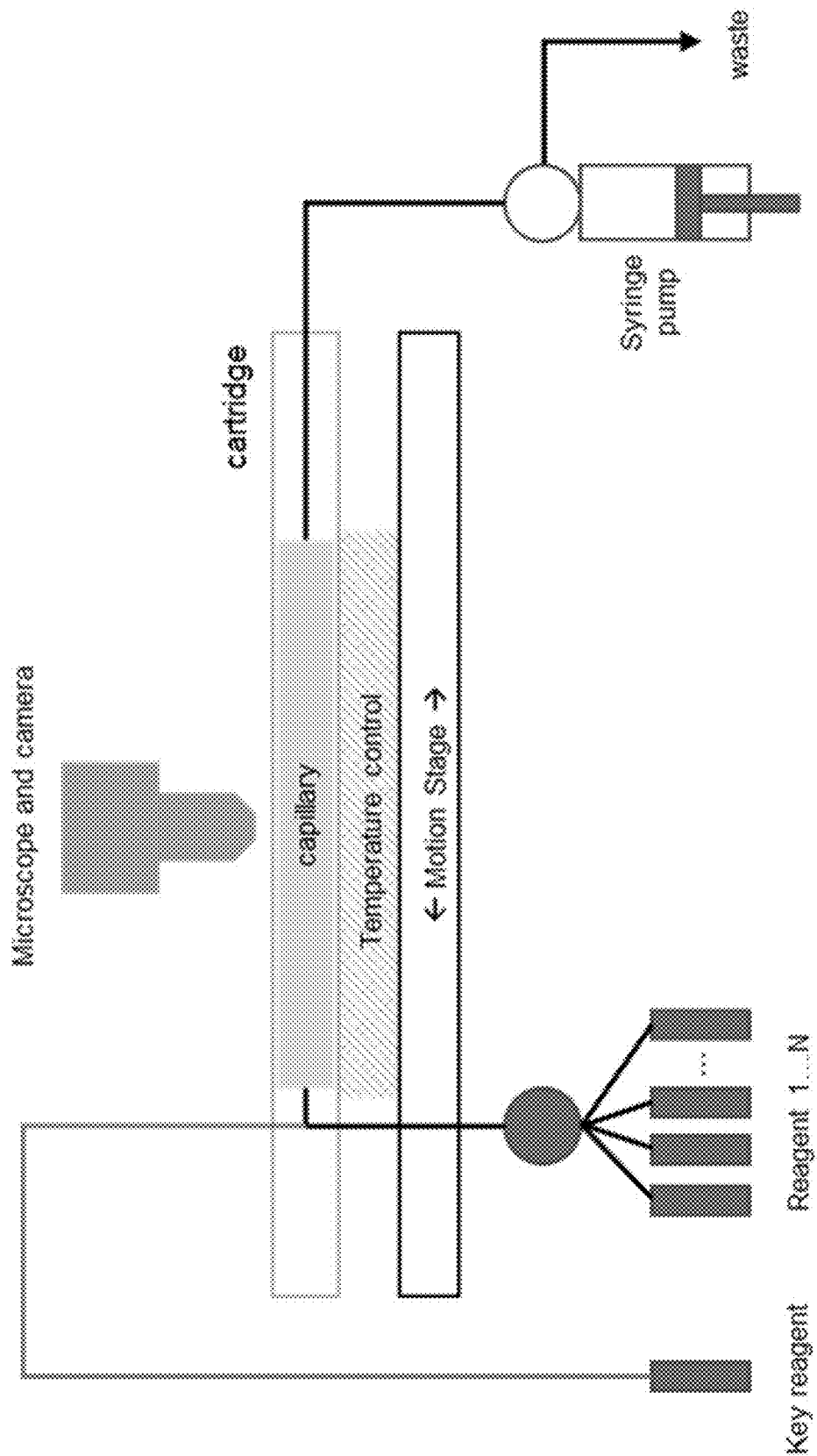
FIG. 33 illustrates one non-limiting example of a system that comprises a capillary flow cell, a microscope setup, and a temperature control mechanism.

FIG. 33 illustrates a non-limiting example of a capillary flow cell cartridge-based fluidics system used in combination with a microscope setup, where the cartridge incorporates or mates with a temperature control component such as a metal plate that makes contact with the capillaries within the cartridge and serves as a heat source/sink. The microscope setup consists of an illumination system (e.g., including a laser, LED, or halogen lamp, etc., as a light source), an objective lens, an imaging system (e.g., a CMOS or CCD camera), and a translation stage to move the cartridge relative to the optical system, which allows, e.g., fluorescence and/or bright field images to be acquired for different regions of the capillary flow cells as the stage is moved.

Temperature Control Modules:

In some implementations the disclosed systems will include temperature control functionality for the purpose of facilitating the accuracy and reproducibility of assay or analysis results. Examples of temperature control components that may be incorporated into the instrument system (or capillary flow cell cartridge) design include, but are not limited to, resistive heating elements, infrared light sources, Peltier heating or cooling devices, heat sinks, thermistors, thermocouples, and the like. In some instances, the temperature control module (or "temperature controller") may provide for a programmable temperature change at a specified, adjustable time prior to performing specific assay or analysis steps. In some instances, the temperature controller may provide for programmable changes in temperature over specified time intervals. In some embodiments, the temperature controller may further provide for cycling of temperatures between two or more set temperatures with specified frequency and ramp rates so that thermal cycling for amplification reactions may be performed.

Figure 34:
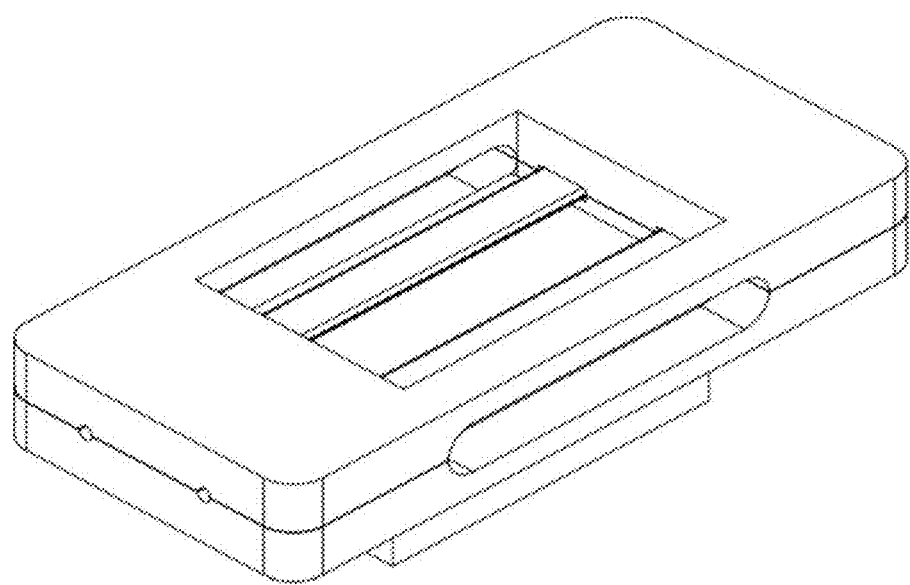
FIG. 34 illustrates one non-limiting example for temperature control of the capillary flow cells through the use of a metal plate that is placed in contact with the flow cell cartridge.

FIG. 34 illustrates one non-limiting example for temperature control of the flow cells (e.g., capillary flow cells or microfluidic device-based flow cells) through the use of a metal plate that is placed in contact with the flow cell cartridge. In some instances, the metal plate may be integrated with the cartridge chassis. In some instances, the metal plate may be temperature controlled using a Peltier or resistive heater.

Figure 35:
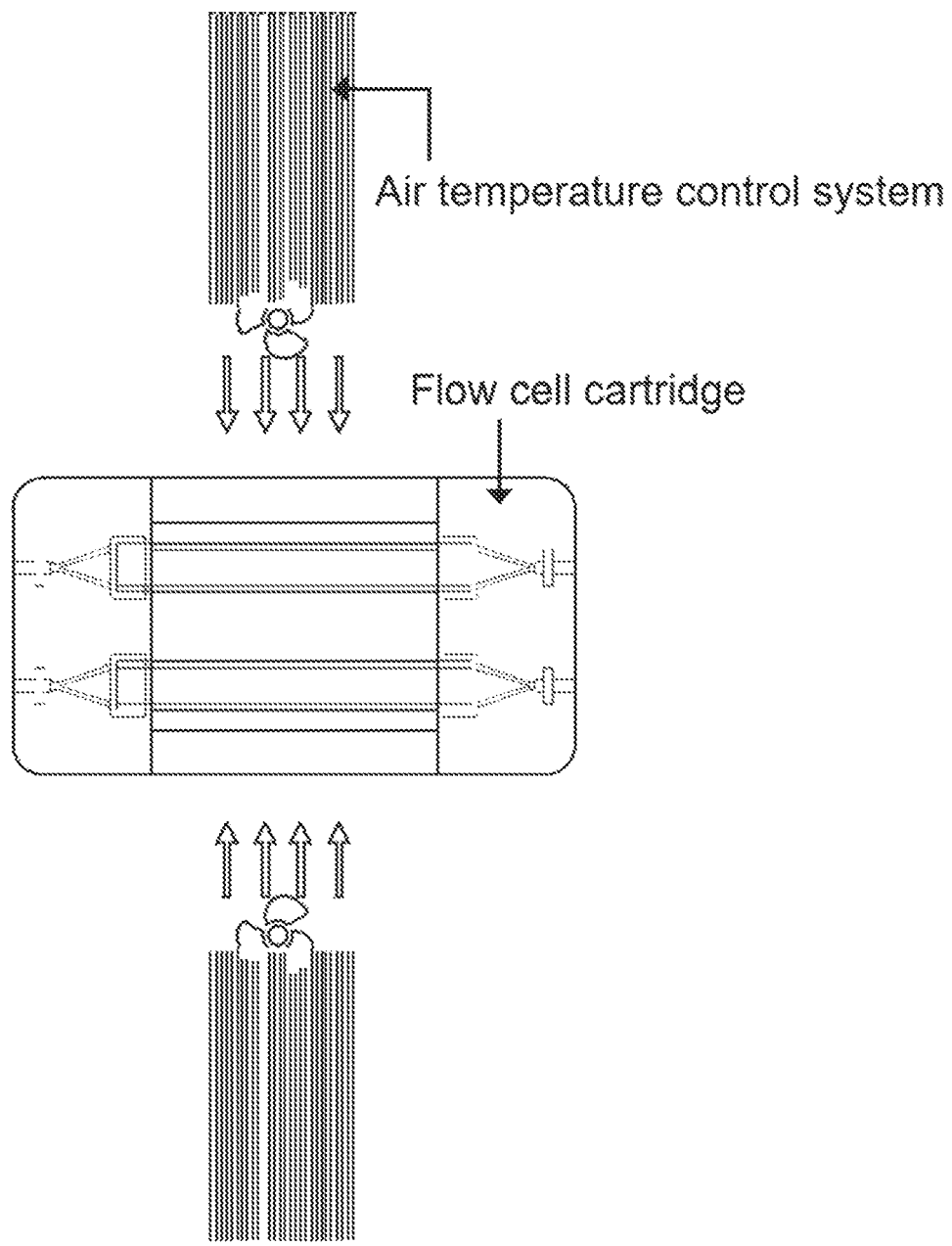
FIG. 35 illustrates one non-limiting approach for temperature control of the capillary flow cells that comprises a non-contact thermal control mechanism.

FIG. 35 illustrates one non-limiting approach for temperature control of the flow cells (e.g., capillary or microfluidic channel flow cells) that comprises a non-contact thermal control mechanism. In this approach, a stream of temperature-controlled air is directed through the flow cell cartridge (e.g., towards a single capillary flow cell device or a microfluidic channel flow cell device) using an air temperature control system. The air temperature control system comprises a heat exchanger, e.g., a resistive heater coil, fins attached to a Peltier device, etc., that is capable of heating and/or cooling the air and holding it at a constant, user-specified temperature. The air temperature control system also comprises an air delivery device, such as a fan, that directs the stream of heated or cooled air to the capillary flow cell cartridge. In some instances, the air temperature control system may be set to a constant temperature T1 so that the air stream, and consequently the flow cell or cartridge (e.g., capillary flow cell or microfluidic channel flow cell) is kept at a constant temperature T2, which in some cases may differ from the set temperature T1 depending on the environment temperature, air flow rate, etc. In some instances, two or more such air temperature control systems may be installed around the capillary flow cell device or flow cell cartridge so that the capillary or cartridge may be rapidly cycled between several different temperatures by controlling which one of the air temperature control systems is active at a given time. In another approach, the temperature setting of the air temperature control system may be varied so the temperature of the capillary flow cell or cartridge may be changed accordingly.

Fluid Dispensing Robotics:

In some implementations, the disclosed systems may comprise an automated, programmable fluid-dispensing (or liquid-dispensing) system for use in dispensing reagents or other solutions into, e.g., microplates, capillary flow cell devices and cartridges, microfluidic devices and cartridges, etc. Suitable automated, programmable fluid-dispensing systems are commercially available from a number of vendors, e.g. Beckman Coulter, Perkin Elmer, Tecan, Velocity 11, and many others. In a preferred aspect of the disclosed systems, the fluid-dispensing system further comprises a multichannel dispense head, e.g. a 4 channel, 8 channel, 16 channel, 96 channel, or 384 channel dispense head, for simultaneous delivery of programmable volumes of liquid (e.g. ranging from about 1 microliter to several milliliters) to multiple wells or locations on a flow cell cartridge or microfluidic cartridge.

Cartridge—and/or Microplate-Handling (Pick-and-Place) Robotics:

In some implementations, the disclosed system may comprise a cartridge- and/or microplate-handling robotic system for automated replacement and positioning of microplates, capillary flow cell cartridges, or microfluidic device cartridges in relation to the optical imaging system, or for optionally moving microplates, capillary flow cell cartridges, or microfluidic device cartridges between the optical imaging system and a fluid-dispensing system. Suitable automated, programmable microplate-handling robotic systems are commercially available from a number of vendors, including Beckman Coulter, Perkin Elemer, Tecan, Velocity 11, and many others. In a preferred aspect of the disclosed systems, an automated microplate-handling robotic system is configured to move collections of microwell plates comprising samples and/or reagents to and from, e.g., refrigerated storage units.

Spectroscopy or Imaging Modules:

As indicated above, in some implementations the disclosed analysis systems will include optical imaging capabilities and may also include other spectroscopic measurement capabilities. For example, the disclosed imaging modules may be configured to operate in any of a variety of imaging modes known to those of skill in the art including, but not limited to, bright-field, dark-field, fluorescence, luminescence, or phosphorescence imaging. In some instances, the one or more capillary flow cells or microfluidic devices of a fluidics sub-system comprise a window that allows at least a section of one or more capillaries or one or more fluid channels in each flow cell or microfluidic device to be illuminated and imaged.

In some embodiments, single wavelength excitation and emission fluorescence imaging may be performed. In some embodiments, dual wavelength excitation and emission (or multi-wavelength excitation or emission) fluorescence imaging may be performed. In some instances, the imaging module is configured to acquire video images. The choice of imaging mode may impact the design of the flow cells devices or cartridges in that all or a portion of the capillaries or cartridge will necessarily need to be optically transparent over the spectral range of interest. In some instances, a plurality of capillaries within a capillary flow cell cartridge may be imaged in their entirety within a single image. In some instances, only a single capillary or a subset of capillaries within a capillary flow cell cartridge, or portions thereof, may be imaged within a single image. In some instances, a series of images may be "tiled" to create a single high-resolution image of one, two, several, or the entire plurality of capillaries within a cartridge. In some instances, a plurality of fluid channels within a microfluidic chip may be imaged in their entirety within a single image. In some instances, only a single fluid channel or a subset of fluid channels within a microfluidic chip, or portions thereof, may be imaged within a single image. In some instances, a series of images may be "tiled" to create a single high-resolution image of one, two, several, or the entire plurality of fluid channels within a cartridge.

A spectroscopy or imaging module may comprise, e.g., a microscope equipped with a CMOS of CCD camera. In some instances, the spectroscopy or imaging module may comprise, e.g., a custom instrument such as one of the imaging modules described herein that is configured to perform a specific spectroscopic or imaging technique of interest. In general, the hardware associated with the spectroscopy or imaging module may include light sources, detectors, and other optical components, as well as processors or computers.

Light Sources:

Any of a variety of light sources may be used to provide the imaging or excitation light, including but not limited to, tungsten lamps, tungsten-halogen lamps, arc lamps, lasers, light emitting diodes (LEDs), or laser diodes. In some instances, a combination of one or more light sources, and additional optical components, e.g. lenses, filters, apertures, diaphragms, mirrors, and the like, may be configured as an illumination system (or sub-system).

Detectors:

Any of a variety of image sensors may be used for imaging purposes, including but not limited to, photodiode arrays, charge-coupled device (CCD) cameras, or complementary metal-oxide-semiconductor (CMOS) image sensors. As used herein, "imaging sensors" may be one-dimensional (linear) or two-dimensional array sensors. In many instances, a combination of one or more image sensors, and additional optical components, e.g. lenses, filters, apertures, diaphragms, mirrors, and the like, may be configured as an imaging system (or sub-system). In some instances, e.g., where spectroscopic measurements are performed by the system rather than imaging, suitable detectors may include, but are not limited to, photodiodes, avalanche photodiodes, and photomultipliers.

Other Optical Components:

The hardware components of the spectroscopic measurement or imaging module may also include a variety of optical components for steering, shaping, filtering, or focusing light beams through the system. Examples of suitable optical components include, but are not limited to, lenses, mirrors, prisms, apertures, diffraction gratings, colored glass filters, long-pass filters, short-pass filters, bandpass filters, narrowband interference filters, broadband interference filters, dichroic reflectors, optical fibers, optical waveguides, and the like. In some instances, as noted above, the spectroscopic measurement or imaging module may further comprise one or more translation stages or other motion control mechanisms for the purpose of moving capillary flow cell devices and cartridges relative to the illumination and/or detection/imaging sub-systems, or vice versa.

Total Internal Reflection:

In some instances, the optical module or sub-system may be designed to use all or a portion of an optically transparent wall of the capillaries or microfluidic channels in flow cell devices and cartridges as a waveguide for delivering excitation light to the capillary or channel lumen(s) via total internal reflection. When incident excitation light strikes the surface of the capillary or channel lumen at an angle with respect to a normal to the surface that is larger than the critical angle (determined by the relative refractive indices of the capillary or channel wall material and the aqueous buffer within the capillary or channel), total internal reflection occurs at the surface and the light propagates through the capillary or channel wall along the length of the capillary or channel. Total internal reflection generates an evanescent wave at the lumen surface which penetrates the lumen interior for extremely short distances, and which may be used to selectively excite fluorophores at the surface, e.g., labeled nucleotides that have been incorporated by a polymerase into a growing oligonucleotide through a solid-phase primer extension reaction.

Light-Tight Housings and Environmental Control Chambers:

In some implementations, the disclosed systems may comprise a light-tight housing to prevent stray ambient light from creating glare and obscuring, e.g., relatively faint fluorescence signals. In some implementations, the disclosed systems may comprise an environmental control chamber that enables the system to operate under a tightly controlled temperature, humidity level, etc.

Processors and Computers:

In some instances, the disclosed systems may comprise one or more processors or computers. The processor may be a hardware processor such as a central processing unit (CPU), a graphic processing unit (GPU), a general-purpose processing unit, or a computing platform. The processor may be comprised of any of a variety of suitable integrated circuits, microprocessors, logic devices, field-programmable gate arrays (FPGAs) and the like. In some instances, the processor may be a single core or multi core processor, or a plurality of processors may be configured for parallel processing. Although the disclosure is described with reference to a processor, other types of integrated circuits and logic devices are also applicable. The processor may have any suitable data operation capability. For example, the processor may perform 512 bit, 256 bit, 128 bit, 64 bit, 32 bit, or 16 bit data operations.

The processor or CPU can execute a sequence of machine-readable instructions, which can be embodied in a program or software. The instructions may be stored in a memory location. The instructions can be directed to the CPU, which can subsequently program or otherwise configure the CPU to implement, e.g., the system control methods of the present disclosure. Examples of operations performed by the CPU can include fetch, decode, execute, and write back.

Some processors may comprise a processing unit of a computer system. The computer system may enable cloud-based data storage and/or computing. In some instances, the computer system may be operatively coupled to a computer network ("network") with the aid of a communication interface. The network may be the internet, an intranet and/or extranet, an intranet and/or extranet that is in communication with the internet, or a local area network (LAN). The network in some cases is a telecommunication and/or data network. The network may include one or more computer servers, which may enable distributed computing, such as cloud-based computing.

The computer system may also include computer memory or memory locations (e.g., random-access memory, read-only memory, flash memory), electronic storage units (e.g., hard disk), communication interfaces (e.g., network adapters) for communicating with one or more other systems, and peripheral devices, such as cache, other memory units, data storage units and/or electronic display adapters. In some instances, the communication interface may allow the computer to be in communication with one or more additional devices. The computer may be able to receive input data from the coupled devices for analysis. Memory units, storage units, communication interfaces, and peripheral devices may be in communication with the processor or CPU through a communication bus (solid lines), such as may be incorporated into a motherboard. A memory or storage unit may be a data storage unit (or data repository) for storing data. The memory or storage units may store files, such as drivers, libraries and saved programs. The memory or storage units may store user data, e.g., user preferences and user programs.

The system control, image processing, and/or data analysis methods as described herein can be implemented by way of machine-executable code stored in an electronic storage location of the computer system, such as, for example, in the memory or electronic storage unit. The machine-executable or machine-readable code can be provided in the form of software. During use, the code can be executed by the processor. In some cases, the code can be retrieved from the storage unit and stored in memory for ready access by the processor. In some situations, the electronic storage unit can be precluded, and machine-executable instructions are stored in memory.

In some instances, the code may be pre-compiled and configured for use with a machine having a processer adapted to execute the code. In some instances, the code may be compiled during runtime. The code can be supplied in a programming language that can be selected to enable the code to execute in a pre-compiled or as-compiled fashion.

Some aspects of the systems and methods provided herein can be embodied in software. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

In some instances, the system control, image processing, and/or data analysis methods of the present disclosure may be implemented by way of one or more algorithms. An algorithm may be implemented by way of software upon execution by the central processing unit.

System Control Software:

In some instances, the system may comprise a computer (or processor) and a computer-readable medium that includes code for providing a user interface as well as manual, semi-automated, or fully-automated control of all system functions, e.g., control of the fluid flow control module(s), the temperature control module(s), and/or the spectroscopy or imaging module(s), as well as other data analysis and display options. The system computer or processor may be an integrated component of the system (e.g. a microprocessor or mother board embedded within the instrument) or may be a stand-alone module, for example, a main frame computer, a personal computer, or a laptop computer. Examples of fluid flow control functions provided by the system control software include, but are not limited to, volumetric fluid flow rates, fluid flow velocities, the timing and duration for sample and reagent addition, buffer addition, and rinse steps. Examples of temperature control functions provided by the system control software include, but are not limited to, specifying temperature set point(s) and control of the timing, duration, and ramp rates for temperature changes. Examples of spectroscopic measurement or imaging control functions provided by the system control software include, but are not limited to, autofocus capability, control of illumination or excitation light exposure times and intensities, control of image acquisition rate, exposure time, and data storage options.

Image Processing Software:

In some instances, the system may further comprise a computer (or processor) and computer-readable medium that includes code for providing image processing and analysis capability. Examples of image processing and analysis capability that may be provided by the software include, but are not limited to, manual, semi-automated, or fully-automated image exposure adjustment (e.g. white balance, contrast adjustment, signal-averaging and other noise reduction capability, etc.), automated edge detection and object identification (e.g., for identifying clonally-amplified clusters of fluorescently-labeled oligonucleotides on the lumen surface of capillary flow cell devices), automated statistical analysis (e.g., for determining the number of clonally-amplified clusters of oligonucleotides identified per unit area of the capillary lumen surface, or for automated nucleotide base-calling in nucleic acid sequencing applications), and manual measurement capabilities (e.g. for measuring distances between clusters or other objects, etc.). Optionally, instrument control and image processing/analysis software may be written as separate software modules. In some embodiments, instrument control and image processing/analysis software may be incorporated into an integrated package.

Any of a variety of image processing methods known to those of skill in the art may be used for image processing/pre-processing. Examples include, but are not limited to, Canny edge detection methods, Canny-Deriche edge detection methods, first-order gradient edge detection methods (e.g., the Sobel operator), second order differential edge detection methods, phase congruency (phase coherence) edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), and mathematical analysis algorithms (e.g., Fourier transform, fast Fourier transform, wavelet analysis, auto-correlation, etc.), or any combination thereof.

Nucleic Acid Sequencing Systems & Applications:

Nucleic acid sequencing provides one non-limiting example of an application for the disclosed flow cell devices (e.g., capillary flow cell devices or cartridges and microfluidic devices and cartridges) and imaging systems. Many "second generation" and "third generation" sequencing technologies utilize a massively parallel, cyclic array approach to perform sequencing-by-nucleotide incorporation, in which accurate decoding of a single-stranded template oligonucleotide sequence tethered to a solid support relies on successfully classifying signals that arise from the stepwise addition of A, G, C, and T nucleotides by a polymerase to a complementary oligonucleotide strand. These methods typically require the oligonucleotide template to be modified with a known adapter sequence of fixed length, affixed to a solid support (e.g., the lumen surface(s) of the disclosed capillary flow cell devices or microfluidic chips) in a random or patterned array by hybridization to surface-tethered capture probes (also referred to herein as "adapters" or "primers" tethered to the interior flow cell surfaces) of known sequence that are complementary to that of the adapter sequence, and then probed through a cyclic series of single base addition primer extension reactions that use, e.g., fluorescently-labeled nucleotides to identify the sequence of bases in the template oligonucleotides. These processes thus require the use of miniaturized fluidics systems that offer precise, reproducible control of the timing of reagent introduction to the flow cell in which the sequencing reactions are performed, and small volumes to reduce or minimize the consumption of costly reagents.

Existing commercially-available NGS flow cells are constructed from layers of glass that have been etched, lapped, and/or processed by other methods to meet the tight dimensional tolerances required for imaging, cooling, and/or other requirements. When flow cells are used as consumables, the costly manufacturing processes required for their fabrication result in costs per sequencing run that are too high to make sequencing routinely accessible to scientists and medical professionals in the research and clinical fields.

This disclosure provides an example of a low-cost flow cell architecture that includes low cost glass or polymer capillaries or microfluidic channels, fluidics adapters, and cartridge chassis. Utilizing glass or polymer capillaries that are extruded in their final cross-sectional geometry may eliminate the need for multiple high-precision and costly glass manufacturing processes. Robustly constraining the orientation of the capillaries or microfluidic channels and providing convenient fluidic connections using molded plastic and/or elastomeric components further reduces cost. Laser bonding the components of the polymer cartridge chassis provides a fast and efficient means of sealing the capillary or the microfluidic channels and structurally-stabilizing the capillaries or channels and flow cell cartridge without requiring the use of fasteners or adhesives.

The disclosed devices and systems may be configured to perform nucleic acid sequencing using any of a variety of "sequencing-by-nucleotide incorporation", "sequencing-by-nucleotide binding", "sequencing-by-nucleotide base-pairing", and "sequencing-by-avidity" sequencing biochemistries. The improvements in flow cell device design disclosed herein, e.g., comprising hydrophilic coated surfaces that maximize foreground signals for, e.g., fluorescently-labeled nucleic acid clusters disposed thereon, while minimizing background signal may give rise to improvements in CNR for images used for base-calling purposes, in combination with improvements in optical imaging system design for fast dual-surface flow cell imaging (comprising simultaneous or near-simultaneous imaging of the interior flow cell surfaces) achieved through improved objective lens and/or tube lens designs that provide for larger depth of field and larger fields-of-view, and reduced reagent consumption (achieved through improved flow cell design) may give rise to dramatic improvements in base-calling accuracy, shortened imaging cycle times, shortened overall sequencing reaction cycle times, and higher throughput nucleic acid sequencing at reduced cost per base.

In some instances, the disclosed hydrophilic, polymer coated flow cell devices used in combination with the optical imaging systems disclosed herein may confer one or more of the following additional advantages for a nucleic acid sequencing system: (i) decreased fluidic wash times (due to reduced non-specific binding, and thus faster sequencing cycle times), (ii) decreased imaging times (and thus faster turnaround times for assay readout and sequencing cycles), (iii) decreased overall work flow time requirements (due to decreased cycle times), (iv) decreased detection instrumentation costs (due to the improvements in CNR), (v) improved readout (base-calling) accuracy (due to improvements in CNR), (vi) improved reagent stability and decreased reagent usage requirements (and thus reduced reagents costs), and (vii) fewer run-time failures due to nucleic acid amplification failures.

The methods, devices, and systems disclosed herein for performing nucleic acid sequencing are suitable for a variety of sequencing applications and for sequencing nucleic acid molecules derived from any of a variety of samples and sources. Nucleic acids, in some instances, may be extracted from any of a variety of biological samples, e.g., blood samples, saliva samples, urine samples, cell samples, tissue samples, and the like. For example, the disclosed devices and systems may be used for the analysis of nucleic acid molecules derived from any of a variety of different cell, tissue, or sample types known to those of skill in the art. For example, nucleic acids may be extracted from cells, or tissue samples comprising one or more types of cells, derived from eukaryotes (such as animals, plants, fungi, protista), archaebacteria, or eubacteria. In some cases, nucleic acids may be extracted from prokaryotic or eukaryotic cells, such as adherent or non-adherent eukaryotic cells. Nucleic acids are variously extracted from, for example, primary or immortalized rodent, porcine, feline, canine, bovine, equine, primate, or human cell lines. Nucleic acids may be extracted from any of a variety of different cell, organ, or tissue types (e.g., white blood cells, red blood cells, platelets, epithelial cells, endothelial cells, neurons, glial cells, astrocytes, fibroblasts, skeletal muscle cells, smooth muscle cells, gametes, or cells from the heart, lungs, brain, liver, kidney, spleen, pancreas, thymus, bladder, stomach, colon, or small intestine). Nucleic acids may be extracted from normal or healthy cells. Alternately or in combination, acids are extracted from diseased cells, such as cancerous cells, or from pathogenic cells that are infecting a host. Some nucleic acids may be extracted from a distinct subset of cell types, e.g., immune cells (such as T cells, cytotoxic (killer) T cells, helper T cells, alpha beta T cells, gamma delta T cells, T cell progenitors, B cells, B-cell progenitors, lymphoid stem cells, myeloid progenitor cells, lymphocytes, granulocytes, Natural Killer cells, plasma cells, memory cells, neutrophils, eosinophils, basophils, mast cells, monocytes, dendritic cells, and/or macrophages, or any combination thereof), undifferentiated human stem cells, human stem cells that have been induced to differentiate, rare cells (e.g., circulating tumor cells (CTCs), circulating epithelial cells, circulating endothelial cells, circulating endometrial cells, bone marrow cells, progenitor cells, foam cells, mesenchymal cells, or trophoblasts). Other cells are contemplated and consistent with the disclosure herein.

Nucleic acids may optionally be attached to one or more non-nucleotide moieties such as labels and other small molecules, large molecules (such as proteins, lipids, sugars, etc.), and solid or semi-solid supports, for example through covalent or non-covalent linkages with either the 5' or 3' end of the nucleic acid. Labels include any moiety that is detectable using any of a variety of detection methods known to those of skill in the art, and thus renders the attached oligonucleotide or nucleic acid similarly detectable. Some labels, e.g., fluorophores, emit electromagnetic radiation that is optically detectable or visible. Alternately or in combination, some labels comprise a mass tag that renders the labeled oligonucleotide or nucleic acid visible in mass spectral data, or a redox tag that renders the labeled oligonucleotide or nucleic acid detectable by amperometry or voltametry. Some labels comprise a magnetic tag that facilitates separation and/or purification of the labeled oligonucleotide or nucleic acid. The nucleotide or polynucleotide is often not attached to a label, and the presence of the oligonucleotide or nucleic acid is directly detected.

Flow Cell Devices Configured for Sequencing:

In some instances, one or more flow cell devices according to the present disclosure may be configured for nucleic acid sequencing applications, e.g., wherein two or more interior flow cell device surfaces comprise hydrophilic polymer coatings that further comprise one or more capture oligonucleotides, e.g., adapter/primer oligonucleotides, or any other oligonucleotides as disclosed herein. In some instances, the hydrophilic, polymer-coated surfaces of the disclosed flow cell devices may comprise a plurality of oligonucleotides tethered thereto that have been selected for use in sequencing a eukaryotic genome. In some instances, the hydrophilic, polymer-coated surfaces of the disclosed flow cell devices may comprise a plurality of oligonucleotides tethered thereto that have been selected for use in sequencing a prokaryotic genome or portion thereof. In some instances, the hydrophilic, polymer-coated surfaces of the disclosed flow cell devices may comprise a plurality of oligonucleotides tethered thereto that have been selected for use in sequencing a viral genome or portion thereof. In some instances, the hydrophilic, polymer-coated surfaces of the disclosed flow cell devices may comprise a plurality of oligonucleotides tethered thereto that have been selected for use in sequencing a transcriptome.

In some instances, a flow cell device of the present disclosure may comprise a first surface in an orientation generally facing the interior of the flow channel, a second surface in an orientation generally facing the interior of the flow channel and further generally facing or parallel to the first surface, a third surface generally facing the interior of a second flow channel, and a fourth surface, generally facing the interior of the second flow channel and generally opposed to or parallel to the third surface; wherein said second and third surfaces may be located on or attached to opposite sides of a generally planar substrate which may be a reflective, transparent, or translucent substrate. In some instances, an imaging surface or imaging surfaces within a flow cell may be located within the center of a flow cell or within or as part of a division between two subunits or subdivisions of a flow cell, wherein said flow cell may comprise a top surface and a bottom surface, one or both of which may be transparent to such detection mode as may be utilized; and wherein a surface comprising oligonucleotides adapters/primers tethered to one or more polymer coatings may be placed or interposed within the lumen of the flow cell. In some instances, the top and/or bottom surfaces do not include attached oligonucleotide adapters/primers. In some instances, said top and/or bottom surfaces do comprise attached oligonucleotide adapters/primers. In some instances, either said top or said bottom surface may comprise attached oligonucleotide adapters/primers. A surface or surfaces placed or interposed within the lumen of a flow cell may be located on or attached to one side, to an opposite side, or to both sides of a generally planar substrate which may be a reflective, transparent, or translucent substrate.

In general, at least one layer of the one or more layers of low nonspecific binding coating on the flow cell device surfaces may comprise functional groups for covalently or non-covalently attaching oligonucleotide molecules, e.g., adapter or primer sequences, or the at least one layer may already comprise covalently or non-covalently attached oligonucleotide adapter or primer sequences at the time that it is deposited on the support surface. In some instances, the oligonucleotides tethered to the polymer molecules of at least one third layer may be distributed at a plurality of depths throughout the layer.

In some instances, the oligonucleotide adapter or primer molecules are covalently coupled to the polymer in solution, i.e., prior to coupling or depositing the polymer on the surface. In some instances, the oligonucleotide adapter or primer molecules are covalently coupled to the polymer after it has been coupled to or deposited on the surface. In some instances, at least one hydrophilic polymer layer comprises a plurality of covalently-attached oligonucleotide adapter or primer molecules. In some instances, at least two, at least three, at least four, or at least five layers of hydrophilic polymer comprise a plurality of covalently-attached adapter or primer molecules.

In some instances, the oligonucleotide adapter or primer molecules may be coupled to the one or more layers of hydrophilic polymer using any of a variety of suitable conjugation chemistries known to those of skill in the art. For example, the oligonucleotide adapter or primer sequences may comprise moieties that are reactive with amine groups, carboxyl groups, thiol groups, and the like. Examples of suitable amine-reactive conjugation chemistries that may be used include, but are not limited to, reactions involving isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester groups. Examples of suitable carboxyl-reactive conjugation chemistries include, but are not limited to, reactions involving carbodiimide compounds, e.g., water soluble EDC (1-ethyl-3-(3-dimethylaminopropyl)carbodiimide.HCL). Examples of suitable sulfydryl-reactive conjugation chemistries include maleimides, haloacetyls and pyridyl disulfides.

One or more types of oligonucleotide molecules may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, and/or molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

In some instances, the tethered oligonucleotide adapter and/or primer sequences may range in length from about 10 nucleotides to about 100 nucleotides. In some instances, the tethered oligonucleotide adapter and/or primer sequences may be at least 10, at least 20, at least 30, at least 40, at least 50, at least 60, at least 70, at least 80, at least 90, or at least 100 nucleotides in length. In some instances, the tethered oligonucleotide adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter and/or primer sequences may range from about 20 nucleotides to about 80 nucleotides. Those of skill in the art will recognize that the length of the tethered oligonucleotide adapter and/or primer sequences may have any value within this range, e.g., about 24 nucleotides.

In some instances, the number of coating layers and/or the material composition of each layer is chosen so as to adjust the resultant surface density of oligonucleotide adapters/primers (or other attached molecules) on the coated interior flow cell surfaces. In some instances, the surface density of oligonucleotide adapters/primers may range from about 1,000 primer molecules per $\mu m^2$ to about 1,000,000 primer molecules per $\mu m^2$. In some instances, the surface density of oligonucleotide primers may be at least 1,000, at least 10,000, at least 100,000, or at least 1,000,000 molecules per $\mu m^2$. In some instances, the surface density of oligonucleotide primers may be at most 1,000,000, at most 100,000, at most 10,000, or at most 1,000 molecules per $\mu m^2$. Any of the lower and upper values described in this paragraph may be combined to form a range included within the present disclosure, for example, in some instances the surface density of primers may range from about 10,000 molecules per $\mu m^2$ to about 100,000 molecules per $\mu m^2$. Those of skill in the art will recognize that the surface density of primer molecules may have any value within this range, e.g., about 455,000 molecules per $\mu m^2$. In some instances, the surface properties of the capillary or channel lumen coating, including the surface density of tethered oligonucleotide primers, may be adjusted to improve or optimize, e.g., solid-phase nucleic acid hybridization specificity and efficiency, and/or solid-phase nucleic acid amplification rate, specificity, and efficiency.

In some instances, the tethered adapter or primer sequences may comprise modifications designed to facilitate the specificity and efficiency of nucleic acid amplification as performed on the low-binding supports. For example, in some instances the primer may comprise polymerase stop points such that the stretch of primer sequence between the surface conjugation point and the modification site is always in single-stranded form and functions as a loading site for 5' to 3' helicases in some helicase-dependent isothermal amplification methods. Other examples of primer modifications that may be used to create polymerase stop points include, but are not limited to, an insertion of a PEG chain into the backbone of the primer between two nucleotides towards the 5' end, insertion of an abasic nucleotide (i.e., a nucleotide that has neither a purine nor a pyrimidine base), or a lesion site which can be bypassed by the helicase.

Nucleic Acid Hybridization:

In some instances, the hydrophilic, polymer coated flow cell device surfaces disclosed herein may provide advantages when used alone or in combination with improved buffer formulations for performing solid-phase nucleic acid hybridization and/or solid-phase nucleic acid amplification reactions as part of genotyping or nucleic acid sequencing applications. In some instances, the polymer-coated flow cell devices disclosed herein may provide advantages in terms of improved nucleic acid hybridization rate and specificity, and improved nucleic acid amplification rates and specificity that may be achieved through one or more of the following additional aspects of the present disclosure: (i) primer design (e.g., sequence and/or modifications), (ii) control of tethered primer density on the solid support, (iii) the surface composition of the solid support, (iv) the surface polymer density of the solid support, (v) the use of improved hybridization conditions before and during amplification, and/or (vi) the use of improved amplification formulations that decrease non-specific primer amplification or increase template amplification efficiency.

In some instances, it may be desirable to vary the surface density of tethered oligonucleotide adapters or primers on the coated flow cell surfaces and/or the spacing of the tethered adapters or primers away from the coated flow cell surface (e.g., by varying the length of a linker molecule used to tether the adapter or primers to the surface) in order to "tune" the support for optimal performance when, e.g., using a given amplification method. In some instances, adjusting the surface density of tethered oligonucleotide adapters or primers may impact the level of specific and/or non-specific amplification observed on the surface in a manner that varies according to the amplification method selected. In some instances, the surface density of tethered oligonucleotide adapters or primers may be varied by adjusting the ratio of molecular components used to create the support surface. For example, in the case that an oligonucleotide primer—PEG conjugate is used to create the final layer of a low-binding support, the ratio of the oligonucleotide primer—PEG conjugate to a non-conjugated PEG molecule may be varied. The resulting surface density of tethered primer molecules may then be estimated or measured using any of a variety of techniques known to those of skill in the art. Examples include, but are not limited to, the use of radio-isotope labeling and counting methods, covalent coupling of a cleavable molecule that comprises an optically-detectable tag (e.g., a fluorescent tag) that may be cleaved from a support surface of defined area, collected in a fixed volume of an appropriate solvent, and then quantified by comparison of fluorescence signals to that for a calibration solution of known optical tag concentration, or using fluorescence imaging techniques provided that care has been taken with the labeling reaction conditions and image acquisition settings to ensure that the fluorescence signals are linearly related to the number of fluorophores on the surface (e.g., that there is no significant self-quenching of the fluorophores on the surface).

In some instances, the use of the disclosed hydrophilic, polymer-coated flow cell devices, either alone or in combination with improved or optimized buffer formulations, may yield relative hybridization rates that range from about 2× to about 20× faster than that for a conventional hybridization protocol. In some instances, the relative hybridization rate may be at least 2x, at least 3x, at least 4x, at least 5x, at least 6x, at least 7x, at least 8x, at least 9x, at least 10x, at least 12x, at least 14x, at least 16x, at least 18x, at least 20x, at least 25x, at least 30x, or at least 40x that for a conventional hybridization protocol.

In some instances, the use of the disclosed hydrophilic, polymer-coated flow cell devices, either alone or in combination with improved or optimized buffer formulations, may yield total hybridization reaction times (i.e., the time required to reach 90%, 95%, 98%, or 99% completion of the hybridization reaction) of less than 60 minutes, 50 minutes, 40 minutes, 30 minutes, 20 minutes, 15 minutes, 10 minutes, or 5 minutes for any of these completion metrics.

In some instances, the use of the disclosed hydrophilic, polymer-coated flow cell devices, either alone or in combination with improved or optimized buffer formulations, may yield improved hybridization specificity compared to that for a conventional hybridization protocol. In some instances, the hybridization specificity that may be achieved is better than 1 base mismatch in 10 hybridization events, 1 base mismatch in 20 hybridization events, 1 base mismatch in 30 hybridization events, 1 base mismatch in 40 hybridization events, 1 base mismatch in 50 hybridization events, 1 base mismatch in 75 hybridization events, 1 base mismatch in 100 hybridization events, 1 base mismatch in 200 hybridization events, 1 base mismatch in 300 hybridization events, 1 base mismatch in 400 hybridization events, 1 base mismatch in 500 hybridization events, 1 base mismatch in 600 hybridization events, 1 base mismatch in 700 hybridization events, 1 base mismatch in 800 hybridization events, 1 base mismatch in 900 hybridization events, 1 base mismatch in 1,000 hybridization events, 1 base mismatch in 2,000 hybridization events, 1 base mismatch in 3,000 hybridization events, 1 base mismatch in 4,000 hybridization events, 1 base mismatch in 5,000 hybridization events, 1 base mismatch in 6,000 hybridization events, 1 base mismatch in 7,000 hybridization events, 1 base mismatch in 8,000 hybridization events, 1 base mismatch in 9,000 hybridization events, or 1 base mismatch in 10,000 hybridization events.

In some instances, the use of the disclosed hydrophilic, polymer-coated flow cell devices, either alone or in combination with improved or optimized buffer formulations, may yield improved hybridization efficiency (e.g., the fraction of available oligonucleotide primers on the support surface that are successfully hybridized with target oligonucleotide sequences) compared to that for a conventional hybridization protocol. In some instances, the hybridization efficiency that may be achieved is better than 50%, 60%, 70%, 80%, 85%, 90%, 95%, 98%, or 99% for any of the input target oligonucleotide concentrations specified below and in any of the hybridization reaction times specified above. In some instances, e.g., wherein the hybridization efficiency is less than 100%, the resulting surface density of target nucleic acid sequences hybridized to the support surface may be less than the surface density of oligonucleotide adapter or primer sequences on the surface.

In some instances, use of the disclosed hydrophilic, polymer-coated flow cell devices for nucleic acid hybridization (or nucleic acid amplification) applications using conventional hybridization (or amplification) protocols, or improved or optimized hybridization (or amplification) protocols, may lead to a reduced requirement for the input concentration of target (or sample) nucleic acid molecules contacted with the support surface. For example, in some instances, the target (or sample) nucleic acid molecules may be contacted with the support surface at a concentration ranging from about 10 pM to about 1 µM (i.e., prior to annealing or amplification). In some instances, the target (or sample) nucleic acid molecules may be administered at a concentration of at least 10 pM, at least 20 pM, at least 30 pM, at least 40 pM, at least 50 pM, at least 100 pM, at least 200 pM, at least 300 pM, at least 400 pM, at least 500 pM, at least 600 pM, at least 700 pM, at least 800 pM, at least 900 pM, at least 1 nM, at least 10 nM, at least 20 nM, at least 30 nM, at least 40 nM, at least 50 nM, at least 60 nM, at least 70 nM, at least 80 nM, at least 90 nM, at least 100 nM, at least 200 nM, at least 300 nM, at least 400 nM, at least 500 nM, at least 600 nM, at least 700 nM, at least 800 nM, at least 900 nM, or at least 1 µM. In some instances, the target (or sample) nucleic acid molecules may be administered at a concentration of at most 1 µM, at most 900 nM, at most 800 nm, at most 700 nM, at most 600 nM, at most 500 nM, at most 400 nM, at most 300 nM, at most 200 nM, at most 100 nM, at most 90 nM, at most 80 nM, at most 70 nM, at most 60 nM, at most 50 nM, at most 40 nM, at most 30 nM, at most 20 nM, at most 10 nM, at most 1 nM, at most 900 pM, at most 800 pM, at most 700 pM, at most 600 pM, at most 500 pM, at most 400 pM, at most 300 pM, at most 200 pM, at most 100 pM, at most 90 pM, at most 80 pM, at most 70 pM, at most 60 pM, at most 50 pM, at most 40 pM, at most 30 pM, at most 20 pM, or at most 10 pM. Any of the lower and upper values described in this paragraph may be combined to form a range included within the present disclosure, for example, in some instances the target (or sample) nucleic acid molecules may be administered at a concentration ranging from about 90 pM to about 200 nM. Those of skill in the art will recognize that the target (or sample) nucleic acid molecules may be administered at a concentration having any value within this range, e.g., about 855 nM.

In some instances, the use of the disclosed hydrophilic, polymer-coated flow cell devices, either alone or in combination with improved or optimized hybridization buffer formulations, may result in a surface density of hybridized target (or sample) oligonucleotide molecules (i.e., prior to performing any subsequent solid-phase or clonal amplification reaction) ranging from about from about 0.0001 target oligonucleotide molecules per $\mu m^2$ to about 1,000,000 target oligonucleotide molecules per $\mu m^2$. In some instances, the surface density of hybridized target oligonucleotide molecules may be at least 0.0001, at least 0.0005, at least 0.001, at least 0.005, at least 0.01, at least 0.05, at least 0.1, at least 0.5, at least 1, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per $\mu m^2$. In some instances, the surface density of hybridized target oligonucleotide molecules may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, at most 100, at most 90, at most 80, at most 70, at most 60, at most 50, at most 40, at most 30, at most 20, at most 10, at most 5, at most 1, at most 0.5, at most 0.1, at most 0.05, at most 0.01, at most 0.005, at most 0.001, at most 0.0005, or at most 0.0001 molecules per $\mu m^2$. Any of the lower and upper values described in this paragraph may be combined to form a range included within the present disclosure, for example, in some instances the surface density of hybridized target oligonucleotide molecules may range from about 3,000 molecules per $\mu m^2$ to about 20,000 molecules per $\mu m^2$. Those of skill in the art will recognize that the surface density of hybridized target oligonucleotide molecules may have any value within this range, e.g., about 2,700 molecules per $\mu m2$.

Stated differently, in some instances the use of the disclosed low-binding supports alone or in combination with improved or optimized hybridization buffer formulations may result in a surface density of hybridized target (or sample) oligonucleotide molecules (i.e., prior to performing any subsequent solid-phase or clonal amplification reaction) ranging from about 100 hybridized target oligonucleotide molecules per $mm^2$ to about $1 \times 10^{12}$ hybridized target oligonucleotide molecules per $mm^2$. In some instances, the surface density of hybridized target oligonucleotide molecules may be at least 100, at least 500, at least 1,000, at least 4,000, at least 5,000, at least 6,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ molecules per $mm^2$. In some instances, the surface density of hybridized target oligonucleotide molecules may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per $mm^2$. Any of the lower and upper values described in this paragraph may be combined to form a range included within the present disclosure, for example, in some instances the surface density of hybridized target oligonucleotide molecules may range from about 5,000 molecules per $mm^2$ to about 50,000 molecules per $mm^2$. Those of skill in the art will recognize that the surface density of hybridized target oligonucleotide molecules may have any value within this range, e.g., about 50,700 molecules per $mm^2$.

In some instances, the target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 0.6 kb in length, at least 0.7 kb in length, at least 0.8 kb in length, at least 0.9 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, at least 20 kb in length, at least 30 kb in length, or at least 40 kb in length, or any intermediate value spanned by the range described herein, e.g., at least 0.85 kb in length.

In some instances, the target (or sample) oligonucleotide molecules (or nucleic acid molecules) may comprise single-stranded or double-stranded, multimeric nucleic acid molecules (e.g., concatamers) further comprising repeats of a regularly occurring monomer unit. In some instances, the single-stranded or double-stranded, multimeric nucleic acid molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, at least 20 kb in length, at least 30 kb in length, or at least 40 kb in length, or any intermediate value spanned by the range described herein, e.g., about 2.45 kb in length.

In some instances, the target (or sample) oligonucleotide molecules (or nucleic acid molecules) may comprise single-stranded or double-stranded multimeric nucleic acid molecules (e.g., concatamers) comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 17. Thus, in some instances, the surface density of hybridized target sequences in terms of the number of copies of a target sequence per unit area of the support surface may exceed the surface density of oligonucleotide primers even if the hybridization efficiency is less than 100%.

Nucleic Acid Surface Amplification (NASA):

As used herein, the phrase "nucleic acid surface amplification" (NASA) is used interchangeably with the phrase "solid-phase nucleic acid amplification" (or simply "solid-phase amplification"). In some aspects of the present disclosure, nucleic acid amplification formulations are described which, in combination with the disclosed hydrophilic, polymer-coated flow cell devices, provide for improved amplification rates, amplification specificity, and amplification efficiency. As used herein, specific amplification refers to amplification of template library oligonucleotide strands that have been tethered to the solid support either covalently or non-covalently. As used herein, non-specific amplification refers to amplification of primer-dimers or other non-template nucleic acids. As used herein, amplification efficiency is a measure of the percentage of tethered oligonucleotides on the support surface that are successfully amplified during a given amplification cycle or amplification reaction. Nucleic acid amplification performed on surfaces disclosed herein may obtain amplification efficiencies of at least 50%, 60%, 70%, 80%, 90%, 95%, or greater than 95%, such as 98% or 99%.

Any of a variety of thermal cycling or isothermal nucleic acid amplification schemes may be used with the disclosed low-binding supports. Examples of nucleic acid amplification methods that may be utilized with the disclosed low-binding supports include, but are not limited to, polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, or single-stranded binding (SSB) protein-dependent amplification.

In some instances, improvements in amplification rate, amplification specificity, and amplification efficiency may be achieved using the disclosed hydrophilic, polymer-coated flow cell devices, either alone or in combination with formulations of the amplification reaction components. In addition to inclusion of nucleotides, one or more polymerases, helicases, single-stranded binding proteins, etc. (or any combination thereof), the amplification reaction mixture may be adjusted in a variety of ways to achieve improved performance including, but not limited to, choice of buffer type, buffer pH, organic solvent mixtures, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

The use of the disclosed hydrophilic, polymer-coated flow cell devices, alone or in combination with improved or optimized amplification reaction formulations, may yield increased amplification rates compared to those obtained using conventional supports and amplification protocols. In some instances, the relative amplification rates that may be achieved may be at least 2×, at least 3×, at least 4×, at least 5×, at least 6×, at least 7×, at least 8×, at least 9×, at least 10×, at least 12×, at least 14×, at least 16×, at least 18×, or at least 20× that for use of conventional supports and amplification protocols for any of the amplification methods described above.

In some instances, the use of the disclosed hydrophilic, polymer-coated flow cell devices, alone or in combination with improved or optimized buffer formulations, may yield total amplification reaction times (i.e., the time required to reach 90%, 95%, 98%, or 99% completion of the amplification reaction) of less than 180 mins, 120 mins, 90 min, 60 minutes, 50 minutes, 40 minutes, 30 minutes, 20 minutes, 15 minutes, 10 minutes, 5 minutes, 3 minutes, 1 minute, 50 s, 40 s, 30 s, 20 s, or 10 s for any of these completion metrics.

In some instances, the use of the disclosed low-binding supports alone or in combination with improved or optimized amplification buffer formulations may enable faster amplification reaction times (i.e., the times required to reach 90%, 95%, 98%, or 99% completion of the amplification reaction) of no more than 60 minutes, 50 minutes, 40 minutes, 30 minutes, 20 minutes, or 10 minutes. Similarly, use of the disclosed low-binding supports alone or in combination with improved or optimized buffer formulations may enable amplification reactions to be completed in some cases in no more than 2, 3, 4, 5, 6, 7, 8, 9, 10, 15, or no more than 30 cycles.

In some instances, the use of the disclosed hydrophilic, polymer-coated flow cell devices, alone or in combination with improved or optimized amplification reaction formulations, may yield increased specific amplification and/or decreased non-specific amplification compared to that obtained using conventional supports and amplification protocols. In some instances, the resulting ratio of specific amplification-to-non-specific amplification that may be achieved is at least 4:1 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1,000:1.

In some instances, the use of the disclosed hydrophilic, polymer-coated flow cell devices, alone or in combination with improved or optimized amplification reaction formulations, may yield increased amplification efficiency compared to that obtained using conventional supports and amplification protocols. In some instances, the amplification efficiency that may be achieved is better than 50%, 60%, 70% 80%, 85%, 90%, 95%, 98%, or 99% in any of the amplification reaction times specified above.

In some instances, the clonally-amplified target (or sample) oligonucleotide molecules (or nucleic acid molecules) hybridized to the oligonucleotide adapter or primer molecules attached to the hydrophilic, polymer-coated flow cell device surfaces may range in length from about 0.02 kilobases (kb) to about 20 kb or from about 0.1 kilobases (kb) to about 20 kb. In some instances, the clonally-amplified target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., at least 0.85 kb in length.

In some instances, the clonally-amplified target (or sample) oligonucleotide molecules (or nucleic acid molecules) may comprise single-stranded or double-stranded, multimeric nucleic acid molecules (e.g., concatamers) further comprising repeats of a regularly occurring monomer unit. In some instances, the clonally-amplified single-stranded or double-stranded, multimeric nucleic acid molecules may be at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., about 2.45 kb in length.

In some instances, the clonally-amplified target (or sample) oligonucleotide molecules (or nucleic acid molecules) may comprise single-stranded or double-stranded multimeric nucleic acid (e.g., concatamers) molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 12. Thus, in some instances, the surface density of clonally-amplified target sequences in terms of the number of copies of a target sequence per unit area of the support surface may exceed the surface density of oligonucleotide primers even if the hybridization and/or amplification efficiencies are less than 100%.

In some instances, the use of the disclosed hydrophilic, polymer-coated flow cell devices, alone or in combination with improved or optimized amplification reaction formulations, may yield increased clonal copy number compared to that obtained using conventional supports and amplification protocols. In some instances, e.g., wherein the clonally-amplified target (or sample) oligonucleotide molecules comprise concatenated, multimeric repeats of a monomeric target sequence, the clonal copy number may be substantially smaller than compared to that obtained using conventional supports and amplification protocols. Thus, in some instances, the clonal copy number may range from about 1 molecule to about 100,000 molecules (e.g., target sequence molecules) per amplified colony. In some instances, the clonal copy number may be at least 1, at least 5, at least 10, at least 50, at least 100, at least 500, at least 1,000, at least 2,000, at least 3,000, at least 4,000, at least 5,000, at least 6,000, at least 7,000, at least 8,000, at least 9,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, or at least 100,000 molecules per amplified colony. In some instances, the clonal copy number may be at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,000, at most 8,000, at most 7,000, at most 6,000, at most 5,000, at most 4,000, at most 3,000, at most 2,000, at most 1,000, at most 500, at most 100, at most 50, at most 10, at most 5, or at most 1 molecule per amplified colony. Any of the lower and upper values described in this paragraph may be combined to form a range included within the present disclosure, for example, in some instances the clonal copy number may range from about 2,000 molecules to about 9,000 molecules. Those of skill in the art will recognize that the clonal copy number may have any value within this range, e.g., about 2,220 molecules in some instances, or about 2 molecules in others.

As noted above, in some instances the amplified target (or sample) oligonucleotide molecules (or nucleic acid molecules) may comprise concatenated, multimeric repeats of a monomeric target sequence. In some instances, the amplified target (or sample) oligonucleotide molecules (or nucleic acid molecules) may comprise a plurality of molecules each of which comprises a single monomeric target sequence. Thus, the use of the disclosed hydrophilic, polymer-coated flow cell devices, alone or in combination with improved or optimized amplification reaction formulations, may result in a surface density of target sequence copies that ranges from about 100 target sequence copies per mm$^2$ to about $1 \times 10^{12}$ target sequence copies per mm$^2$. In some instances, the surface density of target sequence copies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ of clonally amplified target sequence molecules per mm$^2$. In some instances, the surface density of target sequence copies may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 target sequence copies per mm². Any of the lower and upper values described in this paragraph may be combined to form a range included within the present disclosure, for example, in some instances the surface density of target sequence copies may range from about 1,000 target sequence copies per mm² to about 65,000 target sequence copies mm². Those of skill in the art will recognize that the surface density of target sequence copies may have any value within this range, e.g., about 49,600 target sequence copies per mm².

In some instances, the use of the disclosed low-binding supports alone or in combination with improved or optimized amplification buffer formulations may result in a surface density of clonally-amplified target (or sample) oligonucleotide molecules (or clusters) ranging from about from about 100 molecules per mm2 to about $1 \times 10^{12}$ colonies per mm². In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ molecules per mm². In some instances, the surface density of clonally-amplified molecules may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per mm². Any of the lower and upper values described in this paragraph may be combined to form a range included within the present disclosure, for example, in some instances the surface density of clonally-amplified molecules may range from about 5,000 molecules per mm² to about 50,000 molecules per mm². Those of skill in the art will recognize that the surface density of clonally-amplified colonies may have any value within this range, e.g., about 48,800 molecules per mm².

In some instances. the use of the disclosed hydrophilic, polymer-coated flow cell devices, alone or in combination with improved or optimized amplification reaction formulations, may yield signal from the amplified and labeled nucleic acid populations (e.g., a fluorescence signal) that has a coefficient of variance of no greater than 50%, such as 50%, 40%, 30%, 20%, 15%, 10%, 5%, or less than 5%.

Similarly, in some instances the use of the disclosed hydrophilic, polymer-coated flow cell devices, alone or in combination with improved or optimized amplification reaction formulations, may yield signal from the amplified and non-labeled nucleic acid populations that has a coefficient of variance of no greater than 50%, such as 50%, 40%, 30%, 20%, 10%, 5%, or less than 5%.

Fluorescence Imaging of Hydrophilic, Polymer-Coated Flow Cell Device Surfaces:

The disclosed hydrophilic, polymer-coated flow cell devices comprising, e.g., clonal clusters of labeled target nucleic acid molecules disposed thereon may be used in any of a variety of nucleic acid analysis applications, e.g., nucleic acid base discrimination, nucleic acid base classification, nucleic acid base calling, nucleic acid detection applications, nucleic acid sequencing applications, and nucleic acid-based (genetic and genomic) diagnostic applications. In many of these applications, fluorescence imaging techniques may be used to monitor hybridization, amplification, and/or sequencing reactions performed on the low-binding supports. Fluorescence imaging may be performed using any of the optical imaging modules disclosed herein, as well as a variety of fluorophores, fluorescence imaging techniques, and other fluorescence imaging instruments known to those of skill in the art.

In some instances, the performance of nucleic acid hybridization and/or amplification reactions using the disclosed hydrophilic, polymer-coated flow cell devices and reaction buffer formulations may be assessed using fluorescence imaging techniques, where the contrast-to-noise ratio (CNR) of the images provides a key metric in assessing amplification specificity and non-specific binding on the support. CNR is commonly defined as: CNR=(Signal−Background)/Noise. The background term is commonly taken to be the signal measured for the interstitial regions surrounding a particular feature (diffraction limited spot, DLS) in a specified region of interest (ROI). As noted above, while signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times should be reduced or minimized). At high CNR, the imaging time required to reach accurate signal discrimination (and thus accurate base-calling in the case of sequencing applications) can be drastically reduced even with moderate improvements in CNR.

In most ensemble-based sequencing approaches, the background term is typically measured as the signal associated with 'interstitial' regions. In addition to "interstitial" background ($B_{inter}$), "intrastitial" background ($B_{intra}$) exists within the discrete regions occupied by amplified DNA colonies. The combination of these two background signal terms dictates the achievable CNR in the image, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the foreground signal from the ROI, and the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (i.e., (S)—$B_{inter}$ in the FOV) yields a discernable feature that can be classified. In some instances, the intrastitial background ($B_{intra}$) can contribute a confounding fluorescence signal that is not specific to the target of interest but is present in the same ROI, thus making it far more difficult to average and subtract.

The implementation of nucleic acid amplification on the hydrophilic, polymer-coated substrate surfaces of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low nonspecific binding support surfaces, optionally used in combination with improved hybridization and/or amplification reaction buffer formulations, may lead to improvements in CNR by a factor of 2, 5, 10, 100, 200, 500, or 1000-fold over those achieved using conventional supports and hybridization, amplification, and/or sequencing protocols. Although described here in the context of using fluorescence imaging as the read-out or detection mode, the same principles apply to the use of the disclosed low nonspecific binding supports and nucleic acid hybridization and amplification formulations for other detection modes as well, including both optical and non-optical detection modes.

Alternative Sequencing Biochemistries:

In addition to the sequencing-by-nucleotide incorporation approach described above, the disclosed flow cell devices and optical imaging systems are compatible with other emerging nucleic acid sequencing biochemistries as well. Examples include the "sequencing-by-nucleotide binding" approach described in U.S. Pat. No. 10,655,176 B2, and the "sequencing-by-avidity" approach described in U.S. Pat. No. 10,768,173 B2.

The "sequencing-by-nucleotide binding" approach, as currently being developed by Omniome, Inc. (San Diego, Calif.) is based on performing repetitive cycles of detecting a stabilized complex that forms at each position along the template (e.g. a ternary complex that includes the primed template (tethered to a sample support structure), a polymerase, and a cognate nucleotide for the position), under conditions that prevent covalent incorporation of the cognate nucleotide into the primer, and then extending the primer to allow detection of the next position along the template. In the sequencing-by-binding approach, detection of the nucleotide at each position of the template occurs prior to extension of the primer to the next position. Generally, the methodology is used to distinguish the four different nucleotide types that can be present at positions along a nucleic acid template by uniquely labelling each type of ternary complex (i.e. different types of ternary complexes differing in the type of nucleotide it contains) or by separately delivering the reagents needed to form each type of ternary complex. In some instances, the labeling may comprise fluorescence labeling of, e.g., the cognate nucleotide or the polymerase that participate in the ternary complex. The approach is thus compatible with the disclosed flow cell devices and imaging systems.

The "sequencing-by-avidity" approach, as currently being developed by Element Biosciences, Inc. (San Diego, Calif.) relies on the increased avidity (or "functional affinity") derived from forming a complex comprising a plurality of individual non-covalent binding interactions. Element's approach is based on the detection of a multivalent binding complex formed between a fluorescently-labeled polymer-nucleotide conjugate, a polymers, and a plurality of primed target nucleic acid molecules tethered to a sample support structure, which allows the detection/base-calling step to be separated from the nucleotide incorporation step. Fluorescence imaging is used to detect the bound complex and thereby determine the identity of the N+1 nucleotide in the target nucleic acid sequence (where the primer extension strand is N nucleotides in length). Following the imaging step, the multivalent binding complex is disrupted and washed away, the correct blocked nucleotide is incorporated into the primer extension strand, and the cycle is repeated.

Nucleic Acid Sequencing System Performance:

In some instances, the disclosed nucleic acid sequencing systems, comprising one or more of the disclosed flow cell devices used in combination with one or more of the disclosed optical imaging systems, and optionally utilizing one of the emerging sequencing biochemistries such as the "sequencing-by-trapping" (or "sequencing-by-avidity") approach described above, may provide improved nucleic acid sequencing performance in terms of, e.g., reduced sample input requirements, reduced image acquisition cycle time, reduced sequencing reaction cycle time, reduced sequencing run time, improved base-calling accuracy, reduced reagent consumption and cost, higher sequencing throughput, and reduced sequencing cost.

Nucleic Acid Sample Input (pM):

In some instances, the sample input requirements for the disclosed system may be significantly reduced due to the improved hybridization and amplification efficiencies that may be attained, and the high CNR images that may be acquired for base-calling, using the disclosed hydrophilic, polymer coated flow cell devices and imaging systems. In some instances, the nucleic acid sample input requirement for the disclosed systems may range from about 1 pM to about 10,000 pM. In some instances, the nucleic acid sample input requirement may be at least 1 pM, at least 2 pM, at least 5 pM, at least 10 pM, at least 20 pM, at least 50 pM, at least 100 pM, at least 200 pM, at least 500 pM, at least 1,000 pM, at least 2,000 pM, at least 5,000 pM, at least 10,000 pM. In some instances, the nucleic acid sample input requirement for the disclosed systems may be at most 10,000 pM, at most 5,000 pM, at most 2,000 pM, at most 1,000 pM, at most 500 pM, at most 200 pM, at most 100 pM, at most 50 pM, at most 20 pM, at most 10 pM, at most 5 pM, at most 2 pM, or at most 1 pM. Any of the lower and upper values described in this paragraph may be combined to form a range included within the present disclosure, for example, in some instances the nucleic acid sample input requirement for the disclosed systems may range from about 5 pM to about 500 pM. Those of skill in the art will recognize that the nucleic acid sample input requirement may have any value within this range, e.g., about 132 pM. In one exemplary instance, a nucleic acid sample input of about 100 pM is sufficient to generate signals for reliable base-calling.

Nucleic Acid Sample Input (Nanograms):

In some instances, the nucleic acid sample input requirement for the disclosed systems may range from about 0.05 nanograms to about 1,000 nanograms. In some instances, the nucleic acid sample input requirement may be at least 0.05 nanograms, at least 0.1 nanograms, at least 0.2 nanograms, at least 0.4 nanograms, at least 0.6 nanograms, at least 0.8 nanograms, at least 1.0 nanograms, at least 2 nanograms, at least 4 nanograms, at least 6 nanograms, at least 8 nanograms, at least 10 nanograms, at least 20 nanograms, at least 40 nanograms, at least 60 nanograms, at least 80 nanograms, at least 100 nanograms, at least 200 nanograms, at least 400 nanograms, at least 600 nanograms, at least 800 nanograms, or at least 1,000 nanograms. In some instances, the nucleic acid sample input requirement may be at most 1,000 nanograms, at most 800 nanograms, at most 600 nanograms, at most 400 nanograms, at most 200 nanograms, at most 100 nanograms, at most 80 nanograms, at most 60 nanograms, at most 40 nanograms, at most 20 nanograms, at most 10 nanograms, at most 8 nanograms, at most 6 nanograms, at most 4 nanograms, at most 2 nanograms, at most 1 nanograms, at most 0.8 nanograms, at most 0.6 nanograms, at most 0.4 nanograms, at most 0.2 nanograms, at most 0.1 nanograms, or at most 0.05 nanograms. Any of the lower and upper values described in this paragraph may be combined to form a range included within the present disclosure, for example, in some instances the nucleic acid sample input requirement for the disclosed systems may range from about 0.6 nanograms to about 400 nanograms. Those of skill in the art will recognize that the nucleic acid sample input requirement may have any value within this range, e.g., about 2.65 nanograms.

FOV Images Required to Tile Flow Cell:

In some instances, the field-of-view (FOV) of the disclosed optical imaging module is sufficiently large that a multi-channel (or multi-lane) flow cell (i.e., the fluid channel portions thereof) of the present disclosure may be imaged by tiling from about 10 FOV images (or "frames") to about 1,000 FOV images (or "frames"). In some instances, an image of the entire multi-channel flow cell may require tiling at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1,000 FOV images (or "frames"). In some instances, an image of the entire multi-channel flow cell may require tiling at most 1,000, at most 950, at most 900, at most 850, at most 800, at most 750, at most 700, at most 650, at most 600, at most 550, at most 500, at most 450, at most 400, at most 350, at most 300, at most 250, at most 200, at most 150, at most 100, at most 90, at most 80, at most 80, at most 70, at most 60, at most 50, at most 40, at most 30, at most 20, or at most 10 FOV images (or "frames"). Any of the lower and upper values described in this paragraph may be combined to form a range included within the present disclosure, for example, in some instances an image of the entire multi-channel flow cell may require tiling from about 30 to about 100 FOV images. Those of skill in the art will recognize that in some instances the number of required FOV images may have any value within this range, e.g., about 54 FOV images.

Imaging Cycle Time:

In some instances, the combination of large FOV, image sensor response sensitivity, and/or fast FOV translation times enables shortened imaging cycle times (i.e., the time required to acquire a sufficient number of FOV images to tile the entire multichannel flow cell (or the fluid channel portions thereof). In some instances, the imaging cycle time may range from about 10 seconds to about 10 minutes. In some instances, the imaging cycle time may be at least 10 seconds at least 20 seconds, at least 30 seconds, at least 40 seconds, at least 50 seconds, at least 1 minute, at least 2 minutes, at least 3 minutes, at least 4 minutes, at least 5 minutes, at least 6 minutes, at least 7 minutes, at least 8 minutes, at least 9 minutes, or at least 10 minutes. In some instances, the imaging cycle time may be at most 10 minutes, at most 9 minutes, at most 8 minutes, at most 7 minutes, at most 6 minutes, at most 5 minutes, at most 4 minutes, at most 3 minutes, at most 2 minutes, at most 1 minute, at most 50 second, at most 40 second, at most 30 seconds, at most 20 seconds, or at most 10 seconds. Any of the lower and upper values described in this paragraph may be combined to form a range included within the present disclosure, for example, in some instances the imaging cycle time may range from about 20 seconds to about 1 minute. Those of skill in the art will recognize that in some instances the imaging cycle time may have any value within this range, e.g., about 57 seconds.

Sequencing Cycle Time:

In some instances, shortened sequencing reaction steps, e.g., due to reduced wash time requirements for the disclosed hydrophilic, polymer-coated flow cells, may result in shortened overall sequencing cycle times. In some instances, the sequencing cycle times for the disclosed systems may range from about 1 minute to about 60 minutes. In some instances, the sequencing cycle time may be at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, or at least 60 minutes. In some instances, the sequencing reaction cycle time may be at most 60 minutes, at most 55 minutes, at most 50 minutes, at most 45 minutes, at most 40 minutes, at most 35 minutes, at most 30 minutes, at most 25 minutes, at most 20 minutes, at most 15 minutes, at most 10 minutes, at most 9 minutes, at most 8 minutes, at most 7 minutes, at most 6 minutes, at most 5 minutes, at most 4 minutes, at most 3 minutes, at most 2 minutes, or at most 1 minutes. Any of the lower and upper values described in this paragraph may be combined to form a range included within the present disclosure, for example, in some instances the sequencing cycle time may range from about 2 minutes to about 15 minutes. Those of skill in the art will recognize that in some instances the sequencing cycle time may have any value within this range, e.g., about 1 minute, 12 seconds.

Sequencing Read Length:

In some instances, the enhanced CNR images that may be achieved using the disclosed hydrophilic, polymer-coated flow cell devices in combination with the disclosed imaging systems, and in some cases, the use of milder sequencing biochemistries, may enable longer sequencing read lengths for the disclosed systems. In some instances, the maximum (single read) read length may range from about 50 bp to about 500 bp. In some instances, the maximum (single read) read length may be at least 50 bp, at least 100 bp, at least 150 bp, at least 200 bp, at least 250 bp, at least 300 bp, at least 350 bp, at least 400 bp, at least 450 bp, or at least 500 bp. In some instances, the maximum (single read) read length is at most 500 bp, at most 450 bp, at most 400 bp, at most 350 bp, at most 300 bp, at most 250 bp, at most 200 bp, at most 150 bp, at most 100 bp, or at most 50 bp. Any of the lower and upper values described in this paragraph may be combined to form a range included within the present disclosure, for example, in some instances the maximum (single read) read length may range from about 100 bp to about 450 bp. Those of skill in the art will recognize that in some instances the maximum (single read) read length may have any value within this range, e.g., about 380 bp.

Sequencing Run Time:

In some instances, the sequencing run time for the disclosed nucleic acid sequencing systems may range from about 8 hours to about 20 hours. In some instances, the sequencing run time is at least 8 hours, at least 9 hours, at least 10 hours, at least 12 hours, at least 14 hours, at least 16 hours, at least 18 hours, or at least 20 hours. In some instances, the sequencing run time is at most 20 hours, at most 18 hours, at most 16 hours, at most 14 hours, at most 12 hours, at most 10 hours, at most 9 hours, or at most 8 hours. Any of the lower and upper values described in this paragraph may be combined to form a range included within the present disclosure, for example, in some instances the sequencing run time may range from about 10 hours to about 16 hours. Those of skill in the art will recognize that in some instances the sequencing run time may have any value within this range, e.g., about 7 hours, 35 minutes.

Average Base-Calling Accuracy:

In some instances, the disclosed nucleic acid sequencing systems may provide an average base-calling accuracy of at least 80%, at least 85%, at least 90%, at least 92%, at least 94%, at least 96%, at least 98%, at least 99%, at least 99.5%, at least 99.8%, or at least 99.9% correct over the course of a sequencing run. In some instances, the disclosed nucleic acid sequencing systems may provide an average base-calling accuracy of at least 80%, at least 85%, at least 90%, at least 92%, at least 94%, at least 96%, at least 98%, at least 99%, at least 99.5%, at least 99.8%, or at least 99.9% correct per every 1,000 bases, 10,0000 bases, 25,000 bases, 50,000 bases, 75,000 bases, or 100,000 bases called.

Average Q-Score:

In some instances, the disclosed nucleic acid sequencing systems may provide a more accurate base readout. In some instances, for example, the disclosed nucleic acid sequencing systems may provide an average Q-score for base-calling accuracy over a sequencing run that ranges from about 20 to about 50. In some instances, the average Q-score may be at least 20, at least 25, at least 30, at least 35, at least 40, at least 45, or at least 50. Those of skill in the art will recognize that the average Q-score may have any value within this range, e.g., about 32.

Q-Score Vs. % Nucleotides Identified:

In some instances, the disclosed nucleic acid sequencing systems may provide a Q-score of greater than 30 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 35 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 40 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 45 for at least 50%, at least 60%, at least 70%, at least 80%, at least 85%, at least 90%, at least 95%, at least 98%, or at least 99% of the terminal (or N+1) nucleotides identified. In some instances, the disclosed compositions and methods for nucleic acid sequencing may provide a Q-score of greater than 50 for at least 50%, at least 60%, at least 70%, at least 80%, at least 85%, at least 90%, at least 95%, at least 98%, or at least 99% of the terminal (or N+1) nucleotides identified.

Reagent Consumption:

In some instances, the disclosed nucleic acid sequencing systems may have lower reagent consumption rates and costs due to, e.g., the use of the disclosed flow cell devices and fluidic systems that minimize fluid channel volumes and dead volumes. In some instances, the disclosed nucleic acid sequencing systems may thus require an average of at least 5% less, at least 10% less, at least 15% less, at least 20% less, at least 25% less, at least 30% less, at least 35% less, at least 40% less, at least 45% less, or at least 50% less reagent by volume per Gbase sequenced that that consumed by an Illumina MiSeq sequencer.

Sequencing Throughput:

In some instances, the disclosed nucleic acid sequencing systems may provide a sequencing throughput ranging from about 50 Gbase/run to about 200 Gbase/run. In some instances, the sequencing throughput may be at least 50 Gbase/run, at least 75 Gbase/run, at least 100 Gbase/run, at least 125 Gbase/run, at least 150 Gbase/run, at least 175 Gbase/run, or at least 200 Gbase/run. In some instances, the sequencing throughput may be at most 200 Gbase/run, at most 175 Gbase/run, at most 150 Gbase/run, at most 125 Gbase/run, at most 100 Gbase/run, at most 75 Gbase/run, or at most 50 Gbase/run. Any of the lower and upper values described in this paragraph may be combined to form a range included within the present disclosure, for example, in some instances the sequencing throughput may range from about 75 Gbase/run to about 150 Gbase/run. Those of skill in the art will recognize that in some instances the sequencing throughput may have any value within this range, e.g., about 119 Gbase/run.

Sequencing Cost:

In some instances, the disclosed nucleic acid sequencing systems may provide nucleic acid sequencing at a cost ranging from about $5 per Gbase to about $30 per Gbase. In some instances, the sequencing cost may be at least $5 per Gbase, at least $10 per Gbase, at least $15 per Gbase, at least $20 per Gbase, at least $25 per Gbase, or at least $30 per Gbase. In some instances, the sequencing cost may be at most $30 per Gbase, at most $25 per Gbase, at most $20 per Gbase, at most $15 per Gbase, at most $10 per Gbase, or at most $30 per Gbase. Any of the lower and upper values described in this paragraph may be combined to form a range included within the present disclosure, for example, in some instances the sequencing cost may range from about $10 per Gbase to about $15 per Gbase. Those of skill in the art will recognize that in some instances the sequencing cost may have any value within this range, e.g., about $7.25 per Gbase.

EXAMPLES

These examples are provided for illustrative purposes only and not to limit the scope of the claims provided herein.

Example 1—Design Specifications for a Fluorescence Imaging Module for Genomics Applications A non-limiting example of design specifications for a fluorescence imaging module of the present disclosure is provided in Table 1.

TABLE 1

Examples of design specifications for a fluorescence imaging module for genomics applications.

| Design Parameter | Specification |
| --- | --- |
| Numerical aperture | ≥0.3 |
| Image quality | Diffraction limited |
| Field-of-view (FOV) | >2.0 mm$^2$ |
| Image plane curvature | Best focal plane within 100 nm for >90% of the FOV, within 150 nm for 99% of the FOV, and within 200 nm for the entire FOV |
| Image distortion | <0.5% across the FOV |
| Magnification | 2x to 20x |
| Camera pixel size at sample plane | ≥2 x optical system modulation transfer function (MTF) limit |
| Coverslip thickness | >700 μm |
| Number of fluorescence imaging channels | ≥3 |
| Chromatic focal plane difference at camera between all imaging channels | ≤100 nm equivalent at sample plane |
| Number of AF channels | 1 |
| Imaging time | ≤2 seconds per FOV |
| Autofocus | Single step autofocus with error correction |
| Autofocus accuracy | <100 nm |
| Scanning stage step and settle time | <0.4 seconds |
| Channel-specific optimized tube lens | 1 per imaging channel |
| Illumination optical path | Liquid light guide with underfilled entrance aperture |

Example 2—Fabrication of Glass Microfluidic Flow Cell Devices

Figure 36A:
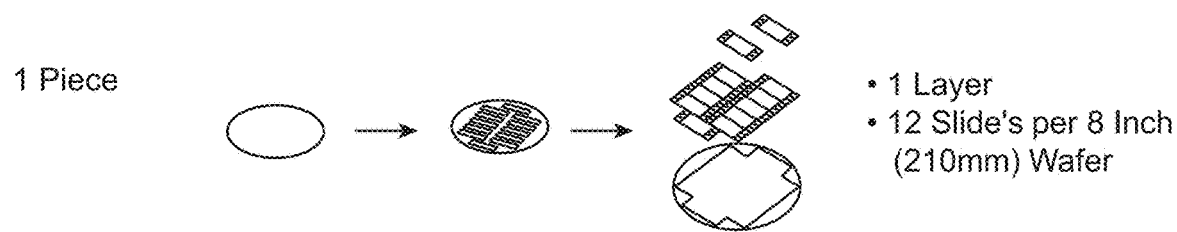
FIGS. 36A-36C illustrates non-limiting examples of flow cell device fabrication.
Figure 36B:
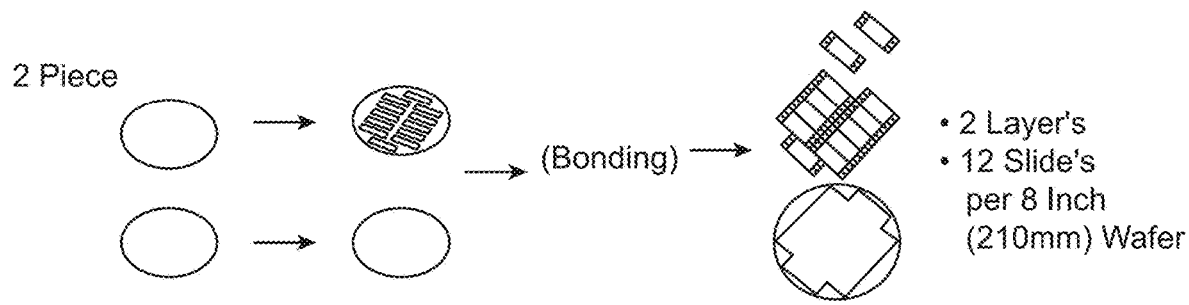
Figure 36C:
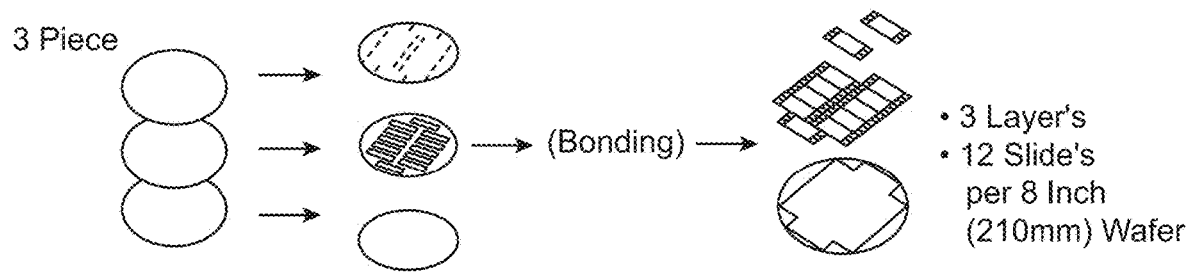

Wafer-scale fabrication of microfluidic devices for use as flow cells can be constructed from, for example, one, two, or three layers of glass, e.g., borosilicate glass, fused-silica glass, or quartz, using one of the processed illustrated in FIGS. 36A-36C and a processing technique such as focused femtosecond laser photoablation and/or laser glass bonding.

In FIG. 36A, a first wafer is processed with a laser (e.g., that produces femtosecond laser radiation) to ablate the wafer material and provide a patterned surface. The patterned wafer surface may comprise a plurality of microfluidic devices (e.g., 12 devices per 210 mm diameter wafer), each of which may comprise a plurality of fluid channels. The processed wafer may then be diced to create individual microfluidic chips comprising open fluid channels that may optionally be subsequently sealed, e.g., by sealing with a film or by clamping the device to another support surface.

In FIG. 36B, a first wafer is processed to create a patterned surface which may then be placed in contact with and bonded to a second wafer to seal the fluid channels. Depending on the materials used, e.g., glass wafers, silicon wafers, etc., the bonding may be performed using, e.g., a thermal bonding process, an anodic bonding process, a laser glass bonding process, etc. The second wafer covers and/or seals the grooves, indentations, and/or apertures on the wafer having the patterned surface to form fluid channels and/or fluid chambers (e.g., the interior portion) of the device at the interface of the two wafer components. The bonded structure may then be diced into individual microfluidic chips, e.g., 12 microfluidic chips per 210 mm diameter wafer.

In FIG. 36C, the first wafer is processed to create a pattern of fluid channels that are cut or etched through the full thickness of the wafer (i.e., open on either surface of the wafer). The first wafer is then sandwiched between and bonded to a second wafer on one side and a third wafer on the other side. Depending on the materials used, e.g., glass wafers, silicon wafers, etc., the bonding may be performed using, e.g., a thermal bonding process, an anodic bonding process, a laser glass bonding process, etc. The second and third wafers cover and/or seal the grooves, indentations, and/or apertures in the first wafer to form fluid channels and/or fluid chambers (e.g., the interior portions) of the device. The bonded structure may then be diced into individual microfluidic chips, e.g., 12 microfluidic chips per 210 mm diameter wafer.

Example 3—Coating Flow Cell Surfaces with a Hydrophilic Polymer Coating

Glass flow cell devices were coated by washing prepared glass channels with KOH, followed by rinsing with ethanol and then silanization for 30 minutes at 65° C. Fluid channel surfaces were activated with EDC-NHS for 30 min., followed by grafting of oligonucleotide primers by incubation of the activated surface with 5 μm primer for 20 min., and then passivation with 30 μm of an amino-terminated polyethylene glycol (PEG-NH2).

Multilayer surfaces are made following the approach described above, where following the PEG-NH2 passivation step, a multi-armed PEG-NETS is flowed through the fluid channels, followed by another addition of the PEG-NH2, optionally followed by another incubation with PEG-NETS, and optionally followed by another incubation with multi-armed PEG-NH2. For these surfaces, the primer may be grafted at any step, and especially following the last addition of multi-armed PEG-NH2.

Example 4—Flow Cell Devices for Nucleic Acid Sequencing

Figure 37A:
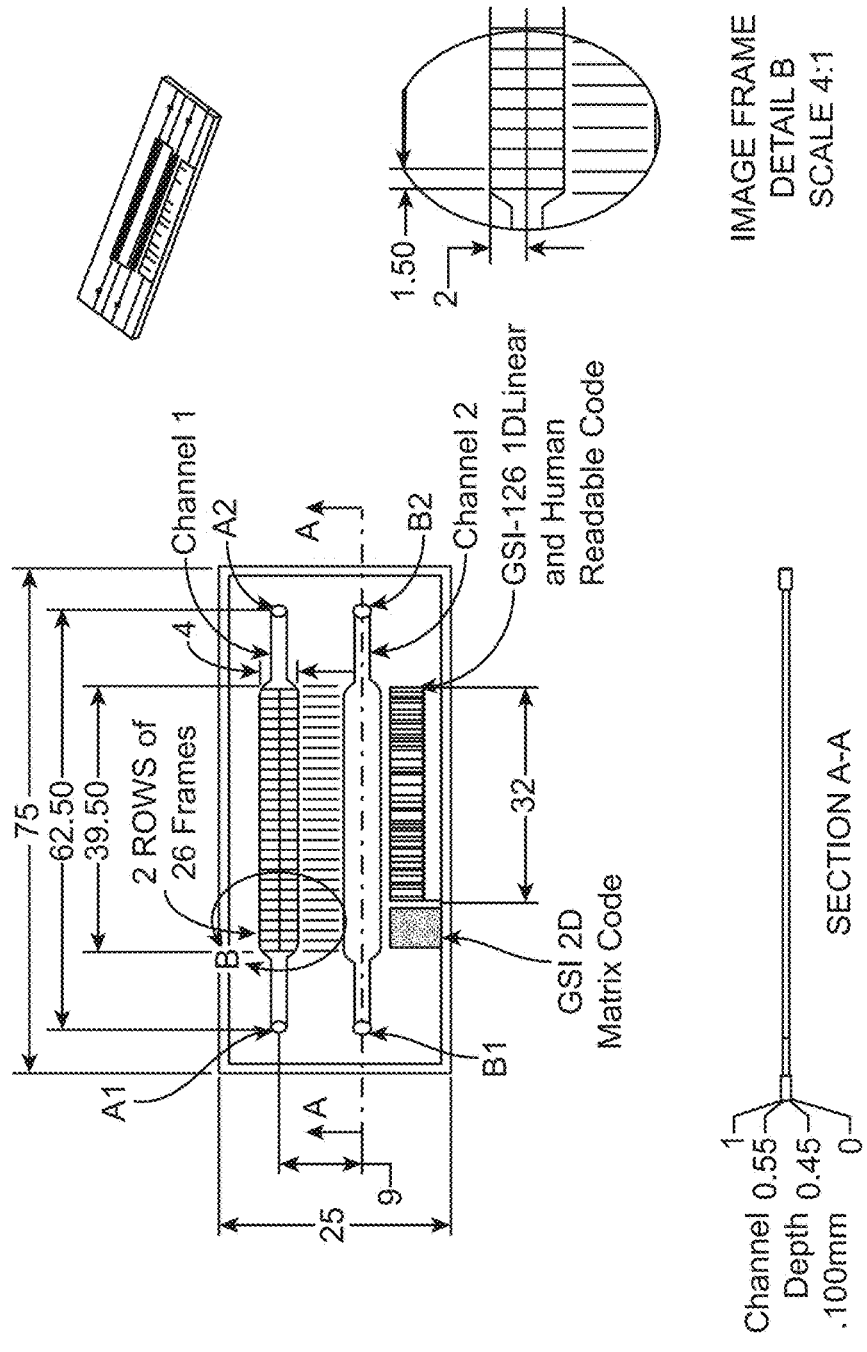
FIGS. 37A-37C illustrates non-limiting examples of glass flow cell designs.

FIG. 37A illustrates a non-limiting example of a one-piece glass microfluidic chip/flow cell design. In this design, fluid channels and inlet/outlet holes may be fabricated using, e.g., focused femtosecond laser radiation. There are two fluid channels ("lanes") in the flow cell device, and each fluid channel comprises, e.g., 2 rows of 26 frames each (i.e., where a "frame" is the image area equivalent to the field-of-view for a corresponding imaging module) each, such that tiling 2×26=52 images suffices to image an entire fluid channel. The fluid channel can have, e.g., a depth of about 100 μm. Fluid channel 1 has an inlet hole A1 and an outlet hole A2, and fluid channel 2 has an inlet hole B1 and an outlet hole B2. The flow cell device may also comprise a 1D linear, human-readable and/or machine-readable barcode, and optionally a 2D matrix barcode.

Figure 37B:
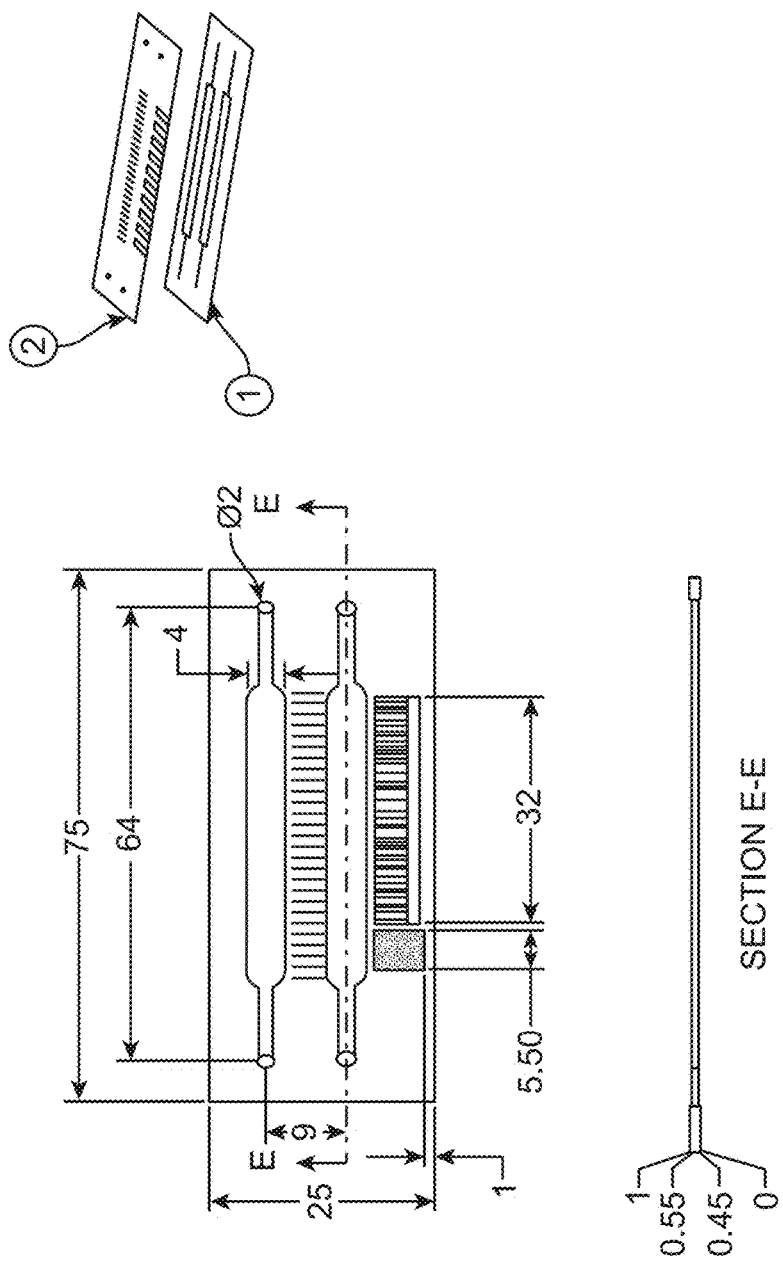

FIG. 37B illustrates a non-limiting example of a two-piece glass microfluidic chip/flow cell design. In this design, fluid channels and inlet/outlet holes may be fabricated using, e.g., focused femtosecond laser photoablation or photolithography and chemical etching processes. The 2 pieces can be bonded together using any of a variety of techniques as described above. The inlet and outlet holes may be positioned on the top layer of the structure and oriented in such a way that they are in fluid communication with at least one of the fluid channels and/or fluid chambers formed in the interior portion of the device. There are two fluid channels in the flow cell device, and as with the device illustrated in FIG. 37A, each fluid channel comprises, e.g., 2 rows with 26 frames in each row. The fluid channels can have, e.g., a depth of about 100 μm. Fluid channel 1 has an inlet hole A1 and an outlet hole A2, and fluid channel 2 has an inlet hole B1 and an outlet hole B2. The flow cell device may also comprise a 1D linear, human-readable and/or machine-readable barcode, and optionally a 2D matrix barcode.

Figure 37C:
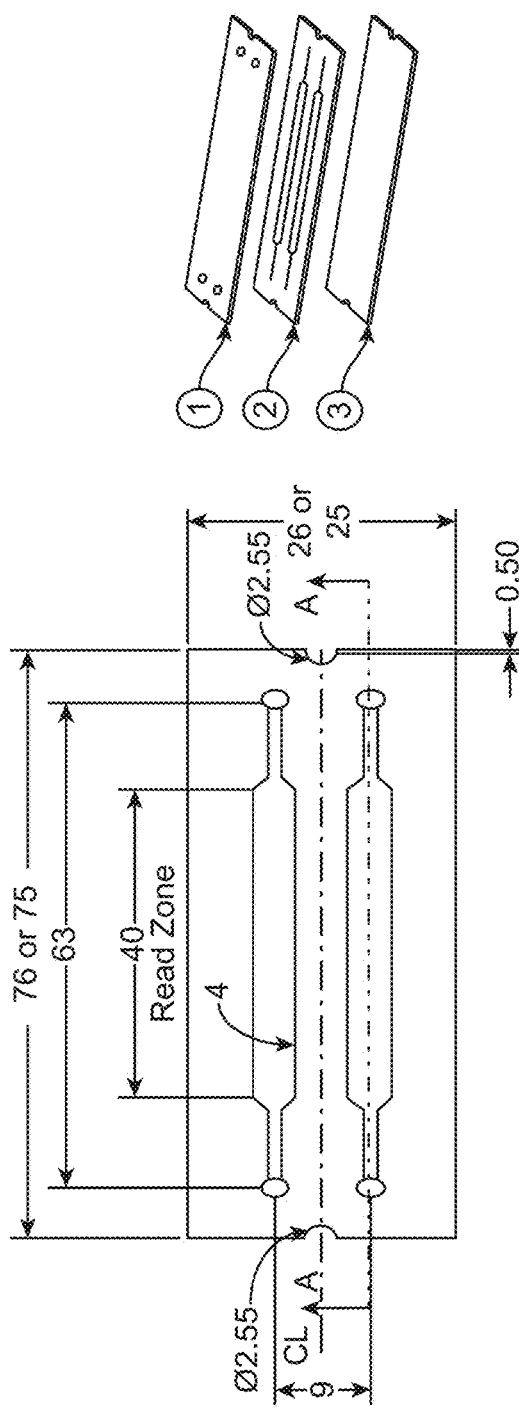
Figure 37C:
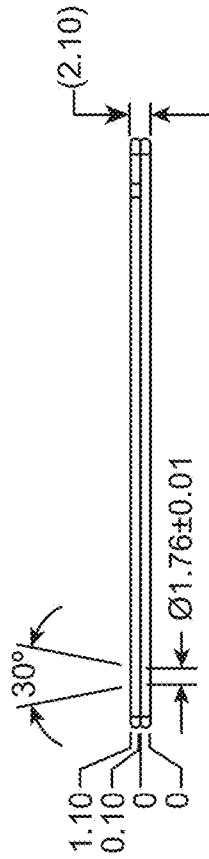

FIG. 37C illustrates a non-limiting example of a three-piece glass microfluidic chip/flow cell design. In this design, fluid channels and inlet/outlet holes may be fabricated using, e.g., focused femtosecond laser photoablation or photolithography and chemical etching processes. The 3 pieces can be bonded together using any of a variety of techniques as described above. The first wafer (comprising a through-pattern of fluid channels or fluid chambers) can be sandwiched between and bonded to a second wafer on one side and a third wafer on the other side. The inlet and outlet holes may be positioned on the top layer of the structure and oriented in a way such that they are in fluid communication with at least one of the fluid channels and/or fluid chambers formed in the interior portion of the device. There are two fluid channels in the flow cell device, and as with the devices illustrated in FIGS. 37A and 37B, each fluid channel has 2 rows with 26 frames in each row. The fluid channel can have a depth of, e.g., about 100 μm. Fluid channel 1 has an inlet hole A1 and an outlet hole A2, and fluid channel 2 has an inlet hole B1 and an outlet hole B2. The flow cell device may also comprise a 1D linear, human-readable and/or machine-readable barcode, and optionally a 2D matrix barcode.

Example 5—Imaging of Nucleic Acid Clusters in a Capillary Flow Cell

Figure 38:
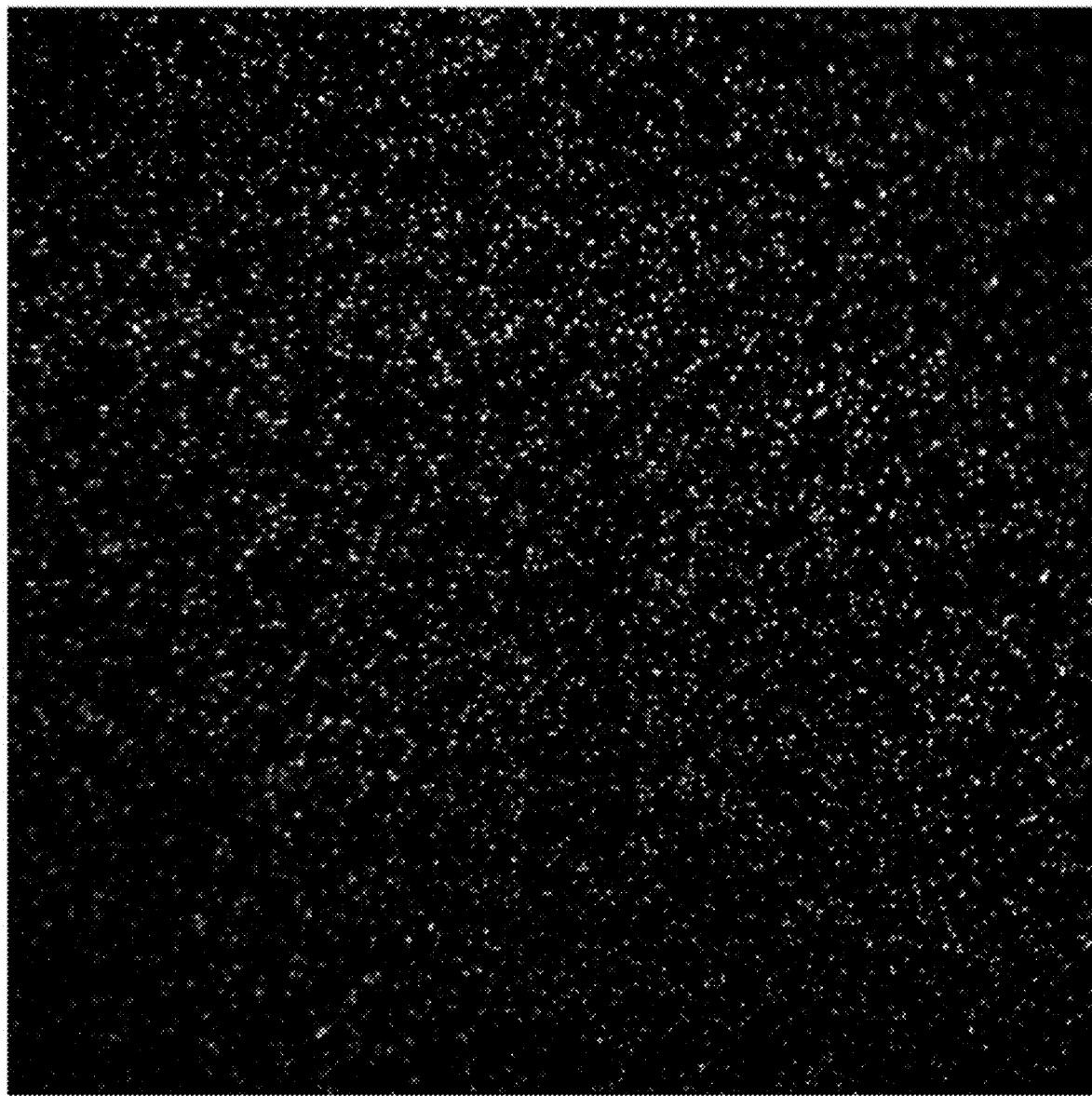
FIG. 38 illustrates visualization of cluster amplification in a capillary lumen.

Nucleic acid clusters were established within a capillary and subjected to fluorescence imaging. A flow device having a capillary tube was used for the test. An example of the resulting cluster images is presented in FIG. 38. The figure demonstrated that nucleic acid clusters formed by amplification within the lumen of a capillary flow cell device as disclosed herein can be reliably formed and visualized.

Example 6—Plastic Sample Support Structures

In some instances, the disclosed samples support structures may be fabricated from a polymer. Examples of materials from which the sample support structure, e.g., a capillary flow cell device, may be fabricated include, but are not limited to, polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), or any combination thereof. Various compositions comprising both glass and plastic substrates are also contemplated.

Modification of a polymer surface for the surface coating purposes disclosed herein involves making surfaces reactive with other chemical groups (—R), including amines. When prepared on an appropriate substrate, these reactive surfaces can be stored long term at room temperature, for example, for at least 3 months or more in some instances. Such surfaces can be further grafted with R-PEG and R-primer oligomer for on-surface amplification of nucleic acids, as described elsewhere herein. Plastic surfaces, such as cyclic olefin polymer (COP), may be modified using any of a variety of methods known in the art. For example, they can be treated with Ti: Sapphire laser ablation, UV-mediated ethylene glycol methacrylate photografting, plasma treatment, or mechanical agitation (e.g., sand blasting, or polishing, etc.) to create hydrophilic surfaces that can remain reactive for months towards a variety of chemical groups, such as amines. These groups may then allow conjugation of passivation polymers such as PEG, or biomolecules such as DNA or proteins, without loss of biochemical activity. For example, attachment of DNA primer oligomers allows DNA amplification on a passivated plastic surface while reducing or minimizing the non-specific adsorption of proteins, fluorophore molecules, or other hydrophobic molecules.

Additionally, in some instances, surface modification can be combined with, e.g., laser printing or UV masking, to create patterned surfaces. This allows patterned attachment of DNA oligomers, proteins, or other moieties, providing for surface-based enzymatic activity, binding, detection, or processing. For example, DNA oligomers may be used to amplify DNA only within patterned features, or to capture amplified long DNA concatemers in a patterned fashion. In some embodiments, enzyme islands may be generated in the patterned areas that are capable of reacting with solution-based substrates. Because plastic surfaces are especially amenable to these processing modes, in some embodiments as contemplated herein, plastic sample support surfaces or flow cell devices may be recognized as being particularly advantageous.

Furthermore, plastic can be injection molded, embossed, stamped, or 3D printed to form any shape, including microfluidic devices, much more easily than glass substrates, and thus can be used to create surfaces for the binding and analysis of biological samples in multiple configurations, e.g., sample-to-result microfluidic chips for biomarker detection or DNA sequencing.

Specific and localized DNA amplification on modified plastic surfaces can be performed to produce nucleic acid spots with an ultra-high contrast to noise ratio and very low background when probed with fluorescent labels.

Hydrophilized and amine-reactive cyclic olefin polymer surface with amine-primer and amine-PEG can be prepared and has been demonstrated to support rolling circle amplification. When probed with fluorophore labeled primers, or when labeled dNTPs were added to the hybridized primers by a polymerase, bright spots of DNA amplicons were observed that exhibited signal to noise ratios greater than 100 with backgrounds that are extremely low, indicating highly specific amplification, and ultra-low levels of non-specific protein and hydrophobic fluorophore binding, which are hallmarks of the high accuracy detection required for systems such as fluorescence-based DNA sequencers.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. An imaging system, comprising:
   a) an objective lens;
   b) at least one image sensor configured to obtain an image of nucleic acid molecules, proteins, or a combination thereof;
   c) at least one tube lens disposed in an optical path between the objective lens and the at least one image sensor; and
   d) a flow cell comprising a first interior surface and a second interior surface, wherein said first interior surface comprises a first set of said nucleic acid molecules, proteins, or a combination thereof covalently coupled thereto, and said second interior surface comprises a second set of said nucleic acid molecules, said proteins, or said combination thereof covalently coupled thereto;

wherein said imaging system has a numerical aperture (NA) of less than 0.6 and a field-of-view (FOV) of greater than 3.0 mm², and wherein the at least one tube lens is configured to correct imaging performance such that images of the first interior surface of the flow cell and the second interior surface of the flow cell have substantially the same optical resolution.

2. The imaging system of claim 1, wherein the flow cell has a wall thickness of at least 700 μm and a fluid-filled gap between the first interior surface and the second interior surface of at least 50 μm.

3. The imaging system of claim 1, wherein the images of the first interior surface and the second interior surface are acquired without moving an optical compensator into said optical path between said objective lens and said at least one image sensor.

4. The imaging system of claim 1, wherein the imaging system has a numerical aperture (NA) of greater than 0.3.

5. The imaging system of claim 1, wherein the imaging system has a field-of-view (FOV) of greater than 3.5 mm².

6. The imaging system of claim 5, wherein the optical resolution of the images of the first interior surface and the second interior surface are diffraction-limited across the FOV in its entirety.

7. The imaging system of claim 1, wherein the at least one tube lens comprises, in order, an asymmetric convex-convex lens, a convex-plano lens, an asymmetric concave-concave lens, and an asymmetric convex-concave lens.

8. The imaging system of claim 1, wherein the imaging system comprises two or more tube lenses which are designed to provide optimal imaging performance for the first interior surface and the second interior surface at two or more fluorescence wavelengths.

9. The imaging system of claim 1, further comprising a focusing mechanism configured to refocus the imaging system between acquiring images of the first interior surface and the second interior surface.

10. The imaging system of claim 1, wherein the imaging system is configured to image two or more fields-of-view on at least one of the first interior surface or the second interior surface.

11. The imaging system of claim 1, wherein the first interior surface and second interior surface of the flow cell are coated with a hydrophilic coating layer, and wherein said hydrophilic coating layer comprises labeled nucleic acid colonies disposed thereon at a surface density of greater than 10,000 nucleic acid colonies per mm².

12. The imaging system of claim 11, wherein an image of the first interior surface or the second interior surface acquired using the imaging system shows a contrast to noise ratio (CNR) of at least 5 when the nucleic acid colonies are labeled with cyanine dye 3 (Cy3), the imaging system comprises a dichroic mirror and bandpass filter set optimized for Cy3 emission, and the image is acquired under non-signal saturating conditions while the first interior surface or the second interior surface are immersed in 25 mM ACES, pH 7.4 buffer.

13. The imaging system of claim 11, wherein said imaging system comprises 1, 2, 3, or 4 imaging channels configured to detect nucleic acid colonies disposed on at least one of said first interior surface and said second interior surface that has been labeled with 1, 2, 3, or 4 distinct detectable labels.

14. The imaging system of claim 11, wherein the imaging system is used to monitor a sequencing-by-avidity, sequencing-by-nucleotide base-pairing, sequencing-by-nucleotide binding, or sequencing-by-nucleotide incorporation reaction on at least one of the first interior surface and the second interior surface and detect a bound or incorporated nucleotide base.

15. The imaging system of claim 11, wherein the imaging system is used to perform nucleic acid sequencing.

16. The imaging system of claim 11, wherein the imaging system is used to determine a genotype of a sample, wherein determining the genotype of the sample comprises preparing a nucleic acid molecule extracted from the sample for sequencing, and then sequencing the nucleic acid molecule.

17. The imaging system of claim 1, wherein the at least one image sensor comprises pixels having a pixel dimension chosen such that a spatial sampling frequency for the imaging system is at least twice an optical resolution of the imaging system.

18. The imaging system of claim 1, wherein a combination of the objective lens and the at least one tube lens is configured to optimize a modulation transfer function in the spatial frequency range from 700 cycles per mm to 1100 cycles per mm in the sample plane.

19. The imaging system of claim 1, wherein the at least one tube lens is designed to correct modulation transfer function (MTF) at one or more specified spatial frequencies, defocus, spherical aberration, chromatic aberration, coma, astigmatism, field curvature, image distortion, image contrast-to-noise ratio (CNR), or any combination thereof, for a combination of the objective lens and the at least one tube lens.

20. The imaging system of claim 1, wherein said first interior surface and said second interior surface comprise nucleic acid molecules, proteins, or a combination thereof immobilized thereto.

21. The imaging system of claim 1, wherein said first interior surface of said flow cell is disposed in said optical path between said objective lens and said second interior surface of said flow cell.

22. The imaging system of claim 1, further comprising a liquid between said first interior surface and said second interior surface.

23. The imaging system of claim 1, wherein said flow cell is a capillary flow cell.

24. The imaging system of claim 1, further comprising a liquid between said first interior surface and said second interior surface.

25. The imaging system of claim 1, wherein at least one optical element is in a permanent position between the objective lens and the at least one image sensor.

26. The imaging system of claim 25, wherein the at least one optical element comprises the at least one tube lens.

27. The imaging system of claim 26, wherein said first interior surface and said second interior surface comprise nucleic acid molecules, proteins, or a combination thereof immobilized thereto.

28. The imaging system of claim 26, wherein said first interior surface of said flow cell is disposed in said optical path between said objective lens and said second interior surface of said flow cell.

29. The imaging system of claim 26, further comprising a liquid between said first interior surface and said second interior surface.

30. The imaging system of claim 1, further comprising a first linker coupled to said first set of said nucleic acid molecules, said proteins, or said combination thereof, wherein said first linker is covalently coupled to said first interior surface.

31. The imaging system of claim 30, wherein said first linker comprises polyethylene glycol (PEG).

32. The imaging system of claim 1, further comprising a fluorescent light filter.

33. The imaging system of claim 1, wherein at least one of said first set of said nucleic acid molecules, said proteins, or said combination thereof covalently coupled thereto and said second set of said nucleic acid molecules, said proteins, or said combination thereof covalently coupled thereto comprise a label detectable by said imaging system.

34. The imaging system of claim 1, further comprising a fluorescence excitation filter that is configured to selectively transmit a fluorescent light emitted by a fluorescent label coupled to at least one of said first set of said nucleic acid molecules, said proteins, or said combination thereof and said second set of said nucleic acid molecules, said proteins, or said combination thereof.

* * * * *